United States Patent
Patzke et al.

(10) Patent No.: US 12,281,321 B2
(45) Date of Patent: Apr. 22, 2025

(54) FRATAXIN EXPRESSION CONSTRUCTS HAVING ENGINEERED PROMOTERS AND METHODS OF USE THEREOF

(71) Applicant: VOYAGER THERAPEUTICS, INC., Lexington, MA (US)

(72) Inventors: Holger Patzke, Lexington, MA (US); Jinzhao Hou, Lexington, MA (US); Hongxing Wang, Lexington, MA (US); Yanqun Shu, Lexington, MA (US); Martin Goulet, Lexington, MA (US); Dinah Wen-Yee Sah, Lexington, MA (US)

(73) Assignee: Voyager Therapeutics, Inc., Lexington, MA (US)

( * ) Notice: Subject to any disclaimer, the term of this patent is extended or adjusted under 35 U.S.C. 154(b) by 936 days.

(21) Appl. No.: 17/279,878

(22) PCT Filed: Sep. 27, 2019

(86) PCT No.: PCT/US2019/053681
§ 371 (c)(1),
(2) Date: Mar. 25, 2021

(87) PCT Pub. No.: WO2020/069461
PCT Pub. Date: Apr. 2, 2020

(65) Prior Publication Data
US 2021/0395776 A1    Dec. 23, 2021

Related U.S. Application Data

(60) Provisional application No. 62/901,769, filed on Sep. 17, 2019, provisional application No. 62/738,519, filed on Sep. 28, 2018.

(51) Int. Cl.
| | | |
|---|---|---|
| *C12N 15/86* | (2006.01) | |
| *A61K 47/02* | (2006.01) | |
| *A61K 47/10* | (2017.01) | |
| *A61K 48/00* | (2006.01) | |
| *C07K 14/47* | (2006.01) | |

(52) U.S. Cl.
CPC .............. *C12N 15/86* (2013.01); *A61K 47/02* (2013.01); *A61K 47/10* (2013.01); *A61K 48/005* (2013.01); *C07K 14/47* (2013.01); *C12N 2830/008* (2013.01)

(58) Field of Classification Search
CPC ......... C12N 15/86; A61K 47/02; A61K 47/10
See application file for complete search history.

(56) References Cited

U.S. PATENT DOCUMENTS

| | | |
|---|---|---|
| 5,064,764 A | 11/1991 | Besnainon et al. |
| 5,474,935 A | 12/1995 | Chatterjee et al. |
| 5,587,308 A | 12/1996 | Carter et al. |
| 5,652,224 A | 7/1997 | Wilson et al. |
| 5,658,785 A | 8/1997 | Johnson |
| 5,688,676 A | 11/1997 | Zhou et al. |
| 5,691,176 A | 11/1997 | Lebkowski et al. |
| 5,693,531 A | 12/1997 | Chiorini et al. |
| 5,741,683 A | 4/1998 | Zhou et al. |
| 5,756,283 A | 5/1998 | Wilson et al. |
| 5,856,152 A | 1/1999 | Wilson et al. |
| 5,858,351 A | 1/1999 | Podsakoff et al. |
| 5,858,775 A | 1/1999 | Johnson |
| 5,866,552 A | 2/1999 | Wilson et al. |
| 5,866,696 A | 2/1999 | Carter et al. |
| 5,871,982 A | 2/1999 | Wilson et al. |
| 5,952,221 A | 9/1999 | Kurtzman et al. |
| 5,962,313 A | 10/1999 | Podsakoff et al. |
| 5,989,540 A | 11/1999 | Carter et al. |
| 6,083,716 A | 7/2000 | Wilson et al. |
| 6,143,548 A | 11/2000 | O'Riordan et al. |
| 6,143,567 A | 11/2000 | Van Agthoven et al. |
| 6,146,874 A | 11/2000 | Zolotukhin et al. |
| 6,156,303 A | 12/2000 | Russell et al. |
| 6,174,527 B1 | 1/2001 | Wilson et al. |
| 6,180,613 B1 | 1/2001 | Kaplitt et al. |

(Continued)

FOREIGN PATENT DOCUMENTS

| | | |
|---|---|---|
| EP | 1046711 A2 | 10/2000 |
| EP | 1164195 A2 | 12/2001 |

(Continued)

OTHER PUBLICATIONS

Lagator et al. Predicting bacterial promoter function and evolution from random sequences. ELife 0: 1-25. (Year: 2022).*
Gray et al. Optimizing Promoters for Recombinant Adeno-Associated Virus-Mediated Gene Expression in the Peripheral and Central Nervous System Using Self-Complementary Vectors. Human Gene Therapy 22: 1143-1153. (Year: 2011).*
Wang et al. Functional Roles of the AAV2 Inverted Terminal Repeat in Messenger RNA Transport and Transgene Expression. Molecular Therapy 21: Abstract 75. (Year: 2013).*
Belbellaa et al., "Correction of half the cardiomyocytes fully rescue Friedreich Ataxia mitochondrial cardiomyopathy through cell-autonomous mechanisms," Apr. 15, 2019;28(8):1274-1285.

(Continued)

*Primary Examiner* — Arthur S Leonard
*Assistant Examiner* — Keenan A Bates
(74) *Attorney, Agent, or Firm* — Finnegan, Henderson, Farabow, Garrett & Dunner, LLP

(57) ABSTRACT

The disclosure relates to compositions and methods for altering, e.g., enhancing, the expression of frataxin (FXN), whether in vitro and/or in vivo including, but not limited to, the exploitation of engineered promoters. Such compositions include delivery via administration of an adeno-associated viral (AAV) particle. The compositions and methods of the present disclosure are useful in the treatment of subjects diagnosed with, or suspected of having Friedreich's ataxia or another neuromuscular or neurological condition resulting from a deficiency in the quantity and/or function of frataxin or associated with decreased expression or protein levels of frataxin.

42 Claims, 12 Drawing Sheets

Specification includes a Sequence Listing.

(56) References Cited

U.S. PATENT DOCUMENTS

| | | |
|---|---|---|
| 6,194,191 B1 | 2/2001 | Zhang et al. |
| 6,200,560 B1 | 3/2001 | Couto et al. |
| 6,204,059 B1 | 3/2001 | Samulski et al. |
| 6,211,163 B1 | 4/2001 | Podsakoff et al. |
| 6,251,677 B1 | 6/2001 | Wilson et al. |
| 6,258,595 B1 | 7/2001 | Gao et al. |
| 6,261,551 B1 | 7/2001 | Wilson et al. |
| 6,265,389 B1 | 7/2001 | Burke |
| 6,270,996 B1 | 8/2001 | Wilson et al. |
| 6,274,354 B1 | 8/2001 | Wilson et al. |
| 6,281,010 B1 | 8/2001 | Gao et al. |
| 6,325,998 B1 | 12/2001 | Podsakoff et al. |
| 6,335,011 B1 | 1/2002 | Podsakoff et al. |
| 6,365,394 B1 | 4/2002 | Gao et al. |
| 6,387,368 B1 | 5/2002 | Wilson et al. |
| 6,399,385 B1 | 6/2002 | Croyle et al. |
| 6,410,300 B1 | 6/2002 | Samulski et al. |
| 6,416,992 B1 | 7/2002 | Mejza |
| 6,428,988 B1 | 8/2002 | Wilson et al. |
| 6,436,392 B1 | 8/2002 | Engelhardt et al. |
| 6,436,394 B1 | 8/2002 | Henderson et al. |
| 6,468,524 B1 | 10/2002 | Chiorini et al. |
| 6,468,771 B1 | 10/2002 | Einerhand et al. |
| 6,475,769 B1 | 11/2002 | Wilson et al. |
| 6,482,634 B1 | 11/2002 | Wilson et al. |
| 6,485,966 B2 | 11/2002 | Gao et al. |
| 6,503,888 B1 | 1/2003 | Kaplitt et al. |
| 6,509,150 B1 | 1/2003 | Salvetti et al. |
| 6,521,426 B1 | 2/2003 | Ciliberto et al. |
| 6,555,525 B2 | 4/2003 | Burke |
| 6,566,118 B1 | 5/2003 | Atkinson et al. |
| 6,582,692 B1 | 6/2003 | Podsakoff et al. |
| 6,593,123 B1 | 7/2003 | Wright et al. |
| 6,610,290 B2 | 8/2003 | Podsakoff et al. |
| 6,642,051 B1 | 11/2003 | Lynch et al. |
| 6,660,514 B1 | 12/2003 | Zolotukhin et al. |
| 6,660,521 B2 | 12/2003 | Brough et al. |
| 6,670,176 B1 | 12/2003 | Samulski et al. |
| 6,676,935 B2 | 1/2004 | Henderson et al. |
| 6,699,706 B1 | 3/2004 | Brooks |
| 6,710,036 B2 | 3/2004 | Kurtzman et al. |
| 6,723,551 B2 | 4/2004 | Kotin et al. |
| 6,726,907 B1 | 4/2004 | Zhang et al. |
| 6,753,419 B1 | 6/2004 | Toniatti et al. |
| 6,759,237 B1 | 7/2004 | Wilson et al. |
| 6,846,665 B1 | 1/2005 | Horer et al. |
| 6,855,314 B1 | 2/2005 | Chiorini et al. |
| 6,887,463 B2 | 5/2005 | Wilson et al. |
| 6,897,045 B2 | 5/2005 | Engelhardt et al. |
| 6,943,019 B2 | 9/2005 | Wilson et al. |
| 6,953,690 B1 | 10/2005 | Gao et al. |
| 6,984,517 B1 | 1/2006 | Chiorini et al. |
| 6,995,006 B2 | 2/2006 | Atkinson et al. |
| 7,015,026 B2 | 3/2006 | O'Riordan et al. |
| 7,022,519 B2 | 4/2006 | Gao et al. |
| 7,048,920 B2 | 5/2006 | Yu et al. |
| 7,056,502 B2 | 6/2006 | Hildinger et al. |
| 7,070,998 B2 | 7/2006 | Johnson et al. |
| 7,091,030 B2 | 8/2006 | Setiawan et al. |
| 7,094,604 B2 | 8/2006 | Snyder et al. |
| 7,105,345 B2 | 9/2006 | Wilson et al. |
| 7,112,321 B2 | 9/2006 | Wang et al. |
| 7,125,705 B2 | 10/2006 | Colosi |
| 7,125,706 B2 | 10/2006 | Zhang et al. |
| 7,169,612 B2 | 1/2007 | Kostenis et al. |
| 7,186,552 B2 | 3/2007 | Wilson et al. |
| 7,198,951 B2 | 4/2007 | Gao et al. |
| 7,223,585 B2 | 5/2007 | Coffey |
| 7,235,393 B2 | 6/2007 | Gao et al. |
| 7,238,526 B2 | 7/2007 | Wilson et al. |
| 7,241,447 B1 | 7/2007 | Engelhardt et al. |
| 7,247,472 B2 | 7/2007 | Wilson et al. |
| 7,271,002 B2 | 9/2007 | Kotin et al. |
| 7,282,199 B2 | 10/2007 | Gao et al. |
| 7,291,498 B2 | 11/2007 | Roy et al. |
| 7,300,797 B2 | 11/2007 | van Agthoven et al. |
| 7,306,794 B2 | 12/2007 | Wilson et al. |
| 7,319,002 B2 | 1/2008 | Wilson et al. |
| 7,326,555 B2 | 2/2008 | Konz, Jr. et al. |
| 7,344,872 B2 | 3/2008 | Gao et al. |
| 7,419,817 B2 | 9/2008 | Chiorini et al. |
| 7,419,956 B2 | 9/2008 | Ohtaki et al. |
| 7,445,930 B2 | 11/2008 | Zhang et al. |
| 7,479,554 B2 | 1/2009 | Chiorini et al. |
| 7,491,508 B2 | 2/2009 | Roy et al. |
| 7,510,872 B2 | 3/2009 | Clark et al. |
| 7,510,875 B2 | 3/2009 | Zhang et al. |
| 7,579,181 B2 | 8/2009 | O'Riordan et al. |
| 7,625,570 B1 | 12/2009 | Schaffer et al. |
| 7,638,120 B2 | 12/2009 | Liu et al. |
| 7,662,627 B2 | 2/2010 | Johnson et al. |
| 7,704,492 B2 | 4/2010 | Podsakoff et al. |
| 7,704,721 B2 | 4/2010 | Wright et al. |
| 7,732,129 B1 | 6/2010 | Zhang et al. |
| 7,790,449 B2 | 9/2010 | Gao et al. |
| 7,803,622 B2 | 9/2010 | Engelhardt et al. |
| 7,838,277 B2 | 11/2010 | Gao et al. |
| 7,888,096 B2 | 2/2011 | Wu et al. |
| 7,901,921 B2 | 3/2011 | Coffey et al. |
| 7,906,111 B2 | 3/2011 | Wilson et al. |
| 7,968,333 B2 | 6/2011 | Yu et al. |
| 8,105,574 B2 | 1/2012 | Wilson et al. |
| 8,110,351 B2 | 2/2012 | Bosnes |
| 8,137,948 B2 | 3/2012 | Qu et al. |
| 8,163,543 B2 | 4/2012 | Urabe et al. |
| 8,231,880 B2 | 7/2012 | Roy et al. |
| 8,236,495 B2 | 8/2012 | Nochumson et al. |
| 8,241,622 B2 | 8/2012 | Engelhardt et al. |
| 8,273,344 B2 | 9/2012 | Wang et al. |
| 8,283,151 B2 | 10/2012 | Schmidt et al. |
| 8,298,818 B2 | 10/2012 | Boye et al. |
| 8,318,480 B2 | 11/2012 | Gao et al. |
| 8,318,687 B2 | 11/2012 | Tabira et al. |
| 8,394,386 B2 | 3/2013 | Wilson |
| 8,409,842 B2 | 4/2013 | Clark et al. |
| 8,470,310 B2 | 6/2013 | Roy et al. |
| 8,476,418 B2 | 7/2013 | Mueller et al. |
| 8,512,981 B2 | 8/2013 | Hermens et al. |
| 8,524,219 B2 | 9/2013 | Roy et al. |
| 8,524,446 B2 | 9/2013 | Gao et al. |
| 8,603,459 B2 | 12/2013 | Wilson et al. |
| 8,614,101 B2 | 12/2013 | Vandine et al. |
| 8,637,255 B2 | 1/2014 | Wilson et al. |
| 8,642,314 B2 | 2/2014 | Bakker et al. |
| 8,685,734 B2 | 4/2014 | Coffey et al. |
| 8,697,417 B2 | 4/2014 | Bakker et al. |
| 8,697,665 B2 | 4/2014 | Roma et al. |
| 8,834,863 B2 | 9/2014 | Roy et al. |
| 8,846,030 B2 | 9/2014 | Engelhardt et al. |
| 8,846,389 B2 | 9/2014 | Chiorini et al. |
| 8,865,881 B2 | 10/2014 | Balazs et al. |
| 8,906,387 B2 | 12/2014 | Kay et al. |
| 8,906,675 B2 | 12/2014 | Gao et al. |
| 8,927,514 B2 | 1/2015 | Chatterjee et al. |
| 8,962,330 B2 | 2/2015 | Gao et al. |
| 8,962,332 B2 | 2/2015 | Gao et al. |
| 8,999,678 B2 | 4/2015 | Vandenberghe et al. |
| 9,034,836 B2 | 5/2015 | Dodge et al. |
| 9,050,299 B2 | 6/2015 | Bankiewicz |
| 9,051,542 B2 | 6/2015 | Wright et al. |
| 9,056,892 B2 | 6/2015 | Pun et al. |
| 9,066,966 B2 * | 6/2015 | Puccio ............... A61K 31/7088 |
| 9,080,183 B2 | 7/2015 | Klein et al. |
| 9,089,667 B2 | 7/2015 | Bankiewicz et al. |
| 9,102,943 B2 | 8/2015 | Shinmura et al. |
| 9,102,949 B2 | 8/2015 | Gao et al. |
| 9,115,373 B2 | 8/2015 | Hermens et al. |
| 9,163,260 B2 | 10/2015 | Wilson et al. |
| 9,217,155 B2 | 12/2015 | Gao et al. |
| 9,217,159 B2 | 12/2015 | Roy et al. |
| 9,228,174 B2 | 1/2016 | Noordman et al. |
| 9,233,174 B2 | 1/2016 | Chen et al. |
| 9,238,800 B2 | 1/2016 | Bossis et al. |
| 9,260,724 B2 | 2/2016 | Bakker et al. |

(56) References Cited

U.S. PATENT DOCUMENTS

| | | |
|---|---|---|
| 9,283,357 B2 | 3/2016 | Stedman et al. |
| 9,415,119 B2 | 8/2016 | Passini et al. |
| 9,434,928 B2 | 9/2016 | Mendell et al. |
| 9,439,979 B2 | 9/2016 | Chiorini et al. |
| 9,441,206 B2 | 9/2016 | Grieger et al. |
| 9,441,244 B2 | 9/2016 | Schaffer et al. |
| 9,447,433 B2 | 9/2016 | Hirsch et al. |
| 9,457,103 B2 | 10/2016 | Schaffer et al. |
| 9,458,517 B2 | 10/2016 | Schaffer et al. |
| 9,464,119 B2 | 10/2016 | Sonntag et al. |
| 9,475,845 B2 | 10/2016 | Asokan et al. |
| 9,486,541 B2 | 11/2016 | Hutton et al. |
| 9,493,788 B2 | 11/2016 | Gao et al. |
| 9,504,762 B2 | 11/2016 | Colosi et al. |
| 9,506,052 B2 | 11/2016 | Samulski et al. |
| 9,506,083 B2 | 11/2016 | Arbetman et al. |
| 9,528,126 B2 | 12/2016 | Qu et al. |
| 9,540,659 B2 | 1/2017 | Davidson et al. |
| 9,546,112 B2 | 1/2017 | Voit et al. |
| 9,546,369 B2 | 1/2017 | Gao et al. |
| 9,567,376 B2 | 2/2017 | Cronin et al. |
| 9,567,607 B2 | 2/2017 | Wilson et al. |
| 9,580,691 B2 | 2/2017 | Bakker et al. |
| 9,585,971 B2 | 3/2017 | Deverman et al. |
| 9,587,250 B2 | 3/2017 | Gao et al. |
| 9,587,282 B2 | 3/2017 | Schaffer et al. |
| 9,593,346 B2 | 3/2017 | Roy et al. |
| 9,596,835 B2 | 3/2017 | Gao et al. |
| 9,597,363 B2 | 3/2017 | Roy et al. |
| 9,598,468 B2 | 3/2017 | Weigel-Van Aken et al. |
| 9,598,703 B2 | 3/2017 | Garcia et al. |
| 9,611,302 B2 | 4/2017 | Srivastava et al. |
| 9,617,561 B2 | 4/2017 | Roy et al. |
| 9,623,120 B2 | 4/2017 | Chatterjee et al. |
| 9,624,274 B2 | 4/2017 | Lux et al. |
| 9,629,930 B2 | 4/2017 | Gregory et al. |
| 9,636,370 B2 | 5/2017 | Mccown et al. |
| 9,670,507 B2 | 6/2017 | Xiao et al. |
| 9,677,088 B2 | 6/2017 | Nakai et al. |
| 9,677,089 B2 | 6/2017 | Gao et al. |
| 9,682,193 B2 | 6/2017 | Anand et al. |
| 9,695,220 B2 | 7/2017 | Vandenberghe et al. |
| 9,701,984 B2 | 7/2017 | Gao et al. |
| 9,708,627 B2 | 7/2017 | Hermens et al. |
| 9,719,070 B2 | 8/2017 | Vandenberghe et al. |
| 9,719,106 B2 | 8/2017 | Wilson et al. |
| 9,725,485 B2 | 8/2017 | Srivastava et al. |
| 9,732,345 B2 | 8/2017 | Martin et al. |
| 9,737,618 B2 | 8/2017 | Wilson et al. |
| 9,745,590 B2 | 8/2017 | Kay et al. |
| 9,775,918 B2 | 10/2017 | Zhong et al. |
| 9,777,291 B2 | 10/2017 | Chatterjee et al. |
| 9,783,824 B2 | 10/2017 | Kay et al. |
| 9,783,825 B2 | 10/2017 | Chatterjee et al. |
| 9,790,472 B2 | 10/2017 | Gao et al. |
| 9,803,218 B2 | 10/2017 | Chatterjee et al. |
| 10,000,757 B2 | 6/2018 | Naldini et al. |
| 10,041,090 B2 | 8/2018 | Gao et al. |
| 10,208,318 B2 | 2/2019 | Barkats |
| 10,337,027 B2 | 7/2019 | Puccio et al. |
| 10,407,724 B2 * | 9/2019 | Hatchwell ............ C12Q 1/6883 |
| 10,563,222 B2 | 2/2020 | Yang et al. |
| 11,116,852 B2 | 9/2021 | Schauer et al. |
| 11,118,192 B2 | 9/2021 | Kirn et al. |
| 2001/0006955 A1 | 7/2001 | Wilson et al. |
| 2001/0049144 A1 | 12/2001 | Rivera et al. |
| 2002/0019050 A1 | 2/2002 | Gao et al. |
| 2002/0037867 A1 | 3/2002 | Wilson et al. |
| 2002/0081721 A1 | 6/2002 | Allen et al. |
| 2002/0090717 A1 | 7/2002 | Gao et al. |
| 2002/0102714 A1 | 8/2002 | Wilson et al. |
| 2002/0131961 A1 | 9/2002 | Wilson et al. |
| 2003/0013189 A1 | 1/2003 | Wilson et al. |
| 2003/0032613 A1 | 2/2003 | Gao et al. |
| 2003/0092161 A1 | 5/2003 | Gao et al. |
| 2003/0100115 A1 | 5/2003 | Raj et al. |
| 2003/0119191 A1 | 6/2003 | Gao et al. |
| 2003/0138772 A1 | 7/2003 | Gao et al. |
| 2004/0043490 A1 | 3/2004 | Shimada |
| 2004/0057931 A1 | 3/2004 | Wilson et al. |
| 2004/0136963 A1 | 7/2004 | Wilson et al. |
| 2004/0171807 A1 | 9/2004 | Gao et al. |
| 2005/0261218 A1 * | 11/2005 | Esau ...................... A61P 37/00 536/23.1 |
| 2006/0003451 A1 | 1/2006 | Gao et al. |
| 2006/0204479 A1 | 9/2006 | Wilson et al. |
| 2007/0004042 A1 | 1/2007 | Gao et al. |
| 2008/0008684 A1 | 1/2008 | Wilson et al. |
| 2008/0050343 A1 | 2/2008 | Wilson et al. |
| 2008/0050345 A1 | 2/2008 | Wilson et al. |
| 2008/0075737 A1 | 3/2008 | Gao et al. |
| 2009/0215871 A1 | 8/2009 | Wilson et al. |
| 2009/0275107 A1 | 11/2009 | Lock et al. |
| 2009/0317417 A1 | 12/2009 | Vandenberghe et al. |
| 2010/0247490 A1 | 9/2010 | Roy et al. |
| 2010/0278791 A1 | 11/2010 | Wilson et al. |
| 2010/0278971 A1 | 11/2010 | Song et al. |
| 2011/0136227 A1 | 6/2011 | Bakker et al. |
| 2011/0171262 A1 | 7/2011 | Bakker et al. |
| 2011/0223135 A1 | 9/2011 | Roy et al. |
| 2011/0229971 A1 | 9/2011 | Knop et al. |
| 2012/0046349 A1 | 2/2012 | Bell et al. |
| 2012/0058102 A1 | 3/2012 | Wilson et al. |
| 2012/0093853 A1 | 4/2012 | Wilson et al. |
| 2012/0137379 A1 | 5/2012 | Gao et al. |
| 2012/0244131 A1 | 9/2012 | Delacote et al. |
| 2012/0258046 A1 | 10/2012 | Mutzke |
| 2013/0023033 A1 | 1/2013 | Wilson et al. |
| 2013/0045186 A1 | 2/2013 | Gao et al. |
| 2013/0101558 A1 | 4/2013 | Gao et al. |
| 2013/0109658 A1 | 5/2013 | Testi et al. |
| 2013/0136729 A1 | 5/2013 | French et al. |
| 2013/0195801 A1 | 8/2013 | Gao et al. |
| 2013/0196932 A1 | 8/2013 | Testi |
| 2013/0296532 A1 | 11/2013 | Hermens et al. |
| 2013/0323226 A1 | 12/2013 | Wilson et al. |
| 2013/0323302 A1 | 12/2013 | Constable et al. |
| 2014/0031418 A1 | 1/2014 | Wilson et al. |
| 2014/0044680 A1 | 2/2014 | Roy et al. |
| 2014/0065105 A1 | 3/2014 | Wilson et al. |
| 2014/0087361 A1 | 3/2014 | Dobbelaer et al. |
| 2014/0099666 A1 | 4/2014 | Rossomando et al. |
| 2014/0107186 A1 | 4/2014 | Garcia et al. |
| 2014/0221462 A1 | 8/2014 | Puccio et al. |
| 2014/0296486 A1 | 10/2014 | Gao et al. |
| 2014/0336245 A1 | 11/2014 | Mingozzi et al. |
| 2014/0341852 A1 | 11/2014 | Srivastava et al. |
| 2014/0342434 A1 | 11/2014 | Hermens et al. |
| 2015/0005369 A1 | 1/2015 | Muzyczka et al. |
| 2015/0023924 A1 | 1/2015 | High et al. |
| 2015/0065562 A1 | 3/2015 | Yazicioglu et al. |
| 2015/0079038 A1 | 3/2015 | Deverman et al. |
| 2015/0118287 A1 | 4/2015 | Hammond et al. |
| 2015/0139952 A1 | 5/2015 | Webster |
| 2015/0151007 A1 | 6/2015 | Dodge et al. |
| 2015/0159173 A1 | 6/2015 | Vandenberghe et al. |
| 2015/0196671 A1 | 7/2015 | Byrne et al. |
| 2015/0203553 A1 | 7/2015 | Chiorini |
| 2015/0238610 A1 | 8/2015 | Sista et al. |
| 2015/0307898 A2 | 10/2015 | Hermens et al. |
| 2015/0313969 A1 | 11/2015 | Puccio et al. |
| 2015/0315610 A1 | 11/2015 | Nishie et al. |
| 2015/0374803 A1 | 12/2015 | Wolfe |
| 2016/0032319 A1 | 2/2016 | Wright et al. |
| 2016/0108373 A1 | 4/2016 | Bennett et al. |
| 2016/0153992 A1 | 6/2016 | Buening et al. |
| 2016/0166709 A1 | 6/2016 | Davidson et al. |
| 2016/0256534 A1 | 9/2016 | Bankiewicz et al. |
| 2016/0271192 A1 | 9/2016 | Roy et al. |
| 2016/0273058 A1 | 9/2016 | Akashika et al. |
| 2016/0289275 A1 | 10/2016 | Chiorini et al. |
| 2016/0296694 A1 | 10/2016 | Bankiewicz et al. |
| 2016/0331897 A1 | 11/2016 | Anand et al. |
| 2016/0333372 A1 | 11/2016 | Srivastava et al. |

(56) References Cited

U.S. PATENT DOCUMENTS

| | | |
|---|---|---|
| 2016/0333373 A1 | 11/2016 | Farley et al. |
| 2016/0333375 A1 | 11/2016 | Chen |
| 2016/0334417 A1 | 11/2016 | Rouillon et al. |
| 2016/0340393 A1 | 11/2016 | Schaffer et al. |
| 2016/0340692 A1 | 11/2016 | Wang et al. |
| 2016/0347822 A1 | 12/2016 | Crystal et al. |
| 2016/0354487 A1 | 12/2016 | Zhang et al. |
| 2016/0355796 A1 | 12/2016 | Davidson et al. |
| 2016/0361439 A1 | 12/2016 | Agbandje-Mckenna et al. |
| 2016/0367661 A1 | 12/2016 | Flavell et al. |
| 2016/0369297 A1 | 12/2016 | Byrne et al. |
| 2016/0369298 A1 | 12/2016 | Marsic et al. |
| 2016/0369299 A1 | 12/2016 | Boye et al. |
| 2016/0375110 A1 | 12/2016 | High et al. |
| 2016/0375151 A1 | 12/2016 | Schaffer et al. |
| 2016/0376323 A1 | 12/2016 | Schaffer et al. |
| 2016/0376608 A1 | 12/2016 | Chou et al. |
| 2017/0000904 A1 | 1/2017 | Wilson et al. |
| 2017/0007669 A1 | 1/2017 | Sarkar et al. |
| 2017/0007720 A1 | 1/2017 | Boye et al. |
| 2017/0021037 A1 | 1/2017 | Wang et al. |
| 2017/0028082 A1 | 2/2017 | Wilson et al. |
| 2017/0043037 A1 | 2/2017 | Kariko et al. |
| 2017/0044504 A1 | 2/2017 | Schaffer et al. |
| 2017/0051259 A1 | 2/2017 | Wang et al. |
| 2017/0067028 A1 | 3/2017 | Ballon et al. |
| 2017/0071972 A1 | 3/2017 | Buj Bello et al. |
| 2017/0073703 A1 | 3/2017 | Chatterjee et al. |
| 2017/0087219 A1 | 3/2017 | Bunting et al. |
| 2017/0088858 A1 | 3/2017 | Gao et al. |
| 2017/0095538 A1 | 4/2017 | Colosi et al. |
| 2017/0096646 A1 | 4/2017 | Roy et al. |
| 2017/0096683 A1 | 4/2017 | Scaria et al. |
| 2017/0105927 A1 | 4/2017 | Thorne et al. |
| 2017/0112946 A1 | 4/2017 | Ikeda et al. |
| 2017/0121734 A1 | 5/2017 | Cairns et al. |
| 2017/0128528 A1 | 5/2017 | Samulski |
| 2017/0128581 A1 | 5/2017 | Freskgard et al. |
| 2017/0128594 A1 | 5/2017 | Wright |
| 2017/0130208 A1 | 5/2017 | Potter et al. |
| 2017/0130245 A1 | 5/2017 | Kotin et al. |
| 2017/0145414 A1 | 5/2017 | Collard et al. |
| 2017/0145440 A1 | 5/2017 | Hermens et al. |
| 2017/0151348 A1 | 6/2017 | Kaspar et al. |
| 2017/0151416 A1 | 6/2017 | Kutikov et al. |
| 2017/0152525 A1 | 6/2017 | Hermens et al. |
| 2017/0157213 A1 | 6/2017 | Dickson et al. |
| 2017/0157267 A1 | 6/2017 | Kay et al. |
| 2017/0159026 A1 | 6/2017 | Kay et al. |
| 2017/0159027 A1 | 6/2017 | Wilson et al. |
| 2017/0159072 A9 | 6/2017 | Arbeit et al. |
| 2017/0165377 A1 | 6/2017 | Gao et al. |
| 2017/0166871 A1 | 6/2017 | Nishie et al. |
| 2017/0166925 A1 | 6/2017 | Gao et al. |
| 2017/0166926 A1 | 6/2017 | Deverman et al. |
| 2017/0166927 A1 | 6/2017 | Gao et al. |
| 2017/0183636 A1 | 6/2017 | Roy et al. |
| 2017/0191039 A1 | 7/2017 | Gao et al. |
| 2017/0191079 A1 | 7/2017 | Vandenberghe et al. |
| 2017/0198304 A1 | 7/2017 | Wilson et al. |
| 2017/0204144 A1 | 7/2017 | Deverman et al. |
| 2017/0211092 A1 | 7/2017 | Chatterjee et al. |
| 2017/0211093 A1 | 7/2017 | Chatterjee et al. |
| 2017/0211094 A1 | 7/2017 | Chatterjee et al. |
| 2017/0211095 A1 | 7/2017 | Chatterjee et al. |
| 2017/0216458 A1 | 8/2017 | Kaspar et al. |
| 2017/0218395 A1 | 8/2017 | Byrne et al. |
| 2017/0226160 A1 | 8/2017 | Sonntag et al. |
| 2017/0232072 A1 | 8/2017 | Ikeda et al. |
| 2017/0232117 A1 | 8/2017 | Arbetman et al. |
| 2017/0240885 A1 | 8/2017 | Deverman et al. |
| 2017/0240921 A1 | 8/2017 | Gao et al. |
| 2017/0246322 A1 | 8/2017 | Mendell et al. |
| 2017/0247664 A1 | 8/2017 | Wright et al. |
| 2017/0258996 A1 | 9/2017 | Anand et al. |
| 2017/0260545 A1 | 9/2017 | Qu et al. |
| 2017/0274024 A1 | 9/2017 | McCown et al. |
| 2017/0275337 A1 | 9/2017 | Srivastava et al. |
| 2017/0298323 A1 | 10/2017 | Vandenberghe et al. |
| 2017/0304464 A1 | 10/2017 | Kügler |
| 2017/0306354 A1 | 10/2017 | Gao et al. |
| 2017/0306355 A1 | 10/2017 | Davidson et al. |
| 2017/0321290 A1 | 11/2017 | Lubelski et al. |
| 2018/0050117 A1 | 2/2018 | Puccio et al. |
| 2018/0327752 A1 | 11/2018 | Pillay et al. |
| 2018/0339066 A1 | 11/2018 | Torbett et al. |
| 2019/0008919 A1 | 1/2019 | Kassab |
| 2019/0038773 A1 | 2/2019 | Esteves et al. |
| 2020/0165576 A1 | 5/2020 | Gradinaru et al. |
| 2021/0189423 A1 | 6/2021 | Matilla Dueñas et al. |
| 2021/0346519 A1 | 11/2021 | Mingozzi et al. |

FOREIGN PATENT DOCUMENTS

| | | | |
|---|---|---|---|
| EP | 1279740 A1 | 1/2003 | |
| EP | 1847614 A1 | 10/2007 | |
| EP | 1849872 A1 | 10/2007 | |
| EP | 1857552 A1 | 11/2007 | |
| EP | 1944043 A1 | 7/2008 | |
| EP | 2166101 A2 * | 3/2010 | ......... C12N 15/8216 |
| EP | 1696036 B1 | 4/2010 | |
| EP | 2186283 A2 | 5/2010 | |
| EP | 2524037 A1 | 11/2012 | |
| EP | 2359866 B1 | 7/2013 | |
| EP | 2660325 A2 | 11/2013 | |
| EP | 2383346 B1 | 10/2014 | |
| EP | 2814958 A1 | 12/2014 | |
| EP | 2198016 B1 | 5/2015 | |
| EP | 2871239 A9 | 6/2015 | |
| EP | 2879719 A1 | 6/2015 | |
| EP | 2212348 B1 | 7/2015 | |
| EP | 2598525 B1 | 8/2015 | |
| EP | 3058959 A1 | 8/2016 | |
| EP | 1453547 B1 | 9/2016 | |
| EP | 2220241 B1 | 9/2016 | |
| EP | 2325298 B1 | 10/2016 | |
| EP | 2007795 B1 | 11/2016 | |
| EP | 2176283 B1 | 11/2016 | |
| EP | 2292779 B1 | 11/2016 | |
| EP | 3067417 A3 | 11/2016 | |
| EP | 2220242 B1 | 12/2016 | |
| EP | 2737071 B1 | 3/2017 | |
| EP | 2933336 B1 | 3/2017 | |
| EP | 3134431 A1 | 3/2017 | |
| EP | 2531604 B1 | 4/2017 | |
| EP | 3168298 A1 | 5/2017 | |
| EP | 2301582 B1 | 7/2017 | |
| EP | 2250256 B1 | 8/2017 | |
| EP | 2292780 B1 | 8/2017 | |
| EP | 2311967 B1 | 9/2017 | |
| EP | 2943567 B1 | 9/2017 | |
| EP | 3215602 A1 | 9/2017 | |
| EP | 3219801 A1 | 9/2017 | |
| EP | 3224376 A1 | 10/2017 | |
| EP | 3230441 A1 | 10/2017 | |
| EP | 3235827 A2 | 10/2017 | |
| EP | 2527457 B1 | 2/2019 | |
| EP | 3132043 B1 | 3/2019 | |
| JP | 2017-532966 | 11/2017 | |
| JP | 2017-533715 | 11/2017 | |
| JP | 2017-535291 | 11/2017 | |
| TW | 201919714 A | 6/2019 | |
| WO | 1993009239 A1 | 5/1993 | |
| WO | 1995034670 A2 | 12/1995 | |
| WO | 1996017947 A1 | 6/1996 | |
| WO | 1996023810 A1 | 8/1996 | |
| WO | 1996030540 A2 | 10/1996 | |
| WO | 1998010088 A1 | 3/1998 | |
| WO | 1999015685 A1 | 4/1999 | |
| WO | 1999027110 A1 | 6/1999 | |
| WO | 1999043360 A1 | 9/1999 | |
| WO | 1999058700 A1 | 11/1999 | |
| WO | 1999060146 A1 | 11/1999 | |
| WO | 1999061595 A2 | 12/1999 | |

(56) References Cited

FOREIGN PATENT DOCUMENTS

| | | |
|---|---|---|
| WO | 2000024916 A1 | 5/2000 |
| WO | 2000066780 A2 | 11/2000 |
| WO | 2000075353 A1 | 12/2000 |
| WO | 2001023001 A2 | 4/2001 |
| WO | 2001025465 A1 | 4/2001 |
| WO | 2001032711 A2 | 5/2001 |
| WO | 2001036623 A2 | 5/2001 |
| WO | 2001042444 A2 | 6/2001 |
| WO | 2001014539 A3 | 9/2001 |
| WO | 2001068888 A2 | 9/2001 |
| WO | 2001096587 A2 | 12/2001 |
| WO | 2002012525 A2 | 2/2002 |
| WO | 2002014487 A2 | 2/2002 |
| WO | 2002020748 A2 | 3/2002 |
| WO | 2002070719 A2 | 9/2002 |
| WO | 2002071843 A1 | 9/2002 |
| WO | 2003010320 A2 | 2/2003 |
| WO | 2003024502 A2 | 3/2003 |
| WO | 2003042397 A2 | 5/2003 |
| WO | 2003087382 A1 | 10/2003 |
| WO | 2003087383 A1 | 10/2003 |
| WO | 2004044003 A2 | 5/2004 |
| WO | 2004083441 A2 | 9/2004 |
| WO | 2004108922 A2 | 12/2004 |
| WO | 2004111248 A2 | 12/2004 |
| WO | 2005005610 A2 | 1/2005 |
| WO | 2005012537 A2 | 2/2005 |
| WO | 2005111220 A2 | 11/2005 |
| WO | 2006102072 A2 | 9/2006 |
| WO | 2007130519 A2 | 11/2007 |
| WO | 2009030025 A1 | 3/2009 |
| WO | 2009073104 A2 | 6/2009 |
| WO | 2007148971 A8 | 7/2009 |
| WO | 2009134681 A2 | 11/2009 |
| WO | 2010109053 A1 | 9/2010 |
| WO | 2011038187 A1 | 3/2011 |
| WO | 2011054976 A2 | 5/2011 |
| WO | 2011122950 A1 | 10/2011 |
| WO | WO 2011133890 A1 | 10/2011 |
| WO | 2012057363 A1 | 5/2012 |
| WO | 2012114090 A1 | 8/2012 |
| WO | 2012144446 A1 | 10/2012 |
| WO | 2013078199 A2 | 5/2013 |
| WO | 2013164793 A2 | 11/2013 |
| WO | 2013170078 A1 | 11/2013 |
| WO | WO 2014144486 A2 | 9/2014 |
| WO | 2014160092 A1 | 10/2014 |
| WO | 2014168953 A1 | 10/2014 |
| WO | 2014170470 A1 | 10/2014 |
| WO | 2014170480 A1 | 10/2014 |
| WO | 2014172669 A1 | 10/2014 |
| WO | 2014186579 A1 | 11/2014 |
| WO | 2014194132 A1 | 12/2014 |
| WO | 2014201252 A2 | 12/2014 |
| WO | 2015012924 A2 | 1/2015 |
| WO | 2015013148 A2 | 1/2015 |
| WO | 2015018503 A1 | 2/2015 |
| WO | 2014186746 A9 | 3/2015 |
| WO | 2015038625 A1 | 3/2015 |
| WO | 2015038958 A1 | 3/2015 |
| WO | WO 2015040002 A1 | 3/2015 |
| WO | 2015031686 A9 | 4/2015 |
| WO | 2015044292 A1 | 4/2015 |
| WO | 2015060722 A1 | 4/2015 |
| WO | 2015108610 A1 | 7/2015 |
| WO | 2015114365 A1 | 8/2015 |
| WO | 2015121501 A1 | 8/2015 |
| WO | 2015124546 A1 | 8/2015 |
| WO | 2015137802 A1 | 9/2015 |
| WO | 2015164786 A1 | 10/2015 |
| WO | 2015127128 A9 | 11/2015 |
| WO | 2015196179 A1 | 12/2015 |
| WO | 2016019364 A1 | 2/2016 |
| WO | 2016054554 A1 | 4/2016 |
| WO | 2016054557 A1 | 4/2016 |
| WO | 2016065001 A1 | 4/2016 |
| WO | 2016073693 A2 | 5/2016 |
| WO | 2016081811 A1 | 5/2016 |
| WO | 2016081927 A2 | 5/2016 |
| WO | 2016115382 A1 | 7/2016 |
| WO | WO-2016115503 A1 * | 7/2016 ......... A61K 31/7088 |
| WO | 2016122791 A1 | 8/2016 |
| WO | 2016126857 A1 | 8/2016 |
| WO | 2016130591 A2 | 8/2016 |
| WO | 2016137949 A1 | 9/2016 |
| WO | 2016145217 A1 | 9/2016 |
| WO | 2016154055 A1 | 9/2016 |
| WO | 2016154344 A1 | 9/2016 |
| WO | WO 2016/150964 A1 | 9/2016 |
| WO | 2016164609 A2 | 10/2016 |
| WO | 2016168728 A2 | 10/2016 |
| WO | 2016172008 A1 | 10/2016 |
| WO | 2016172155 A1 | 10/2016 |
| WO | WO 2016172659 A1 | 10/2016 |
| WO | 2016179496 A1 | 11/2016 |
| WO | 2016183297 A1 | 11/2016 |
| WO | 2016191418 A1 | 12/2016 |
| WO | 2016196507 A1 | 12/2016 |
| WO | 2017004514 A1 | 1/2017 |
| WO | 2017005806 A1 | 1/2017 |
| WO | 2017015102 A1 | 1/2017 |
| WO | 2017019876 A1 | 2/2017 |
| WO | 2017019994 A2 | 2/2017 |
| WO | 2017023724 A1 | 2/2017 |
| WO | 2017024198 A1 | 2/2017 |
| WO | 2017058892 A2 | 4/2017 |
| WO | 2017070476 A2 | 4/2017 |
| WO | 2017070516 A1 | 4/2017 |
| WO | 2017070525 A1 | 4/2017 |
| WO | 2017070678 A1 | 4/2017 |
| WO | 2017075335 A1 | 5/2017 |
| WO | 2017083423 A1 | 5/2017 |
| WO | WO 2017/075338 A2 | 5/2017 |
| WO | WO 2017/077451 A1 | 5/2017 |
| WO | 2017093330 A1 | 6/2017 |
| WO | 2017096039 A1 | 6/2017 |
| WO | 2017100671 A1 | 6/2017 |
| WO | 2017100674 A1 | 6/2017 |
| WO | 2017100676 A1 | 6/2017 |
| WO | 2017100704 A1 | 6/2017 |
| WO | 2017112948 A1 | 6/2017 |
| WO | WO 2017106236 A1 | 6/2017 |
| WO | 2017122789 A1 | 7/2017 |
| WO | 2017123934 A1 | 7/2017 |
| WO | 2017136202 A1 | 8/2017 |
| WO | 2017136536 A1 | 8/2017 |
| WO | 2017139381 A1 | 8/2017 |
| WO | 2017143100 A1 | 8/2017 |
| WO | 2017147477 A1 | 8/2017 |
| WO | 2017151884 A1 | 9/2017 |
| WO | 2017152149 A1 | 9/2017 |
| WO | 2017155973 A1 | 9/2017 |
| WO | 2017160360 A2 | 9/2017 |
| WO | 2017165167 A1 | 9/2017 |
| WO | 2017165859 A1 | 9/2017 |
| WO | WO 2017161273 A1 | 9/2017 |
| WO | 2017172733 A1 | 10/2017 |
| WO | 2017172772 A1 | 10/2017 |
| WO | 2017173043 A1 | 10/2017 |
| WO | 2017173283 A1 | 10/2017 |
| WO | 2017180854 A1 | 10/2017 |
| WO | 2017181162 A1 | 10/2017 |
| WO | 2017184879 A1 | 10/2017 |
| WO | 2017190031 A1 | 11/2017 |
| WO | 2017192699 A1 | 11/2017 |
| WO | 2017192750 A1 | 11/2017 |
| WO | WO 2018/089527 A1 | 5/2018 |
| WO | WO 2018152333 A1 | 8/2018 |
| WO | WO 2018156654 A1 | 8/2018 |
| WO | 2019006043 A1 | 1/2019 |
| WO | 2019006182 A1 | 1/2019 |
| WO | 2019046069 A1 | 3/2019 |
| WO | WO 2019/079240 A1 | 4/2019 |
| WO | WO 2019067840 A1 | 4/2019 |

(56) References Cited

FOREIGN PATENT DOCUMENTS

| WO | WO 2019028306 A2 | 7/2019 |
|---|---|---|
| WO | WO 2019/222329 A1 | 11/2019 |
| WO | WO 2019/222444 A2 | 11/2019 |
| WO | WO 2020069461 A1 | 2/2020 |

OTHER PUBLICATIONS

Cherif et al., "Increased frataxin expression induced in Friedreich Ataxia cells by platinum TALE-VP64s or platinum TALE-SunTag," Mol Ther Nucleic Acids. Sep. 7, 2018;12:19-32.

Cossee et al., "Inactivation of the Friedreich ataxia mouse gene leads to early embryonic lethality without iron accumulation," Hum Mol Genet. May 1, 2000;9(8):1219-26.

Flytzanis et al., "Broad gene expression throughout the mouse and marmoset brain after intravenous delivery of engineered AAV capsids," bioRxiv. Jun. 17, 2020. doi: https://doi.org/10.1101/2020.06.16.152975.

Gerard et al., "An AAV9 coding for frataxin clearly improved the symptoms and prolonged the life of Friedreich ataxia mouse models." Mol Ther Methods Clin Dev. Oct. 8, 2014;1:14044.

Gessler et al., "Intravenous Infusion of AAV for Widespread Gene Delivery to the Nervous System," Methods Mol Biol. 2019;1950:143-163.

Gray et al., "Optimizing promoters for recombinant adeno-associated virus-mediated gene expression in the peripheral and central nervous system using self-complementary vectors," Hum Gene Ther. Sep. 2011;22(9):1143-1153.

Guo et al., "Characterization of a new N-terminally acetylated extra-mitochondrial isoform of frataxin in human erythrocytes," Sci Rep. Nov. 19, 2018;8(1):17043.

Haery et al., "Adeno-Associated Virus Technologies and Methods for Targeted Neuronal Manipulation," Front. Neuroanat., Nov. 26, 2019.

Legrand et al., "Significance of NT-proBNP and High-sensitivity Troponin in Friedreich Ataxia," J Clin Med. May 28, 2020;9(6):1630.

Maguire et al., "Gene therapy for the nervous system: challenges and new strategies," Neurotherapeutics. Oct. 2014;11(4):817-39.

Matsuzaki et al., "Intravenous administration of the adeno-associated virus-PHP.B capsid fails to upregulate transduction efficiency in the marmoset brain," Neurosci Lett. Feb. 5, 2018;665:182-188.

Muzyczka et al., "Custom adeno-associated virus capsids: the next generation of recombinant vectors with novel tropism," Hum Gene Ther. Apr. 2005;16(4):408-16.

Passini et al., "Widespread gene delivery and structure-specific patterns of expression in the brain after intraventricular injections of neonatal mice with an adeno-associated virus vector," J Virol. Dec. 2001;75(24):12382-92.

Patzke, "Intravenous delivery of AAV gene therapy to cerebellum and peripheral tissues critical for the treatment of Friedreich's ataxia" International Ataxia Research Conference [oral presentation], Sep. 30, 2017. Pisa, Italy.

Piguet et al., "Clinical gene therapy for neurodegenerative diseases: past, present, and future," Hum Gene Ther. Nov. 2017;28(11):988-1003.

Piguet et al., "Rapid and Complete Reversal of Sensory Ataxia by Gene Therapy in a Novel Model of Friedreich Ataxia," Mol Ther. Aug. 1, 2018;26(8):1940-1952.

Powell et al." AAV capsid-promoter interactions determine CNS cell selective gene expression in vivo," Mol Ther. May 6, 2020;28(5):1373-1380.

Puccio et al., "Mouse models for Friedreich ataxia exhibit cardiomyopathy, sensory nerve defect and Fe-S enzyme deficiency followed by intramitochondrial iron deposits," Nat Genet. Feb. 2001;27(2):181-6.

Qu et al., "Characteristics and advantages of adeno-associated virus vector-mediated gene therapy for neurodegenerative diseases," Neural Regen Res. Jun. 2019;14(6):931-938.

Salami et al., Stress-induced Mouse Model of the Cardiac Manifestations of Friedreich's Ataxia Corrected by AAV-mediated Gene Therapy. Hum Gene Ther. Aug. 2020;31(15-16):819-827.

Shen et al., "Activating frataxin expression by single-stranded siRNAs targeting the GAA repeat expansion," Bioorg Med Chem Lett Sep. 15, 2018;28(17):2850-2855.

International Search Report and Written Opinion of the International Searching Authority received in International application No. PCT/US2019/053681, mailed Mar. 9, 2020 (18 pages).

Office Action received in JP Application No. 2021-517461 dated Sep. 5, 2023.

Han et al., "Enhanced Efficacy from Gene Therapy in Pompe Disease Using Coreceptor Blockade," Hum Gene Ther.Jan. 2015, 26(1):26-35.

Hastie et al., "Adeno-Associated Virus at 50: A Golden Anniversary of Discovery, Research, and Gene Therapy Success-A Personal Perspective," Hum Gene Ther. May 2015, 26(5):257-65.

Hastie et al., "Recombinant adeno-associated virus vectors in the treatment of rare diseases," Expert Opin Orphan Drugs. 2015;3(6):675-689.

Hauck et al., "Generation and characterization of chimeric recombinant AAV vectors," Mol Ther. Mar. 2003;7 (3):419-25.

Haurigot et al., "Whole body correction of mucopolysaccharidosis IIIA by intracerebrospinal fluid gene therapy," The Journal of Clinical Investigation. 2013; 123(8): 3254-3271.

Heim et al., "Engineering green fluorescent protein for improved brightness, longer wavelengths and fluorescence resonance energy transfer," Curr Biol. Feb. 1, 1996;6(2): 178-82.

Heim et al., "Wavelength mutations and posttranslational autoxidation of green fluorescent protein," Proceedings of the National Academy of Sciences. Dec. 20, 1994;91(26): 12501-4.

Heller et al., "Human alpha 7 integrin gene (ITGA7) delivered by adeno-associated virus extends survival of severely affected dystrophin/utrophin deficient mice," Oct. 2015;26(1):647-56.

Hemphill et al., "Adeno-associated virus gene therapy vector scAAVIGF-1 for transduction of equine articular chondrocytes and RNA-seq analysis," Osteoarthritis Cartilage. May 2016;24(5): 902-11.

Herrera-Carrillo et al., "Improving miRNA delivery by optimizing miRNA expression cassettes in viral vectors," Hum Gene Ther Methods. Aug. 1, 2017;28(4): 177-90.

Hickey et al., "Tropism of engineered and evolved recombinant AAV serotypes in the rd1 mouse and ex vivo primate retina," Gene Ther. Dec. 2017;24(12):787-800.

Hinderer et al., "Delivery of an Adeno-Associated Virus Vector into Cerebrospinal Fluid Attenuates Central Nervous System Disease in Mucopolysaccharidosis Type II Mice," Hum Gene Ther. Nov. 2016;27(11): 906-915.

Hinderer et al., "Evaluation of intrathecal routes of administration for adeno-associated virus vectors in large animals," Hum Gene Ther. Jan. 1, 2018;29(1): 15-24.

Hinderer et al., "Neonatal Systemic AAV Induces Tolerance to CNS Gene Therapy in Mps I Dogs and Nonhuman Primates," Molecular Therapy. Aug. 1, 2015;23(8): 1298-307.

Hinderer et al., "Widespread gene transfer in the central nervous system of cynomolgus macaques following delivery of AAV9 into the cisterna magna," Molecular therapy-Methods & Clinical Development. 2014; 1:1-9.

Hirsch et al., "Delivering Transgenic DNA Exceeding the Carrying Capacity of AAV Vectors," Methods Mol Biol. 2016;1382:21-39.

Hordeaux et al., "Efficient central nervous system AAVrh10-mediated intrathecal gene transfers in adult and neonate rats," Gene Ther. Apr. 2015, 22(4): 316-24.

Hordeaux et al., "Long-term neurologic and cardiac correction by intrathecal gene therapy in Pompe disease," Acta Neuropathol Commun Sep. 6, 2017(5):66.

Hordeaux et al., "The GPI-linked protein LY6A (SCA-1) drives AAV-PHP.B transport across the blood-brain barrier," Molecular Therapy. May 8, 2019;27(5):912-21.

Hosaka et al., "Localized Intra-Arterial Gene Delivery Using AAV," Methods Mol Biol. 2019; 1937:259-265.

(56) References Cited

OTHER PUBLICATIONS

Hrabovska et al., "Delivery of human acetylcholinesterase by adeno-associated virus to the acetylcholinesterase knockout mouse," Chemico-Biological Interactions. 2005; 157-158:71-78.
Huang et al., "Characterization of the Adeno-Associated Virus 1 and 6 Sialic Acid Binding Site," J Virol. May 12, 2016;90(11):5219-30.
Huang et al., "Delivering genes across the blood-brain barrier: LY6A, a novel cellular receptor for AAV-PHP.B capsids," PloS one. Nov. 14, 2019; 14(11): 1-17.
Huang et al., "Targeting Visceral Fat by Intraperitoneal Delivery of Novel AAV Serotype Vector Restricting Off-Target Transduction in Liver," Mol Ther Methods Clin Dev. Jun. 19, 2017;6:68-78.
Hudry et al., "Efficient gene transfer to the central nervous system by single stranded Anc80L65," Mol Ther Meth Clin Dev. Jul. 15, 2018:197-209.
Hudry et al., "Exosome-associated AAV vector as a robust and convenient neuroscience tool," Gene Ther. Apr. 2016;23(4):380-92.
Hudry et al., "Therapeutic AAV Gene Transfer to the Nervous System: A Clinical Reality," Neuron. Mar. 6, 2019;101 (5):839-862.
Ibrahim et al., "Stable liver specific expression of human IDOL in humanized mice raises plasma cholesterol," Cardiovasc Res. May 2016; 110(1):23-9.
International Search Report and Written Opinion in PCT/US2016/013671, mailed Jun. 23, 2016, 11 pages.
International Search Report and Written Opinion in PCT/US2018/045088, mailed Feb. 15, 2019, 54 pages.
International Search Report and Written Opinion in PCT/US2018/053312, mailed Feb. 8, 2019, 12 pages.
Ishizu et al., "Targeted Genome Replacement via Homolgy-directed Repair in Non-dividing Cardiomyocytes," Sci Rep. Aug. 24, 2017;7(1):9363.
Ito et al., "HMGB1 facilitates repair of mitochondrial DNA damage and extends the lifespan of mutant ataxin-1 knock-in mice," EMBO Mol Med. Dec. 2015;7(1):78-101.
Ito et al., "In utero gene therapy rescues microcephaly caused by Pqbp1-hypofunction in neural stem progenitor cells," Mol Psychiatry. Apr. 2015, 20(4):459-71.
Iwayama et al., "Adeno associated virus 9-based gene therapy delivers a functional monocarboxylate transporter 8 which improves thyroid hormone availability to the brain of Mct8 deficient mice," Thyroid. Sep. 2016; 26(9): 1311-9.
Jackson et al. "Better Targeting, Better Efficiency for Wide-Scale Neuronal Transduction with the Synapsin Promoter and AAV-PHP.B," Front Mol Neurosci. Nov. 2016;6:116.
Jeong et al., "Matricellular Protein CCN5 Reverses Established Cardiac Fibrosis," J Am Coll Cardiol. Apr. 5, 2016;67 (13): 1556-68.
Jin et al., "Direct LC/MS Analysis for Complete Characterization of Recombinant Adeno-Associated Virus Capsid Proteins," Hum Gene Ther Methods. Oct. 2017;28(5): 255-267.
Jungmann et al., "Protocol for efficient generation and characterization of adeno-associated viral (AAV) vectors," Hum Gene Ther Methods. Oct. 2017;28(5):235-246.
Kailasan et al., "Parvovirus Family Conundrum: What makes a killer?" Annu Rev Virol. Nov. 2015;2(1): 425-50.
Kailasan et al., "Structure of an Enteric Pathogen, Bovine Parvovirus," J Virol. Mar. 2015, 89(5):2603-14.
Kajigaya et al., "Self-assembled B19 parvovirus capsids, produced in a baculovirus system, are antigenically and immunogenically similar to native virions," Proc Natl Acad Sci U S A. Jun. 1, 1991;88(11):4646-50.
Kanaan et al., "Rationally Engineered AAV Capsids Improve Transduction and Volumetric Spread in the CNS," Molecular Therapy—Nucleic Acids, Sep. 15, 2017;8:184-97.
Kaplitt et al., "Long-term gene expression and phenotypic correction using adeno-associated virus vectors in the mammalian brain," Nat Genet. Oct. 1994;8(2): 148-54.
Karamuthil-Melethil et al., "Novel Vector Design and Hexosaminidase Variant Enabling Self-Complementary Adeno-Associated Virus for the Treatment of Tay-Sachs Disease," Hum Gene Ther. Jul. 2016;27(7):509-21.
Katz et al., "AAV gene transfer delays disease onset in a TPP1-deficient canine model of the late infantile form of Batten Disease," Sci Transl Med. Nov. 2015;7(313): 1-23.
Katz et al., "Use of Adeno-Associated Virus Vector for Cardiac Gene Delivery in Large Animal Surgical Models of Heart Failure," Hum Gene Ther Clin Dev. Sep. 1, 2017;28(3): 157-64.
Keravala et al., "Evaluating AAV Hybrid Variants for Improved Tropism after Intravitreal Gene Delivery to the Retina," Molecular Therapy, May 1, 2015;23:S127-8.
Kim et al., "Mutagenic Analysis of an Adeno-Associated Virus Variant Capable of Simultaneously Promoting Immune Resistance and Robust Gene Delivery," Hum Gene Ther. Jan. 2018;29(1): 25-41.
Sun et al., "Preclinical Development of New Therapy for Glycogen Storage Diseases," Curr Gene Ther. Jan. 2015, 15(4):338-47.
Suzuki et al., "Cochlear gene therapy with ancestral AAV in adult mice: complete transduction of inner hair cells without cochlear dysfunction," Apr. 3, 2017;7:1-12.
Tadokoro et al., "Subpial Adeno-associated Virus 9 (AAV9) Vector Delivery in Adult Mice," J Vis Exp. Jul. 1, 20173; (125):1-9.
Talla et al., "Complex I Subunit Gene Therapy with NDUFA6 Ameliorates Neurodegeneration in EAE," Invest Ophthalmol Vis Sci. Jan. 2015, 22;56(2):1129-40.
Tarantal et al., "Systemic and Persistent Muscle Gene Expression in Rhesus Monkeys with a Liver De-targeted Adeno-Associated Virus (AAV) Vector," Hum Gene Ther. May 2017;28(5):385-391.
Tardieu et al., "Intracerebral gene therapy in children with mucopolysaccharidosis type IIIB syndrome: an uncontrolled phase 1/2 clinical trial," Lancet Neurol. Sep. 2017; 16(9):712-720.
Tervo et al., "A Designer AAV Variant Permits Efficient Retrograde Access to Projection Neurons," Neuron. Oct. 19, 2016;92(2):372-382.
Thorne et al., "Gene Therapy," Adv Biochem Eng Biotechnol. 2018: 165:351-399.
Todd et al., "Correcting Neuromuscular Deficits With Gene Therapy in Pompe Disease," Ann Neurol. Aug. 2015, 78 (2):222-34.
Tordo et al., "A novel adeno-associated virus capsid with enhanced neurotropism corrects a lysosomal transmembrane enzyme deficiency," Brain Jul. 1, 2018; 141(7):2014-2031.
Tratschin et al., "Adeno-associated virus vector for high-frequency integration, expression, and rescue of genes in mammalian cells," Mol Cell Biol. Nov. 1985;5(11):3251-60.
Tse et al., "Mapping and engineering function domains of the assembly-activating protein of adeno-associated viruses," J. Virol. Jun. 29, 2018;92(14): 1-18.
Tse et al., "Structure-guided evolution of antigenically distinct adeno-associated virus variants for immune evasion," Proceedings of the National Academy of Sciences. Jun. 13, 2017; 114(24): E4812-21.
Tu et al., "Role of capsid proteins in parvoviruses infection," Virol J. Aug. 2015, 4;12: 114:1-8.
UniProt [Online], Database accession No. Q16595, Last Updated Jul. 15, 1999, 16 pages.
Urabe et al., "Scalable generation of high-titer recombinant adeno-associated virus type 5 in insect cells," J Virol. Feb. 2006;80(4): 1874-85.
Valdmanis et al., "Future of rAAV gene therapy: Platform for RNAi, Gene Editing and Beyond," Hum Gene Ther. Apr. 2017;28(4):361-372.
Van Der Loo et al., "Progress and challenges in viral vector manufacturing," Hum Mol Genet. Apr. 2016;25(R1): R42-52.
Van Lieshout et al., "A Novel Triple-Mutant AAV6 Capsid Induces Rapid and Potent Transgene Expression in the Muscle and Respiratory Tract of Mice," Mol Ther Meth Clin Dev. Jun. 15, 2018;9:323-9.
Vandamme et al., "Unraveling the complex story of immune responses to AAV vectors trial after trial," Hum Gene Ther. Nov. 1, 2017;28(11): 1061-74.

(56) References Cited

OTHER PUBLICATIONS

Vandendriessche et al., "Efficacy and safety of adeno-associated viral vectors based on serotype 8 and 9 vs. lentiviral Vectors for hemophilia B gene therapy," J Thromb Haemost. Jan. 2007;5(1): 16-24.
Vercauteren et al., "Superior in vivo Transduction of Human Hepatocytes Using Engineered AAV3 Capsid," Mol Ther. Jun. 2016;24(6): 1042-9.
Verhelle et al., "AAV9 delivered bispecific nanobody attenuates amyloid burden in the gelsolin amyloidosis mouse model," Hum Mol Genet. Apr. 2017; 26(7): 1353-1364.
Wang et al., "A Rationally Engineered Capsid Variant of AAV9 for Systemic CNS-Directed and Peripheral Tissue- Detargeted Gene Delivery in Neonates," Mol Ther Methods Clin Dev. Mar. 16, 2018;9:234-246.
Wang et al., "AAV gene therapy corrects OTC deficiency and prevents liver fibrosis in aged OTC-knock out heterozygous mice," Mol Genet Metab. Apr. 2017; 120(4):299-305.
Wang et al., "Comparative study of liver gene transfer with AAV vectors based on endogenous and engineered AAV capsids," Mol Ther. Dec. 2015;23(12): 1877-87.
Wang et al., "Direct brain infusion can be enhanced with focused ultrasound and microbubbles," J Cereb Blood Flow Metab. Feb. 2016;37(2):706-714.
Wang et al., "Direct interaction of human serum proteins with AAV virions to enhance AAV transduction: immediate impact on clinical applications," Gene Ther. Jan. 2017;24(1):49-59.
Wang et al., "Human Bocavirus 1 Is a Novel Helper for Adeno-Associated Virus Replication," J Virol. Sep. 15, 2017;91 (18):1-18.
Wang et al., "Noninvasive, neuron-specific gene therapy can be facilitated by focused ultrasound and recombinant adeno-associated virus," Gene Therapy. Jan. 2015;22(1): 104-10.
Wang et al., "Productive life cycle of adeno-associated virus serotype 2 in the complete absence of a conventional polyadenylation signal," J Gen Virol. Sep. 2015;96(9):2780-7.
Wang et al., "Widespread spinal cord transduction by intrathecal injection of rAAV delivers efficacious RNAi therapy for amyotrophic lateral sclerosis," Human Molecular Genetics. 2014; 23(3):668-681.
Wasilko et al., "The titerless infected-cells preservation and scale-up (TIPS) method for large-scale production of NO-sensitive human soluble guanylate cyclase (sGC) from insect cells infected with recombinant baculovirus," Protein Expr Purif. Jun. 2009;65(2): 122-32.
Watakabe et al., "Comparative analyses of adeno-associated viral vector serotypes 1, 2, 5, 8 and 9 in marmoset, mouse and macaque cerebral cortex," Neurosci Res.Apr. 2015, 93:144-57.
Watanabe et al., "Protein Phosphatase Inhibitor-1 Gene Therapy in a Swine Model of Nonischemic Heart Failure," Journal of the American College of Cardiology. Oct. 3, 2017;70(14): 1744-56.
Watson et al., "Adeno-associated Virus Vectors Efficiently Transduce Mouse and Rabbit Sensory Neurons Coinfected with Herpes Simplex Virus 1 following Peripheral Inoculation," J Virol. Aug. 12, 2016;90(17): 7894-901.
Weber-Adrian et al., "Gene delivery to the spinal cord using MRI-guided focused ultrasound," Gene Ther. Jul. 2015, 22(7): 568-77.
Woodard et al., "Heparan Sulfate Binding Promotes Accumulation of Intravitreally Delivered Adeno-associated Viral Vectors at the Retina for Enhanced Transduction but Weakly Influences Tropism," J Virol. Oct. 14, 2016;90 (21): 9878-9888.
Wooley et al., "A directed evolution approach to select for novel Adeno-associated virus capsids on an HIV-1 producer T cell line," J Virol. Methods. Dec. 1, 2017;250:47-54.
Wu et al., "Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush," Front Mol Neurosci. Jul. 5, 2016;9:1-18.
Wu et al., "Mutational analysis of the adeno-associated virus type 2 (AAV2) capsid gene and construction of AAV2 vectors with altered tropism," J Virol. Sep. 2000;74(18): 8635-47.
Xiao et al., "Disruption of microtubules post virus entry enhances adeno-associated virus vector transduction," Hum Gene Ther. Apr. 2016;27(4):309-24.
Xie et al., "MicroRNA-regulated, systemically delivered rAAV9: a step closer to CNS-restricted transgene expression," Mol Ther. Mar. 2011; 19(3):526-35.
Xie et al., "Short DNA Hairpins Compromise Recombinant Adeno-Associated Virus Genome Homogeneity," Mol Ther. Jun. 7, 2017;25(6): 1363-74.
Xie et al., "The 2.8 Å Electron Microscopy Structure of Adeno-Associated Virus-DJ Bound by a Heparinoid Pentasaccharide," Mol Ther Methods Clin Dev. Mar. 8, 2017;5:1-12.
Xie et al., "The atomic structure of adeno-associated virus (AAV-2), a vector for human gene therapy," Proc Natl Acad Sci U S A. Aug. 6, 2002;99(16): 10405-10.
Yalvac et al., "AAV1.NT-3 gene therapy attenuates spontaneous autoimmune peripheral polyneuropathy," Gene Ther. Jan. 2016;23(1):95-102.
Yan et al., "Human Bocavirus Type-1 Capsid Facilitates the Transduction of Ferret Airways by Adeno-Associated Virus Genomes," Hum Gene Ther. Aug. 1, 2017;28(8):612-25.
Adachi et al., "Drawing a high-resolution functional map of adeno-associated virus capsid by massively parallel sequencing," Nat Commun. 2014;5:3075.
Adamson-Small et al., "Sodium chloride enhances rAAV production in a serum-free suspension manufacturing platform using the Herpes Simplex Virus System," Hum Gene Ther Methods, Feb. 2017;28(1): 1-14.
Afione et al., "Identification and Mutagenesis of the Adeno-Associated Virus 5 Sialic Acid Binding Region," J Virol. Feb. 2015, 89(3): 1660-72.
Ahmad et al., "Engineered Expression of Broadly Neutralizing Antibodies Against Human Immunodeficiency Virus," Annu Rev Virol. Sep. 29, 2017;4(1):491-510.
Ahmed et al., "rAAV gene therapy in a Canavan's disease mouse model reveals immune impairments and an extended pathology beyond the central nervous system," Mol Ther. Jun. 2016;24(6): 1030-41.
Al et al., "A Scalable and Accurate Method for Quantifying Vector Genomes of Recombinant Adeno-Associated Viruses in Crude Lysate," Hum Gene Ther Methods. Jun. 1, 2017;28(3): 139-47.
Al et al., "Adeno-associated virus serotype rh. 10 displays strong muscle tropism following intraperitoneal delivery," Sci Rep. Jan. 2017;7:40336.
Alton et al., "Repeated nebulisation of non-viral CFTR gene therapy in patients with cystic fibrosis: a randomised, double-blind, placebo-controlled, phase 2b trial," Lancet Respir Med. Sep. 2015;3(9): 684-91.
Altschul et al., "Basic local alignment search tool," J Mol Biol. Oct. 5, 1990;215(3): 403-10.
Alves et al., "Ultramicroscopy as a Novel Tool to Unravel the Tropism of AAV Gene Therapy Vectors in the Brain," Sci Rep. Jun. 20, 2016;6:28272.
Aoyama et al., "Wnt11 gene therapy with adeno-associated virus 9 improves the survival of mice with myocarditis induced by coxsackievirus B3 through the suppression of the inflammatory reaction," J Mol Cell Cardiol. Jul. 2015; 84:45-51.
Armbruster et al., "Efficacy and biodistribution analysis of intracerebroventricular administration of an optimized scAAV9-SMN1 vector in a mouse model of spinal muscular atrophy," Mol Ther Methods Clin Dev. Sep. 2016;3:16060.
Arruda et al., "Obstacles and future of gene therapy for hemophilia," Expert Opin Orphan Drugs. 2015;3 (9):997-1010.
Asokan et al., "The AAV vector toolkit: poised at the clinical crossroads," Mol Ther. Apr. 2012;20(4): 699-708.
Aubourg, P., "Gene therapy for rare central nervous system diseases comes to age," Endocr Dev. 2016;30:141-6.
Aydemir et al., "Mutants at the 2-fold interface of AAV2 structural proteins suggest a role in viral transcription for AAV capsids," J Virol. Jul. 2016;90(16): 7196-204.

(56) References Cited

OTHER PUBLICATIONS

Bankiewicz et al., "AAV Viral Vector Delivery to the Brain by Shape-conforming MR-guided Infusions," J Control Release. Oct. 28, 2016;240:434-442.
Bantel-Schaal et al., "Human adeno-associated virus type 5 is only distantly related to other known primate helper-dependent parvoviruses," J Virol. Feb. 1999;73(2):939-47.
Bartel et al., "Directed evolution of novel adeno-associated viruses for therapeutic gene delivery," Gene Ther. Jun. 2012;19(6):694-700.
Baum et al., "Advances in salivary gland gene therapy - oral and systemic implications," Expert Opinion on Biological Therapy. 2015; 15(10): 1443-54.
Baum et al., "Early responses to adenoviral-mediated transfer of the aquaporin-1 cDNA for radiation-induced salivary hypofunction," Proc Natl Acad Sci U S A. Nov. 20, 2012; 109(47): 19403-7.
Bedbrook et al., "Viral Strategies for Targeting the Central and Peripheral Nervous Systems," Annu Rev Neurosci. Jul. 8, 2018;41:323-348.
Bell et al., "Effects of self-complementarity, codon optimization, transgene, and dose on liver transduction with AAV8," Hum Gene Ther Methods. Dec. 2016;27(6):228-237.
Belmonte et al., "Brains, genes, and primates," Neuron. May 6, 2015;86(3):617-31.
Bennett et al., "Thermal Stability as a Determinant of AAV Serotype Identity," Mol Ther Methods Clin Dev. Jul. 24, 2017;6:171-182.
Bennett et al., "Understanding capsid assembly and genome packaging for adeno-associated viruses," Future virology. Jun. 1, 2017; 12(6):283-97.
Bensky et al., "Targeted gene delivery to the enteric nervous system using AAV: a comparison across serotypes and capsid mutants," Mol Ther. Mar. 2015;23(3):488-500.
Bentley, D.L., "Coupling mRNA processing with transcription in time and space," Nature Reviews Genetics. Mar. 2014; 15(3): 163-75.
Berge et al., "Pharmaceutical salts," J Pharm Sci. Jan. 1977;66(1):1-19.
Berry et al., "Cellular transduction mechanisms of adeno-associated viral vectors," Curr Opin Virol. Dec. 2016;21:54-60.
Betley et al., "Adeno-associated viral vectors for mapping, monitoring, and manipulating neural circuits," Hum Gene Ther. Jun. 2011;22(6): 669-77.
Bevan et al., "Systemic gene delivery in large species for targeting spinal cord, brain, and peripheral tissues for pediatric disorders," Mol Ther. Nov. 2011; 19(11): 1971-80.
Bey et al., "Efficient CNS targeting in adult mice by intrathecal infusion of single-stranded AAV9-GFP for gene therapy of neurological disorders," Gene Ther. Gene therapy. May 2017;24(5):325-32.
Blair et al., "The current state of biomarker research for Friedreich's ataxia: a report from the 2018 FARA biomarker meeting," Future Sci OA. Jun. 28, 2019;5(6): FSO398.
Bosch et al., "Self-Complementary AAV9 Gene Delivery Partially Corrects Pathology Associated with Juvenile Neuronal Ceroid Lipofuscinosis (CLN3)," J Neurosci. Sep. 14, 2016;36(37):9669-82.
Bradbury et al., "Biomarkers for disease progression and AAV therapeutic efficacy in feline Sandhoff disease," Exp Neurol. Jan. 2015, 263: 102-12.
Brady et al., "Antibody gene transfer with adeno-associated viral vectors as a method for HIV prevention," Immunol Rev. Jan. 2017;275(1): 324-333.
Brulet et al., "NEUROD1 Instructs Neuronal Conversion in Non-Reactive Astrocytes," Stem Cell Reports. Jun. 6, 2017;8(6): 1506-15.
Buclez et al., "Rapid, scalable, and low-cost purification of recombinant adeno-associated virus produced by baculovirus expression vector system," Mol Ther Methods Clin Dev. May 2016;3:16035.
Büning et al., "Capsid Modifications for Targeting and Improving the Efficacy of AAV Vectors," Molecular Therapy—Methods & Clinical Development. Mar. 15, 2019;12:248-65.

Burg et al., "Atomic structure of rationally engineered gene delivery vector, AAV2.5," Journal of Structural Biology. Sep. 2018 203(3):236-241.
Burnham et al. "Analytical ultracentrifugation as an approach to characterize recombinant adeno-associated viral vectors," Hum Gene Ther Methods. Dec. 2015;26(6):228-42.
Cabral-Miranda et al., "rAAV8-733-Mediated Gene Transfer of CHIP/Stub-1 Prevents Hippocampal Neuronal Death in Experimental Brain Ischemia," Mol Ther. Feb. 2017;25(2):392-400.
Callaway, "Transneuronal circuit tracing with neurotropic viruses," Curr Opin Neurobiol. Dec. 2008; 18(6):617-23.
Carillo et al., "The Multiple Sequence Alignment Problem in Biology," Siam J. Appl. Math. Oct. 1988;48(5): 1073-82.
Carter, B.J., "Adeno-associated virus and the development of adeno-associated virus vectors: a historical perspective," Mol Ther. Dec. 2004; 10(6): 981-9.
Carvalho et al., "Evaluating efficiencies of dual AAV approaches for retinal targeting," Front Neursci. Sep. 8, 2017;11:503.
Castle et al., "Controlling AAV Tropism in the Nervous System with Natural and Engineered Capsids," Methods Mol Biol. 2016; 1382:133-49.
Fenno et al., "The development and application of optogenetics," Annu Rev Neurosci. 2011;34:389-412.
Foust et al., "Intravascular AAV9 preferentially targets neonatal neurons and adult astrocytes," Nat Biotechnol. Jan. 2009;27(1):59-65.
Foust et al., "Therapeutic AAV9-mediated Suppression of Mutant SOD1 Slows Disease Progression and Extends Survival in Models of Inherited ALS," Molecular Therapy. Dec. 1, 2013;21(12):2148-59.
Francis et al., "N-Acetylaspartate supports the Energetic Demands of Developmental Myelination via Oligodendroglial Aspartoacyclase," Neurobiol Dis. Oct. 4, 2016;96:323-334.
Fu et al., "Differential prevalence of antibodies against adeno-associated virus in healthy children and patients with mucopolysaccharidosis III: perspective for AAV-mediated gene therapy," Human Gene Ther Clin Dev. Dec. 1, 2017;28 (4): 187-96.
Fu et al., "Functional correction of neurological and somatic disorders at later stages of disease in Mps Iiia mice by systemic scAAV9-hSGSH gene delivery," Mol Ther Methods Clin Dev. Jun. 2016;3:16036.
Gadalla et al., "Development of a Novel AAV Gene Therapy Cassette with Improved Safety Features and Efficacy in a Mouse Model of Rett Syndrome," Mol Ther Methods Clin Dev. Apr. 2, 20172;5:180-190.
Galli et al., "Strategies to optimize capsid protein expression and single stranded DNA formation of Adeno-associated virus in Saccharomyces cerevisiae," J Appl Microbiol. Aug. 1, 2017;123(2):414-28.
GenBank Accession No. BC023633.2, publicly available Jul. 15, 2006, 3 pages.
GenBank Accession No. EF550208.1, publicly available Oct. 14, 2009, 3 pages.
GenBank Accession No. NM_000144.4, publicly available Oct. 21, 2018, 5 pages.
GenBank Accession No. X00182.1, publicly available Nov. 14, 2006, 3 pages.
GenBank Accession No. X17403.1, publicly available Jul. 26, 2016, 95 pages.
George et al., "Gene therapy for hemophilia: past, present and future," Semin Hematol. Jan. 2016; 53(1):46-54.
Gessler et al., "Gene Therapy for the Treatment of Neurological Disorders: Metabolic Disorders," Methods Mol Biol. 2016;1382:429-65.
Gessler et al., "Redirecting N-acetylaspartate metabolism in the central nervous system normalizes myelination and rescues Canavan disease," JCI Insight. Feb. 2017;2(3): e90807.
Gil-Farina et al., "Recombinant AAV Integration Is Not Associated With Hepatic Genotoxicity in Nonhuman Primates and Patients," Mol Ther. Jun. 2016;24(6): 1100-5.
Giles et al., "Mapping an adeno-associated virus 9-specific neutralizing epitope to develop next-generation gene delivery vectors," J Virol. Oct. 15, 2018;92(20): e01011-18.

(56) References Cited

OTHER PUBLICATIONS

Gilkes et al., "Mucopolysaccharidosis IIIB confers enhanced neonatal intracranial transduction by AAV8 but not by 5, 9 or rh10," Gene Ther. Mar. 2016;23(3):263-71.
Gilkes et al., "Preferred Transduction with AAV8 and AAV9 Via Thalamic Administration in the Mps Iiib Model: A Comparison of Four rAAV Serotypes," Mol Genet Metab Rep. Dec. 7, 2015;6:48-54.
Golebiowski et al., "Direct intracranial injection of AAVrh8 encoding monkey ß-N-acetylhexosaminidase causes neurotoxicity in primate brain," Hum Gene Ther. Jun. 1, 2017;28(6): 510-22.
Gombash et al., "Systemic gene delivery transduces the enteric nervous system of guinea pigs and cynomolgus macaques," Gene Ther. Oct. 2017;24(10):640-8.
Gombash et al., "Systemic Gene Therapy for Targeting the CNS," Methods Mol Biol. 2016; 1382:231-7 (abstract).
Gong et al., "Intrathecal Adeno-Associated Viral Vector-Mediated Gene Delivery for Adrenomyeloneuropathy," Hum Gene Ther. May 2019;30(5): 544-555.
Goulet et al., "Comparison of CNS Transduction by Different AAV Capsids in Mouse and Non-Human Primate," Molecular Therapy. May 1, 2015;23:S37.
Gowanlock et al., "A designer AAV variant permits efficient retrograde access to projection neurons," Neuron. Oct. 19, 2016;92(2):372-382.
Gray-Edwards et al., "AAV gene therapy in a sheep model of Tay-Sachs disease," Human Gene Therapy. Mar. 2018;29(3):312-326.
Greig et al., "Impact of intravenous infusion time on AAV8 vector pharmacokinetics, safety, and liver transduction in cynomolgus macaques," Mol Ther Methods Clin Dev. Dec. 2016;3: 16079.
Greig et al., "Intramuscular administration of AAV overcomes pre-existing neutralizing antibodies in rhesus macaques," Vaccine. Dec. 2016;34(50):6323-6329.
Grieger et al., "Production of Recombinant Adeno-associated Virus Vectors Using Suspension HEK293 Cells and Continuous Harvest of Vector From the Culture Media for Gmp Fix and FLT1 Clinical Vector," Mol Ther. Feb. 2016;24 (2):287-97.
Griesenbach et al., "Cystic Fibrosis Gene Therapy in the UK and Elsewhere," Hum Gene Ther. May 1, 2015; 26(5): 266-275.
Grimm et al., "E Pluribus Unum: 50 years of research, millions of viruses and one goal - tailored acceleration of AAV evolution," Mol Ther. Dec. 2015;23(12): 1819-1831.
Grimm et al., "Progress in adeno-associated virus type 2 vector production: promises and prospects for clinical use," Hum Gene Ther. Oct. 1, 19990; 10(15):2445-50.
Grimm et al., "Small but increasingly mighty—latest advances in AAV vector research, design and evolution," Hum Gene Ther. Nov. 2017;28(11): 1075-1086.
Grimson et al., "MicroRNA targeting specificity in mammals: determinants beyond seed pairing," Mol Cell. Jul. 6, 2007;27(1): 91-105.
Grosse et al., "Relevance of assembly-activating protein for Adeno-associated virus vector production and capsid protein stability in mammalian and insect cells," J Virol. Oct. 15, 2017;91(20): e01198-17.
Gruntman et al., "Delivery of Adeno-associated virus gene therapy by intravascular limb infusion methods," Hum Gene Ther Clin Dev Sep. 2015;26(3): 159-64.
Gruntman et al., "Retro-Orbital Venous Sinus Delivery of rAAV9 Mediates High-Level Transduction of Brain and Retina Compared with Temporal Vein Delivery in Neonatal Mouse Pups," Hum Gene Ther. Mar. 2017;28(3):228-230.
Gruntman et al., "Stability and Compatibility of Recombinant Adeno-Associated Virus Under Conditions Commonly Encountered in Human Gene Therapy Trials," Hum Gene Ther Methods. Apr. 2015, 26(2):71-6.
GTEx Consortium, "Genetic effects on gene expression across human tissues," Nature. Oct. 11, 2017;550 (7675):204-213.
Guggino et al., "A Preclinical Study in Rhesus Macaques for Cystic Fibrosis to Assess Gene Transfer and Transduction by AAV1 and AAV5 with a Dual-Luciferase Reporter System," Hum Gene Ther Clin Dev. Sep. 1, 2017;28 (3): 145-56.
Gurda et al., "Evaluation of AAV-mediated gene therapy for central nervous system disease in canine mucopolysaccharidosis VII," Mol Ther. Feb. 2016;24(2):206-16.
Haas, M.J., "Reversing (heart) failure in Friedreich's ataxia," Science-Business exchange (2014) 7:1-3.
Hagedorn et al., "S/MAR element facilitates episomal long-term persistence of Adeno-associated viral (AAV) vector genomes in proliferating cells," Hum Gene Ther. Dec. 2017;28(12): 1169-1179.
Hagg et al., "Using AAV vectors expressing the beta 2-adrenoceptor or associated G alpha proteins to modulate skeletal muscle mass and muscle fiber size," Sci Rep. Mar. 2016;6:23042.
Hai et al., "Long-term transduction of miniature pig parotid glands using serotype 2 adeno-associated viral vectors," J Gene Med. Jun. 2009; 11(6):506-14.
Halder et al., "Structure of neurotropic adeno-associated virus AAVrh.8," J Struct Biol. Oct. 2015; 192(1):21-36.
Cearley et al., "A single injection of an adeno-associated virus vector into nuclei with divergent connections results in widespread vector distribution in the brain and global correction of a neurogenetic disease," J Neurosci. Sep. 12, 2007;27(37):9928-40.
Chai et al., "Application of polyploid adeno-associated virus vectors for transduction enhancement and neutralizing antibody evasion," J Control Release. Sep. 28, 2017;262:348-56.
Challis et al., "Systemic AAV vectors for widespread and targeted gene delivery in rodents," Nat Protoc. Feb. 2019; 14(2):379-414.
Chamberlain et al., "Expressing transgenes that exceed the packaging capacity of AAV capsids," Hum Gene Ther Methods. Feb. 2016;27(1): 1-12.
Chan et al., "Engineered AAVs for efficient noninvasive gene delivery to the central and peripheral nervous systems," Nature Neuroscience. Aug. 1, 2017;20(8): 1172-9.
Chandler et al., "Recombinant Adeno-Associated Viral integration and genotoxicity: insights from animal models," Hum Gene Ther. Apr. 2017;28(4): 314-322.
Chandler et al., "Systemic AAV9 gene therapy improves the lifespan of mice with Niemann-Pick disease, type C1," Hum Mol Genet. Jan. 2017;26(1):52-64.
Chandran et al. "Gene therapy in the nervous system: failures and successes," Adv Exp Med Biol. 2017;1007:241-257.
Chandran et al., "Site Specific Modification of Adeno-Associated Virus Enables Both Fluorescent Imaging of Viral Particles and Characterization of the Capsid Interactome," Sci Rep. Nov. 7, 2017;7(1): 14766.
Chen et al., "Efficient Gene Delivery and Expression in Pancreas and Pancreatic Tumors by Capsid-optimized AAV8 Vectors," Human Gene Therapy Methods. Feb. 1, 2017;28(1):49-59.
Chen et al., "Viral Vectors for Gene Transfer," Curr Protoc Mouse Biol. Dec. 2018;8(4): e58.
Chiorini et al., "Adeno-Associated Virus (AAV) Type 5 Rep Protein Cleaves a Unique Terminal Resolution Site Compared with Other AAV Serotypes," J Virol. May 1999;73(5): 4293-8.
Chiorini et al., "Cloning and characterization of adeno-associated virus type 5," J Virol. Feb. 1999; 73(2): 1309-19.
Chiorini et al., "Cloning of adeno-associated virus type 4 (AAV4) and generation of recombinant AAV4 particles," J Virol. Sep. 1997;71(9):6823-33.
Chiuchiolo et al., "Gene therapy for alpha-1 antitrypsin deficiency lung disease," Ann Am Thorac Soc. Aug. 2016; 13 Suppl 4:S352-69.
Choi et al., "AAV Hybrid Serotypes: Improved Vectors for Gene Delivery," Curr Gene Ther. Jun. 2005; 5(3): 299-310.
Choudhury et al., "In Vivo Selection Yields AAV-B1 Capsid for Central Nervous System and Muscle Gene Therapy," Mol Ther. Aug. 2016;24(7): 1247-57.
Choudhury et al., "Widespread central nervous system gene transfer and silencing after systemic delivery of novel AAV-AS vectors," Mol Ther. Apr. 2016;24(4): 726-35.
Clement et al., "Manufacturing of recombinant adeno-associated viral vectors for clinical trials," Mol Ther Methods Clin Dev. Mar. 2016;3:16002.

(56) References Cited

OTHER PUBLICATIONS

Conlon et al., "Transfer of Therapeutic Genes into Fetal Rhesus Monkeys using Recombinant Adeno-Associated Type I Viral Vectors," Hum Gene Ther Clin Dev. Dec. 2016;27(4): 152-159.

Corti et al., "Evaluation of Readministration of a Recombinant Adeno-Associated Virus Vector Expressing Acid Alpha-Glucosidase in Pompe Disease: Preclinical to Clinical Planning," Human Gene Therapy Clin Dev Sep. 2015;26 (3): 185-193.

Cuende et al., "Cell, tissue and gene products with marketing authorization in 2018 worldwide," Cytotherapy. Nov. 2018;20(11): 1401-1413.

D'COSTA et al., "Practical utilization of recombinant AAV vector reference standards: focus on vector genome titration by free ITR qPCR," Mol Ther Methods Clin Dev. Mar. 2016;5:16019.

Dang et al., "In vivo dynamics of AAV-mediated gene delivery to sensory neurons of the trigeminal ganglia," Sci Rep. Apr. 19, 2017;7(1):927.

Dashkoff et al., "Tailored transgene expression to specific cell types in the central nervous system after peripheral injection with AAV9," Mol Ther Methods Clin Dev. Dec. 2016;3:16081.

Davidsson et al., "A novel process of viral vector barcoding and library preparation enables high-diversity library generation and recombination-free paired-end sequencing," Sci Rep. Nov. 2016;6:3563.

Davis et al., "Rational design and engineering of a modified adeno-associated virus (AAV1)-based vector system for enhanced retrograde gene delivery," Neurosurgery. Feb. 2015; 76(2):216-25.

Dayton et al., "More expansive gene transfer to the rat CNS: AAV PHP.EB vector dose-response and comparison to AAV PHP.B," Gene Ther. Aug. 2018;25(5): 392-400.

De Leeuw et al., "rAAV-compatible MiniPromoters for Restricted Expression in the Brain and Eye," Mol Brain. May 10, 2016;9(1): 1-13.

De Silva et al., "Single residue AAV capsid mutation improves transduction of photoreceptors in the Abca4-/- mouse and bipolar cells in the rd1 mouse and human retina ex vivo," Gene Ther. Nov. 2016;23(11): 767-774.

Deng et al., "Replication of an autonomous human parvovirus in non-dividing human airway epithelium is facilitated through the DNA damage and repair pathways," PLOS Pathog. Jan. 2016; 12(1): e1005399.

Devereux et al., "A comprehensive set of sequence analysis programs for the VAX," Nucleic Acids Res. Jan. 11, 1984;12(1 Pt 1):387-95.

Deverman et al., "Cre-dependent selection yields AAV variants for widespread gene transfer to the adult brain," Nat Biotechnol. Feb. 2016;34(2):204-9.

Deverman et al., "Gene therapy for neurological disorders: progress and prospects," Nat Rev Drug Discov. Sep. 2018; 17(9):641-59.

Dimidschstein et al., "A viral strategy for targeting and manipulating interneurons across vertebrate species," Nat Neurosci. Dec. 2016; 19(12): 1743-1749.

Dinculescu et al., "AAV-mediated clarin-1 expression in the mouse retina: Implications for USH3A gene therapy," PoS One. Feb. 2016; 11(2): e0148874.

Ding et al., "Biochemical Characterization of Junonia Coenia Densovirus Nonstructural Protein NS-1.," J. Virol., Jan. 1, 2002;76(1):338-45.

Doerfler et al., "Copackaged AAV9 Vectors Promote Simultaneous Immune Tolerance and Phenotypic Correction of Pompe Disease," Hum Gene Ther. Jan. 2016;27(1):43-59.

Donsante et al., "Intracerebroventricular delivery of self-complementary adeno-associated virus serotype 9 to the adult rat brain," Gene Ther. May 2016;23(5):401-7.

Drouin et al., "Cryo-electron microscopy reconstruction and stability studies of Wild-Type and R432A Variant of AAV2 Reveals Capsid Structural Stability is a Major Factor in Genome Packaging," J Virol. Sep. 2016;90(19):8542-51.

Du et al., "Delivery of Gba Gene Using AAV9 Vector Therapy as a Treatment Strategy in Mouse Models of Gaucher disease," Hum Gene Ther. Feb. 1, 2019;30(2): 155-67.

Durost et al., "Gene therapy with an AAV vector expressing human IL-2 alters immune system homeostasis in humanized mice," Hum Gene Ther. Mar. 2018;29(3):352-365.

Earley et al., "Adeno-Associated Virus Assembly-Activating Protein Is Not an Essential Requirement for Capsid Assembly of AAV Serotypes 4, 5 and 11," J Virol. Jan. 2017;91(3): e01980-16.

Earley et al., "Identification and Characterization of Nuclear and Nucleolar Localization Signals in the Adeno- Associated Virus Serotype 2 Assembly-Activating Protein," J Virol. Mar. 2015, 89(6):3038-48.

Eichler et al., "Hematopoietic Stem-Cell Gene Therapy for Cerebral Adrenoleukodystrophy," N Engl J Med. Oct. 26, 2017;377(17):1630-8.

Eichler et al., "The complete connectome of a learning and memory centre in an insect brain," Nature. Aug. 9, 2017;548(7666): 175-182.

El-Shamayleh et al., "Strategies for targeting primate neural circuits with viral vectors," J Neurophysiol. Jul. 2016; 116(1): 122-34.

Extended European Search Report in EP16737993.2, mailed May 11, 2018, 9 pages.

Fargnoli et al., "Liquid jet delivery method featuring S100 gene therapy in the rodent model following acute myocardial infarction," Gene Ther. Feb. 2016;23(2): 151-7.

Federici et al., "Robust spinal motor neuron transduction following intrathecal delivery of AAV9 in pigs," Gene therapy. Aug. 2012; 19(8): 852-9.

Marsic et al., "Altering Tropism of rAAV by Directed Evolution," Methods of Mol Biol. 2016; 1382: 151-73 (abstract).

Martelli et al., "Understanding the genetic and molecular pathogenesis of Friedreich's ataxia through animal and cellular models," Dis Model Mech. Mar. 2012;5(2): 165-76.

Mason et al., "Delivery and evaluation of recombinant adeno-associated viral vectors in the equine distal extremity for the treatment of laminitis," Equine Vet J. Jan. 2017;49(1):79-86.

Massaro et al., "Fetal gene therapy for neurodegenerative disease of infants," Nat Med. Sep. 2018;24(9): 1317-23.

Matsuzaki et al., "Neurotropic Properties of AAV-PHP.B Are Shared among Diverse Inbred Strains of Mice," Mol Ther. Apr. 10, 2019;27(4):700-4.

McClements et al., "A fragmented adeno-associated viral dual vector strategy for treatment of diseases caused by mutations in large genes leads to expression of hybrid transcripts," J Genet Syndr Gene Ther. Nov. 2016;7(5): 1-16.

Meadows et al., "A GLP-compliant toxicology and biodistribution study: systemic delivery of an rAAV9 vector for the treatment of mucopolysaccharidosis IIIB," Hum Gene Ther Clin Dev. Dec. 2015;26(4):228-42.

Mendell et al., "Follistatin Gene Therapy for Sporadic Inclusion Body Myositis Improves Functional Outcomes," Mol Ther. Apr. 2017;25(4): 870-879.

Merkel et al., "Trafficking of AAV vectors across a model of the blood-brain barrier; a comparative study of transcytosis and transduction using primary human brain endothelial cells," J Neurochem. Jan. 2017; 140(2):216-230.

Merten et al., "Viral vectors for gene therapy and gene modification approaches," Biochem Eng J. Apr. 2016; 108:98-115.

Meyer et al., "Improving Single Injection CSF Delivery of AAV9-mediated Gene Therapy for Sma: A Dose-response Study in Mice and Nonhuman Primates," Mol Ther. Mar. 2015, 23(3):477-87.

Michelfelder et al., "Peptide ligands incorporated into the threefold spike capsid domain to re-direct gene transduction of AAV and AAV9 in vivo," PLoS One. 2011;6(8): 1-11.

Mietzsch et al., "OneBac 2.0: Sf9 Cell Lines for Production of AAV1, AAV2 and AAV8 Vectors with Minimal Encapsidation of Foreign DNA," Hum Gene Ther Methods. Feb. 2017;28(1): 15-22.

Mietzsch et al., "OneBac 2.0: Sf9 cell lines for production of AAV5 vectors with enhanced infectivity and minimal encapsidation of foreign DNA, " Hum Gene Ther. 2015 Oct. 26(10):688-97.

Mingozzi et al., "Adeno-associated viral vectors at the frontier between tolerance and immunity," Front Immunol. Mar. 2015, 6:1-3.

(56) References Cited

OTHER PUBLICATIONS

Mingozzi et al., "Overcoming the Host Immune Response to Adeno-Associated Virus Gene Delivery Vectors: The Race Between Clearance, Tolerance, Neutralization, and Escape," Annu Rev Virol Sep. 29, 2017;4(1):511-534.
Miyanohara et al., "Potent Spinal Parenchymal AAV9-mediated Gene Delivery by Subpial Injection in Adult Rats and Pigs," Mol Ther Methods Clin Dev. Jul. 13, 2016;3:1-10.
Moffett et al., "Hit-and-run programming of therapeutic cytoreagents using mRNA nanocarriers," Nat Commun. Aug. 30, 2017;8(1): 1-13.
Mondo et al., "Selective Neuronal Uptake and Distribution of AAVrh8, AAV9, and AAVrh10 in Sheep After Intra-Striatal Administration," J Huntingtons Dis. 2018;7(4):309-319.
Morabito et al., "AAV-PHP.B-Mediated Global-Scale Expression in the Mouse Nervous System Enables GBA1 Gene Therapy for Wide Protection from Synucleinopathy," Mol Ther. Aug. 10, 2017;25(12):2727-2742.
Muralidharan et al., "Unique glycan signatures regulate adeno-associated virus tropism in the developing brain," J Virol. Apr. 2015;89(7):3976-87.
Murlidharan et al., "Glymphatic Fluid Transport Controls Paravascular Clearance of AAV Vectors from the Brain," JCI Insight. Sep. 8, 2016;1-11.
Muzyczka et al., "AAV's Golden Jubilee," Mol Ther. May 2015;23(5):807-8.
Myers et al., "Optimal alignments in linear space," Comput Appl Biosci. Mar. 1988;4(1): 11-7.
Naidoo et al., "Extensive Transduction and Enhanced Spread of a Modified AAV2 Capsid in the Non-human Primate CNS," Mol Ther. 22018 Oct 3;26(10):2418-30.
Nambiar et al., "Characteristics of minimally oversized adeno-associated virus vectors encoding human Factor VIII generated using producer cell lines and triple transfection," Hum Gene Ther Methods. Feb. 2017;28(1):23-38.
Nery et al., "New methods for investigation of neuronal migration in embryonic brain explants," J Neurosci Methods. Jan. 2015, 239:80-4.
Neuberger et al., "Establishment of two quantitative nested qPCR assays targeting the human EPO transgene," Gene Ther. Apr. 2016;23(4):330-9.
Nicolson et al., "Identification and validation of small molecules that enhance recombinant Adeno-associated virus transduction following high throughput screen," J Virol. Jul. 2016; 90(16):7019-31.
Nygaard et al., "A universal system to select gene-modified hepatocytes in vivo," Sci Transl Med. Jun. 2016; 8 (342): 1-22.
Ojala et al., "Adeno-associated virus vectors and neurological gene therapy," Neuroscientist. 2014; 1:1-15.
Ojala et al., "In Vivo Selection of a Computationally Designed Schema Aav Library Yields a Novel Variant for Infection of Adult Neural Stem Cells in the SVZ," Molecular Therapy. Jan. 3, 2018;26(1):304-19.
Oliva et al., "An automated classification of the structure of protein loops," J Mol Biol. Mar. 7, 1997;266(4):814-30.
Osmon et al., "Systemic Gene Transfer of a Hexosaminidase Variant Using a scAAV9.47 Vector Corrects GM2 Gangliosidosis in Sandhoff Mice," Hum Gene Ther. Jul. 2016;27(7):497-508.
Pacouret et al., "Aav-Id: A Rapid and Robust Assay for Batch-to-Batch Consistency Evaluation of AAV Preparations," Mol Ther. Jun. 7, 2017;25(6): 1375-86.
Pan et al., "Gene therapy restores auditory and vestibular function in a mouse model of Usher syndrome type 1c," Nat Biotechnol. Mar. 2017;35(3):264-272.
Parr et al., "Tumor-selective transgene expression in vivo mediated by an E2F-responsive adenoviral vector," Nat Med. Oct. 1997;3(10):1145-9.
Paulk et al., "Bioengineered AAV Capsids with Combined High Human Liver Transduction In Vivo and Unique Humoral Seroreactivity," Mol Ther. Jan. 3, 2018;26(1):289-303.

Penaud-Budloo et al., "Accurate identification and quantification of DNA species by next-generation sequencing in adeno-associated viral vectors produced in insect cells," Hum Gene Ther Methods. Jun. 1, 2017;28(3): 148-62.
Petit et al., "Rod Outer Segment Development Influences AAV-Mediated Photoreceptor Transduction After Subretinal Injection," Hum Gene Ther. Jun. 1, 2017;28(6):464-81.
Pierce et al., "The status of RPE65 Gene Therapy Trials: Safety and Efficacy," Cold Spring Harb Perspect Med. 2015 Sept;5(9):1-21.
Pierson et al., "Resolving adeno-associated viral particle diversity with charge detection mass spectrometry," Anal Chem. Jul. 2016;88(13):6718-25.
Pillay et al., "AAV serotypes have distinctive interactions with domains of the cellular receptor AAVR," J Virol. Sep. 15, 2017;91(18): 10-128.
Pillay et al., "An essential receptor for adeno-associated virus infection," Nature. Feb. 2016; 530(7588): 108-12.
Pillay et al., "Host determinants of adeno-associated viral vector entry," Curr Opin Virol. Jun. 30, 2017;24:124-131.
Platt et al., "Embryonic disruption of the candidate dyslexia susceptibility gene homolog Kiaa0319-like results in neuronal migration disorders," Neuroscience. Sep. 17, 2013;248:585-93.
Pleger et al., "Cardiac AAV9-S100A1 gene therapy rescues post-oschemic heart failure in a preclinical large animal model," Science Translational Medicine, Jul. 20, 2011;3(92): 117-126.
Poon et al., "Distribution of Kiaa0319-like immunoreactivity in the adult mouse brain -- a novel protein encoded by the putative dyslexia susceptibility gene KIAA0319-like," Histol Histopathol. Aug. 2011;26(8):953-63.
Poon et al., "Dyslexia-associated kiaa0319-like protein interacts with axon guidance receptor nogo receptor 1," Cell Mol Neurobiol. Jan. 2011;31(1):27-35.
Potter et al., "Systemic delivery of dysferlin overlap vectors provides long-term gene expression and functional improvement for dysferlinopathy," Hum Gene Ther. Jul. 1, 2018;29(7):749-62.
Pourshafie et al., "Systemic Delivery of MicroRNA Using Recombinant Adeno-associated Virus Serotype 9 to Treat Neuromuscular Diseases in Rodents," J Vis Exp. Aug. 10, 2018;(138): 1-7.
Powell et al., "Characterization of a novel adeno-associated viral vector with preferential oligodendrocyte tropism," Gene Ther. Nov. 2016;23(11): 807-14.
Powell et al., "Viral expression cassette elements to enhance transgene target specificity and expression in gene therapy," Discov Med. Jan. 2015; 19(102): 49-57.
Pozsgai et al., "B-sarcoglycan gene transfer decreases fibrosis and restores force in LGMD2E mice," Gene Ther. Jan. 2016;23(1):57-66.
Ramos et al., "Gene therapy for Duchenne muscular dystrophy," Exp Opin Orphan Drugs. 2015;3(11): 1255-1266.
Rashnonejad et al., "Large-Scale Production of Adeno-Associated Viral Vector Serotype-9 Carrying the Human Survival Motor Neuron Gene," Mol Biotechnol. Jan. 2016;58(1):30-6.
Reichel et al., "AAV8 can induce innate and adaptive immune response in the primate eye," Mol Ther. Dec. 6, 2017;25(12):2648-60.
Reid et al., "miRNA mediated post-transcriptional silencing of transgenes leads to increased adeno-associated viral vector yield and targeting specificity," Gene Ther. Aug. 2017;24(8):462-9.
Ren et al., "Adeno-associated virus-mediated BMP-7 and SOX9 in vitro co-transfection of human degenerative intervertebral disc cells," Genet Mol Res. Apr. 22, 2015; 14(2): 3736-44.
Rincon et al., "Widespread transduction of astrocytes and neurons in the mouse central nervous system after systemic delivery of a self-complementary AAV-PHP.B vector," Gene Ther. Apr. 2018;25(2): 83-92.
Rockwell et al., "AAV-Mediated Gene Delivery in a Feline Model of Sandhoff Disease Corrects Lysosomal Storage in the Central Nervous System," ASN Neuro. Apr. 2015, 7(2): 1-13.
Ronzitti et al., "A translationally optimized AAV-UGT1 vector drives safe and long-lasting correction of Crigler-Najjar syndrome," Mol Ther Methods Clin Dev. Jul. 2016; 3: 1-10.

(56) References Cited

OTHER PUBLICATIONS

Rosario et al., "Microglia-specific Targeting by Novel Capsid-modified AAV6 Vectors," Mol Ther Methods Clin Dev. Apr. 13, 2016;3:1-9.
Rosenberg et al., "Gene Therapy for Metachromatic Leukodystrophy," J Neurosci Res. Nov. 2016:94(11): 1169-79.
Ruffing et al., "Assembly of viruslike particles by recombinant structural proteins of adeno-associated virus type 2 in insect cells," J Virol. Dec. 1992;66(12):6922-30.
Rutledge et al., "Infectious clones and vectors derived from adeno-associated virus (AAV) serotypes other than AAV type 2," J Virol. Jan. 1998;72(1):309-19.
Salegio et al., "MRI-Guided Delivery of Viral Vectors," Methods Mol Viol. 2016; 1382:217-30 (abstract).
Samaranch et al., "Cerebellomedullary Cistern Delivery for AAV-Based Gene Therapy: A Technical Note for Nonhuman Primates," Hum Gene Ther Methods. Feb. 2016;27(1): 13-6.
Samaranch et al., "MR-guided parenchymal delivery of adeno-associated viral vector serotype 5 in non-human primate brain," Gene Ther. Apr. 2017;24(4):253-261.
Samulski et al., "Helper-free stocks of recombinant adeno-associated viruses: normal integration does not require viral gene expression," J Virol. Sep. 1989;63(9):3822-8.
Saraiva et al., "Gene Therapy for the CNS Using AAVs: The Impact of Systemic Delivery by AAV9," J Control Release. Nov. 10, 2016;241:94-109.
Savy et al., "Impact of ITR integrity on rAAV8 production using baculovirus/Sf9 cells system," Hum Gene Ther Methods. Oct. 1, 2017;28(5):277-89.
Sawada et al., "Inflammation-induced Reversible Switch of the Neuron-specific Enolase Promoter from Purkinje Neurons to Bergmann Glia," Sci Rep. Jun. 13, 2016;6:1-12.
Schaffer et al., "Molecular engineering of viral gene delivery vehicles," Annu Rev Biomed Eng. 2008; 10:169-94.
Schnepp et al., "Recombinant adeno-associated virus vector genomes take the form of long-lived transcriptionally competent episomes in human muscle," Hum Gene Ther. Jan. 2016;27(1):32-42.
Shen et al., "Analysis of the Cis and Trans Requirements for DNA Replication at the Right End Hairpin of the Human Bocavirus 1 Genome," J Virol. Aug. 2016; 90(17):7761-77.
Shen et al., "Functional Analysis of the Putative Integrin Recognition Motif on Adeno-associated virus 9," J Biol Chem. Jan. 2015, 290(3): 1496-504.
Shen et al., "Inhibition of pathological brain angiogenesis through systemic delivery of AAV vector expressing soluble FLT1," Gene Therapy. Nov. 2, 20152(11):893-900.
Shinohara et al., "Effects of Neutralizing Antibody Production on AAV-PHP.B-Mediated Transduction of the Mouse Central Nervous System," Mol Neurobiol. Jun. 2019; 56:4203-14.
Sinnett et al., "Improved MECP2 Gene Therapy Extends the Survival of MeCP2-Null Mice without Apparent Toxicity after Intracisternal Delivery," Mol Ther Methods Clin Dev. Apr. 19, 2017;5:106-115.
Siu et al., "Improved gene delivery to adult mouse spinal cord through the use of engineered hybrid adeno-associated viral serotypes," Gene Ther. Jun. 2017;24(6):361-9.
Smith et al., "A simplified baculovirus-AAV expression vector system coupled with one-step affinity purification yields high-titer rAAV stocks from insect cells," Mol Ther. Nov. 2009; 17(11): 1888-96.
Smith et al., "Gene transfer properties and structural modeling of human stem cell-derived AAV," Molecular Therapy. Sep. 2014;22(9): 1625-1634.
Smith et al., "Germline viral "fossils" guide in silico reconstruction of a mid-Cenozoic era marsupial adeno-associated virus," Sci Rep. Jul. 2016;6:1-17.
Sondhi et al., "Genetic Modification of the Lung Directed Toward Treatment of Human Disease," Hum Gene Ther. Jan. 2017;28(1):3-84.
Srivastava et al., "Nucleotide sequence and organization of the adeno-associated virus 2 genome," J Virol. Feb. 1983;45(2):555-64.

Srivastava, A., "Adeno-Associated Virus: The Naturally Occurring Virus Versus the Recombinant Vector," Hum Gene Ther. Jan. 2016;27(1): 1-6.
Srivastava, A., "In Vivo Tissue-tropism of Adeno-associated Viral Vectors," Curr Opin Virol. Sep. 2, 2016;21:75-80.
Steines et al., "CFTR gene transfer with AAV improves early cystic fibrosis pig phenotypes," JCI Insight. Sep. 2016; 1 (14): 1-14.
Su et al., "Recombinant adeno-associated viral (rAAV) vectors mediate efficient gene transduction in cultured neonatal and adult microglia," J Neurochem. Jan. 2016; 136 Suppl 1:49-62.
Summerford et al., "Aavr: A multi-serotype receptor for AAV," Mol Ther. Apr. 2016;24(4):663-6.
Sun et al., "Gene delivery of activated Factor VII Using Alternative AAV Serotype Improves Hemostasis in Hemophiliac Mice with FVIII Inhibitors and AAV Neutralizing antibodies," Hum Gene Ther. Aug. 1, 2017;28(8): 654-66.
Yan et al., "Optimization of recombinant adeno-associated virus mediated expression for large transgenes, using a synthetic promoter and tandem array enhancers," Hum Gene Ther. Jun. 2015;26(6):334-46.
Yang et al., "Sequential adeno-associated viral vector serotype 9-green fluorescent protein gene transfer causes massive inflammation and intense immune response in rat striatum," Hum Gene Ther. Jul. 2016;27(7):528-43.
Yazdan-Shahmorad et al., "Widespread Optogenetic Expression in Macaque Cortex Obtained with MR-Guided, Convection Enhanced Delivery (CED) of AAV vector to the Thalamus," J Neurosci Methods.Jan. 1, 2018;293:347-58.
Ye et al., "Adeno-Associated Virus Vector Mediated Delivery of the HBV Genome Induces Chronic Hepatitis B Virus Infection and Liver Fibrosis in Mice," PLOS One. Jun. 2015, 10(6): 1-16.
Yi et al., "Systemic correction of murine glycogen storage disease type IV by an AAV-mediated gene therapy," Hum Gene Ther. Mar. 2017;28(3): 286-294.
Zeng et al., "Probing the Link between Genomic Cargo, Contact Mechanics and Nanoindentation in Recombinant Adeno-Associated Virus 2," J Phys Chem B. Mar. 2017; 121(8): 1843-1853.
Zerah et al., "Intracerebral Gene therapy using AAV rh. 10-hARSA recombinant vector to treat patients with early- onset forms of metachromatic leukodystrophy: preclinical feasibility and safety assessments in NHP," Hum Gene Ther Clin Dev. Jun. 2015; 26(2): 113-24.
Zhang et al., "Blood-brain barrier shuttle peptides enhance AAV transduction in the brain after systemic administration," Biomaterials. Sep. 2018; 176:71-83.
Zhang et al., "Identification of adeno-associated virus capsid proteins using ZipChip CE/MS," Anal Biochem. Aug. 15, 2018;555:22-25.
Zhao et al., "BPV1 E2 protein enhances packaging of full-length plasmid DNA in BPV1 pseudovirions," Virology. Jul. 5, 2000;272(2):382-93.
Zhou et al., "Comparative Analysis In Vitro of Regulatory Elements That Drive Targeted Gene Expression in Adenovirus-Associated Viral (AAV) Vectors," Mol. Ther. May 1, 2015;23:S77-8.
Zhu et al., "Soluble FLT1 Gene Therapy Alleviates Brain Arteriovenous Malformation Severity," Stroke. May 2017;48 (5):1420-1423.
Zhu et al., "Zika virus has oncolytic activity against glioblastoma stem cells," J Exp Med. Oct. 2, 2017;214(10):2843-57.
Ziegler et al., "Steerable induction of the Thymosin B4/MRTF-A pathway via AAV-based overexpression induces therapeutic neovascularization," Hum Gene Ther. Dec. 1, 2018;29(12): 1407-15.
Zinn et al., "In Silico Reconstruction of the Viral Evolutionary Lineage Yields a Potent Gene Therapy Vector," Cell Reports, Aug. 1, 20151; 12(6): 1056-68.
Zolotukhin et al., "Potential for cellular stress response to hepatic factor VIII expression from AAV vector," Molecular Therapy - Methods & Clinical Development, Jan. 1, 2016;3:1-8.
Zou et al., "Nonstructural Protein NP1 of Human Bocavirus 1 Plays a Critical Role in the Expression of Viral Capsid Proteins," Journal of Virology, May 1, 2016;90(9):4658-69.

(56) References Cited

OTHER PUBLICATIONS

Belbellaa et al., "Correction of half the cardiomycytes fully rescue Friedreich Ataxia mitochondrial cardiomyopathy through cell-autonomous mechanisms," Human Molecular Genetics. Apr. 15, 2019;28(8): 1274-85.
Burk K., "Friedreich Ataxia: current status and future prospects," Cerebellum Ataxias. Apr. 7, 2017;4:1-9.
Campuzano et al., "Frataxin is reduced in Friedreich ataxia patients and is associated with mitochondrial membranes," Hum Mol Genet. Oct. 1997;6(11): 1771-80.
Campuzano et al., "Friedreich's ataxia: autosomal recessive disease caused by an intronic GAA triplet repeat expansion," Science. Mar. 8, 1996;271(5254): 1423-7.
Cherif et al., "Increased frataxin expression induced in Friedreich Ataxia cells by platinum TALE-VP64s or platinum TALE-SunTag," Mol Ther Nuc Acids Sep. 7, 2018;12:19-32.
Cook et al., "Friedreich's ataxia: clinical features, pathogenesis and management," Br Med Bull. Dec. 1, 2017;124 (1): 19-30.
Corben et al., "Consensus clinical management guidelines for Friedreich ataxia," Orphanet J Rare Dis. Nov. 30, 2014;9:1-12.
Cossee et al., "Evolution of the Friedreich's ataxia trinucleotide repeat expansion: founder effect and premutations," Proc Natl Acad Sci USA. Jul. 8, 1997;94(14):7452-7.
Delatycki et al., "Direct evidence that mitochondrial iron accumulation occurs in Friedreich ataxia," Ann Neurol. May 1999;45(5): 673-5.
Delatycki et al., "Friedreich ataxia: an overview," J Med Genet. Jan. 2000;37(1):1-8.
Durr et al., "Clinical and genetic abnormalities in patients with Friedreich's ataxia," N Engl J Med. Oct. 17, 1996;335 (16): 1169-75.
Filla et al.,"The relationship between trinucleotide (GAA) repeat length and clinical features in Friedreich ataxia," Am J Hum Genet. Sep. 1996;59(3):554-60.
Grabczyk et al., "The GAA*TTC triplet repeat expanded in Friedreich's ataxia impedes transcription elongation by T7 RNA polymerase in a length and supercoil dependent manner," Nucleic Acids Res. Jul. 15, 2000;28(14):2815-22.
Harding et al., "Friedreich's ataxia: a clinical and genetic study of 90 families with an analysis of early diagnostic criteria and intrafamilial clustering of clinical features," Brain. Sep. 1981; 104(3):589-620.
Kim et al., "Points to Consider in Designing and Conducting Juvenile Toxicology Studies," Int J Toxicol. Jul. 2017/ Aug. 36(4): 325-339.
Koeppen Ah., "Friedreich's ataxia: pathology, pathogenesis, and molecular genetics," J Neurol Sci. Apr. 15, 2011;303 (1-2):1-12.
Lazaropoulos et al., "Frataxin levels in peripheral tissue in Friedreich ataxia," Ann Clin Transl Neurol. Aug. 2015;2 (8):831-42.
Martelli et al., "Dysregulation of cellular iron metabolism in Friedreich ataxia: from primary iron-sulfur cluster deficit to mitochondrial iron accumulation," Front Pharmacol. Jun. 3, 2014;5:1-11.
Pandolfo M., "Friedreich ataxia: the clinical picture," J Neurol. Mar. 2009;256 Suppl 1:3-8.
Perdomini et al., "Prevention and reversal of severe mitochondrial cardiomyopathy by gene therapy in a mouse model of Friedreich's ataxia," Nat Med. May 2014;20(5): 542-7.
Piguet et al., "Rapid and complete reversal of sensory ataxia by gene therapy in a novel model of Friedreich ataxia," Mol Ther. Aug. 1, 2018;26(8): 1940-52.
Reetz et al., "Biological and clinical characteristics of the European Friedreich's Ataxia Consortium for Translational Studies (EFACTS) cohort: a cross-sectional analysis of baseline data," Lancet Neurol. Feb. 2015; 14(2): 174-82.
Yandim et al., "Gene regulation and epigenetics in Friedreich's ataxia," J Neurochem. Aug. 2013; 126 Suppl 1:21-42.
Zhu et al., "Friedreich's ataxia with chorea and myoclonus caused by a compound heterozygosity for a novel deletion and the trinucleotide GAA expansion," Mov Disord. May 2002; 17(3): 585-9.

Kirnbauer et al., "Virus-like particles of bovine papillomavirus type 4 in prophylactic and therapeutic immunization," Virology. May 1, 1996;219(1): 37-44.
Knezevic et al., "Adeno-associated Virus Serotype 9—Driven Expression of BAG3 Improves Left Ventricular Function in Murine Hearts with Left Ventricular Dysfunction Secondary to a Myocardial Infarction," JACC Basic Transl Sci. Dec. 2016;1(7):647-656.
Ko et al., "AAV8-mediated expression of N-acetylglucosamine-1-phosphate transferase attenuates bone loss in a mouse model of mucolipidosis II," Mol Genet Metab. Apr. 2016; 117(4):447-55.
Kohlbrenner et al., "Production and Characterization of Vectors Based on the Cardiotropic AAV Serotype 9," Methods Mol Biol. 2017; 1521:91-107.
Kondratov et al., "Direct head-to-head evaluation of recombinant Adeno-associated viral (rAAV) vectors manufactured in human vs insect cells," Molecular Therapy. Dec. 6, 2017;25(12):2661-75.
Korbelin et al., "Pulmonary targeting of adeno-associated viral vectors by next-generation sequencing-guided screening of random capsid displayed peptide libraries," Molecular Therapy. Jun. 1, 2016;24(6): 1050-61.
Kothari et al., "Iodine-124 Labeled Adeno-Associated Virus: A Promising Tool for Tracking Gene Therapy," Journal of Nuclear Medicine. May 2015, 56 (supplement 3), 494-494.
Kothari et al., "Radioiodinated Capsids Facilitate In Vivo Non-Invasive Tracking of Adeno-Associated Gene Transfer Vectors," Sci Rep. Jan. 2017;7:39594.
Kotin et al., "Large-scale recombinant adeno-associated virus production," Hum Mol Genet. Apr. 15, 2011;20(R1): R2-6.
Kotin et al., "Manufacturing clinical grade recombinant adeno-associated virus using invertebrate cell lines," Hum Gene Ther. Apr. 2017;28(4):350-360.
Kotterman et al., "Enhanced cellular secretion of AAV2 by expression of foreign viral envelope proteins," Biochemical Engineering Journal, Jan. 15, 2015;93:108-14.
Kou et al., "Catalytic Immunoglobulin Gene Delivery in a Mouse Model of Alzheimer's Disease: Prophylactic and Therapeutic Applications," Molecular Neurobiology, Feb. 2015;51:43-56.
Kozak, M., "Interpreting cDNA sequences: some insights from studies on translation," Mamm Genome. Aug. 1996;7 (8):563-74.
Kozak, M., "Point mutations define a sequence flanking the AUG initiator codon that modulates translation by eukaryotic ribosomes," Cell. Jan. 31, 1986;44(2):283-92.
Kozak, M., "The scanning model for translation: an update," J Cell Biol. Feb. 1989; 108(2):229-41.
Kurosaki et al., "Optimization of adeno-associated virus vector-mediated gene transfer to the respiratory tract," Gene Ther. May 2017;24(5):290-297.
Lahteenvuo et al., "Advances and Challenges in Cardiovascular gene therapy," Hum Gene Ther. Nov. 1, 2017;28 (11): 1024-32.
Lai et al., "Aquaporin gene therapy corrects Sjogren's syndrome phenotype in mice," PNAS. May 2016; 113 (20):5694-9.
Landau et al., "In vivo zinc finger nuclease mediated targeted integration of a glucose-6-phosphatase transgene promotes survival in mice with glycogen storage disease type 1a," Mol Ther. Apr. 2016;24(4):697-706.
Landegger et al., "A synthetic AAV vector enables safe and efficient gene transfer to the mammalian inner ear," Nat Biotechnol. Mar. 2017;35(3):280-284.
Le Pichon et al., "Loss of dual leucine zipper kinase signaling is protective in animal models of neurodegenerative disease," Sci Transl Med. Aug. 16, 2017;9(403).
Lee et al., "A neuron-specific gene therapy relieves motor deficits in pompe disease mice," Mol Neurobiol. Jun. 2018;55(6):5299-5309.
Lentz et al., "Insight into the Mechanism of Inhibition of Adeno-Associated Virus by the Mre11/Rad50/Nbs1 Complex," J Virol. Jan. 2015, 89(1): 181-94.
Levacic et al., "Minicircle Versus Plasmid DNA Delivery by Receptor-Targeted Polyplexes," Hum Gene Ther. Oct. 2017;28(10): 862-874.
Li et al., "Efficient and targeted transduction of nonhuman primate liver with systemically delivered optimized AAV3B vectors," Mol Ther. Dec. 2015;23(12): 1867-76.

(56) References Cited

OTHER PUBLICATIONS

Li et al., "Engineering and selection of shuffled AAV genomes: a new strategy for producing targeted biological nanoparticles," Mol Ther. Jul. 2008; 16(7): 1252-60.

Li et al., "Production and characterization of novel recombinant adeno-associated virus replicative-form genomes: a eukaryotic source of DNA for gene transfer," PLOS One. Aug. 1, 2013;8(8): e69879.

Li et al., "Site directed mutagenesis of surface-exposed lysine residues leads to improved transduction by AAV2 but not AAV8 vectors in murine hepatocytes in vivo," Hum Gene Ther Methods. Dec. 2015;26(6):211-20.

Li et al., "The impact of rare variation on gene expression across tissues," Nature. Oct. 11, 2017;550(7675):239-243.

Liguore et al., "AAV-PHP.B Administration Results in a Differential Pattern of CNS Biodistribution in Non-human Primates Compared with Mice," Molecular Therapy. Nov. 6, 2019;27(11):2018-37.

Ling et al., "Development of Optimized AAV Serotype Vectors for High-Efficiency Transduction at Further Reduced Doses," Hum Gene Ther Methods. Aug. 2016;27(4): 143-9.

Ling et al., "Enhanced Transgene Expression from Recombinant Single-Stranded D-Sequence-Substituted Adeno- Associated Virus Vectors in Human Cell Lines In Vitro and in Murine Hepatocytes In Vivo," J Virol. Jan. 2015, 89 (2):952-61.

Ling et al., "High-Efficiency Transduction of Primary Human Hematopoietic Stem/Progenitor Cells by AAV6 Vectors: Strategies for Overcoming Donor-Variation and Implications in Genome Editing," Sci Rep. Oct. 2016; 6:35495.

Ling et al., "Strategies to generate high-titer, high-potency recombinant AAV3 serotype vectors," Mol Ther Methods Clin Dev. May 2016;3:16029.

Liu et al., "Single cell transcriptomics reconstructs fate conversion from fibroblast to cardiomyocyte," Nature. Nov. 2, 2017;551(7678): 100-4.

Liu et al., "Vectored Intracerebral Immunization with the Anti-Tau Monoclonal Antibody PHF1 Markedly Reduces Tau Pathology in Mutant Tau Transgenic Mice," J Neurosci. Dec. 2016;36(49): 12425-12435.

Logan et al., "Identification of liver-specific enhancer-promoter activity in the 3' untranslated region of the wild-type AAV2 genome," Nat Genet. Aug. 1, 2017;49(8): 1267-73.

Loring et al., "Development of rAAV2-CFTR: History of the First rAAV Vector Product to be Used in Humans," Hum Gene Ther Methods. Apr. 2016;27(2):49-58.

Lu et al., "A 5' Noncoding Exon Containing Engineered Intron Enhances Transgene Expression from Recombinant AAV Vectors in vivo," Hum Gene Ther. Jan. 2017;28(1): 125-134.

Lukashcuk et al., "AAV9-mediated central nervous system-targeted gene delivery via cisterna magna route in mice," Mol Ther Methods Clin Dev. Feb. 17, 2016;3:15055.

Luo et al., "AAVS1-Targeted Plasmid Integration in AAV Producer Cell Lines," Hum Gene Ther Methods. Jun. 2017;28 (3): 124-138.

Luo et al., "Genetic dissection of neural circuits," Neuron. Mar. 13, 2008; 57(5):634-60.

Mack et al., "Minimally Effective Dose of Systemic AAV8-MTM1 Needed To Prolong Survival and Correct Severe Muscle Pathology in a Canine Model of X-Linked Myotubular Myopathy," Molecular Therapy. May 1, 2015;23:S201.

Mack et al., "Systemic AAV8-Mediated Gene Therapy Drives Whole-Body Correction of Myotubular Myopathy in Dogs," Mol Ther. Apr. 2017;25(4): 839-854.

Magnani et al., "Dengue virus evades AAV-mediated neutralizing antibody prophylaxis in rhesus monkeys," Mol Ther. Oct. 4, 2017;25(10):2323-31.

Majowicz et al., "Successful Repeated Hepatic Gene Delivery in Mice and Non-human Primates Achieved by Sequential Administration of AAV5ch and AAV1," Mol Ther. Aug. 2, 2017;25(8): 1831-42.

Mao et al., "Single point mutation in adeno-associated viral vectors - DJ capsid leads to improvement for gene delivery in vivo," BMC Biotechnol. Jan. 2016; 16:1-8.

Marcos-Contreras et al., "Sustained correction of FVII deficiency in dogs using AAV-mediated expression of zymogen FVII," Blood. Feb. 2016; 127(5):565-71.

\* cited by examiner

FRATAXIN EXPRESSION CONSTRUCTS HAVING ENGINEERED PROMOTERS AND METHODS OF USE THEREOF

CROSS REFERENCE TO RELATED APPLICATIONS

This application is a U.S. national stage entry under 35 U.S.C. § 371 of international application number PCT/US2019/053681, filed Sep. 27, 2019, which designates the U.S. and claims the benefit of U.S. Provisional Patent Application No. 62/738,519, filed Sep. 28, 2018, entitled FRATAXIN COMPOSITIONS AND METHODS OF USE THEREOF, and U.S. Provisional Patent Application No. 62/901,769, filed Sep. 17, 2019, entitled FRATAXIN EXPRESSION CONSTRUCTS HAVING ENGINEERED PROMOTERS AND METHODS OF USE THEREOF, the contents of each of which are incorporated herein by reference in their entirety.

REFERENCE TO THE SEQUENCE LISTING

The present application is being filed along with a Sequence Listing in electronic format. The Sequence Listing file, entitled 20571019PCTSEQLST.txt, was created on Sep. 27, 2019, and is 6,732,273 bytes in size. The information in electronic format of the Sequence Listing is incorporated herein by reference in its entirety.

FIELD OF THE DISCLOSURE

The invention relates to frataxin-based compositions and methods related to enhancing the expression of frataxin (FXN) whether in vitro or in vivo at least in part via the exploitation of novel engineered promoters. Such frataxin-based compositions may be delivered in an adeno-associated viral (AAV) vector. In other embodiments, a frataxin-based composition, such as an AAV-frataxin composition, is used to treat a subject in need thereof, such as a human subject diagnosed with Friedreich's Ataxia or other neurological condition resulting from a deficiency in the quantity and/or function of frataxin, or as a research tool in the study of diseases or conditions in cells or animal models of such disease or condition.

BACKGROUND

Friedreich's Ataxia (FA), as first described by German physician Nikolas Friedreich in the 1860s, is an autosomal recessive inherited disease that causes progressive damage to the nervous system. See Parkinson et al., *Journal of Neurochemistry*, 2013, 126 (Suppl. 1), 103-117, the contents of which are herein incorporated by reference in their entirety. Onset usually occurs at puberty, and almost always by age 25. See Campuzano, et al., Science, 271.5254 (Mar. 8, 1996): 1423, the contents of which are herein incorporated by reference in their entirety. FA typically results from the degeneration of nervous tissue in the spinal cord due to reduced expression of the mitochondrial protein frataxin (FXN) in sensory neurons that (through connections with the cerebellum) direct muscle movement of the arms and legs. See Koeppen, Arnulf; *J Neurol Sci.*, 2011, Apr. 15; 303(1-2): 1-12, the contents of which are herein incorporated by reference in their entirety. The spinal cord becomes thinner and peripheral nerve cells lose some of their myelin sheath, which is the insulating covering on some nerve cells that helps conduct nerve impulses. Initial symptoms of FA include poor coordination such as gait disturbance, poor balance, leg weakness, decreased walking, impaired coordination, dysarthria, nystagmus, impaired sensation, kyphoscoliosis, and foot deformities. See Parkinson et al., *Journal of Neurochemistry*, 2013, 126 (Suppl. 1), 103-117. FA is also associated with scoliosis, heart disease, and diabetes. The disease generally progresses until a wheelchair is required for mobility. Incidence of FA among Caucasian populations is between about 1 in 20,000 and about 1 in 50,000, with a deduced carrier frequency of about 1 in 120 in European populations. See Nageshwaran and Festenstein, *Frontiers in Neurology*, Vol. 6, Art. 262 (2015); Campuzano, et al., Science, 271.5254 (Mar. 8, 1996): 1423, the contents of each of which are herein incorporated by reference in their entirety.

The expansion of an intronic GAA triplet repeat in the FXN gene is the genetic cause of reduced expression of frataxin resulting in FA. See Parkinson et al., *Journal of Neurochemistry*, 2013, 126 (Suppl. 1), 103-117. Over time, the deficiency causes the aforementioned symptoms, as well as frequent fatigue due to effects on cellular metabolism.

Sclerosis and degeneration are most frequent in dorsal root ganglia, spinocerebellar tracts, lateral corticospinal tracts, and posterior columns. See Sandi et al., *Frontiers in Genetics*, Vol. 5, Art. 165 (June 2014), the contents of which are herein incorporated by reference in their entirety.

Progressive destruction of dorsal root ganglia causes thinning of dorsal roots, degeneration of dorsal columns, trans-synaptic atrophy of nerve cells in Clarke's column and dorsal spinocerebellar fibers, atrophy of gracile and cuneate nuclei, and neuropathy of sensory nerves. See Koeppen, Arnulf; *J Neurol Sci.*, 2011, Apr. 15; 303(1-2): 1-12, the contents of which are herein incorporated by reference in their entirety. The lesion of the dentate nucleus consists of progressive and selective atrophy of large glutamatergic neurons and grumose degeneration of corticonuclear synaptic terminals that contain gamma-aminobutyric acid (GABA). Small GABA-ergic neurons and their projection fibers in the dentato-olivary tract survive. Atrophy of Betz cells and corticospinal tracts constitute a second lesion. Currently, no effective treatments exist for FA and patients are most often simply monitored for symptom management.

Consequently, there remains a long felt need in the art to develop pharmaceutical compositions and methods for the treatment of FXN related disorders and to ameliorate deficiencies of the protein in patients afflicted with FA. Adeno-associated viruses (AAVs) have emerged as one of the most widely studied and utilized viral particles for delivery of therapeutically effective polypeptides to mammalian cells. See, e.g., Tratschin et al., Mol. Cell Biol., 5(11):3251-3260 (1985) and Grimm et al., Hum. Gene Ther., 10(15):2445-2450 (1999), the contents of each of which are incorporated herein by reference in their entirety. As such, this modality is well suited to exploitation toward treatment of FA and the delivery of frataxin and frataxin related proteins and peptides.

SUMMARY

In some aspects, the present disclosure provides AAV viral genomes comprising at least one inverted terminal repeat (ITR) and a payload region, wherein the payload region encodes a frataxin protein. In some embodiments, the AAV viral genome comprises a 5' ITR, an engineered promoter, a payload region, and a 3' ITR. The encoded frataxin protein may be a human (*Homo sapiens*) frataxin, a cynomolgus monkey (*Macaca fascicularis*) frataxin, or a rhesus monkey (*Macaca mulatta*) frataxin, a synthetic (non-naturally occurring) frataxin, or a derivative thereof, e.g., a variant that retains one or more function of a wild-type frataxin. In some embodiments, the frataxin protein may be at least partially humanized.

The engineered promoter of the AAV viral genome may be derived from a cytomegalovirus (CMV) promoter, a chicken β-actin (CBA) promoter, or a frataxin (FXN) promoter. In some embodiments, the engineered promoter is a promoter variant or a derivative of a parent promoter sequence.

In some embodiments, the engineered promoter is derived from a CMV promoter.

In some embodiments, the engineered promoter is derived from a CBA promoter.

In some embodiments, the engineered promoter is derived from a FXN promoter.

An engineered promoter of the AAV viral genome as described herein, may comprise a sequence as given by any of SEQ ID NO: 1734-1777. In some embodiments, the engineered promoter comprises a sequence having at least 90% sequence identity to any of SEQ ID NO: 1734-1777. In some embodiments, the engineered promoter comprises a sequence having at least 95% sequence identity to any of SEQ ID NO: 1734-1777. In some embodiments, the engineered promoter comprises a sequence having at least 99% sequence identity to any of SEQ ID NO: 1734-1777. In some embodiments, the engineered promoter may consist of any of SEQ ID NO: 1734-1777. In some embodiments, the engineered promoter is derived from a CMV promoter and may comprise a sequence as given by any of SEQ ID NO: 1743-1751, 1767, and 1772-1774. In some embodiments, the engineered promoter comprises SEQ ID NO: 1777. In some embodiments, the engineered promoter is derived from a CBA promoter and may comprise a sequence as given by any of SEQ ID NO: 1734-1742, 1760-1766, 1768, and 1775-1776. In some embodiments, the engineered promoter is derived from a FXN promoter and may comprise a sequence as given by any of SEQ ID NO: 1752-1759 and 1769-1770.

In some embodiments, the engineered promoter comprises a sequence as given by SEQ ID NO: 1738. In some embodiments, the engineered promoter comprises a sequence which has at least 90% sequence identity to SEQ ID NO: 1738. In some embodiments, the engineered promoter comprises a sequence which has at least 95% sequence identity to SEQ ID NO: 1738. In some embodiments, the engineered promoter comprises a sequence which has at least 99% sequence identity to SEQ ID NO: 1738. In some embodiments, the engineered promoter consists of SEQ ID NO: 1738.

In some embodiments, the engineered promoter comprises a sequence as given by SEQ ID NO: 1740. In some embodiments, the engineered promoter comprises a sequence which has at least 90% sequence identity to SEQ ID NO: 1740. In some embodiments, the engineered promoter comprises a sequence which has at least 95% sequence identity to SEQ ID NO: 1740. In some embodiments, the engineered promoter comprises a sequence which has at least 99% sequence identity to SEQ ID NO: 1740. In some embodiments, the engineered promoter consists of SEQ ID NO: 1740.

In some embodiments, the engineered promoter comprises a sequence as given by SEQ ID NO: 1742. In some embodiments, the engineered promoter comprises a sequence which has at least 90% sequence identity to SEQ ID NO: 1742. In some embodiments, the engineered promoter comprises a sequence which has at least 95% sequence identity to SEQ ID NO: 1742. In some embodiments, the engineered promoter comprises a sequence which has at least 99% sequence identity to SEQ ID NO: 1742. In some embodiments, the engineered promoter consists of SEQ ID NO: 1742.

In some embodiments, the engineered promoter comprises a sequence as given by SEQ ID NO: 1750. In some embodiments, the engineered promoter comprises a sequence which has at least 90% sequence identity to SEQ ID NO: 1750. In some embodiments, the engineered promoter comprises a sequence which has at least 95% sequence identity to SEQ ID NO: 1750. In some embodiments, the engineered promoter comprises a sequence which has at least 99% sequence identity to SEQ ID NO: 1750. In some embodiments, the engineered promoter consists of SEQ ID NO: 1750.

In some embodiments, the engineered promoter comprises a sequence as given by SEQ ID NO: 1756. In some embodiments, the engineered promoter comprises a sequence which has at least 90% sequence identity to SEQ ID NO: 1756. In some embodiments, the engineered promoter comprises a sequence which has at least 95% sequence identity to SEQ ID NO: 1756. In some embodiments, the engineered promoter comprises a sequence which has at least 99% sequence identity to SEQ ID NO: 1756. In some embodiments, the engineered promoter consists of SEQ ID NO: 1756.

An engineered promoter as described herein, may have a length of 50-1400 nucleotides (nt). In some embodiments, the engineered promoter is derived from a CMV promoter and is 50-700 nt in length. In, some embodiments, the engineered promoter is derived from a CMV promoter and is 109 nt in length. In some embodiments, the engineered promoter is derived from a CBA promoter and is 100-700 nt in length. In some embodiments, the engineered promoter is derived from a CBA promoter and is 100-400 nt in length. In some embodiments, the engineered promoter is derived from a CBA promoter and is 100 nt in length. In some embodiments, the engineered promoter is derived from a CBA promoter and is 200-350 nt in length. In some embodiments, the engineered promoter is derived from a CBA promoter and is 260 nt in length. In some embodiments, the engineered promoter is derived from a CBA promoter and is 332 nt in length. In some embodiments, the engineered promoter is derived from a FXN promoter and is 200-1400 nt in length. In some embodiments, the engineered promoter is 950-1150 nt in length. In some embodiments, the engineered promoter is derived from a FXN promoter and is 1060 nt in length.

In some embodiments, the engineered promoter comprises an enhancer region.

Engineered promoters and payload regions encoding frataxin may be incorporated into an AAV viral genome.

In some embodiments, the AAV viral genome comprises, in addition to an engineered promoter and a payload region, a 5' ITR, an enhancer, an intron, at least one miR binding site (e.g., one, two, or three miR binding sites), a polyA sequence, a filler sequence and a 3' ITR. In some embodiments, the AAV viral genome comprises multiple miR binding sites (an "miR binding site series") that may appear consecutively or separated by one or more nucleotides. In some embodiments, the 5' ITR and/or the 3' ITR is an AAV2 ITR.

In some embodiments, the viral genome comprises at least one ITR sequence. In some embodiments, the ITR may be an AAV2 ITR. In some embodiments, the 5' ITR may be an AAV2 ITR. In some embodiments, the 3' ITR may be an AAV2 ITR. In some embodiments, the 5' and/or the 3' ITR may be 141 nt in length. In some embodiments, the 5' ITR comprises a sequence at least 95%, at least 99%, or 100% identical to SEQ ID NO: 1811. In some embodiments, the 3' ITR comprises a sequence at least 95%, at least 99%, or 100% identical to SEQ ID NO: 1812.

In some embodiments, an ITR to ITR sequence comprises an intron/exon region. In some embodiments, the intron/exon region may be an enhancer sequence. As a non-limiting example, an enhancer sequence may comprise two or more subcomponents, such as, but not limited to, an ie1 exon (e.g., exon 1), an ie1 intron (e.g., intron 1), a human beta-globin intron (e.g., intron 2), and/or a human beta globin exon (e.g., exon 3), or a fragment thereof. In some embodiments, the intron/exon region comprises a sequence at least 90%, at least 95%, at least 99%, or 100% identical to a sequence as given by any of SEQ ID NOs: 1815-1821. In some embodiments, the enhancer comprises a sequence at least 90%, at least 95%, at least 99%, or 100% identical to a sequence as given by any of SEQ ID NOs: 1815-1821. In some embodiments, the enhancer comprises a sequence at least 90%, at least 95%, at least 99%, or 100% identical to SEQ ID NO: 1777. In some embodiments, the intron/exon region comprises one or more human beta-globin sequences, e.g., a sequence at least 90%, at least 95%, at least 99%, or 100% identical to SEQ ID NOs: 1820 and/or 1821. In some embodiments, the intron may comprise a sequence as given by any of SEQ ID NO: 1815-1821. In some embodiments, the intron has a sequence at least 90%, at least 95%, at leas 99%, or 100% identical to SEQ ID NO: 1816. In some embodiments, the intron may consist of SEQ ID NO: 1816.

In some embodiments, a miR binding site series comprises at least one miR122 binding site sequence. In some embodiments, the at least one miR122 binding site comprises a sequence at least 90%, at least 95%, at least 99%, or 100% identical to SEQ ID NO: 1827. In some embodiments, the at least one miR122 binding site consists of SEQ ID NO: 1827. In some embodiments, the AAV vector genome comprises three copies of a miR122 binding site, e.g., three copies of SEQ ID NO: 1827 or a variant thereof having at least 90% sequence identity. In some embodiments, the miR binding site series may comprise a sequence having at least 90%, at least 95%, at least 99%, or 100% identical to SEQ ID NO: 1826. In some embodiments, the miR binding site series may consist of SEQ ID NO: 1826.

In some embodiments, the polyA sequence is a human growth hormone (hGH) polyA sequence. In some embodiments, the viral genome comprises a hGH polyA sequence at least 90%, at least 95%, at least 99%, or 100% identical to SEQ ID NO: 1828. In some embodiments, the polyA sequence consists of SEQ ID NO: 1828.

In some embodiments, the AAV viral genome further comprises a filler sequence, e.g., an albumin filler sequence. In some embodiments, the filler sequence may comprise a sequence at least 90%, at least 95%, at least 99%, or 100% identical to a sequence as given by any of SEQ ID NOs: 1829-1842. In some embodiments, the filler sequence may comprise a sequence at least 90%, at least 95%, at least 99% or 100% identical to SEQ ID NO: 1838. In some embodiments, the filler sequence may consist of SEQ ID NO: 1838. In some embodiments, the filler sequence may comprise a sequence at least 90%, at least 95%, at least 99% or 100% identical to SEQ ID NO: 1839. In some embodiments, the filler sequence may consist of SEQ ID NO: 1839. In some embodiments, the filler sequence may comprise a sequence at least 90%, at least 95%, at least 99% or 100% identical to SEQ ID NO: 1840. In some embodiments, the filler sequence may consist of SEQ ID NO: 1840. In some embodiments, the filler sequence may comprise a sequence at least 90%, at least 95%, at least 99% or 100% identical to SEQ ID NO: 1841. In some embodiments, the filler sequence may consist of SEQ ID NO: 1841.

In some embodiments, an AAV viral genome may comprise a sequence as given by any of SEQ ID NO: 1778-1810. In some embodiments, the AAV viral genome comprises a sequence that has at least 80%, at least 85%, at least 90%, at least 95%, or at least 99% sequence identity to any of SEQ ID NO: 1778-1810. In some embodiments, the AAV viral genome comprises a sequence that has 80-85%, 80-90%, 80-95%, 80-99%, 80-100%, 90-95%, 90-99%, or 90-100% sequence identity to any of SEQ ID NOs: 1778-1810. An AAV viral genome wherein the encoded frataxin is a *Cynomolgus* sp. frataxin may comprise a sequence as given by any of SEQ ID NO: 1778-1795. In some embodiments, the AAV viral genome comprises a sequence that has at least 80%, at least 85%, at least 90%, at least 95%, or at least 99% sequence identity to any of SEQ ID NO: 1778-1795. In some embodiments, the AAV viral genome comprises a sequence that has 80-85%, 80-90%, 80-95%, 80-99%, 80-100%, 90-95%, 90-99%, or 90-100% sequence identity to any of SEQ ID NOs: 1778-1795. An AAV viral genome wherein the encoded frataxin is a human frataxin may comprise a sequence as given by any of SEQ ID NO: 1796-1810. In some embodiments, the AAV viral genome comprises a sequence that has at least 80%, at least 85%, at least 90%, at least 95%, or at least 99% sequence identity to any of SEQ ID NO: 1796-1810. In some embodiments, the AAV viral genome comprises a sequence that has 80-85%, 80-90%, 80-95%, 80-99%, 80-100%, 90-95%, 90-99%, or 90-100% sequence identity to any of SEQ ID NOs: 1796-1810.

In some embodiments, the AAV viral genome may comprise a sequence at least 90%, at least 95%, at least 99% or 100% identical to SEQ ID NO: 1797. In some embodiments, the AAV viral genome may consist of SEQ ID NO: 1797. In some embodiments, the AAV viral genome may comprise a sequence at least 90%, at least 95%, at least 99% or 100% identical to SEQ ID NO: 1801. In some embodiments, the AAV viral genome may consist of SEQ ID NO: 1801. In some embodiments, the AAV viral genome may comprise a sequence at least 90%, at least 95%, at least 99% or 100% identical to SEQ ID NO: 1808. In some embodiments, the AAV viral genome may consist of SEQ ID NO: 1808. In some embodiments, the AAV viral genome may comprise a sequence at least 90%, at least 95%, at least 99% or 100% identical to SEQ ID NO: 1809. In some embodiments, the AAV viral genome may consist of SEQ ID NO: 1809.

In some embodiments, a payload region of an AAV vector genome encoding frataxin comprises a nucleic acid sequence at least 80%, at least 85%, at least 90%, at least 95%, or at least 99% identical to a sequence as given by any of SEQ ID NOs: 1822-1824. In some embodiments, a payload region of an AAV vector genome encoding frataxin comprises a nucleic acid sequence as given by any of SEQ ID NOs: 1822-1824. In some embodiments, the nucleic acid sequence encoding frataxin comprises SEQ ID NO: 1822. In some embodiments, the nucleic acid sequence encoding frataxin comprises SEQ ID NO: 1823. In some embodiments, the nucleic acid sequence encoding frataxin comprises SEQ ID NO: 1824. In some embodiments, the nucleic acid sequence encoding frataxin comprises a fragment of SEQ ID NO: 1728, 1729, or 1730, or a variant thereof having at least 80%, at least 85%, at least 90%, at least 95%, or at least 99% sequence identity thereto. In some embodiments, the nucleic acid sequence encoding frataxin comprises a fragment of SEQ ID NO: 1728. In some embodiments, the nucleic acid sequence encoding frataxin comprises nucleotides 221-853 of SEQ ID NO: 1728.

In some embodiments, a payload region of an AAV vector genome comprises a nucleic acid sequence that encodes a frataxin polypeptide having at least 80%, at least 85%, at least 90%, at least 95%, or at least 99% sequence identity to SEQ ID NO: 1725, 1726, or 1727. In some embodiments, a payload region of an AAV vector genome comprises a nucleic acid sequence that encodes a frataxin polypeptide of SEQ ID NO: 1725, 1726, or 1727. In some embodiments the AAV vector genome comprises a nucleic acid sequence that encodes a frataxin polypeptide comprising SEQ ID NO: 1725. In some embodiments, a payload region of an AAV vector genome comprises a nucleic acid sequence that encodes a frataxin polypeptide having at least 80%, 85%, 90%, 95%, or 99% sequence identity to SEQ ID NO: 1731, 1732, or 1733. In some embodiments, a payload region of an AAV vector genome comprises a nucleic acid sequence that encodes a frataxin polypeptide of SEQ ID NO: 1731, 1732, or 1733.

Viral genomes comprising engineered promoters or promoter variants may be incorporated into an AAV particle, wherein the AAV particle comprises a viral genome and a capsid. In some embodiments, the capsid comprises a sequence as shown in Table 1 or is selected from the group consisting of SEQ ID NO: 1-1724. Non-limiting examples of capsids include AAV9, AAV9 K449R, AAVPHP.B, AAVPHP.N, VOY101 (having an amino acid sequence of SEQ ID NO: 1 and/or having a nucleic acid sequence of SEQ ID NO: 1722), and/or VOY201 (having an amino acid sequence of SEQ ID NO: 1724 and/or having a nucleic acid sequence of SEQ ID NO: 1723). In some embodiments, the capsid is encoded by a nucleic acid sequence selected from SEQ ID NO: 4, 135, 1722, and 1723. In some embodiments, the capsid may have an amino acid sequence as given by any of SEQ ID NO: 1, 2, 3, 9, 136, or 1724. In some embodiments, the capsid comprises an amino acid sequence as given by SEQ ID NO: 136. In some embodiments, the capsid comprises an amino acid sequence encoded by a nucleic acid sequence as given by SEQ ID NO: 135. In some embodiments, the capsid comprises an amino acid sequence as given by SEQ ID NO: 9. In some embodiments, the capsid comprises an amino acid sequence as given by SEQ ID NO: 3. In some embodiments, the capsid comprises an amino acid sequence encoded by a nucleic acid sequence as given by SEQ ID NO: 4. In some embodiments, the capsid comprises an amino acid sequence as given by SEQ ID NO: 2. In some embodiments, the capsid comprises an amino acid sequence as given by SEQ ID NO: 1. In some embodiments, the capsid comprises an amino acid sequence encoded by a nucleic acid sequence as given by SEQ ID NO: 1722. In some embodiments, the capsid comprises an amino acid sequence encoded by a nucleic acid sequence as given by SEQ ID NO: 1723. In some embodiments, the capsid comprises an amino acid sequence as given by SEQ ID NO: 1724.

In some embodiments, the AAV particles described herein may be used in a pharmaceutical composition. In some embodiments, the pharmaceutical composition comprises sodium chloride, sodium phosphate, potassium chloride, potassium phosphate and poloxamer 188. In some embodiments, the pharmaceutical composition comprises 192 mM sodium chloride, 10 mM sodium phosphate, 2.7 mM potassium chloride, 2 mM potassium phosphate and 0.001% poloxamer 188 (v/v). In some embodiments, the sodium phosphate of the composition is dibasic. In some embodiments, the potassium phosphate of the composition is monobasic. In some embodiments, the pH of the pharmaceutical composition is between 7.3-7.7. In some embodiments, the pH of the pharmaceutical composition is 7.4

In some embodiments, the AAV particle may comprise a vector genome as given by SEQ ID NO: 1797 and a VOY101 capsid. In some embodiments, a pharmaceutical composition comprising the AAV particle comprising a vector genome given by SEQ ID NO: 1797 and a VOY101 capsid, comprises sodium chloride, sodium phosphate, potassium chloride, potassium phosphate and poloxamer 188; optionally wherein the pharmaceutical composition comprises 192 mM sodium chloride, 10 mM sodium phosphate, 2.7 mM potassium chloride, 2 mM potassium phosphate and 0.001% poloxamer 188 (v/v), and wherein the pH of the composition is 7.4.

In some embodiments, the AAV particle may comprise a vector genome as given by SEQ ID NO: 1801 and a VOY101 capsid. In some embodiments, a pharmaceutical composition comprising the AAV particle comprising a vector genome given by SEQ ID NO: 1801 and a VOY101 capsid, comprises sodium chloride, sodium phosphate, potassium chloride, potassium phosphate and poloxamer 188; optionally wherein the pharmaceutical composition comprises 192 mM sodium chloride, 10 mM sodium phosphate, 2.7 mM potassium chloride, 2 mM potassium phosphate and 0.001% poloxamer 188 (v/v), and wherein the pH of the composition is 7.4.

In some embodiments, the AAV particle may comprise a vector genome as given by SEQ ID NO: 1808 and a VOY101 capsid. In some embodiments, a pharmaceutical composition comprising the AAV particle comprising a vector genome given by SEQ ID NO: 1808 and a VOY101 capsid, comprises sodium chloride, sodium phosphate, potassium chloride, potassium phosphate and poloxamer 188; optionally wherein the pharmaceutical composition comprises 192 mM sodium chloride, 10 mM sodium phosphate, 2.7 mM potassium chloride, 2 mM potassium phosphate and 0.001% poloxamer 188 (v/v), and wherein the pH of the composition is 7.4.

In some embodiments, the AAV particle may comprise a vector genome as given by SEQ ID NO: 1809 and a VOY101 capsid. In some embodiments, a pharmaceutical composition comprising the AAV particle comprising a vector genome given by SEQ ID NO: 1809 and a VOY101 capsid, comprises sodium chloride, sodium phosphate, potassium chloride, potassium phosphate and poloxamer 188; optionally wherein the pharmaceutical composition comprises 192 mM sodium chloride, 10 mM sodium phosphate, 2.7 mM potassium chloride, 2 mM potassium phosphate and 0.001% poloxamer 188 (v/v), and wherein the pH of the composition is 7.4.

Pharmaceutical compositions and/or the AAV particles of this disclosure may be used to treat a neurological or neuromuscular disorder, such as, but not limited to Friedreich's Ataxia.

In some embodiments, AAV particles of the present disclosure are used to treat a disorder or condition associated with decreased frataxin expression or protein levels. In some embodiments, the disorder or condition associated with decreased frataxin expression or protein levels is a neurological or neuromuscular disorder. In some embodiments, the disorder or condition associated with decreased frataxin protein levels is FA or frataxin deficiency. In some embodiments, administration of AAV particles may result in enhanced frataxin expression in a target cell to a level 0.5-3×

(e.g., 0.5-1×, 1-1.5×, 1.5-2×, 2-2.5×, 2.5-3×) of frataxin expression in an equivalent target cell of a normal subject not suffering from a disorder associated with decreased frataxin levels. In some embodiments, administration of AAV particles may result in frataxin expression in a target cell of approximately 5.5-32.8 ng/mg protein.

The details of various aspects or embodiments of the present disclosure are set forth below. Other features, objects, and advantages of the disclosure will be apparent from the description and the claims. In the description, the singular forms also include the plural unless the context clearly dictates otherwise. Unless defined otherwise, all technical and scientific terms used herein have the same meaning as commonly understood by one of ordinary skill in the art in the field of this disclosure. In the case of conflict, the present description will control.

BRIEF DESCRIPTION OF THE DRAWINGS

The foregoing and other objects, features and advantages will be apparent from the following description of particular embodiments presented herein, as illustrated in the accompanying drawings. The drawings are not necessarily to scale, emphasis instead being placed upon illustrating the principles of various embodiments described herein.

DETAILED DESCRIPTION

I. Compositions

Adeno-Associated Viral (AAV) Vectors

Figure 1A:
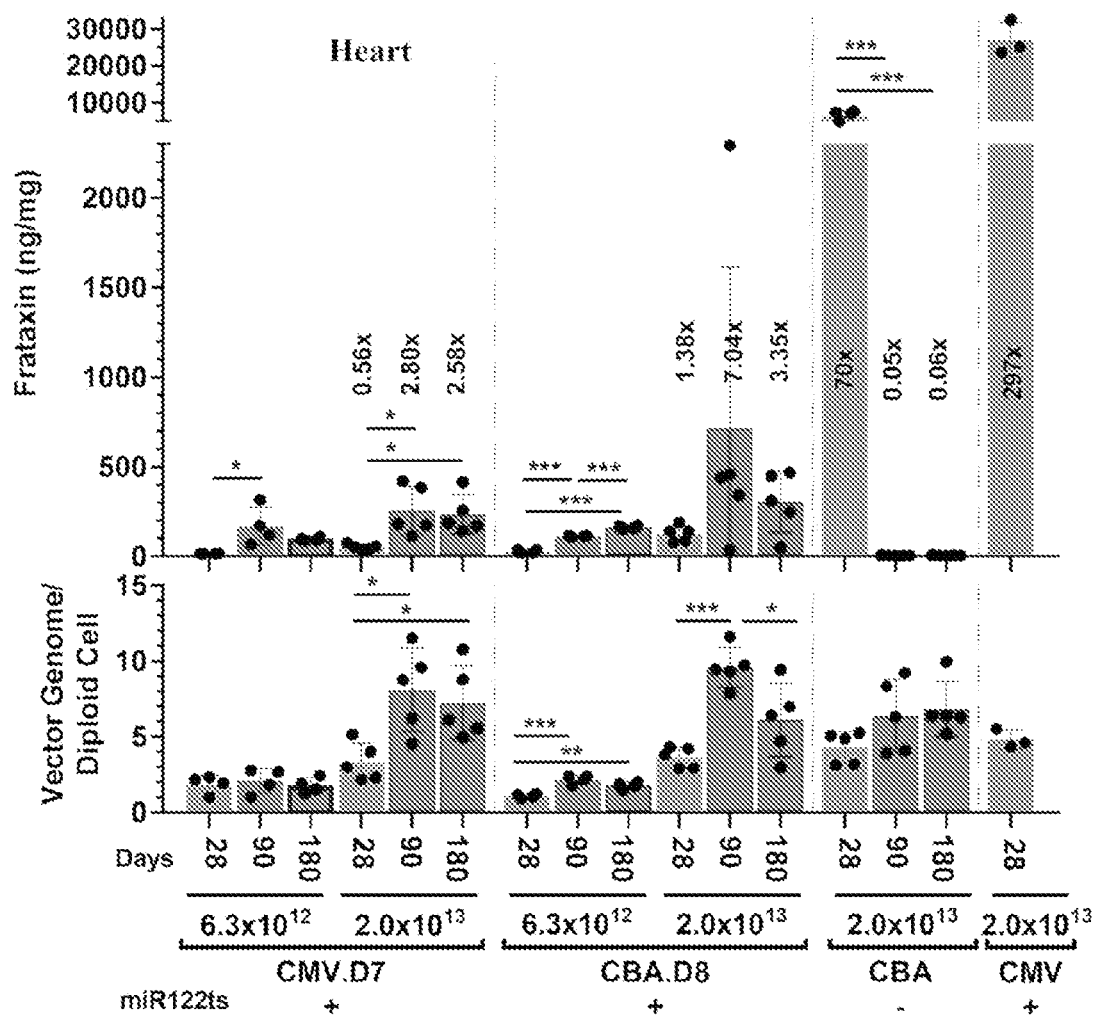
FIG. 1A presents graphs showing quantification results for frataxin expression levels (ng/mg) by ELISA and for AAV biodistribution (VG/DC) by quantitative PCR, for heart tissues.
Figure 1B:
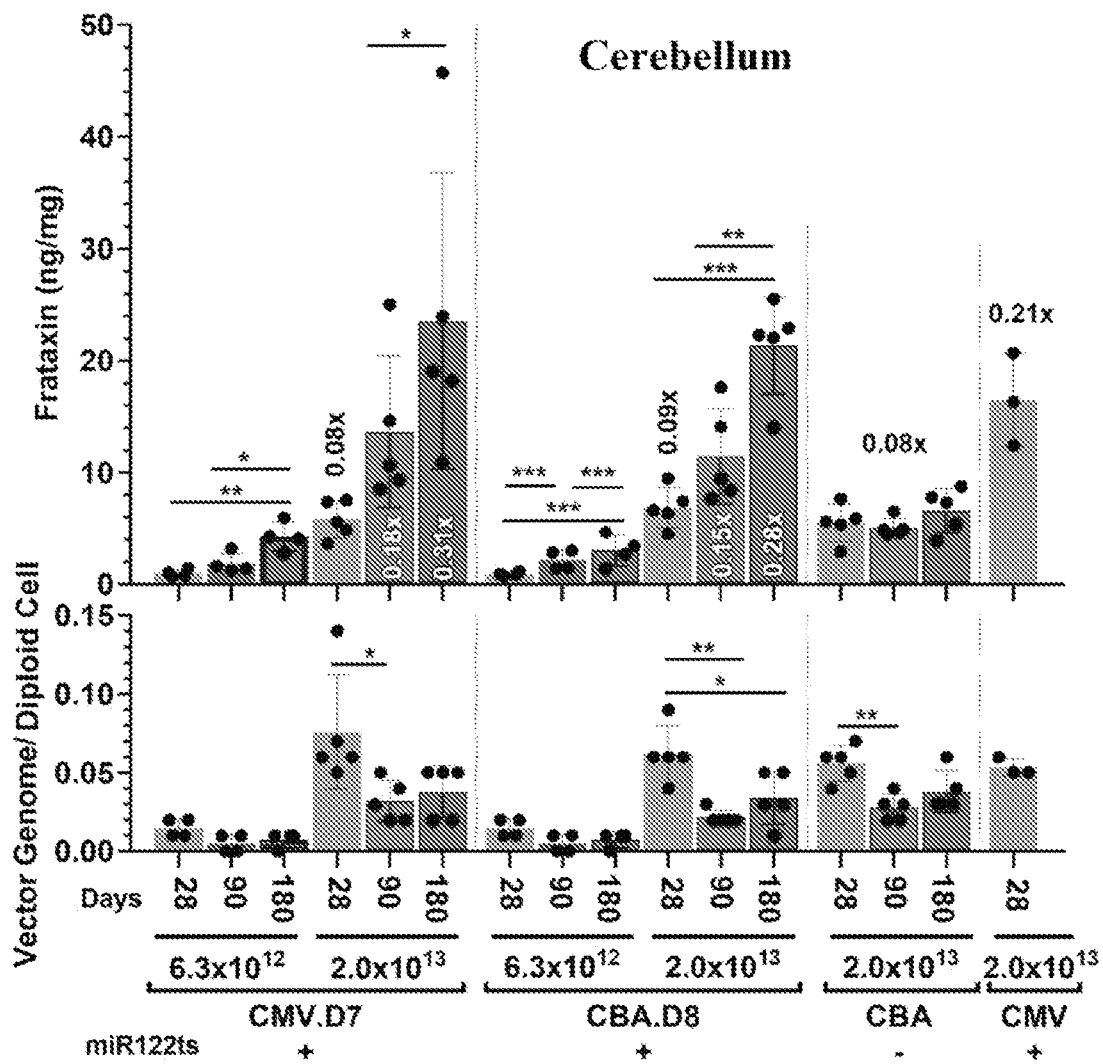
FIG. 1B presents graphs showing quantification results for frataxin expression levels (ng/mg) by ELISA and for AAV biodistribution (VG/DC) by quantitative PCR, for tissue of the cerebellum.
Figure 1C:
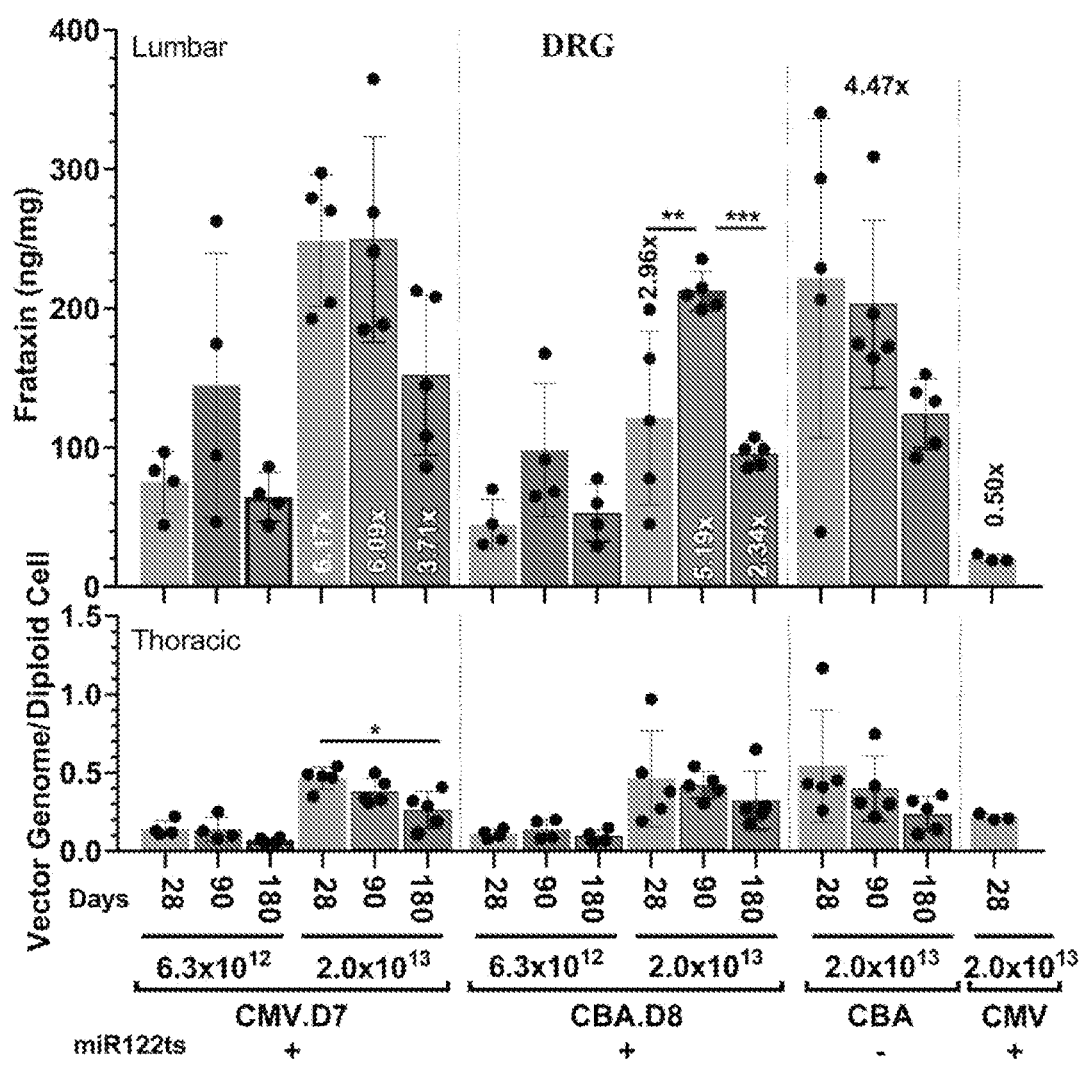
FIG. 1C presents graphs showing quantification results for frataxin expression levels (ng/mg) by ELISA and for AAV biodistribution (VG/DC) by quantitative PCR, for dorsal root ganglia (DRG).
Figure 1D:
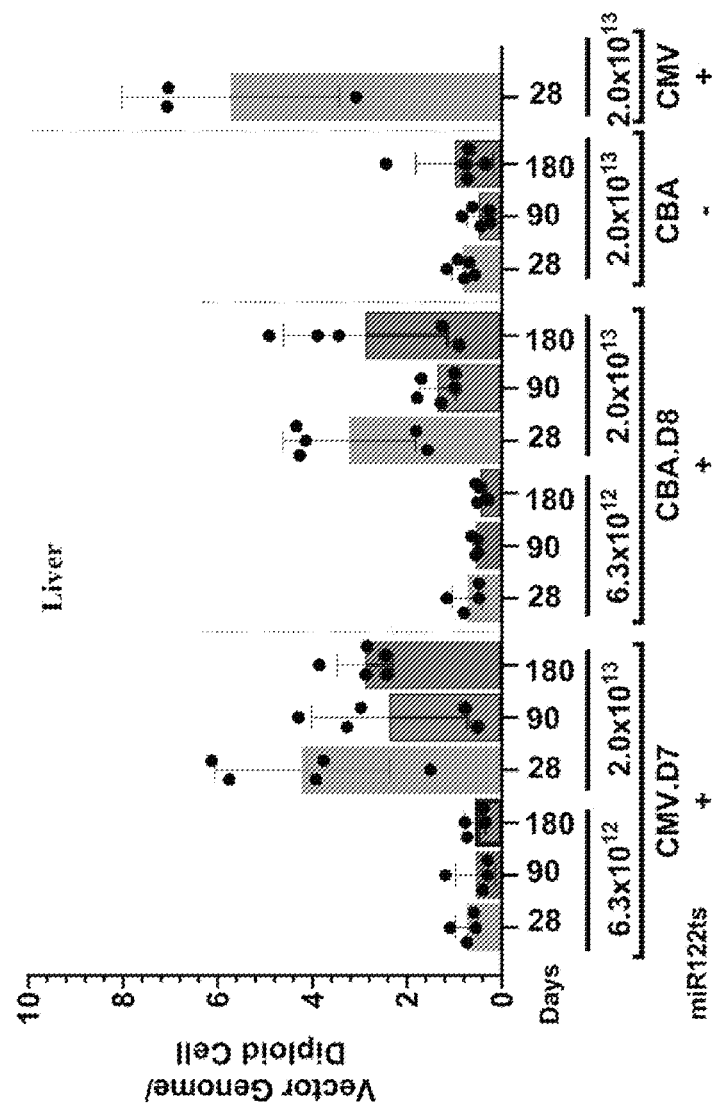
FIG. 1D presents graphs showing quantification results for frataxin expression levels (ng/mg) by ELISA and for AAV biodistribution (VG/DC) by quantitative PCR, for liver tissues.

Viruses of the Parvoviridae family are small non-enveloped icosahedral capsid viruses characterized by a single stranded DNA genome. Parvoviridae family viruses consist of two subfamilies: Parvoviridae, which infect vertebrates, and Densovirinae, which infect invertebrates. This virus family may be used as a biological tool due to a relatively simple structure that may be manipulated with standard molecular biology techniques. The genome of the virus may be modified to contain a minimum of components for the assembly of a functional recombinant virus, or viral particle, which is loaded with or engineered to express or deliver a desired nucleic acid construct or payload, e.g., a transgene, polypeptide-encoding polynucleotide, or FXN, which may be delivered to a target cell, tissue, or organism. In some embodiments, the target cell is a CNS cell. In some embodiments, the target tissue is a CNS tissue.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are hereby incorporated by reference in their entirety.

The Parvoviridae family comprises the Dependovirus genus which includes adeno-associated viruses (AAVs) capable of replication in vertebrate hosts including, but not limited to, human, primate, bovine, canine, equine, and ovine species.

An adeno-associated virus (AAV) is a dependent parvovirus (like other parvoviruses) which is a single stranded non-enveloped DNA virus having a genome of about 5000 nucleotides in length and which contains two open reading frames encoding the proteins responsible for replication (Rep) and the structural protein of the capsid (Cap). The open reading frames are flanked by two Inverted Terminal Repeat (ITR) sequences, which serve as the origin of replication of the viral genome. The wild-type AAV viral genome comprises nucleotide sequences for two open reading frames, one for the four non-structural Rep proteins (Rep78, Rep68, Rep52, Rep40, encoded by Rep genes) and one for the three capsid, or structural, proteins (VP1, VP2, VP3, encoded by capsid genes or Cap genes). The Rep proteins are important for replication and packaging, while the capsid proteins are assembled to create the protein shell of the AAV, or AAV capsid. Alternative splicing and alternate initiation codons and promoters result in the generation of four different Rep proteins from a single open reading frame and the generation of three capsid proteins from a single open reading frame. Though it varies by AAV serotype, as a non-limiting example, for AAV9/hu.14 (SEQ ID NO: 123 of U.S. Pat. No. 7,906,111, the contents of which are herein incorporated by reference in their entirety) VP1 refers to amino acids 1-736, VP2 refers to amino acids 138-736, and VP3 refers to amino acids 203-736. In other words, VP1 is the full length capsid sequence, while VP2 and VP3 are shorter components of the whole. As a result, changes in the sequence in the VP3 region, are also changes to VP1 and VP2, however, the percent difference as compared to the parent sequence will be greatest for VP3 since it is the shortest sequence of the three. Though described here in relation to the amino acid sequence, the nucleic acid sequence encoding these proteins can be similarly described. Together, the three capsid proteins assemble to create the AAV capsid protein. While not wishing to be bound by theory, the AAV capsid protein typically comprises a molar ratio of 1:1:10 of VP1:VP2:VP3. As used herein, an "AAV serotype" is defined primarily by the AAV capsid. In some instances, the ITRs are also specifically described by the AAV serotype (e.g., AAV2/9).

The AAV vector typically requires a co-helper (e.g., adenovirus) to undergo productive infection in infected cells. In the absence of such helper functions, the AAV virions essentially enter host cells but do not integrate into the cells' genome. As used herein, the term "AAV vector" or "AAV particle" comprises a capsid and a viral genome comprising a polynucleotide payload. As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide or multi-polypeptide, e.g., FXN.

AAV vectors have been investigated for delivery because of several unique features. Non-limiting examples of the features include (i) the ability to infect both dividing and non-dividing cells; (ii) a broad host range for infectivity, including human cells; (iii) wild-type AAV has not been associated with any disease and has not been shown to replicate in infected cells; (iv) the lack of cell-mediated immune response against the vector, and (v) the non-integrative nature in a host chromosome thereby reducing potential for long-term genetic alterations. Moreover, infection with AAV vectors has minimal influence on changing the pattern of cellular gene expression (Stilwell and Samulski et al., Biotechniques, 2003, 34, 148, the contents of which are herein incorporated by reference in their entirety).

Typically, AAV vectors for FXN delivery may be recombinant viral vectors which are replication defective as they lack sequences encoding functional Rep and Cap proteins within the viral genome. In some cases, the defective AAV vectors may lack most or all coding sequences and essentially only contain one or two AAV ITR sequences and a payload sequence. In certain embodiments, the viral genome encodes FXN. For example, the viral genome encodes human FXN.

In one embodiment, the AAV particles of the present disclosure may be introduced into mammalian cells.

AAV vectors may be modified to enhance the efficiency of delivery. Such modified AAV vectors of the present disclosure can be packaged efficiently and can be used to successfully infect the target cells at high frequency and with minimal toxicity.

In other embodiments, AAV particles of the present disclosure may be used to deliver FXN to the central nervous system (see, e.g., U.S. Pat. No. 6,180,613; the contents of which is herein incorporated by reference in its entirety).

AAV Serotypes

AAV particles of the present disclosure may comprise or be derived from any natural or recombinant AAV serotype. According to the present disclosure, the AAV particles may utilize or be based on a serotype or include a peptide selected from any of the following: VOY101, VOY201, AAV9, AAV9 K449R, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhER1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv1-12, AAV CLv1-3, AAV CLv-13, AAV Clv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9, and variants or hybrids/chimeras/combinations thereof.

In some embodiments, an AAV serotype used in a composition disclosed herein may be, or comprise, a sequence as described in U.S. Patent Application Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22), AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2

(US20030138772 SEQ ID NO: 59), AAV42-2 (US20030138772 SEQ ID NO: 9), or variants or hybrids/chimeras/combinations thereof.

In some embodiments, the AAV serotype may be, or comprise, a sequence as described in U.S. Patent Application Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh.10 (SEQ ID NO: 9 and 25 of US20150159173), rh.13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu.13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, or hu.48R3, or a variant or hybrid/chimera/combination thereof.

In some embodiments, the AAV serotype may be, or comprise, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), or AAV8 (SEQ ID NO: 7 of U.S. Pat. No. 7,198,951), or a variant or hybrid/chimera/combination thereof.

In some embodiments, the AAV serotype may be the AAV9 sequence as described by N Pulicherla et al. (Molecular Therapy 19(6):1070-1078 (2011), the contents of which are herein incorporated by reference in their entirety), or may be a variant thereof, such as but not limited to, AAV9.9, AAV9.11, AAV9.13, AAV9.16, AAV9.24, AAV9.45, AAV9.47, AAV9.61, AAV9.68, or AAV9.84.

In some embodiments, the AAV serotype may be, or comprise, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or a derivative or a variant or hybrid/chimera/combination thereof.

In some embodiments, the AAV serotype may be, or comprise, a sequence as described in U.S. Patent Application Publication No. US20140359799, the contents of which are herein incorporated by reference in their entirety, such as, but not limited to, AAV8 (SEQ ID NO: 1 of US20140359799), AAVDJ (SEQ ID NO: 2 and 3 of US20140359799), or variants thereof.

In some embodiments, the serotype may be AAVDJ or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations effective to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, the AAV-DJ sequence described in U.S. Pat. No. 7,588,772 may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the AAV serotype may be, or comprise, a sequence of AAV4 as described in International Publication No. WO1998011244, the contents of which are herein incorporated by reference in their entirety, such as, but not limited to AAV4 (SEQ ID NO: 1-20 of WO1998011244).

In some embodiments, the AAV serotype may be, or comprise, a mutation in the AAV2 sequence to generate AAV2G9 as described in International Publication No. WO2014144229 and herein incorporated by reference in its entirety.

In some embodiments, the AAV serotype may be, or comprise, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu.10 (SEQ ID NO: 156 and 56 of WO2005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu.17 (SEQ ID NO:4 of WO2005033321), AAV33.4/hu.15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu.19 (SEQ ID NO: 133 of WO2005033321), AAV5-22/rh.58 (SEQ ID No: 27 of WO2005033321), AAV5-3/rh.57 (SEQ ID NO: 105 of WO2005033321), AAV5-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu.10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu.19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO2005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh.12, AAVrh.17, AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, or AAVrh14. Non limiting examples of variants include SEQ ID NO: 13, 15, 17, 19, 24, 36, 40, 45, 47, 48, 51, 52, 53, 54, 60, 61, 62, 64, 65, 66, 67, 68, 69, 70, 71, 72, 73, 74, 75, 76, 77, 79, 80, 82, 89, 90, 93, 94, 95, 98, 100, 101, 109, 110, 111, 112, 113, 118, 119, 120, 124, 126, 131, 139, 142, 151, 154, 158, 161, 162, 165, 166, 167, 168, 169, 170, 171, 172, 173, 174, 175, 176, 177, 178, 179, 180, 181, 182, 183, 202, 204, 205, 206, 207, 208, 209, 210, 211, 212, 215, 219, 224, 225, 226, 227, 228, 229, 230, 231, 232, 233, 234, 235 or 236 of WO2005033321, the contents of which are herein incorporated by reference in their entirety.

In some embodiments, the AAV serotype may be, or comprise, a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV serotype may be, or comprise, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO:50 of U.S. Pat. No. 9,233,131), AAVhEr1.7 (SEQ ID NO:51 of U.S. Pat. No. 9,233,131), AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of U.S. Pat. No. 9,233,131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV serotype may be, or comprise, a sequence as described in U.S. Patent Application Publication No. US20150376607, the contents of which are herein incorporated by reference in their entirety, such as, but not limited to, AAV-PAEC (SEQ ID NO:1 of US20150376607), AAV-LK01 (SEQ ID NO:2 of US20150376607), AAV-LK02 (SEQ ID NO:3 of US20150376607), AAV-LK03 (SEQ ID NO:4 of US20150376607), AAV-LK04 (SEQ ID NO:5 of US20150376607), AAV-LK05 (SEQ ID NO:6 of US20150376607), AAV-LK06 (SEQ ID NO:7 of US20150376607), AAV-LK07 (SEQ ID NO:8 of US20150376607), AAV-LK08 (SEQ ID NO:9 of US20150376607), AAV-LK09 (SEQ ID NO:10 of US20150376607), AAV-LK10 (SEQ ID NO:11 of US20150376607), AAV-LK11 (SEQ ID NO:12 of US20150376607), AAV-LK12 (SEQ ID NO:13 of US20150376607), AAV-LK13 (SEQ ID NO:14 of US20150376607), AAV-LK14 (SEQ ID NO:15 of US20150376607), AAV-LK15 (SEQ ID NO:16 of US20150376607), AAV-LK16 (SEQ ID NO:17 of US20150376607), AAV-LK17 (SEQ ID NO:18 of US20150376607), AAV-LK18 (SEQ ID NO:19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO:23 of US20150376607), AAV-PAEC7 (SEQ ID NO:24 of US20150376607), AAV-PAEC8 (SEQ ID NO:25 of US20150376607), AAV-PAEC11 (SEQ ID NO:26 of US20150376607), AAV-PAEC12 (SEQ ID NO:27, of US20150376607), or variants thereof.

In some embodiments, the AAV serotype may be, or comprise, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV serotype may be, or have, a sequence as described in U.S. Patent Application Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV serotype may be, or have, a sequence as described in U.S. Patent Application Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV serotype may be, or comprise, a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV serotype may be or may comprise a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV serotype may be, or comprise, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, AAV capsid serotype selection or use may be from a variety of species. In one embodiment, the AAV may be an avian AAV (AAAV). The AAAV serotype may be, or have, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, or 14 of U.S. Pat. No. 9,238,800), or variants thereof.

In one embodiment, the AAV may be a bovine AAV (BAAV). The BAAV serotype may be, or have, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In some embodiments, the AAV may be a caprine AAV. The caprine AAV serotype may be, or have, a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In some embodiments, the AAV may be engineered as a hybrid AAV from two or more parental serotypes. In one embodiment, the AAV may be AAV2G9 which comprises sequences from AAV2 and AAV9. The AAV2G9 AAV serotype may be, or have, a sequence as described in U.S. Patent Application Publication No. US20160017005, the contents of which are herein incorporated by reference in their entirety.

In one embodiment, the AAV may be a serotype generated by the AAV9 capsid library with mutations in amino acids 390-627 (VP1 numbering) as described by Pulicherla et al. (Molecular Therapy 19(6):1070-1078 (2011), the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399I), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L), or AAV9.95 (T1605A; F535L).

In some embodiments, the AAV serotype may be, or comprise, a sequence as described in International Publication No. WO2016049230, the contents of which are herein incorporated by reference in their entirety, such as, but not limited to AAVF1/HSC1 (SEQ ID NO: 2 and 20 of WO2016049230), AAVF2/HSC2 (SEQ ID NO: 3 and 21 of WO2016049230), AAVF3/HSC3 (SEQ ID NO: 5 and 22 of WO2016049230), AAVF4/HSC4 (SEQ ID NO: 6 and 23 of WO2016049230), AAVF5/HSC5 (SEQ ID NO: 11 and 25 of WO2016049230), AAVF6/HSC6 (SEQ ID NO: 7 and 24 of WO2016049230), AAVF7/HSC7 (SEQ ID NO: 8 and 27 of WO2016049230), AAVF8/HSC8 (SEQ ID NO: 9 and 28 of WO2016049230), AAVF9/HSC9 (SEQ ID NO: 10 and 29 of WO2016049230), AAVF11/HSC11 (SEQ ID NO: 4 and 26 of WO2016049230), AAVF12/HSC12 (SEQ ID NO: 12 and 30 of WO2016049230), AAVF13/HSC13 (SEQ ID NO: 14 and 31 of WO2016049230), AAVF14/HSC14 (SEQ ID NO: 15 and 32 of WO2016049230), AAVF15/HSC15 (SEQ ID NO: 16 and 33 of WO2016049230), AAVF16/HSC16 (SEQ ID NO: 17 and 34 of WO2016049230), AAVF17/HSC17 (SEQ ID NO: 13 and 35 of WO2016049230), or variants or derivatives thereof.

In some embodiments, the AAV serotype may be, or comprise, a sequence as described in U.S. Pat. No. 8,734,809, the contents of which are herein incorporated by reference in their entirety, such as, but not limited to, AAV CBr-E1 (SEQ ID NO: 13 and 87 of U.S. Pat. No. 8,734,809), AAV CBr-E2 (SEQ ID NO: 14 and 88 of U.S. Pat. No. 8,734,809), AAV CBr-E3 (SEQ ID NO: 15 and 89 of U.S. Pat. No. 8,734,809), AAV CBr-E4 (SEQ ID NO: 16 and 90 of U.S. Pat. No. 8,734,809), AAV CBr-E5 (SEQ ID NO: 17 and 91 of U.S. Pat. No. 8,734,809), AAV CBr-e5 (SEQ ID NO: 18 and 92 of U.S. Pat. No. 8,734,809), AAV CBr-E6 (SEQ ID NO: 19 and 93 of U.S. Pat. No. 8,734,809), AAV CBr-E7 (SEQ ID NO: 20 and 94 of U.S. Pat. No. 8,734,809), AAV CBr-E8 (SEQ ID NO: 21 and 95 of U.S. Pat. No. 8,734,809), AAV CLv-D1 (SEQ ID NO: 22 and 96 of U.S. Pat. No. 8,734,809), AAV CLv-D2 (SEQ ID NO: 23 and 97 of U.S. Pat. No. 8,734,809), AAV CLv-D3 (SEQ ID NO: 24 and 98 of U.S. Pat. No. 8,734,809), AAV CLv-D4 (SEQ ID NO: 25 and 99 of U.S. Pat. No. 8,734,809), AAV CLv-D5 (SEQ ID NO: 26 and 100 of U.S. Pat. No. 8,734,809), AAV CLv-D6 (SEQ ID NO: 27 and 101 of U.S. Pat. No. 8,734,809), AAV CLv-D7 (SEQ ID NO: 28 and 102 of U.S. Pat. No. 8,734,809), AAV CLv-D8 (SEQ ID NO: 29 and 103 of U.S. Pat. No. 8,734,809), AAV CUT-E1 (SEQ ID NO: 13 and 87 of U.S. Pat. No. 8,734,809), AAV CLv-R1 (SEQ ID NO: 30 and 104 of U.S. Pat. No. 8,734,809), AAV CLv-R2 (SEQ ID NO: 31 and 105 of U.S. Pat. No. 8,734,809), AAV CLv-R3 (SEQ ID NO: 32 and 106 of U.S. Pat. No. 8,734,809), AAV CLv-R4 (SEQ ID NO: 33 and 107 of U.S. Pat. No. 8,734,809), AAV CLv-R5 (SEQ ID NO: 34 and 108 of U.S. Pat. No. 8,734,809), AAV CLv-R6 (SEQ ID NO: 35 and 109 of U.S. Pat. No. 8,734,809), AAV CLv-R7 (SEQ ID NO: 36 and 110 of U.S. Pat. No. 8,734,809), AAV CLv-R8 (SEQ ID NO: 37 and 111 of U.S. Pat. No. 8,734,809), AAV CLv-R9 (SEQ ID NO: 38 and 112 of U.S. Pat. No. 8,734,809), AAV CLg-F1 (SEQ ID NO: 39 and 113 of U.S. Pat. No. 8,734,809), AAV CLg-F2 (SEQ ID NO: 40 and 114 of U.S. Pat. No. 8,734,809), AAV CLg-F3 (SEQ ID NO: 41 and 115 of U.S. Pat. No. 8,734,809), AAV CLg-F4 (SEQ ID NO: 42 and 116 of U.S. Pat. No. 8,734,809), AAV CLg-F5 (SEQ ID NO: 43 and 117 of U.S. Pat. No. 8,734,809), AAV CLg-F6 (SEQ ID NO: 43 and 117 of U.S. Pat. No. 8,734, 809), AAV CLg-F7 (SEQ ID NO: 44 and 118 of U.S. Pat. No. 8,734,809), AAV CLg-F8 (SEQ ID NO: 43 and 117 of U.S. Pat. No. 8,734,809), AAV CSp-1 (SEQ ID NO: 45 and 119 of U.S. Pat. No. 8,734,809), AAV CSp-10 (SEQ ID NO: 46 and 120 of U.S. Pat. No. 8,734,809), AAV CSp-11 (SEQ ID NO: 47 and 121 of U.S. Pat. No. 8,734,809), AAV CSp-2 (SEQ ID NO: 48 and 122 of U.S. Pat. No. 8,734,809), AAV CSp-3 (SEQ ID NO: 49 and 123 of U.S. Pat. No. 8,734,809), AAV CSp-4 (SEQ ID NO: 50 and 124 of U.S. Pat. No. 8,734,809), AAV CSp-6 (SEQ ID NO: 51 and 125 of U.S. Pat. No. 8,734,809), AAV CSp-7 (SEQ ID NO: 52 and 126 of U.S. Pat. No. 8,734,809), AAV CSp-8 (SEQ ID NO: 53 and 127 of U.S. Pat. No. 8,734,809), AAV CSp-9 (SEQ ID NO: 54 and 128 of U.S. Pat. No. 8,734,809), AAV CHt-2 (SEQ ID NO: 55 and 129 of U.S. Pat. No. 8,734,809), AAV CHt-3 (SEQ ID NO: 56 and 130 of U.S. Pat. No. 8,734,809), AAV CKd-1 (SEQ ID NO: 57 and 131 of U.S. Pat. No. 8,734,809), AAV CKd-10 (SEQ ID NO: 58 and 132 of U.S. Pat. No. 8,734,809), AAV CKd-2 (SEQ ID NO: 59 and 133 of U.S. Pat. No. 8,734,809), AAV CKd-3 (SEQ ID NO: 60 and 134 of U.S. Pat. No. 8,734,809), AAV CKd-4 (SEQ ID NO: 61 and 135 of U.S. Pat. No. 8,734,809), AAV CKd-6 (SEQ ID NO: 62 and 136 of U.S. Pat. No. 8,734,809), AAV CKd-7 (SEQ ID NO: 63 and 137 of U.S. Pat. No. 8,734,809), AAV CKd-8 (SEQ ID NO: 64 and 138 of U.S. Pat. No. 8,734,809), AAV CLv-1 (SEQ ID NO: 35 and 139 of U.S. Pat. No. 8,734,809), AAV CLv-12 (SEQ ID NO: 66 and 140 of U.S. Pat. No. 8,734,809), AAV CLv-13 (SEQ ID NO: 67 and 141 of U.S. Pat. No. 8,734,809), AAV CLv-2 (SEQ ID NO: 68 and 142 of U.S. Pat. No. 8,734,809), AAV CLv-3 (SEQ ID NO: 69 and 143 of U.S. Pat. No. 8,734,809), AAV CLv-4 (SEQ ID NO: 70 and 144 of U.S. Pat. No. 8,734,809), AAV CLv-6 (SEQ ID NO: 71 and 145 of U.S. Pat. No. 8,734,809), AAV CLv-8 (SEQ ID NO: 72 and 146 of U.S. Pat. No. 8,734,809), AAV CKd-B1 (SEQ ID NO: 73 and 147 of U.S. Pat. No. 8,734,809), AAV CKd-B2 (SEQ ID NO: 74 and 148 of U.S. Pat. No. 8,734,809), AAV CKd-B3 (SEQ ID NO: 75 and 149 of U.S. Pat. No. 8,734,809), AAV CKd-B4 (SEQ ID NO: 76 and 150 of U.S. Pat. No. 8,734,809), AAV CKd-B5 (SEQ ID NO: 77 and 151 of U.S. Pat. No. 8,734,809), AAV CKd-B6 (SEQ ID NO: 78 and 152 of U.S. Pat. No. 8,734,809), AAV CKd-B7 (SEQ ID NO: 79 and 153 of U.S. Pat. No. 8,734,809), AAV CKd-B8 (SEQ ID NO: 80 and 154 of U.S. Pat. No. 8,734,809), AAV CKd-H1 (SEQ ID NO: 81 and 155 of U.S. Pat. No. 8,734,809), AAV CKd-H2 (SEQ ID NO: 82 and 156 of U.S. Pat. No. 8,734,809), AAV CKd-H3 (SEQ ID NO: 83 and 157 of U.S. Pat. No. 8,734,809), AAV CKd-H4 (SEQ ID NO: 84 and 158 of U.S. Pat. No. 8,734,809), AAV CKd-H5 (SEQ ID NO: 85 and 159 of U.S. Pat. No. 8,734,809), AAV CKd-H6 (SEQ ID NO: 77 and 151 of U.S. Pat. No. 8,734,809), AAV CHt-1 (SEQ ID NO: 86 and 160 of U.S. Pat. No. 8,734,809), AAV CLv1-1 (SEQ ID NO: 171 of U.S. Pat. No. 8,734,809), AAV CLv1-2 (SEQ ID NO: 172 of U.S. Pat. No. 8,734,809), AAV CLv1-3 (SEQ ID NO: 173 of U.S. Pat. No. 8,734,809), AAV CLv1-4 (SEQ ID NO: 174 of U.S. Pat. No. 8,734,809), AAV Clv1-7 (SEQ ID NO: 175 of U.S. Pat. No. 8,734,809), AAV Clv1-8 (SEQ ID NO: 176 of U.S. Pat. No. 8,734,809), AAV Clv1-9 (SEQ ID NO: 177 of U.S. Pat. No. 8,734,809), AAV Clv1-10 (SEQ ID NO: 178 of U.S. Pat. No. 8,734,809), AAV.VR-355 (SEQ ID NO: 181 of U.S. Pat. No. 8,734,809), AAV.hu.48R3 (SEQ ID NO: 183 of U.S. Pat. No. 8,734, 809), or variants or derivatives thereof.

In some embodiments, the AAV serotype may be, or comprise, a sequence as described in International Publication No. WO2016065001, the contents of which are herein incorporated by reference in their entirety, such as, but not limited to AAV CHt-P2 (SEQ ID NO: 1 and 51 of WO2016065001), AAV CHt-P5 (SEQ ID NO: 2 and 52 of WO2016065001), AAV CHt-P9 (SEQ ID NO: 3 and 53 of WO2016065001), AAV CBr-7.1 (SEQ ID NO: 4 and 54 of WO2016065001), AAV CBr-7.2 (SEQ ID NO: 5 and 55 of WO2016065001), AAV CBr-7.3 (SEQ ID NO: 6 and 56 of WO2016065001), AAV CBr-7.4 (SEQ ID NO: 7 and 57 of WO2016065001), AAV CBr-7.5 (SEQ ID NO: 8 and 58 of WO2016065001), AAV CBr-7.7 (SEQ ID NO: 9 and 59 of WO2016065001), AAV CBr-7.8 (SEQ ID NO: 10 and 60 of WO2016065001), AAV CBr-7.10 (SEQ ID NO: 11 and 61 of WO2016065001), AAV CKd-N3 (SEQ ID NO: 12 and 62 of WO2016065001), AAV CKd-N4 (SEQ ID NO: 13 and 63 of WO2016065001), AAV CKd-N9 (SEQ ID NO: 14 and 64 of WO2016065001), AAV CLv-L4 (SEQ ID NO: 15 and 65 of WO2016065001), AAV CLv-L5 (SEQ ID NO: 16 and 66 of WO2016065001), AAV CLv-L6 (SEQ ID NO: 17 and 67 of WO2016065001), AAV CLv-K1 (SEQ ID NO: 18 and 68 of WO2016065001), AAV CLv-K3 (SEQ ID NO: 19 and 69 of WO2016065001), AAV CLv-K6 (SEQ ID NO: 20 and 70 of WO2016065001), AAV CLv-M1 (SEQ ID NO: 21 and 71 of WO2016065001), AAV CLv-M11 (SEQ ID NO: 22 and 72 of WO2016065001), AAV CLv-M2 (SEQ ID NO: 23 and 73 of WO2016065001), AAV CLv-M5 (SEQ ID NO: 24 and 74 of WO2016065001), AAV CLv-M6 (SEQ ID NO: 25 and 75 of WO2016065001), AAV CLv-M7 (SEQ ID NO: 26 and 76 of WO2016065001), AAV CLv-M8 (SEQ ID NO: 27 and 77 of WO2016065001), AAV CLv-M9 (SEQ ID NO: 28 and 78 of WO2016065001), AAV CHt-P1 (SEQ ID NO: 29 and 79 of WO2016065001), AAV CHt-P6 (SEQ ID NO: 30 and 80 of WO2016065001), AAV CHt-P8 (SEQ ID NO: 31 and 81 of WO2016065001), AAV CHt-6.1 (SEQ ID NO: 32 and 82 of WO2016065001), AAV CHt-6.10 (SEQ ID NO: 33 and 83 of WO2016065001), AAV CHt-6.5 (SEQ ID NO: 34 and 84 of WO2016065001), AAV CHt-6.6 (SEQ ID NO: 35 and 85 of WO2016065001), AAV CHt-6.7 (SEQ ID NO: 36 and 86 of WO2016065001), AAV CHt-6.8 (SEQ ID NO: 37 and 87 of WO2016065001), AAV CSp-8.10 (SEQ ID NO: 38 and 88 of WO2016065001), AAV CSp-8.2 (SEQ ID NO: 39 and 89 of WO2016065001), AAV CSp-8.4 (SEQ ID NO: 40 and 90 of WO2016065001), AAV CSp-8.5 (SEQ ID NO: 41 and 91 of WO2016065001), AAV CSp-8.6 (SEQ ID NO: 42 and 92 of WO2016065001), AAV CSp-8.7 (SEQ ID NO: 43 and 93 of WO2016065001), AAV CSp-8.8 (SEQ ID NO: 44 and 94 of WO2016065001), AAV CSp-8.9 (SEQ ID NO: 45 and 95 of WO2016065001), AAV CBr-B7.3 (SEQ ID NO: 46 and 96 of WO2016065001), AAV CBr-B7.4 (SEQ ID NO: 47 and 97 of WO2016065001), AAV3B (SEQ ID NO: 48 and 98 of WO2016065001), AAV4 (SEQ ID NO: 49 and 99 of WO2016065001), AAV5 (SEQ ID NO: 50 and 100 of WO2016065001), or variants or derivatives thereof.

In some embodiments, the AAV particle may be or comprise a serotype selected from any of those found in Table 1.

In some embodiments, the AAV particle may comprise a sequence, fragment, or variant of any sequence in Table 1.

In some embodiments, the AAV particle may be encoded by a sequence, fragment, or variant of any sequence in Table 1.

In the DNA and RNA sequences referenced and/or described herein, the single letter symbol has the following description: A for adenine; C for cytosine; G for guanine; T for thymine; U for Uracil; W for weak bases such as adenine or thymine; S for strong nucleotides such as cytosine and guanine; M for amino nucleotides such as adenine and cytosine; K for keto nucleotides such as guanine and thymine; R for purines adenine and guanine; Y for pyrimidine cytosine and thymine; B for any base that is not A (e.g., cytosine, guanine, and thymine); D for any base that is not C (e.g., adenine, guanine, and thymine); H for any base that is not G (e.g., adenine, cytosine, and thymine); V for any base that is not T (e.g., adenine, cytosine, and guanine); N for any nucleotide (which is not a gap); and Z is for zero.

In any of the amino acid sequences referenced and/or described herein, the single letter symbol has the following description: G (Gly) for Glycine; A (Ala) for Alanine; L (Leu) for Leucine; M (Met) for Methionine; F (Phe) for Phenylalanine; W (Trp) for Tryptophan; K (Lys) for Lysine; Q (Gln) for Glutamine; E (Glu) for Glutamic Acid; S (Ser) for Serine; P (Pro) for Proline; V (Val) for Valine; I (Ile) for Isoleucine; C (Cys) for Cysteine; Y (Tyr) for Tyrosine; H (His) for Histidine; R (Arg) for Arginine; N (Asn) for Asparagine; D (Asp) for Aspartic Acid; T (Thr) for Threonine; B (Asx) for Aspartic acid or Asparagine; J (Xle) for Leucine or Isoleucine; O (Pyl) for Pyrrolysine; U (Sec) for Selenocysteine; X (Xaa) for any amino acid; and Z (Glx) for Glutamine or Glutamic acid.

TABLE 1

Representative AAV Serotypes

| Serotype | SEQ ID NO | Reference Information |
| --- | --- | --- |
| VOY101 | 1 or 1722 | — |
| VOY201 | 1723 or 1724 | — |
| PHP.N/PHP.B-DGT | 2 | WO2017100671 SEQ ID NO: 46 |
| AAVPHP.B or G2B-26 | 3 | WO2015038958 SEQ ID NO: 8 and 13 |
| AAVPHP.B | 4 | WO2015038958 SEQ ID NO: 9 |
| AAVG2B-13 | 5 | WO2015038958 SEQ ID NO: 12 |
| AAVTH1.1-32 | 6 | WO2015038958 SEQ ID NO: 14 |
| AAVTH1.1-35 | 7 | WO2015038958 SEQ ID NO: 15 |
| PHP.S/G2A12 | 8 | WO2017100671 SEQ ID NO: 47 |
| AAV9/hu.14 K449R | 9 | WO2017100671 SEQ ID NO: 45 |
| AAV1 | 10 | US20150159173 SEQ ID NO: 11, US20150315612 SEQ ID NO: 202 |
| AAV1 | 11 | US20160017295 SEQ ID NO: 1, US20030138772 SEQ ID NO: 64, US20150159173 SEQ ID NO: 27, US20150315612 SEQ ID NO: 219, U.S. Pat. No. 7,198,951 SEQ ID NO: 5 |
| AAV1 | 12 | US20030138772 SEQ ID NO: 6 |
| AAV1.3 | 13 | US20030138772 SEQ ID NO: 14 |
| AAV10 | 14 | US20030138772 SEQ ID NO: 117 |
| AAV10 | 15 | WO2015121501 SEQ ID NO: 9 |
| AAV10 | 16 | WO2015121501 SEQ ID NO: 8 |
| AAV11 | 17 | US20030138772 SEQ ID NO: 118 |
| AAV12 | 18 | US20030138772 SEQ ID NO: 119 |
| AAV2 | 19 | US20150159173 SEQ ID NO: 7, US20150315612 SEQ ID NO: 211 |
| AAV2 | 20 | US20030138772 SEQ ID NO: 70, US20150159173 SEQ ID NO: 23, US20150315612 SEQ ID NO: 221, US20160017295 SEQ ID NO: 2, U.S. Pat. No. 6,156,303 SEQ ID NO: 4, U.S. Pat. No. 7,198,951 SEQ ID NO: 4, WO2015121501 SEQ ID NO: 1 |
| AAV2 | 21 | U.S. Pat. No. 6,156,303 SEQ ID NO: 8 |
| AAV2 | 22 | US20030138772 SEQ ID NO: 7 |
| AAV2 | 23 | U.S. Pat. No. 6,156,303 SEQ ID NO: 3 |
| AAV2.5T | 24 | U.S. Pat. No. 9,233,131 SEQ ID NO: 42 |
| AAV223.10 | 25 | US20030138772 SEQ ID NO: 75 |
| AAV223.2 | 26 | US20030138772 SEQ ID NO: 49 |
| AAV223.2 | 27 | US20030138772 SEQ ID NO: 76 |
| AAV223.4 | 28 | US20030138772 SEQ ID NO: 50 |
| AAV223.4 | 29 | US20030138772 SEQ ID NO: 73 |
| AAV223.5 | 30 | US20030138772 SEQ ID NO: 51 |
| AAV223.5 | 31 | US20030138772 SEQ ID NO: 74 |
| AAV223.6 | 32 | US20030138772 SEQ ID NO: 52 |
| AAV223.6 | 33 | US20030138772 SEQ ID NO: 78 |
| AAV223.7 | 34 | US20030138772 SEQ ID NO: 53 |
| AAV223.7 | 35 | US20030138772 SEQ ID NO: 77 |
| AAV29.3 | 36 | US20030138772 SEQ ID NO: 82 |
| AAV29.4 | 37 | US20030138772 SEQ ID NO: 12 |
| AAV29.5 | 38 | US20030138772 SEQ ID NO: 83 |
| AAV29.5 (AAVbb.2) | 39 | US20030138772 SEQ ID NO: 13 |
| AAV3 | 40 | US20150159173 SEQ ID NO: 12 |
| AAV3 | 41 | US20030138772 SEQ ID NO: 71, US20150159173 SEQ ID NO: 28, US20160017295 SEQ ID NO: 3, U.S. Pat. No. 7,198,951 SEQ ID NO: 6 |
| AAV3 | 42 | US20030138772 SEQ ID NO: 8 |
| AAV3.3b | 43 | US20030138772 SEQ ID NO: 72 |
| AAV3-3 | 44 | US20150315612 SEQ ID NO: 200 |
| AAV3-3 | 45 | US20150315612 SEQ ID NO: 217 |
| AAV3a | 46 | U.S. Pat. No. 6,156,303 SEQ ID NO: 5 |
| AAV3a | 47 | U.S. Pat. No. 6,156,303 SEQ ID NO: 9 |

TABLE 1-continued

Representative AAV Serotypes

| Serotype | SEQ ID NO | Reference Information |
|---|---|---|
| AAV3b | 48 | U.S. Pat. No. 6,156,303 SEQ ID NO: 6 |
| AAV3b | 49 | U.S. Pat. No. 6,156,303 SEQ ID NO: 10 |
| AAV3b | 50 | U.S. Pat. No. 6,156,303 SEQ ID NO: 1 |
| AAV4 | 51 | US20140348794 SEQ ID NO: 17 |
| AAV4 | 52 | US20140348794 SEQ ID NO: 5 |
| AAV4 | 53 | US20140348794 SEQ ID NO: 3 |
| AAV4 | 54 | US20140348794 SEQ ID NO: 14 |
| AAV4 | 55 | US20140348794 SEQ ID NO: 15 |
| AAV4 | 56 | US20140348794 SEQ ID NO: 19 |
| AAV4 | 57 | US20140348794 SEQ ID NO: 12 |
| AAV4 | 58 | US20140348794 SEQ ID NO: 13 |
| AAV4 | 59 | US20140348794 SEQ ID NO: 7 |
| AAV4 | 60 | US20140348794 SEQ ID NO: 8 |
| AAV4 | 61 | US20140348794 SEQ ID NO: 9 |
| AAV4 | 62 | US20140348794 SEQ ID NO: 2 |
| AAV4 | 63 | US20140348794 SEQ ID NO: 10 |
| AAV4 | 64 | US20140348794 SEQ ID NO: 11 |
| AAV4 | 65 | US20140348794 SEQ ID NO: 18 |
| AAV4 | 66 | US20030138772 SEQ ID NO: 63, US20160017295 SEQ ID NO: 4, US20140348794 SEQ ID NO: 4 |
| AAV4 | 67 | US20140348794 SEQ ID NO: 16 |
| AAV4 | 68 | US20140348794 SEQ ID NO: 20 |
| AAV4 | 69 | US20140348794 SEQ ID NO: 6 |
| AAV4 | 70 | US20140348794 SEQ ID NO: 1 |
| AAV42.2 | 71 | US20030138772 SEQ ID NO: 9 |
| AAV42.2 | 72 | US20030138772 SEQ ID NO: 102 |
| AAV42.3b | 73 | US20030138772 SEQ ID NO: 36 |
| AAV42.3B | 74 | US20030138772 SEQ ID NO: 107 |
| AAV42.4 | 75 | US20030138772 SEQ ID NO: 33 |
| AAV42.4 | 76 | US20030138772 SEQ ID NO: 88 |
| AAV42.8 | 77 | US20030138772 SEQ ID NO: 27 |
| AAV42.8 | 78 | US20030138772 SEQ ID NO: 85 |
| AAV43.1 | 79 | US20030138772 SEQ ID NO: 39 |
| AAV43.1 | 80 | US20030138772 SEQ ID NO: 92 |
| AAV43.12 | 81 | US20030138772 SEQ ID NO: 41 |
| AAV43.12 | 82 | US20030138772 SEQ ID NO: 93 |
| AAV43.20 | 83 | US20030138772 SEQ ID NO: 42 |
| AAV43.20 | 84 | US20030138772 SEQ ID NO: 99 |
| AAV43.21 | 85 | US20030138772 SEQ ID NO: 43 |
| AAV43.21 | 86 | US20030138772 SEQ ID NO: 96 |
| AAV43.23 | 87 | US20030138772 SEQ ID NO: 44 |
| AAV43.23 | 88 | US20030138772 SEQ ID NO: 98 |
| AAV43.25 | 89 | US20030138772 SEQ ID NO: 45 |
| AAV43.25 | 90 | US20030138772 SEQ ID NO: 97 |
| AAV43.5 | 91 | US20030138772 SEQ ID NO: 40 |
| AAV43.5 | 92 | US20030138772 SEQ ID NO: 94 |
| AAV4-4 | 93 | US20150315612 SEQ ID NO: 201 |
| AAV4-4 | 94 | US20150315612 SEQ ID NO: 218 |
| AAV44.1 | 95 | US20030138772 SEQ ID NO: 46 |
| AAV44.1 | 96 | US20030138772 SEQ ID NO: 79 |
| AAV44.5 | 97 | US20030138772 SEQ ID NO: 47 |
| AAV44.5 | 98 | US20030138772 SEQ ID NO: 80 |
| AAV4407 | 99 | US20150315612 SEQ ID NO: 90 |
| AAV5 | 100 | U.S. Pat. No. 7,427,396 SEQ ID NO: 1 |
| AAV5 | 101 | US20030138772 SEQ ID NO: 114 |
| AAV5 | 102 | US20160017295 SEQ ID NO: 5, U.S. Pat. No. 7,427,396 SEQ ID NO: 2, US20150315612 SEQ ID NO: 216 |
| AAV5 | 103 | US20150315612 SEQ ID NO: 199 |
| AAV6 | 104 | US20150159173 SEQ ID NO: 13 |
| AAV6 | 105 | US20030138772 SEQ ID NO: 65, US20150159173 SEQ ID NO: 29, US20160017295 SEQ ID NO: 6, U.S. Pat. No. 6,156,303 SEQ ID NO: 7 |
| AAV6 | 106 | U.S. Pat. No. 6,156,303 SEQ ID NO: 11 |
| AAV6 | 107 | U.S. Pat. No. 6,156,303 SEQ ID NO: 2 |
| AAV6 | 108 | US20150315612 SEQ ID NO: 203 |
| AAV6 | 109 | US20150315612 SEQ ID NO: 220 |
| AAV6.1 | 110 | US20150159173 |
| AAV6.12 | 111 | US20150159173 |
| AAV6.2 | 112 | US20150159173 |
| AAV7 | 113 | US20150159173 SEQ ID NO: 14 |
| AAV7 | 114 | US20150315612 SEQ ID NO: 183 |
| AAV7 | 115 | US20030138772 SEQ ID NO: 2, US20150159173 SEQ ID NO: 30, |

TABLE 1-continued

Representative AAV Serotypes

| Serotype | SEQ ID NO | Reference Information |
|---|---|---|
| | | US20150315612 SEQ ID NO: 181, |
| | | US20160017295 SEQ ID NO: 7 |
| AAV7 | 116 | US20030138772 SEQ ID NO: 3 |
| AAV7 | 117 | US20030138772 SEQ ID NO: 1, |
| | | US20150315612 SEQ ID NO: 180 |
| AAV7 | 118 | US20150315612 SEQ ID NO: 213 |
| AAV7 | 119 | US20150315612 SEQ ID NO: 222 |
| AAV8 | 120 | US20150159173 SEQ ID NO: 15 |
| AAV8 | 121 | US20150376240 SEQ ID NO: 7 |
| AAV8 | 122 | US20030138772 SEQ ID NO: 4, |
| | | US20150315612 SEQ ID NO: 182 |
| AAV8 | 123 | US20030138772 SEQ ID NO: 95, |
| | | US20140359799 SEQ ID NO: 1, |
| | | US20150159173 SEQ ID NO: 31, |
| | | US20160017295 SEQ ID NO: 8, |
| | | U.S. Pat. No. 7,198,951 SEQ ID NO: 7, |
| | | US20150315612 SEQ ID NO: 223 |
| AAV8 | 124 | US20150376240 SEQ ID NO: 8 |
| AAV8 | 125 | US20150315612 SEQ ID NO: 214 |
| AAV-8b | 126 | US20150376240 SEQ ID NO: 5 |
| AAV-8b | 127 | US20150376240 SEQ ID NO: 3 |
| AAV-8h | 128 | US20150376240 SEQ ID NO: 6 |
| AAV-8h | 129 | US20150376240 SEQ ID NO: 4 |
| AAV9 | 130 | US20030138772 SEQ ID NO: 5 |
| AAV9 | 131 | U.S. Pat. No. 7,198,951 SEQ ID NO: 1 |
| AAV9 | 132 | US20160017295 SEQ ID NO: 9 |
| AAV9 | 133 | US20030138772 SEQ ID NO: 100, |
| | | U.S. Pat. No. 7,198,951 SEQ ID NO: 2 |
| AAV9 | 134 | U.S. Pat. No. 7,198,951 SEQ ID NO: 3 |
| AAV9 (AAVhu.14) | 135 | U.S. Pat. No. 7,906,111 SEQ ID NO: 3; |
| | | WO2015038958 SEQ ID NO: 11 |
| AAV9 (AAVhu.14) | 136 | U.S. Pat. No. 7,906,111 SEQ ID NO: 123; |
| | | WO2015038958 SEQ ID NO: 2 |
| AAVA3.1 | 137 | US20030138772 SEQ ID NO: 120 |
| AAVA3.3 | 138 | US20030138772 SEQ ID NO: 57 |
| AAVA3.3 | 139 | US20030138772 SEQ ID NO: 66 |
| AAVA3.4 | 140 | US20030138772 SEQ ID NO: 54 |
| AAVA3.4 | 141 | US20030138772 SEQ ID NO: 68 |
| AAVA3.5 | 142 | US20030138772 SEQ ID NO: 55 |
| AAVA3.5 | 143 | US20030138772 SEQ ID NO: 69 |
| AAVA3.7 | 144 | US20030138772 SEQ ID NO: 56 |
| AAVA3.7 | 145 | US20030138772 SEQ ID NO: 67 |
| AAV29.3 (AAVbb.1) | 146 | US20030138772 SEQ ID NO: 11 |
| AAVC2 | 147 | US20030138772 SEQ ID NO: 61 |
| AAVCh.5 | 148 | US20150159173 SEQ ID NO: 46, |
| | | US20150315612 SEQ ID NO: 234 |
| AAVcy.2 (AAV13.3) | 149 | US20030138772 SEQ ID NO: 15 |
| AAV24.1 | 150 | US20030138772 SEQ ID NO: 101 |
| AAVcy.3 (AAV24.1) | 151 | US20030138772 SEQ ID NO: 16 |
| AAV27.3 | 152 | US20030138772 SEQ ID NO: 104 |
| AAVcy.4 (AAV27.3) | 153 | US20030138772 SEQ ID NO: 17 |
| AAVcy.5 | 154 | US20150315612 SEQ ID NO: 227 |
| AAV7.2 | 155 | US20030138772 SEQ ID NO: 103 |
| AAVcy.5 (AAV7.2) | 156 | US20030138772 SEQ ID NO: 18 |
| AAV16.3 | 157 | US20030138772 SEQ ID NO: 105 |
| AAVcy.6 (AAV16.3) | 158 | US20030138772 SEQ ID NO: 10 |
| AAVcy.5 | 159 | US20150159173 SEQ ID NO: 8 |
| AAVcy.5 | 160 | US20150159173 SEQ ID NO: 24 |
| AAVCy.5R1 | 161 | US20150159173 |
| AAVCy.5R2 | 162 | US20150159173 |
| AAVCy.5R3 | 163 | US20150159173 |
| AAVCy.5R4 | 164 | US20150159173 |
| AAVDJ | 165 | US20140359799 SEQ ID NO: 3, |
| | | U.S. Pat. No. 7,588,772 SEQ ID NO: 2 |
| AAVDJ | 166 | US20140359799 SEQ ID NO: 2, |
| | | U.S. Pat. No. 7,588,772 SEQ ID NO: 1 |
| AAVDJ-8 | 167 | U.S. Pat. No. 7,588,772; |
| | | Grimm et al 2008 |
| AAVDJ-8 | 168 | U.S. Pat. No. 7,588,772; |
| | | Grimm et al 2008 |
| AAVF5 | 169 | US20030138772 SEQ ID NO: 110 |
| AAVH2 | 170 | US20030138772 SEQ ID NO: 26 |
| AAVH6 | 171 | US20030138772 SEQ ID NO: 25 |
| AAVhE1.1 | 172 | U.S. Pat. No. 9,233,131 SEQ ID NO: 44 |
| AAVhEr1.14 | 173 | U.S. Pat. No. 9,233,131 SEQ ID NO: 46 |
| AAVhEr1.16 | 174 | U.S. Pat. No. 9,233,131 SEQ ID NO: 48 |

TABLE 1-continued

Representative AAV Serotypes

| Serotype | SEQ ID NO | Reference Information |
|---|---|---|
| AAVhEr1.18 | 175 | U.S. Pat. No. 9,233,131 SEQ ID NO: 49 |
| AAVhEr1.23 (AAVhEr2.29) | 176 | U.S. Pat. No. 9,233,131 SEQ ID NO: 53 |
| AAVhEr1.35 | 177 | U.S. Pat. No. 9,233,131 SEQ ID NO: 50 |
| AAVhEr1.36 | 178 | U.S. Pat. No. 9,233,131 SEQ ID NO: 52 |
| AAVhEr1.5 | 179 | U.S. Pat. No. 9,233,131 SEQ ID NO: 45 |
| AAVhEr1.7 | 180 | U.S. Pat. No. 9,233,131 SEQ ID NO: 51 |
| AAVhEr1.8 | 181 | U.S. Pat. No. 9,233,131 SEQ ID NO: 47 |
| AAVhEr2.16 | 182 | U.S. Pat. No. 9,233,131 SEQ ID NO: 55 |
| AAVhEr2.30 | 183 | U.S. Pat. No. 9,233,131 SEQ ID NO: 56 |
| AAVhEr2.31 | 184 | U.S. Pat. No. 9,233,131 SEQ ID NO: 58 |
| AAVhEr2.36 | 185 | U.S. Pat. No. 9,233,131 SEQ ID NO: 57 |
| AAVhEr2.4 | 186 | U.S. Pat. No. 9,233,131 SEQ ID NO: 54 |
| AAVhEr3.1 | 187 | U.S. Pat. No. 9,233,131 SEQ ID NO: 59 |
| AAVhu.1 | 188 | US20150315612 SEQ ID NO: 46 |
| AAVhu.1 | 189 | US20150315612 SEQ ID NO: 144 |
| AAVhu.10 (AAV16.8) | 190 | US20150315612 SEQ ID NO: 56 |
| AAVhu.10 (AAV16.8) | 191 | US20150315612 SEQ ID NO: 156 |
| AAVhu.11 (AAV16.12) | 192 | US20150315612 SEQ ID NO: 57 |
| AAVhu.11 (AAV16.12) | 193 | US20150315612 SEQ ID NO: 153 |
| AAVhu.12 | 194 | US20150315612 SEQ ID NO: 59 |
| AAVhu.12 | 195 | US20150315612 SEQ ID NO: 154 |
| AAVhu.13 | 196 | US20150159173 SEQ ID NO: 16, US20150315612 SEQ ID NO: 71 |
| AAVhu.13 | 197 | US20150159173 SEQ ID NO: 32, US20150315612 SEQ ID NO: 129 |
| AAVhu.136.1 | 198 | US20150315612 SEQ ID NO: 165 |
| AAVhu.140.1 | 199 | US20150315612 SEQ ID NO: 166 |
| AAVhu.140.2 | 200 | US20150315612 SEQ ID NO: 167 |
| AAVhu.145.6 | 201 | US20150315612 SEQ ID No: 178 |
| AAVhu.15 | 202 | US20150315612 SEQ ID NO: 147 |
| AAVhu.15 (AAV33.4) | 203 | US20150315612 SEQ ID NO: 50 |
| AAVhu.156.1 | 204 | US20150315612 SEQ ID No: 179 |
| AAVhu.16 | 205 | US20150315612 SEQ ID NO: 148 |
| AAVhu.16 (AAV33.8) | 206 | US20150315612 SEQ ID NO: 51 |
| AAVhu.17 | 207 | US20150315612 SEQ ID NO: 83 |
| AAVhu.17 (AAV33.12) | 208 | US20150315612 SEQ ID NO: 4 |
| AAVhu.172.1 | 209 | US20150315612 SEQ ID NO: 171 |
| AAVhu.172.2 | 210 | US20150315612 SEQ ID NO: 172 |
| AAVhu.173.4 | 211 | US20150315612 SEQ ID NO: 173 |
| AAVhu.173.8 | 212 | US20150315612 SEQ ID NO: 175 |
| AAVhu.18 | 213 | US20150315612 SEQ ID NO: 52 |
| AAVhu.18 | 214 | US20150315612 SEQ ID NO: 149 |
| AAVhu.19 | 215 | US20150315612 SEQ ID NO: 62 |
| AAVhu.19 | 216 | US20150315612 SEQ ID NO: 133 |
| AAVhu.2 | 217 | US20150315612 SEQ ID NO: 48 |
| AAVhu.2 | 218 | US20150315612 SEQ ID NO: 143 |
| AAVhu.20 | 219 | US20150315612 SEQ ID NO: 63 |
| AAVhu.20 | 220 | US20150315612 SEQ ID NO: 134 |
| AAVhu.21 | 221 | US20150315612 SEQ ID NO: 65 |
| AAVhu.21 | 222 | US20150315612 SEQ ID NO: 135 |
| AAVhu.22 | 223 | US20150315612 SEQ ID NO: 67 |
| AAVhu.22 | 224 | US20150315612 SEQ ID NO: 138 |
| AAVhu.23 | 225 | US20150315612 SEQ ID NO: 60 |
| AAVhu.23.2 | 226 | US20150315612 SEQ ID NO: 137 |
| AAVhu.24 | 227 | US20150315612 SEQ ID NO: 66 |
| AAVhu.24 | 228 | US20150315612 SEQ ID NO: 136 |
| AAVhu.25 | 229 | US20150315612 SEQ ID NO: 49 |
| AAVhu.25 | 230 | US20150315612 SEQ ID NO: 146 |
| AAVhu.26 | 231 | US20150159173 SEQ ID NO: 17, US20150315612 SEQ ID NO: 61 |
| AAVhu.26 | 232 | US20150159173 SEQ ID NO: 33, US20150315612 SEQ ID NO: 139 |
| AAVhu.27 | 233 | US20150315612 SEQ ID NO: 64 |
| AAVhu.27 | 234 | US20150315612 SEQ ID NO: 140 |
| AAVhu.28 | 235 | US20150315612 SEQ ID NO: 68 |
| AAVhu.28 | 236 | US20150315612 SEQ ID NO: 130 |
| AAVhu.29 | 237 | US20150315612 SEQ ID NO: 69 |
| AAVhu.29 | 238 | US20150159173 SEQ ID NO: 42, US20150315612 SEQ ID NO: 132 |
| AAVhu.29 | 239 | US20150315612 SEQ ID NO: 225 |
| AAVhu.29R | 240 | US20150159173 |
| AAVhu.3 | 241 | US20150315612 SEQ ID NO: 44 |
| AAVhu.3 | 242 | US20150315612 SEQ ID NO: 145 |
| AAVhu.30 | 243 | US20150315612 SEQ ID NO: 70 |
| AAVhu.30 | 244 | US20150315612 SEQ ID NO: 131 |
| AAVhu.31 | 245 | US20150315612 SEQ ID NO: 1 |

TABLE 1-continued

Representative AAV Serotypes

| Serotype | SEQ ID NO | Reference Information |
|---|---|---|
| AAVhu.31 | 246 | US20150315612 SEQ ID NO: 121 |
| AAVhu.32 | 247 | US20150315612 SEQ ID NO: 2 |
| AAVhu.32 | 248 | US20150315612 SEQ ID NO: 122 |
| AAVhu.33 | 249 | US20150315612 SEQ ID NO: 75 |
| AAVhu.33 | 250 | US20150315612 SEQ ID NO: 124 |
| AAVhu.34 | 251 | US20150315612 SEQ ID NO: 72 |
| AAVhu.34 | 252 | US20150315612 SEQ ID NO: 125 |
| AAVhu.35 | 253 | US20150315612 SEQ ID NO: 73 |
| AAVhu.35 | 254 | US20150315612 SEQ ID NO: 164 |
| AAVhu.36 | 255 | US20150315612 SEQ ID NO: 74 |
| AAVhu.36 | 256 | US20150315612 SEQ ID NO: 126 |
| AAVhu.37 | 257 | US20150159173 SEQ ID NO: 34, US20150315612 SEQ ID NO: 88 |
| AAVhu.37 (AAV106.1) | 258 | US20150315612 SEQ ID NO: 10, US20150159173 SEQ ID NO: 18 |
| AAVhu.38 | 259 | US20150315612 SEQ ID NO: 161 |
| AAVhu.39 | 260 | US20150315612 SEQ ID NO: 102 |
| AAVhu.39 (AAVLG-9) | 261 | US20150315612 SEQ ID NO: 24 |
| AAVhu.4 | 262 | US20150315612 SEQ ID NO: 47 |
| AAVhu.4 | 263 | US20150315612 SEQ ID NO: 141 |
| AAVhu.40 | 264 | US20150315612 SEQ ID NO: 87 |
| AAVhu.40 (AAV114.3) | 265 | US20150315612 SEQ ID No: 11 |
| AAVhu.41 | 266 | US20150315612 SEQ ID NO: 91 |
| AAVhu.41 (AAV127.2) | 267 | US20150315612 SEQ ID NO: 6 |
| AAVhu.42 | 268 | US20150315612 SEQ ID NO: 85 |
| AAVhu.42 (AAV127.5) | 269 | US20150315612 SEQ ID NO: 8 |
| AAVhu.43 | 270 | US20150315612 SEQ ID NO: 160 |
| AAVhu.43 | 271 | US20150315612 SEQ ID NO: 236 |
| AAVhu.43 (AAV128.1) | 272 | US20150315612 SEQ ID NO: 80 |
| AAVhu.44 | 273 | US20150159173 SEQ ID NO: 45, US20150315612 SEQ ID NO: 158 |
| AAVhu.44 (AAV128.3) | 274 | US20150315612 SEQ ID NO: 81 |
| AAVhu.44R1 | 275 | US20150159173 |
| AAVhu.44R2 | 276 | US20150159173 |
| AAVhu.44R3 | 277 | US20150159173 |
| AAVhu.45 | 278 | US20150315612 SEQ ID NO: 76 |
| AAVhu.45 | 279 | US20150315612 SEQ ID NO: 127 |
| AAVhu.46 | 280 | US20150315612 SEQ ID NO: 82 |
| AAVhu.46 | 281 | US20150315612 SEQ ID NO: 159 |
| AAVhu.46 | 282 | US20150315612 SEQ ID NO: 224 |
| AAVhu.47 | 283 | US20150315612 SEQ ID NO: 77 |
| AAVhu.47 | 284 | US20150315612 SEQ ID NO: 128 |
| AAVhu.48 | 285 | US20150159173 SEQ ID NO: 38 |
| AAVhu.48 | 286 | US20150315612 SEQ ID NO: 157 |
| AAVhu.48 (AAV130.4) | 287 | US20150315612 SEQ ID NO: 78 |
| AAVhu.48R1 | 288 | US20150159173 |
| AAVhu.48R2 | 289 | US20150159173 |
| AAVhu.48R3 | 290 | US20150159173 |
| AAVhu.49 | 291 | US20150315612 SEQ ID NO: 209 |
| AAVhu.49 | 292 | US20150315612 SEQ ID NO: 189 |
| AAVhu.5 | 293 | US20150315612 SEQ ID NO: 45 |
| AAVhu.5 | 294 | US20150315612 SEQ ID NO: 142 |
| AAVhu.51 | 295 | US20150315612 SEQ ID NO: 208 |
| AAVhu.51 | 296 | US20150315612 SEQ ID NO: 190 |
| AAVhu.52 | 297 | US20150315612 SEQ ID NO: 210 |
| AAVhu.52 | 298 | US20150315612 SEQ ID NO: 191 |
| AAVhu.53 | 299 | US20150159173 SEQ ID NO: 19 |
| AAVhu.53 | 300 | US20150159173 SEQ ID NO: 35 |
| AAVhu.53 (AAV145.1) | 301 | US20150315612 SEQ ID NO: 176 |
| AAVhu.54 | 302 | US20150315612 SEQ ID NO: 188 |
| AAVhu.54 (AAV145.5) | 303 | US20150315612 SEQ ID No: 177 |
| AAVhu.55 | 304 | US20150315612 SEQ ID NO: 187 |
| AAVhu.56 | 305 | US20150315612 SEQ ID NO: 205 |
| AAVhu.56 (AAV145.6) | 306 | US20150315612 SEQ ID NO: 168 |
| AAVhu.56 (AAV145.6) | 307 | US20150315612 SEQ ID NO: 192 |
| AAVhu.57 | 308 | US20150315612 SEQ ID NO: 206 |
| AAVhu.57 | 309 | US20150315612 SEQ ID NO: 169 |
| AAVhu.57 | 310 | US20150315612 SEQ ID NO: 193 |
| AAVhu.58 | 311 | US20150315612 SEQ ID NO: 207 |
| AAVhu.58 | 312 | US20150315612 SEQ ID NO: 194 |
| AAVhu.6 (AAV3.1) | 313 | US20150315612 SEQ ID NO: 5 |
| AAVhu.6 (AAV3.1) | 314 | US20150315612 SEQ ID NO: 84 |
| AAVhu.60 | 315 | US20150315612 SEQ ID NO: 184 |
| AAVhu.60 (AAV161.10) | 316 | US20150315612 SEQ ID NO: 170 |
| AAVhu.61 | 317 | US20150315612 SEQ ID NO: 185 |
| AAVhu.61 (AAV161.6) | 318 | US20150315612 SEQ ID NO: 174 |

TABLE 1-continued

Representative AAV Serotypes

| Serotype | SEQ ID NO | Reference Information |
|---|---|---|
| AAVhu.63 | 319 | US20150315612 SEQ ID NO: 204 |
| AAVhu.63 | 320 | US20150315612 SEQ ID NO: 195 |
| AAVhu.64 | 321 | US20150315612 SEQ ID NO: 212 |
| AAVhu.64 | 322 | US20150315612 SEQ ID NO: 196 |
| AAVhu.66 | 323 | US20150315612 SEQ ID NO: 197 |
| AAVhu.67 | 324 | US20150315612 SEQ ID NO: 215 |
| AAVhu.67 | 325 | US20150315612 SEQ ID NO: 198 |
| AAVhu.7 | 326 | US20150315612 SEQ ID NO: 226 |
| AAVhu.7 | 327 | US20150315612 SEQ ID NO: 150 |
| AAVhu.7 (AAV7.3) | 328 | US20150315612 SEQ ID NO: 55 |
| AAVhu.71 | 329 | US20150315612 SEQ ID NO: 79 |
| AAVhu.8 | 330 | US20150315612 SEQ ID NO: 53 |
| AAVhu.8 | 331 | US20150315612 SEQ ID NO: 12 |
| AAVhu.8 | 332 | US20150315612 SEQ ID NO: 151 |
| AAVhu.9 (AAV3.1) | 333 | US20150315612 SEQ ID NO: 58 |
| AAVhu.9 (AAV3.1) | 334 | US20150315612 SEQ ID NO: 155 |
| AAV-LK01 | 335 | US20150376607 SEQ ID NO: 2 |
| AAV-LK01 | 336 | US20150376607 SEQ ID NO: 29 |
| AAV-LK02 | 337 | US20150376607 SEQ ID NO: 3 |
| AAV-LK02 | 338 | US20150376607 SEQ ID NO: 30 |
| AAV-LK03 | 339 | US20150376607 SEQ ID NO: 4 |
| AAV-LK03 | 340 | WO2015121501 SEQ ID NO: 12, US20150376607 SEQ ID NO: 31 |
| AAV-LK04 | 341 | US20150376607 SEQ ID NO: 5 |
| AAV-LK04 | 342 | US20150376607 SEQ ID NO: 32 |
| AAV-LK05 | 343 | US20150376607 SEQ ID NO: 6 |
| AAV-LK05 | 344 | US20150376607 SEQ ID NO: 33 |
| AAV-LK06 | 345 | US20150376607 SEQ ID NO: 7 |
| AAV-LK06 | 346 | US20150376607 SEQ ID NO: 34 |
| AAV-LK07 | 347 | US20150376607 SEQ ID NO: 8 |
| AAV-LK07 | 348 | US20150376607 SEQ ID NO: 35 |
| AAV-LK08 | 349 | US20150376607 SEQ ID NO: 9 |
| AAV-LK08 | 350 | US20150376607 SEQ ID NO: 36 |
| AAV-LK09 | 351 | US20150376607 SEQ ID NO: 10 |
| AAV-LK09 | 352 | US20150376607 SEQ ID NO: 37 |
| AAV-LK10 | 353 | US20150376607 SEQ ID NO: 11 |
| AAV-LK10 | 354 | US20150376607 SEQ ID NO: 38 |
| AAV-LK11 | 355 | US20150376607 SEQ ID NO: 12 |
| AAV-LK11 | 356 | US20150376607 SEQ ID NO: 39 |
| AAV-LK12 | 357 | US20150376607 SEQ ID NO: 13 |
| AAV-LK12 | 358 | US20150376607 SEQ ID NO: 40 |
| AAV-LK13 | 359 | US20150376607 SEQ ID NO: 14 |
| AAV-LK13 | 360 | US20150376607 SEQ ID NO: 41 |
| AAV-LK14 | 361 | US20150376607 SEQ ID NO: 15 |
| AAV-LK14 | 362 | US20150376607 SEQ ID NO: 42 |
| AAV-LK15 | 363 | US20150376607 SEQ ID NO: 16 |
| AAV-LK15 | 364 | US20150376607 SEQ ID NO: 43 |
| AAV-LK16 | 365 | US20150376607 SEQ ID NO: 17 |
| AAV-LK16 | 366 | US20150376607 SEQ ID NO: 44 |
| AAV-LK17 | 367 | US20150376607 SEQ ID NO: 18 |
| AAV-LK17 | 368 | US20150376607 SEQ ID NO: 45 |
| AAV-LK18 | 369 | US20150376607 SEQ ID NO: 19 |
| AAV-LK18 | 370 | US20150376607 SEQ ID NO: 46 |
| AAV-LK19 | 371 | US20150376607 SEQ ID NO: 20 |
| AAV-LK19 | 372 | US20150376607 SEQ ID NO: 47 |
| AAV-PAEC | 373 | US20150376607 SEQ ID NO: 1 |
| AAV-PAEC | 374 | US20150376607 SEQ ID NO: 48 |
| AAV-PAEC11 | 375 | US20150376607 SEQ ID NO: 26 |
| AAV-PAEC11 | 376 | US20150376607 SEQ ID NO: 54 |
| AAV-PAEC12 | 377 | US20150376607 SEQ ID NO: 27 |
| AAV-PAEC12 | 378 | US20150376607 SEQ ID NO: 51 |
| AAV-PAEC13 | 379 | US20150376607 SEQ ID NO: 28 |
| AAV-PAEC13 | 380 | US20150376607 SEQ ID NO: 49 |
| AAV-PAEC2 | 381 | US20150376607 SEQ ID NO: 21 |
| AAV-PAEC2 | 382 | US20150376607 SEQ ID NO: 56 |
| AAV-PAEC4 | 383 | US20150376607 SEQ ID NO: 22 |
| AAV-PAEC4 | 384 | US20150376607 SEQ ID NO: 55 |
| AAV-PAEC6 | 385 | US20150376607 SEQ ID NO: 23 |
| AAV-PAEC6 | 386 | US20150376607 SEQ ID NO: 52 |
| AAV-PAEC7 | 387 | US20150376607 SEQ ID NO: 24 |
| AAV-PAEC7 | 388 | US20150376607 SEQ ID NO: 53 |
| AAV-PAEC8 | 389 | US20150376607 SEQ ID NO: 25 |
| AAV-PAEC8 | 390 | US20150376607 SEQ ID NO: 50 |
| AAVpi.1 | 391 | US20150315612 SEQ ID NO: 28 |
| AAVpi.1 | 392 | US20150315612 SEQ ID NO: 93 |
| AAVpi.2 | 393 | US20150315612 SEQ ID NO: 30 |

TABLE 1-continued

Representative AAV Serotypes

| Serotype | SEQ ID NO | Reference Information |
|---|---|---|
| AAVpi.2 | 394 | US20150315612 SEQ ID NO: 95 |
| AAVpi.3 | 395 | US20150315612 SEQ ID NO: 29 |
| AAVpi.3 | 396 | US20150315612 SEQ ID NO: 94 |
| AAVrh.10 | 397 | US20150159173 SEQ ID NO: 9 |
| AAVrh.10 | 398 | US20150159173 SEQ ID NO: 25 |
| AAV44.2 | 399 | US20030138772 SEQ ID NO: 59 |
| AAVrh.10 (AAV44.2) | 400 | US20030138772 SEQ ID NO: 81 |
| AAV42.1B | 401 | US20030138772 SEQ ID NO: 90 |
| AAVrh.12 (AAV42.1b) | 402 | US20030138772 SEQ ID NO: 30 |
| AAVrh.13 | 403 | US20150159173 SEQ ID NO: 10 |
| AAVrh.13 | 404 | US20150159173 SEQ ID NO: 26 |
| AAVrh.13 | 405 | US20150315612 SEQ ID NO: 228 |
| AAVrh.13R | 406 | US20150159173 |
| AAV42.3A | 407 | US20030138772 SEQ ID NO: 87 |
| AAVrh.14 (AAV42.3a) | 408 | US20030138772 SEQ ID NO: 32 |
| AAV42.5A | 409 | US20030138772 SEQ ID NO: 89 |
| AAVrh.17 (AAV42.5a) | 410 | US20030138772 SEQ ID NO: 34 |
| AAV42.5B | 411 | US20030138772 SEQ ID NO: 91 |
| AAVrh.18 (AAV42.5b) | 412 | US20030138772 SEQ ID NO: 29 |
| AAV42.6B | 413 | US20030138772 SEQ ID NO: 112 |
| AAVrh.19 (AAV42.6b) | 414 | US20030138772 SEQ ID NO: 38 |
| AAVrh.2 | 415 | US20150159173 SEQ ID NO: 39 |
| AAVrh.2 | 416 | US20150315612 SEQ ID NO: 231 |
| AAVrh.20 | 417 | US20150159173 SEQ ID NO: 1 |
| AAV42.10 | 418 | US20030138772 SEQ ID NO: 106 |
| AAVrh.21 (AAV42.10) | 419 | US20030138772 SEQ ID NO: 35 |
| AAV42.11 | 420 | US20030138772 SEQ ID NO: 108 |
| AAVrh.22 (AAV42.11) | 421 | US20030138772 SEQ ID NO: 37 |
| AAV42.12 | 422 | US20030138772 SEQ ID NO: 113 |
| AAVrh.23 (AAV42.12) | 423 | US20030138772 SEQ ID NO: 58 |
| AAV42.13 | 424 | US20030138772 SEQ ID NO: 86 |
| AAVrh.24 (AAV42.13) | 425 | US20030138772 SEQ ID NO: 31 |
| AAV42.15 | 426 | US20030138772 SEQ ID NO: 84 |
| AAVrh.25 (AAV42.15) | 427 | US20030138772 SEQ ID NO: 28 |
| AAVrh.2R | 428 | US20150159173 |
| AAVrh.31 (AAV223.1) | 429 | US20030138772 SEQ ID NO: 48 |
| AAVC1 | 430 | US20030138772 SEQ ID NO: 60 |
| AAVrh.32 (AAVC1) | 431 | US20030138772 SEQ ID NO: 19 |
| AAVrh.32/33 | 432 | US20150159173 SEQ ID NO: 2 |
| AAVrh.33 (AAVC3) | 433 | US20030138772 SEQ ID NO: 20 |
| AAVC5 | 434 | US20030138772 SEQ ID NO: 62 |
| AAVrh.34 (AAVC5) | 435 | US20030138772 SEQ ID NO: 21 |
| AAVF1 | 436 | US20030138772 SEQ ID NO: 109 |
| AAVrh.35 (AAVF1) | 437 | US20030138772 SEQ ID NO: 22 |
| AAVF3 | 438 | US20030138772 SEQ ID NO: 111 |
| AAVrh.36 (AAVF3) | 439 | US20030138772 SEQ ID NO: 23 |
| AAVrh.37 | 440 | US20030138772 SEQ ID NO: 24 |
| AAVrh.37 | 441 | US20150159173 SEQ ID NO: 40 |
| AAVrh.37 | 442 | US20150315612 SEQ ID NO: 229 |
| AAVrh.37R2 | 443 | US20150159173 |
| AAVrh.38 (AAVLG-4) | 444 | US20150315612 SEQ ID NO: 7 |
| AAVrh.38 (AAVLG-4) | 445 | US20150315612 SEQ ID NO: 86 |
| AAVrh.39 | 446 | US20150159173 SEQ ID NO: 20, US20150315612 SEQ ID NO: 13 |
| AAVrh.39 | 447 | US20150159173 SEQ ID NO: 3, US20150159173 SEQ ID NO: 36, US20150315612 SEQ ID NO: 89 |
| AAVrh.40 | 448 | US20150159173 SEQ ID NO: 92 |
| AAVrh.40 (AAVLG-10) | 449 | US20150315612 SEQ ID No: 14 |
| AAVrh.43 (AAVN721-8) | 450 | US20150315612 SEQ ID NO: 43, US20150159173 SEQ ID NO: 21 |
| AAVrh.43 (AAVN721-8) | 451 | US20150315612 SEQ ID NO: 163, US20150159173 SEQ ID NO: 37 |
| AAVrh.44 | 452 | US20150315612 SEQ ID NO: 34 |
| AAVrh.44 | 453 | US20150315612 SEQ ID NO: 111 |
| AAVrh.45 | 454 | US20150315612 SEQ ID NO: 41 |
| AAVrh.45 | 455 | US20150315612 SEQ ID NO: 109 |
| AAVrh.46 | 456 | US20150159173 SEQ ID NO: 22, US20150315612 SEQ ID NO: 19 |
| AAVrh.46 | 457 | US20150159173 SEQ ID NO: 4, US20150315612 SEQ ID NO: 101 |
| AAVrh.47 | 458 | US20150315612 SEQ ID NO: 38 |
| AAVrh.47 | 459 | US20150315612 SEQ ID NO: 118 |
| AAVrh.48 | 460 | US20150159173 SEQ ID NO: 44, US20150315612 SEQ ID NO: 115 |
| AAVrh.48.1 | 461 | US20150159173 |

TABLE 1-continued

Representative AAV Serotypes

| Serotype | SEQ ID NO | Reference Information |
|---|---|---|
| AAVrh.48.1.2 | 462 | US20150159173 |
| AAVrh.48.2 | 463 | US20150159173 |
| AAVrh.48 (AAV1-7) | 464 | US20150315612 SEQ ID NO: 32 |
| AAVrh.49 (AAV1-8) | 465 | US20150315612 SEQ ID NO: 25 |
| AAVrh.49 (AAV1-8) | 466 | US20150315612 SEQ ID NO: 103 |
| AAVrh.50 (AAV2-4) | 467 | US20150315612 SEQ ID NO: 23 |
| AAVrh.50 (AAV2-4) | 468 | US20150315612 SEQ ID NO: 108 |
| AAVrh.51 (AAV2-5) | 469 | US20150315612 SEQ ID No: 22 |
| AAVrh.51 (AAV2-5) | 470 | US20150315612 SEQ ID NO: 104 |
| AAVrh.52 (AAV3-9) | 471 | US20150315612 SEQ ID NO: 18 |
| AAVrh.52 (AAV3-9) | 472 | US20150315612 SEQ ID NO: 96 |
| AAVrh.53 | 473 | US20150315612 SEQ ID NO: 97 |
| AAVrh.53 (AAV3-11) | 474 | US20150315612 SEQ ID NO: 17 |
| AAVrh.53 (AAV3-11) | 475 | US20150315612 SEQ ID NO: 186 |
| AAVrh.54 | 476 | US20150315612 SEQ ID NO: 40 |
| AAVrh.54 | 477 | US20150159173 SEQ ID NO: 49, US20150315612 SEQ ID NO: 116 |
| AAVrh.55 | 478 | US20150315612 SEQ ID NO: 37 |
| AAVrh.55 (AAV4-19) | 479 | US20150315612 SEQ ID NO: 117 |
| AAVrh.56 | 480 | US20150315612 SEQ ID NO: 54 |
| AAVrh.56 | 481 | US20150315612 SEQ ID NO: 152 |
| AAVrh.57 | 482 | US20150315612 SEQ ID NO: 26 |
| AAVrh.57 | 483 | US20150315612 SEQ ID NO: 105 |
| AAVrh.58 | 484 | US20150315612 SEQ ID NO: 27 |
| AAVrh.58 | 485 | US20150159173 SEQ ID NO: 48, US20150315612 SEQ ID NO: 106 |
| AAVrh.58 | 486 | US20150315612 SEQ ID NO: 232 |
| AAVrh.59 | 487 | US20150315612 SEQ ID NO: 42 |
| AAVrh.59 | 488 | US20150315612 SEQ ID NO: 110 |
| AAVrh.60 | 489 | US20150315612 SEQ ID NO: 31 |
| AAVrh.60 | 490 | US20150315612 SEQ ID NO: 120 |
| AAVrh.61 | 491 | US20150315612 SEQ ID NO: 107 |
| AAVrh.61 (AAV2-3) | 492 | US20150315612 SEQ ID NO: 21 |
| AAVrh.62 (AAV2-15) | 493 | US20150315612 SEQ ID NO: 33 |
| AAVrh.62 (AAV2-15) | 494 | US20150315612 SEQ ID NO: 114 |
| AAVrh.64 | 495 | US20150315612 SEQ ID No: 15 |
| AAVrh.64 | 496 | US20150159173 SEQ ID NO: 43, US20150315612 SEQ ID NO: 99 |
| AAVrh.64 | 497 | US20150315612 SEQ ID NO: 233 |
| AAVRh.64R1 | 498 | US20150159173 |
| AAVRh.64R2 | 499 | US20150159173 |
| AAVrh.65 | 500 | US20150315612 SEQ ID NO: 35 |
| AAVrh.65 | 501 | US20150315612 SEQ ID NO: 112 |
| AAVrh.67 | 502 | US20150315612 SEQ ID NO: 36 |
| AAVrh.67 | 503 | US20150315612 SEQ ID NO: 230 |
| AAVrh.67 | 504 | US20150159173 SEQ ID NO: 47, US20150315612 SEQ ID NO: 113 |
| AAVrh.68 | 505 | US20150315612 SEQ ID NO: 16 |
| AAVrh.68 | 506 | US20150315612 SEQ ID NO: 100 |
| AAVrh.69 | 507 | US20150315612 SEQ ID NO: 39 |
| AAVrh.69 | 508 | US20150315612 SEQ ID NO: 119 |
| AAVrh.70 | 509 | US20150315612 SEQ ID NO: 20 |
| AAVrh.70 | 510 | US20150315612 SEQ ID NO: 98 |
| AAVrh.71 | 511 | US20150315612 SEQ ID NO: 162 |
| AAVrh.72 | 512 | US20150315612 SEQ ID NO: 9 |
| AAVrh.73 | 513 | US20150159173 SEQ ID NO: 5 |
| AAVrh.74 | 514 | US20150159173 SEQ ID NO: 6 |
| AAVrh.8 | 515 | US20150159173 SEQ ID NO: 41 |
| AAVrh.8 | 516 | US20150315612 SEQ ID NO: 235 |
| AAVrh.8R | 517 | US20150159173, WO2015168666 SEQ ID NO: 9 |
| AAVrh.8R A586R mutant | 518 | WO2015168666 SEQ ID NO: 10 |
| AAVrh.8R R533A mutant | 519 | WO2015168666 SEQ ID NO: 11 |
| BAAV (bovine AAV) | 520 | U.S. Pat. No. 9,193,769 SEQ ID NO: 8 |
| BAAV (bovine AAV) | 521 | U.S. Pat. No. 9,193,769 SEQ ID NO: 10 |
| BAAV (bovine AAV) | 522 | U.S. Pat. No. 9,193,769 SEQ ID NO: 4 |
| BAAV (bovine AAV) | 523 | U.S. Pat. No. 9,193,769 SEQ ID NO: 2 |
| BAAV (bovine AAV) | 524 | U.S. Pat. No. 9,193,769 SEQ ID NO: 6 |
| BAAV (bovine AAV) | 525 | U.S. Pat. No. 9,193,769 SEQ ID NO: 1 |
| BAAV (bovine AAV) | 526 | U.S. Pat. No. 9,193,769 SEQ ID NO: 5 |
| BAAV (bovine AAV) | 527 | U.S. Pat. No. 9,193,769 SEQ ID NO: 3 |
| BAAV (bovine AAV) | 528 | U.S. Pat. No. 9,193,769 SEQ ID NO: 11 |
| BAAV (bovine AAV) | 529 | U.S. Pat. No. 7,427,396 SEQ ID NO: 5 |
| BAAV (bovine AAV) | 530 | U.S. Pat. No. 7,427,396 SEQ ID NO: 6 |
| BAAV (bovine AAV) | 531 | U.S. Pat. No. 9,193,769 SEQ ID NO: 7 |
| BAAV (bovine AAV) | 532 | U.S. Pat. No. 9,193,769 SEQ ID NO: 9 |

TABLE 1-continued

Representative AAV Serotypes

| Serotype | SEQ ID NO | Reference Information |
|---|---|---|
| BNP61 AAV | 533 | US20150238550 SEQ ID NO: 1 |
| BNP61 AAV | 534 | US20150238550 SEQ ID NO: 2 |
| BNP62 AAV | 535 | US20150238550 SEQ ID NO: 3 |
| BNP63 AAV | 536 | US20150238550 SEQ ID NO: 4 |
| caprine AAV | 537 | U.S. Pat. No. 7,427,396 SEQ ID NO: 3 |
| caprine AAV | 538 | U.S. Pat. No. 7,427,396 SEQ ID NO: 4 |
| true type AAV (ttAAV) | 539 | WO2015121501 SEQ ID NO: 2 |
| AAAV (Avian AAV) | 540 | U.S. Pat. No. 9,238,800 SEQ ID NO: 12 |
| AAAV (Avian AAV) | 541 | U.S. Pat. No. 9,238,800 SEQ ID NO: 2 |
| AAAV (Avian AAV) | 542 | U.S. Pat. No. 9,238,800 SEQ ID NO: 6 |
| AAAV (Avian AAV) | 543 | U.S. Pat. No. 9,238,800 SEQ ID NO: 4 |
| AAAV (Avian AAV) | 544 | U.S. Pat. No. 9,238,800 SEQ ID NO: 8 |
| AAAV (Avian AAV) | 545 | U.S. Pat. No. 9,238,800 SEQ ID NO: 14 |
| AAAV (Avian AAV) | 546 | U.S. Pat. No. 9,238,800 SEQ ID NO: 10 |
| AAAV (Avian AAV) | 547 | U.S. Pat. No. 9,238,800 SEQ ID NO: 15 |
| AAAV (Avian AAV) | 548 | U.S. Pat. No. 9,238,800 SEQ ID NO: 5 |
| AAAV (Avian AAV) | 549 | U.S. Pat. No. 9,238,800 SEQ ID NO: 9 |
| AAAV (Avian AAV) | 550 | U.S. Pat. No. 9,238,800 SEQ ID NO: 3 |
| AAAV (Avian AAV) | 551 | U.S. Pat. No. 9,238,800 SEQ ID NO: 7 |
| AAAV (Avian AAV) | 552 | U.S. Pat. No. 9,238,800 SEQ ID NO: 11 |
| AAAV (Avian AAV) | 553 | U.S. Pat. No. 9,238,800 SEQ ID NO: 13 |
| AAAV (Avian AAV) | 554 | U.S. Pat. No. 9,238,800 SEQ ID NO: 1 |
| AAV Shuffle 100-1 | 555 | US20160017295 SEQ ID NO: 23 |
| AAV Shuffle 100-1 | 556 | US20160017295 SEQ ID NO: 11 |
| AAV Shuffle 100-2 | 557 | US20160017295 SEQ ID NO: 37 |
| AAV Shuffle 100-2 | 558 | US20160017295 SEQ ID NO: 29 |
| AAV Shuffle 100-3 | 559 | US20160017295 SEQ ID NO: 24 |
| AAV Shuffle 100-3 | 560 | US20160017295 SEQ ID NO: 12 |
| AAV Shuffle 100-7 | 561 | US20160017295 SEQ ID NO: 25 |
| AAV Shuffle 100-7 | 562 | US20160017295 SEQ ID NO: 13 |
| AAV Shuffle 10-2 | 563 | US20160017295 SEQ ID NO: 34 |
| AAV Shuffle 10-2 | 564 | US20160017295 SEQ ID NO: 26 |
| AAV Shuffle 10-6 | 565 | US20160017295 SEQ ID NO: 35 |
| AAV Shuffle 10-6 | 566 | US20160017295 SEQ ID NO: 27 |
| AAV Shuffle 10-8 | 567 | US20160017295 SEQ ID NO: 36 |
| AAV Shuffle 10-8 | 568 | US20160017295 SEQ ID NO: 28 |
| AAV SM 100-10 | 569 | US20160017295 SEQ ID NO: 41 |
| AAV SM 100-10 | 570 | US20160017295 SEQ ID NO: 33 |
| AAV SM 100-3 | 571 | US20160017295 SEQ ID NO: 40 |
| AAV SM 100-3 | 572 | US20160017295 SEQ ID NO: 32 |
| AAV SM 10-1 | 573 | US20160017295 SEQ ID NO: 38 |
| AAV SM 10-1 | 574 | US20160017295 SEQ ID NO: 30 |
| AAV SM 10-2 | 575 | US20160017295 SEQ ID NO: 10 |
| AAV SM 10-2 | 576 | US20160017295 SEQ ID NO: 22 |
| AAV SM 10-8 | 577 | US20160017295 SEQ ID NO: 39 |
| AAV SM 10-8 | 578 | US20160017295 SEQ ID NO: 31 |
| AAVF1/HSC1 | 579 | WO2016049230 SEQ ID NO: 20 |
| AAVF2/HSC2 | 580 | WO2016049230 SEQ ID NO: 21 |
| AAVF3/HSC3 | 581 | WO2016049230 SEQ ID NO: 22 |
| AAVF4/HSC4 | 582 | WO2016049230 SEQ ID NO: 23 |
| AAVF5/HSC5 | 583 | WO2016049230 SEQ ID NO: 25 |
| AAVF6/HSC6 | 584 | WO2016049230 SEQ ID NO: 24 |
| AAVF7/HSC7 | 585 | WO2016049230 SEQ ID NO: 27 |
| AAVF8/HSC8 | 586 | WO2016049230 SEQ ID NO: 28 |
| AAVF9/HSC9 | 587 | WO2016049230 SEQ ID NO: 29 |
| AAVF11/HSC11 | 588 | WO2016049230 SEQ ID NO: 26 |
| AAVF12/HSC12 | 589 | WO2016049230 SEQ ID NO: 30 |
| AAVF13/HSC13 | 590 | WO2016049230 SEQ ID NO: 31 |
| AAVF14/HSC14 | 591 | WO2016049230 SEQ ID NO: 32 |
| AAVF15/HSC15 | 592 | WO2016049230 SEQ ID NO: 33 |
| AAVF16/HSC16 | 593 | WO2016049230 SEQ ID NO: 34 |
| AAVF17/HSC17 | 594 | WO2016049230 SEQ ID NO: 35 |
| AAVF1/HSC1 | 595 | WO2016049230 SEQ ID NO: 2 |
| AAVF2/HSC2 | 596 | WO2016049230 SEQ ID NO: 3 |
| AAVF3/HSC3 | 597 | WO2016049230 SEQ ID NO: 5 |
| AAVF4/HSC4 | 598 | WO2016049230 SEQ ID NO: 6 |
| AAVF5/HSC5 | 599 | WO2016049230 SEQ ID NO: 11 |
| AAVF6/HSC6 | 600 | WO2016049230 SEQ ID NO: 7 |
| AAVF7/HSC7 | 601 | WO2016049230 SEQ ID NO: 8 |
| AAVF8/HSC8 | 602 | WO2016049230 SEQ ID NO: 9 |
| AAVF9/HSC9 | 603 | WO2016049230 SEQ ID NO: 10 |
| AAVF11/HSC11 | 604 | WO2016049230 SEQ ID NO: 4 |
| AAVF12/HSC12 | 605 | WO2016049230 SEQ ID NO: 12 |
| AAVF13/HSC13 | 606 | WO2016049230 SEQ ID NO: 14 |
| AAVF14/HSC14 | 607 | WO2016049230 SEQ ID NO: 15 |
| AAVF15/HSC15 | 608 | WO2016049230 SEQ ID NO: 16 |

TABLE 1-continued

Representative AAV Serotypes

| Serotype | SEQ ID NO | Reference Information |
| --- | --- | --- |
| AAVF16/HSC16 | 609 | WO2016049230 SEQ ID NO: 17 |
| AAVF17/HSC17 | 610 | WO2016049230 SEQ ID NO: 13 |
| AAV CBr-E1 | 611 | U.S. Pat. No. 8,734,809 SEQ ID NO: 13 |
| AAV CBr-E2 | 612 | U.S. Pat. No. 8,734,809 SEQ ID NO: 14 |
| AAV CBr-E3 | 613 | U.S. Pat. No. 8,734,809 SEQ ID NO: 15 |
| AAV CBr-E4 | 614 | U.S. Pat. No. 8,734,809 SEQ ID NO: 16 |
| AAV CBr-E5 | 615 | U.S. Pat. No. 8,734,809 SEQ ID NO: 17 |
| AAV CBr-e5 | 616 | U.S. Pat. No. 8,734,809 SEQ ID NO: 18 |
| AAV CBr-E6 | 617 | U.S. Pat. No. 8,734,809 SEQ ID NO: 19 |
| AAV CBr-E7 | 618 | U.S. Pat. No. 8,734,809 SEQ ID NO: 20 |
| AAV CBr-E8 | 619 | U.S. Pat. No. 8,734,809 SEQ ID NO: 21 |
| AAV CLv-D1 | 620 | U.S. Pat. No. 8,734,809 SEQ ID NO: 22 |
| AAV CLv-D2 | 621 | U.S. Pat. No. 8,734,809 SEQ ID NO: 23 |
| AAV CLv-D3 | 622 | U.S. Pat. No. 8,734,809 SEQ ID NO: 24 |
| AAV CLv-D4 | 623 | U.S. Pat. No. 8,734,809 SEQ ID NO: 25 |
| AAV CLv-D5 | 624 | U.S. Pat. No. 8,734,809 SEQ ID NO: 26 |
| AAV CLv-D6 | 625 | U.S. Pat. No. 8,734,809 SEQ ID NO: 27 |
| AAV CLv-D7 | 626 | U.S. Pat. No. 8,734,809 SEQ ID NO: 28 |
| AAV CLv-D8 | 627 | U.S. Pat. No. 8,734,809 SEQ ID NO: 29 |
| AAV CLv-E1 | 628 | U.S. Pat. No. 8,734,809 SEQ ID NO: 13 |
| AAV CLv-R1 | 629 | U.S. Pat. No. 8,734,809 SEQ ID NO: 30 |
| AAV CLv-R2 | 630 | U.S. Pat. No. 8,734,809 SEQ ID NO: 31 |
| AAV CLv-R3 | 631 | U.S. Pat. No. 8,734,809 SEQ ID NO: 32 |
| AAV CLv-R4 | 632 | U.S. Pat. No. 8,734,809 SEQ ID NO: 33 |
| AAV CLv-R5 | 633 | U.S. Pat. No. 8,734,809 SEQ ID NO: 34 |
| AAV CLv-R6 | 634 | U.S. Pat. No. 8,734,809 SEQ ID NO: 35 |
| AAV CLv-R7 | 635 | U.S. Pat. No. 8,734,809 SEQ ID NO: 36 |
| AAV CLv-R8 | 636 | U.S. Pat. No. 8,734,809 SEQ ID NO: 37 |
| AAV CLv-R9 | 637 | U.S. Pat. No. 8,734,809 SEQ ID NO: 38 |
| AAV CLg-F1 | 638 | U.S. Pat. No. 8,734,809 SEQ ID NO: 39 |
| AAV CLg-F2 | 639 | U.S. Pat. No. 8,734,809 SEQ ID NO: 40 |
| AAV CLg-F3 | 640 | U.S. Pat. No. 8,734,809 SEQ ID NO: 41 |
| AAV CLg-F4 | 641 | U.S. Pat. No. 8,734,809 SEQ ID NO: 42 |
| AAV CLg-F5 | 642 | U.S. Pat. No. 8,734,809 SEQ ID NO: 43 |
| AAV CLg-F6 | 643 | U.S. Pat. No. 8,734,809 SEQ ID NO: 43 |
| AAV CLg-F7 | 644 | U.S. Pat. No. 8,734,809 SEQ ID NO: 44 |
| AAV CLg-F8 | 645 | U.S. Pat. No. 8,734,809 SEQ ID NO: 43 |
| AAV CSp-1 | 646 | U.S. Pat. No. 8,734,809 SEQ ID NO: 45 |
| AAV CSp-10 | 647 | U.S. Pat. No. 8,734,809 SEQ ID NO: 46 |
| AAV CSp-11 | 648 | U.S. Pat. No. 8,734,809 SEQ ID NO: 47 |
| AAV CSp-2 | 649 | U.S. Pat. No. 8,734,809 SEQ ID NO: 48 |
| AAV CSp-3 | 650 | U.S. Pat. No. 8,734,809 SEQ ID NO: 49 |
| AAV CSp-4 | 651 | U.S. Pat. No. 8,734,809 SEQ ID NO: 50 |
| AAV CSp-6 | 652 | U.S. Pat. No. 8,734,809 SEQ ID NO: 51 |
| AAV CSp-7 | 653 | U.S. Pat. No. 8,734,809 SEQ ID NO: 52 |
| AAV CSp-8 | 654 | U.S. Pat. No. 8,734,809 SEQ ID NO: 53 |
| AAV CSp-9 | 655 | U.S. Pat. No. 8,734,809 SEQ ID NO: 54 |
| AAV CHt-2 | 656 | U.S. Pat. No. 8,734,809 SEQ ID NO: 55 |
| AAV CHt-3 | 657 | U.S. Pat. No. 8,734,809 SEQ ID NO: 56 |
| AAV CKd-1 | 658 | U.S. Pat. No. 8,734,809 SEQ ID NO: 57 |
| AAV CKd-10 | 659 | U.S. Pat. No. 8,734,809 SEQ ID NO: 58 |
| AAV CKd-2 | 660 | U.S. Pat. No. 8,734,809 SEQ ID NO: 59 |
| AAV CKd-3 | 661 | U.S. Pat. No. 8,734,809 SEQ ID NO: 60 |
| AAV CKd-4 | 662 | U.S. Pat. No. 8,734,809 SEQ ID NO: 61 |
| AAV CKd-6 | 663 | U.S. Pat. No. 8,734,809 SEQ ID NO: 62 |
| AAV CKd-7 | 664 | U.S. Pat. No. 8,734,809 SEQ ID NO: 63 |
| AAV CKd-8 | 665 | U.S. Pat. No. 8,734,809 SEQ ID NO: 64 |
| AAV CLv-1 | 666 | U.S. Pat. No. 8,734,809 SEQ ID NO: 65 |
| AAV CLv-12 | 667 | U.S. Pat. No. 8,734,809 SEQ ID NO: 66 |
| AAV CLv-13 | 668 | U.S. Pat. No. 8,734,809 SEQ ID NO: 67 |
| AAV CLv-2 | 669 | U.S. Pat. No. 8,734,809 SEQ ID NO: 68 |
| AAV CLv-3 | 670 | U.S. Pat. No. 8,734,809 SEQ ID NO: 69 |
| AAV CLv-4 | 671 | U.S. Pat. No. 8,734,809 SEQ ID NO: 70 |
| AAV CLv-6 | 672 | U.S. Pat. No. 8,734,809 SEQ ID NO: 71 |
| AAV CLv-8 | 673 | U.S. Pat. No. 8,734,809 SEQ ID NO: 72 |
| AAV CKd-B1 | 674 | U.S. Pat. No. 8,734,809 SEQ ID NO: 73 |
| AAV CKd-B2 | 675 | U.S. Pat. No. 8,734,809 SEQ ID NO: 74 |
| AAV CKd-B3 | 676 | U.S. Pat. No. 8,734,809 SEQ ID NO: 75 |
| AAV CKd-B4 | 677 | U.S. Pat. No. 8,734,809 SEQ ID NO: 76 |
| AAV CKd-B5 | 678 | U.S. Pat. No. 8,734,809 SEQ ID NO: 77 |
| AAV CKd-B6 | 679 | U.S. Pat. No. 8,734,809 SEQ ID NO: 78 |
| AAV CKd-B7 | 680 | U.S. Pat. No. 8,734,809 SEQ ID NO: 79 |
| AAV CKd-B8 | 681 | U.S. Pat. No. 8,734,809 SEQ ID NO: 80 |
| AAV CKd-H1 | 682 | U.S. Pat. No. 8,734,809 SEQ ID NO: 81 |
| AAV CKd-H2 | 683 | U.S. Pat. No. 8,734,809 SEQ ID NO: 82 |
| AAV CKd-H3 | 684 | U.S. Pat. No. 8,734,809 SEQ ID NO: 83 |

TABLE 1-continued

Representative AAV Serotypes

| Serotype | SEQ ID NO | Reference Information |
|---|---|---|
| AAV CKd-H4 | 685 | U.S. Pat. No. 8,734,809 SEQ ID NO: 84 |
| AAV CKd-H5 | 686 | U.S. Pat. No. 8,734,809 SEQ ID NO: 85 |
| AAV CKd-H6 | 687 | U.S. Pat. No. 8,734,809 SEQ ID NO: 77 |
| AAV CHt-1 | 688 | U.S. Pat. No. 8,734,809 SEQ ID NO: 86 |
| AAV CLv1-1 | 689 | U.S. Pat. No. 8,734,809 SEQ ID NO: 171 |
| AAV CLv1-2 | 690 | U.S. Pat. No. 8,734,809 SEQ ID NO: 172 |
| AAV CLv1-3 | 691 | U.S. Pat. No. 8,734,809 SEQ ID NO: 173 |
| AAV CLv1-4 | 692 | U.S. Pat. No. 8,734,809 SEQ ID NO: 174 |
| AAV Clv1-7 | 693 | U.S. Pat. No. 8,734,809 SEQ ID NO: 175 |
| AAV Clv1-8 | 694 | U.S. Pat. No. 8,734,809 SEQ ID NO: 176 |
| AAV Clv1-9 | 695 | U.S. Pat. No. 8,734,809 SEQ ID NO: 177 |
| AAV Clv1-10 | 696 | U.S. Pat. No. 8,734,809 SEQ ID NO: 178 |
| AAV.VR-355 | 697 | U.S. Pat. No. 8,734,809 SEQ ID NO: 181 |
| AAV.hu.48R3 | 698 | U.S. Pat. No. 8,734,809 SEQ ID NO: 183 |
| AAV CBr-E1 | 699 | U.S. Pat. No. 8,734,809 SEQ ID NO: 87 |
| AAV CBr-E2 | 700 | U.S. Pat. No. 8,734,809 SEQ ID NO: 88 |
| AAV CBr-E3 | 701 | U.S. Pat. No. 8,734,809 SEQ ID NO: 89 |
| AAV CBr-E4 | 702 | U.S. Pat. No. 8,734,809 SEQ ID NO: 90 |
| AAV CBr-E5 | 703 | U.S. Pat. No. 8,734,809 SEQ ID NO: 91 |
| AAV CBr-e5 | 704 | U.S. Pat. No. 8,734,809 SEQ ID NO: 92 |
| AAV CBr-E6 | 705 | U.S. Pat. No. 8,734,809 SEQ ID NO: 93 |
| AAV CBr-E7 | 706 | U.S. Pat. No. 8,734,809 SEQ ID NO: 94 |
| AAV CBr-E8 | 707 | U.S. Pat. No. 8,734,809 SEQ ID NO: 95 |
| AAV CLv-D1 | 708 | U.S. Pat. No. 8,734,809 SEQ ID NO: 96 |
| AAV CLv-D2 | 709 | U.S. Pat. No. 8,734,809 SEQ ID NO: 97 |
| AAV CLv-D3 | 710 | U.S. Pat. No. 8,734,809 SEQ ID NO: 98 |
| AAV CLv-D4 | 711 | U.S. Pat. No. 8,734,809 SEQ ID NO: 99 |
| AAV CLv-D5 | 712 | U.S. Pat. No. 8,734,809 SEQ ID NO: 100 |
| AAV CLv-D6 | 713 | U.S. Pat. No. 8,734,809 SEQ ID NO: 101 |
| AAV CLv-D7 | 714 | U.S. Pat. No. 8,734,809 SEQ ID NO: 102 |
| AAV CLv-D8 | 715 | U.S. Pat. No. 8,734,809 SEQ ID NO: 103 |
| AAV CLv-E1 | 716 | U.S. Pat. No. 8,734,809 SEQ ID NO: 87 |
| AAV CLv-R1 | 717 | U.S. Pat. No. 8,734,809 SEQ ID NO: 104 |
| AAV CLv-R2 | 718 | U.S. Pat. No. 8,734,809 SEQ ID NO: 105 |
| AAV CLv-R3 | 719 | U.S. Pat. No. 8,734,809 SEQ ID NO: 106 |
| AAV CLv-R4 | 720 | U.S. Pat. No. 8,734,809 SEQ ID NO: 107 |
| AAV CLv-R5 | 721 | U.S. Pat. No. 8,734,809 SEQ ID NO: 108 |
| AAV CLv-R6 | 722 | U.S. Pat. No. 8,734,809 SEQ ID NO: 109 |
| AAV CLv-R7 | 723 | U.S. Pat. No. 8,734,809 SEQ ID NO: 110 |
| AAV CLv-R8 | 724 | U.S. Pat. No. 8,734,809 SEQ ID NO: 111 |
| AAV CLv-R9 | 725 | U.S. Pat. No. 8,734,809 SEQ ID NO: 112 |
| AAV CLg-F1 | 726 | U.S. Pat. No. 8,734,809 SEQ ID NO: 113 |
| AAV CLg-F2 | 727 | U.S. Pat. No. 8,734,809 SEQ ID NO: 114 |
| AAV CLg-F3 | 728 | U.S. Pat. No. 8,734,809 SEQ ID NO: 115 |
| AAV CLg-F4 | 729 | U.S. Pat. No. 8,734,809 SEQ ID NO: 116 |
| AAV CLg-F5 | 730 | U.S. Pat. No. 8,734,809 SEQ ID NO: 117 |
| AAV CLg-F6 | 731 | U.S. Pat. No. 8,734,809 SEQ ID NO: 117 |
| AAV CLg-F7 | 732 | U.S. Pat. No. 8,734,809 SEQ ID NO: 118 |
| AAV CLg-F8 | 733 | U.S. Pat. No. 8,734,809 SEQ ID NO: 117 |
| AAV CSp-1 | 734 | U.S. Pat. No. 8,734,809 SEQ ID NO: 119 |
| AAV CSp-10 | 735 | U.S. Pat. No. 8,734,809 SEQ ID NO: 120 |
| AAV CSp-11 | 736 | U.S. Pat. No. 8,734,809 SEQ ID NO: 121 |
| AAV CSp-2 | 737 | U.S. Pat. No. 8,734,809 SEQ ID NO: 122 |
| AAV CSp-3 | 738 | U.S. Pat. No. 8,734,809 SEQ ID NO: 123 |
| AAV CSp-4 | 739 | U.S. Pat. No. 8,734,809 SEQ ID NO: 124 |
| AAV CSp-6 | 740 | U.S. Pat. No. 8,734,809 SEQ ID NO: 125 |
| AAV CSp-7 | 741 | U.S. Pat. No. 8,734,809 SEQ ID NO: 126 |
| AAV CSp-8 | 742 | U.S. Pat. No. 8,734,809 SEQ ID NO: 127 |
| AAV CSp-9 | 743 | U.S. Pat. No. 8,734,809 SEQ ID NO: 128 |
| AAV CHt-2 | 744 | U.S. Pat. No. 8,734,809 SEQ ID NO: 129 |
| AAV CHt-3 | 745 | U.S. Pat. No. 8,734,809 SEQ ID NO: 130 |
| AAV CKd-1 | 746 | U.S. Pat. No. 8,734,809 SEQ ID NO: 131 |
| AAV CKd-10 | 747 | U.S. Pat. No. 8,734,809 SEQ ID NO: 132 |
| AAV CKd-2 | 748 | U.S. Pat. No. 8,734,809 SEQ ID NO: 133 |
| AAV CKd-3 | 749 | U.S. Pat. No. 8,734,809 SEQ ID NO: 134 |
| AAV CKd-4 | 750 | U.S. Pat. No. 8,734,809 SEQ ID NO: 135 |
| AAV CKd-6 | 751 | U.S. Pat. No. 8,734,809 SEQ ID NO: 136 |
| AAV CKd-7 | 752 | U.S. Pat. No. 8,734,809 SEQ ID NO: 137 |
| AAV CKd-8 | 753 | U.S. Pat. No. 8,734,809 SEQ ID NO: 138 |
| AAV CLv-1 | 754 | U.S. Pat. No. 8,734,809 SEQ ID NO: 139 |
| AAV CLv-12 | 755 | U.S. Pat. No. 8,734,809 SEQ ID NO: 140 |
| AAV CLv-13 | 756 | U.S. Pat. No. 8,734,809 SEQ ID NO: 141 |
| AAV CLv-2 | 757 | U.S. Pat. No. 8,734,809 SEQ ID NO: 142 |
| AAV CLv-3 | 758 | U.S. Pat. No. 8,734,809 SEQ ID NO: 143 |
| AAV CLv-4 | 759 | U.S. Pat. No. 8,734,809 SEQ ID NO: 144 |
| AAV CLv-6 | 760 | U.S. Pat. No. 8,734,809 SEQ ID NO: 145 |

TABLE 1-continued

Representative AAV Serotypes

| Serotype | SEQ ID NO | Reference Information |
|---|---|---|
| AAV CLv-8 | 761 | U.S. Pat. No. 8,734,809 SEQ ID NO: 146 |
| AAV CKd-B1 | 762 | U.S. Pat. No. 8,734,809 SEQ ID NO: 147 |
| AAV CKd-B2 | 763 | U.S. Pat. No. 8,734,809 SEQ ID NO: 148 |
| AAV CKd-B3 | 764 | U.S. Pat. No. 8,734,809 SEQ ID NO: 149 |
| AAV CKd-B4 | 765 | U.S. Pat. No. 8,734,809 SEQ ID NO: 150 |
| AAV CKd-B5 | 766 | U.S. Pat. No. 8,734,809 SEQ ID NO: 151 |
| AAV CKd-B6 | 767 | U.S. Pat. No. 8,734,809 SEQ ID NO: 152 |
| AAV CKd-B7 | 768 | U.S. Pat. No. 8,734,809 SEQ ID NO: 153 |
| AAV CKd-B8 | 769 | U.S. Pat. No. 8,734,809 SEQ ID NO: 154 |
| AAV CKd-H1 | 770 | U.S. Pat. No. 8,734,809 SEQ ID NO: 155 |
| AAV CKd-H2 | 771 | U.S. Pat. No. 8,734,809 SEQ ID NO: 156 |
| AAV CKd-H3 | 772 | U.S. Pat. No. 8,734,809 SEQ ID NO: 157 |
| AAV CKd-H4 | 773 | U.S. Pat. No. 8,734,809 SEQ ID NO: 158 |
| AAV CKd-H5 | 774 | U.S. Pat. No. 8,734,809 SEQ ID NO: 159 |
| AAV CKd-H6 | 775 | U.S. Pat. No. 8,734,809 SEQ ID NO: 151 |
| AAV CHt-1 | 776 | U.S. Pat. No. 8,734,809 SEQ ID NO: 160 |
| AAV CHt-P2 | 777 | WO2016065001 SEQ ID NO: 1 |
| AAV CHt-P5 | 778 | WO2016065001 SEQ ID NO: 2 |
| AAV CHt-P9 | 779 | WO2016065001 SEQ ID NO: 3 |
| AAV CBr-7.1 | 780 | WO2016065001 SEQ ID NO: 4 |
| AAV CBr-7.2 | 781 | WO2016065001 SEQ ID NO: 5 |
| AAV CBr-7.3 | 782 | WO2016065001 SEQ ID NO: 6 |
| AAV CBr-7.4 | 783 | WO2016065001 SEQ ID NO: 7 |
| AAV CBr-7.5 | 784 | WO2016065001 SEQ ID NO: 8 |
| AAV CBr-7.7 | 785 | WO2016065001 SEQ ID NO: 9 |
| AAV CBr-7.8 | 786 | WO2016065001 SEQ ID NO: 10 |
| AAV CBr-7.10 | 787 | WO2016065001 SEQ ID NO: 11 |
| AAV CKd-N3 | 788 | WO2016065001 SEQ ID NO: 12 |
| AAV CKd-N4 | 789 | WO2016065001 SEQ ID NO: 13 |
| AAV CKd-N9 | 790 | WO2016065001 SEQ ID NO: 14 |
| AAV CLv-L4 | 791 | WO2016065001 SEQ ID NO: 15 |
| AAV CLv-L5 | 792 | WO2016065001 SEQ ID NO: 16 |
| AAV CLv-L6 | 793 | WO2016065001 SEQ ID NO: 17 |
| AAV CLv-K1 | 794 | WO2016065001 SEQ ID NO: 18 |
| AAV CLv-K3 | 795 | WO2016065001 SEQ ID NO: 19 |
| AAV CLv-K6 | 796 | WO2016065001 SEQ ID NO: 20 |
| AAV CLv-M1 | 797 | WO2016065001 SEQ ID NO: 21 |
| AAV CLv-M11 | 798 | WO2016065001 SEQ ID NO: 22 |
| AAV CLv-M2 | 799 | WO2016065001 SEQ ID NO: 23 |
| AAV CLv-M5 | 800 | WO2016065001 SEQ ID NO: 24 |
| AAV CLv-M6 | 801 | WO2016065001 SEQ ID NO: 25 |
| AAV CLv-M7 | 802 | WO2016065001 SEQ ID NO: 26 |
| AAV CLv-M8 | 803 | WO2016065001 SEQ ID NO: 27 |
| AAV CLv-M9 | 804 | WO2016065001 SEQ ID NO: 28 |
| AAV CHt-P1 | 805 | WO2016065001 SEQ ID NO: 29 |
| AAV CHt-P6 | 806 | WO2016065001 SEQ ID NO: 30 |
| AAV CHt-P8 | 807 | WO2016065001 SEQ ID NO: 31 |
| AAV CHt-6.1 | 808 | WO2016065001 SEQ ID NO: 32 |
| AAV CHt-6.10 | 809 | WO2016065001 SEQ ID NO: 33 |
| AAV CHt-6.5 | 810 | WO2016065001 SEQ ID NO: 34 |
| AAV CHt-6.6 | 811 | WO2016065001 SEQ ID NO: 35 |
| AAV CHt-6.7 | 812 | WO2016065001 SEQ ID NO: 36 |
| AAV CHt-6.8 | 813 | WO2016065001 SEQ ID NO: 37 |
| AAV CSp-8.10 | 814 | WO2016065001 SEQ ID NO: 38 |
| AAV CSp-8.2 | 815 | WO2016065001 SEQ ID NO: 39 |
| AAV CSp-8.4 | 816 | WO2016065001 SEQ ID NO: 40 |
| AAV CSp-8.5 | 817 | WO2016065001 SEQ ID NO: 41 |
| AAV CSp-8.6 | 818 | WO2016065001 SEQ ID NO: 42 |
| AAV CSp-8.7 | 819 | WO2016065001 SEQ ID NO: 43 |
| AAV CSp-8.8 | 820 | WO2016065001 SEQ ID NO: 44 |
| AAV CSp-8.9 | 821 | WO2016065001 SEQ ID NO: 45 |
| AAV CBr-B7.3 | 822 | WO2016065001 SEQ ID NO: 46 |
| AAV CBr-B7.4 | 823 | WO2016065001 SEQ ID NO: 47 |
| AAV3B | 824 | WO2016065001 SEQ ID NO: 48 |
| AAV4 | 825 | WO2016065001 SEQ ID NO: 49 |
| AAV5 | 826 | WO2016065001 SEQ ID NO: 50 |
| AAV CHt-P2 | 827 | WO2016065001 SEQ ID NO: 51 |
| AAV CHt-P5 | 828 | WO2016065001 SEQ ID NO: 52 |
| AAV CHt-P9 | 829 | WO2016065001 SEQ ID NO: 53 |
| AAV CBr-7.1 | 830 | WO2016065001 SEQ ID NO: 54 |
| AAV CBr-7.2 | 831 | WO2016065001 SEQ ID NO: 55 |
| AAV CBr-7.3 | 832 | WO2016065001 SEQ ID NO: 56 |
| AAV CBr-7.4 | 833 | WO2016065001 SEQ ID NO: 57 |
| AAV CBr-7.5 | 834 | WO2016065001 SEQ ID NO: 58 |
| AAV CBr-7.7 | 835 | WO2016065001 SEQ ID NO: 59 |
| AAV CBr-7.8 | 836 | WO2016065001 SEQ ID NO: 60 |

TABLE 1-continued

Representative AAV Serotypes

| Serotype | SEQ ID NO | Reference Information |
|---|---|---|
| AAV CBr-7.10 | 837 | WO2016065001 SEQ ID NO: 61 |
| AAV CKd-N3 | 838 | WO2016065001 SEQ ID NO: 62 |
| AAV CKd-N4 | 839 | WO2016065001 SEQ ID NO: 63 |
| AAV CKd-N9 | 840 | WO2016065001 SEQ ID NO: 64 |
| AAV CLv-L4 | 841 | WO2016065001 SEQ ID NO: 65 |
| AAV CLv-L5 | 842 | WO2016065001 SEQ ID NO: 66 |
| AAV CLv-L6 | 843 | WO2016065001 SEQ ID NO: 67 |
| AAV CLv-K1 | 844 | WO2016065001 SEQ ID NO: 68 |
| AAV CLv-K3 | 845 | WO2016065001 SEQ ID NO: 69 |
| AAV CLv-K6 | 846 | WO2016065001 SEQ ID NO: 70 |
| AAV CLv-M1 | 847 | WO2016065001 SEQ ID NO: 71 |
| AAV CLv-M11 | 848 | WO2016065001 SEQ ID NO: 72 |
| AAV CLv-M2 | 849 | WO2016065001 SEQ ID NO: 73 |
| AAV CLv-M5 | 850 | WO2016065001 SEQ ID NO: 74 |
| AAV CLv-M6 | 851 | WO2016065001 SEQ ID NO: 75 |
| AAV CLv-M7 | 852 | WO2016065001 SEQ ID NO: 76 |
| AAV CLv-M8 | 853 | WO2016065001 SEQ ID NO: 77 |
| AAV CLv-M9 | 854 | WO2016065001 SEQ ID NO: 78 |
| AAV CHt-P1 | 855 | WO2016065001 SEQ ID NO: 79 |
| AAV CHt-P6 | 856 | WO2016065001 SEQ ID NO: 80 |
| AAV CHt-P8 | 857 | WO2016065001 SEQ ID NO: 81 |
| AAV CHt-6.1 | 858 | WO2016065001 SEQ ID NO: 82 |
| AAV CHt-6.10 | 859 | WO2016065001 SEQ ID NO: 83 |
| AAV CHt-6.5 | 860 | WO2016065001 SEQ ID NO: 84 |
| AAV CHt-6.6 | 861 | WO2016065001 SEQ ID NO: 85 |
| AAV CHt-6.7 | 862 | WO2016065001 SEQ ID NO: 86 |
| AAV CHt-6.8 | 863 | WO2016065001 SEQ ID NO: 87 |
| AAV CSp-8.10 | 864 | WO2016065001 SEQ ID NO: 88 |
| AAV CSp-8.2 | 865 | WO2016065001 SEQ ID NO: 89 |
| AAV CSp-8.4 | 866 | WO2016065001 SEQ ID NO: 90 |
| AAV CSp-8.5 | 867 | WO2016065001 SEQ ID NO: 91 |
| AAV CSp-8.6 | 868 | WO2016065001 SEQ ID NO: 92 |
| AAV CSp-8.7 | 869 | WO2016065001 SEQ ID NO: 93 |
| AAV CSp-8.8 | 870 | WO2016065001 SEQ ID NO: 94 |
| AAV CSp-8.9 | 871 | WO2016065001 SEQ ID NO: 95 |
| AAV CBr-B7.3 | 872 | WO2016065001 SEQ ID NO: 96 |
| AAV CBr-B7.4 | 873 | WO2016065001 SEQ ID NO: 97 |
| AAV3B | 874 | WO2016065001 SEQ ID NO: 98 |
| AAV4 | 875 | WO2016065001 SEQ ID NO: 99 |
| AAV5 | 876 | WO2016065001 SEQ ID NO: 100 |
| GPV | 877 | U.S. Pat. No. 9,624,274B2 SEQ ID NO: 192 |
| B19 | 878 | U.S. Pat. No. 9,624,274B2 SEQ ID NO: 193 |
| MVM | 879 | U.S. Pat. No. 9,624,274B2 SEQ ID NO: 194 |
| FPV | 880 | U.S. Pat. No. 9,624,274B2 SEQ ID NO: 195 |
| CPV | 881 | U.S. Pat. No. 9,624,274B2 SEQ ID NO: 196 |
| AAV6 | 882 | U.S. Pat. No. 9,546,112B2 SEQ ID NO: 5 |
| AAV6 | 883 | U.S. Pat. No. 9,457,103B2 SEQ ID NO: 1 |
| AAV2 | 884 | U.S. Pat. No. 9,457,103B2 SEQ ID NO: 2 |
| ShH10 | 885 | U.S. Pat. No. 9,457,103B2 SEQ ID NO: 3 |
| ShH13 | 886 | U.S. Pat. No. 9,457,103B2 SEQ ID NO: 4 |
| ShH10 | 887 | U.S. Pat. No. 9,457,103B2 SEQ ID NO: 5 |
| ShH10 | 888 | U.S. Pat. No. 9,457,103B2 SEQ ID NO: 6 |
| ShH10 | 889 | U.S. Pat. No. 9,457,103B2 SEQ ID NO: 7 |
| ShH10 | 890 | U.S. Pat. No. 9,457,103B2 SEQ ID NO: 8 |
| ShH10 | 891 | U.S. Pat. No. 9,457,103B2 SEQ ID NO: 9 |
| rh74 | 892 | U.S. Pat. No. 9,434,928B2 SEQ ID NO: 1, US2015023924A1 SEQ ID NO: 2 |
| rh74 | 893 | U.S. Pat. No. 9,434,928B2 SEQ ID NO: 2, US2015023924A1 SEQ ID NO: 1 |
| AAV8 | 894 | U.S. Pat. No. 9,434,928B2 SEQ ID NO: 4 |
| rh74 | 895 | U.S. Pat. No. 9,434,928B2 SEQ ID NO: 5 |
| rh74 (RHM4-1) | 896 | US2015023924A1 SEQ ID NO: 5, US20160375110A1 SEQ ID NO: 4 |
| rh74 (RHM15-1) | 897 | US2015023924A1 SEQ ID NO: 6, US20160375110A1 SEQ ID NO: 5 |
| rh74 (RHM15-2) | 898 | US2015023924A1 SEQ ID NO: 7, US20160375110A1 SEQ ID NO: 6 |
| rh74 (RHM15-3/RHM15-5) | 899 | US2015023924A1 SEQ ID NO: 8, US20160375110A1 SEQ ID NO: 7 |
| rh74 (RHM15-4) | 900 | US2015023924A1 SEQ ID NO: 9, US20160375110A1 SEQ ID NO: 8 |
| rh74 (RHM15-6) | 901 | US2015023924A1 SEQ ID NO: 10, US20160375110A1 SEQ ID NO: 9 |
| rh74 (RHM4-1) | 902 | US2015023924A1 SEQ ID NO: 11 |
| rh74 (RHM15-1) | 903 | US2015023924A1 SEQ ID NO: 12 |
| rh74 (RHM15-2) | 904 | US2015023924A1 SEQ ID NO: 13 |

TABLE 1-continued

Representative AAV Serotypes

| Serotype | SEQ ID NO | Reference Information |
| --- | --- | --- |
| rh74 (RHM15-3/RHM15-5) | 905 | US2015023924A1 SEQ ID NO: 14 |
| rh74 (RHM15-4) | 906 | US2015023924A1 SEQ ID NO: 15 |
| rh74 (RHM15-6) | 907 | US2015023924A1 SEQ ID NO: 16 |
| AAV2 (comprising lung specific polypeptide) | 908 | US20160175389A1 SEQ ID NO: 9 |
| AAV2 (comprising lung specific polypeptide) | 909 | US20160175389A1 SEQ ID NO: 10 |
| Anc80 | 910 | US20170051257A1 SEQ ID NO: 1 |
| Anc80 | 911 | US20170051257A1 SEQ ID NO: 2 |
| Anc81 | 912 | US20170051257A1 SEQ ID NO: 3 |
| Anc80 | 913 | US20170051257A1 SEQ ID NO: 4 |
| Anc82 | 914 | US20170051257A1 SEQ ID NO: 5 |
| Anc82 | 915 | US20170051257A1 SEQ ID NO: 6 |
| Anc83 | 916 | US20170051257A1 SEQ ID NO: 7 |
| Anc83 | 917 | US20170051257A1 SEQ ID NO: 8 |
| Anc84 | 918 | US20170051257A1 SEQ ID NO: 9 |
| Anc84 | 919 | US20170051257A1 SEQ ID NO: 10 |
| Anc94 | 920 | US20170051257A1 SEQ ID NO: 11 |
| Anc94 | 921 | US20170051257A1 SEQ ID NO: 12 |
| Anc113 | 922 | US20170051257A1 SEQ ID NO: 13 |
| Anc113 | 923 | US20170051257A1 SEQ ID NO: 14 |
| Anc126 | 924 | US20170051257A1 SEQ ID NO: 15 |
| Anc126 | 925 | US20170051257A1 SEQ ID NO: 16 |
| Anc127 | 926 | US20170051257A1 SEQ ID NO: 17 |
| Anc127 | 927 | US20170051257A1 SEQ ID NO: 18 |
| Anc80L27 | 928 | US20170051257A1 SEQ ID NO: 19 |
| Anc80L59 | 929 | US20170051257A1 SEQ ID NO: 20 |
| Anc80L60 | 930 | US20170051257A1 SEQ ID NO: 21 |
| Anc80L62 | 931 | US20170051257A1 SEQ ID NO: 22 |
| Anc80L65 | 932 | US20170051257A1 SEQ ID NO: 23 |
| Anc80L33 | 933 | US20170051257A1 SEQ ID NO: 24 |
| Anc80L36 | 934 | US20170051257A1 SEQ ID NO: 25 |
| Anc80L44 | 935 | US20170051257A1 SEQ ID NO: 26 |
| Anc80L1 | 936 | US20170051257A1 SEQ ID NO: 35 |
| Anc80L1 | 937 | US20170051257A1 SEQ ID NO: 36 |
| AAV-X1 | 938 | U.S. Pat. No. 8,283,151B2 SEQ ID NO: 11 |
| AAV-X1b | 939 | U.S. Pat. No. 8,283,151B2 SEQ ID NO: 12 |
| AAV-X5 | 940 | U.S. Pat. No. 8,283,151B2 SEQ ID NO: 13 |
| AAV-X19 | 941 | U.S. Pat. No. 8,283,151B2 SEQ ID NO: 14 |
| AAV-X21 | 942 | U.S. Pat. No. 8,283,151B2 SEQ ID NO: 15 |
| AAV-X22 | 943 | U.S. Pat. No. 8,283,151B2 SEQ ID NO: 16 |
| AAV-X23 | 944 | U.S. Pat. No. 8,283,151B2 SEQ ID NO: 17 |
| AAV-X24 | 945 | U.S. Pat. No. 8,283,151B2 SEQ ID NO: 18 |
| AAV-X25 | 946 | U.S. Pat. No. 8,283,151B2 SEQ ID NO: 19 |
| AAV-X26 | 947 | U.S. Pat. No. 8,283,151B2 SEQ ID NO: 20 |
| AAV-X1 | 948 | U.S. Pat. No. 8,283,151B2 SEQ ID NO: 21 |
| AAV-X1b | 949 | U.S. Pat. No. 8,283,151B2 SEQ ID NO: 22 |
| AAV-X5 | 950 | U.S. Pat. No. 8,283,151B2 SEQ ID NO: 23 |
| AAV-X19 | 951 | U.S. Pat. No. 8,283,151B2 SEQ ID NO: 24 |
| AAV-X21 | 952 | U.S. Pat. No. 8,283,151B2 SEQ ID NO: 25 |
| AAV-X22 | 953 | U.S. Pat. No. 8,283,151B2 SEQ ID NO: 26 |
| AAV-X23 | 954 | U.S. Pat. No. 8,283,151B2 SEQ ID NO: 27 |
| AAV-X24 | 955 | U.S. Pat. No. 8,283,151B2 SEQ ID NO: 28 |
| AAV-X25 | 956 | U.S. Pat. No. 8,283,151B2 SEQ ID NO: 29 |
| AAV-X26 | 957 | U.S. Pat. No. 8,283,151B2 SEQ ID NO: 30 |
| AAVrh8 | 958 | WO2016054554A1 SEQ ID NO: 8 |
| AAVrh8VP2FC5 | 959 | WO2016054554A1 SEQ ID NO: 9 |
| AAVrh8VP2FC44 | 960 | WO2016054554A1 SEQ ID NO: 10 |
| AAVrh8VP2ApoB100 | 961 | WO2016054554A1 SEQ ID NO: 11 |
| AAVrh8VP2RVG | 962 | WO2016054554A1 SEQ ID NO: 12 |
| AAVrh8VP2Angiopep-2 VP2 | 963 | WO2016054554A1 SEQ ID NO: 13 |
| AAV9.47VP1.3 | 964 | WO2016054554A1 SEQ ID NO: 14 |
| AAV9.47VP2ICAMg3 | 965 | WO2016054554A1 SEQ ID NO: 15 |
| AAV9.47VP2RVG | 966 | WO2016054554A1 SEQ ID NO: 16 |
| AAV9.47VP2Angiopep-2 | 967 | WO2016054554A1 SEQ ID NO: 17 |
| AAV9.47VP2A-string | 968 | WO2016054554A1 SEQ ID NO: 18 |
| AAVrh8VP2FC5 VP2 | 969 | WO2016054554A1 SEQ ID NO: 19 |
| AAVrh8VP2FC44 VP2 | 970 | WO2016054554A1 SEQ ID NO: 20 |
| AAVrh8VP2ApoB100 VP2 | 971 | WO2016054554A1 SEQ ID NO: 21 |
| AAVrh8VP2RVG VP2 | 972 | WO2016054554A1 SEQ ID NO: 22 |
| AAVrh8VP2Angiopep-2 VP2 | 973 | WO2016054554A1 SEQ ID NO: 23 |

TABLE 1-continued

Representative AAV Serotypes

| Serotype | SEQ ID NO | Reference Information |
|---|---|---|
| AAV9.47VP2ICAMg3 VP2 | 974 | WO2016054554A1 SEQ ID NO: 24 |
| AAV9.47VP2RVG VP2 | 975 | WO2016054554A1 SEQ ID NO: 25 |
| AAV9.47VP2Angiopep-2 VP2 | 976 | WO2016054554A1 SEQ ID NO: 26 |
| AAV9.47VP2A-string VP2 | 977 | WO2016054554A1 SEQ ID NO: 27 |
| rAAV-B1 | 978 | WO2016054557A1 SEQ ID NO: 1 |
| rAAV-B2 | 979 | WO2016054557A1 SEQ ID NO: 2 |
| rAAV-B3 | 980 | WO2016054557A1 SEQ ID NO: 3 |
| rAAV-B4 | 981 | WO2016054557A1 SEQ ID NO: 4 |
| rAAV-B1 | 982 | WO2016054557A1 SEQ ID NO: 5 |
| rAAV-B2 | 983 | WO2016054557A1 SEQ ID NO: 6 |
| rAAV-B3 | 984 | WO2016054557A1 SEQ ID NO: 7 |
| rAAV-B4 | 985 | WO2016054557A1 SEQ ID NO: 8 |
| rAAV-L1 | 986 | WO2016054557A1 SEQ ID NO: 9 |
| rAAV-L2 | 987 | WO2016054557A1 SEQ ID NO: 10 |
| rAAV-L3 | 988 | WO2016054557A1 SEQ ID NO: 11 |
| rAAV-L4 | 989 | WO2016054557A1 SEQ ID NO: 12 |
| rAAV-L1 | 990 | WO2016054557A1 SEQ ID NO: 13 |
| rAAV-L2 | 991 | WO2016054557A1 SEQ ID NO: 14 |
| rAAV-L3 | 992 | WO2016054557A1 SEQ ID NO: 15 |
| rAAV-L4 | 993 | WO2016054557A1 SEQ ID NO: 16 |
| AAV9 | 994 | WO2016073739A1 SEQ ID NO: 3 |
| rAAV | 995 | WO2016081811A1 SEQ ID NO: 1 |
| rAAV | 996 | WO2016081811A1 SEQ ID NO: 2 |
| rAAV | 997 | WO2016081811A1 SEQ ID NO: 3 |
| rAAV | 998 | WO2016081811A1 SEQ ID NO: 4 |
| rAAV | 999 | WO2016081811A1 SEQ ID NO: 5 |
| rAAV | 1000 | WO2016081811A1 SEQ ID NO: 6 |
| rAAV | 1001 | WO2016081811A1 SEQ ID NO: 7 |
| rAAV | 1002 | WO2016081811A1 SEQ ID NO: 8 |
| rAAV | 1003 | WO2016081811A1 SEQ ID NO: 9 |
| rAAV | 1004 | WO2016081811A1 SEQ ID NO: 10 |
| rAAV | 1005 | WO2016081811A1 SEQ ID NO: 11 |
| rAAV | 1006 | WO2016081811A1 SEQ ID NO: 12 |
| rAAV | 1007 | WO2016081811A1 SEQ ID NO: 13 |
| rAAV | 1008 | WO2016081811A1 SEQ ID NO: 14 |
| rAAV | 1009 | WO2016081811A1 SEQ ID NO: 15 |
| rAAV | 1010 | WO2016081811A1 SEQ ID NO: 16 |
| rAAV | 1011 | WO2016081811A1 SEQ ID NO: 17 |
| rAAV | 1012 | WO2016081811A1 SEQ ID NO: 18 |
| rAAV | 1013 | WO2016081811A1 SEQ ID NO: 19 |
| rAAV | 1014 | WO2016081811A1 SEQ ID NO: 20 |
| rAAV | 1015 | WO2016081811A1 SEQ ID NO: 21 |
| rAAV | 1016 | WO2016081811A1 SEQ ID NO: 22 |
| rAAV | 1017 | WO2016081811A1 SEQ ID NO: 23 |
| rAAV | 1018 | WO2016081811A1 SEQ ID NO: 24 |
| rAAV | 1019 | WO2016081811A1 SEQ ID NO: 25 |
| rAAV | 1020 | WO2016081811A1 SEQ ID NO: 26 |
| rAAV | 1021 | WO2016081811A1 SEQ ID NO: 27 |
| rAAV | 1022 | WO2016081811A1 SEQ ID NO: 28 |
| rAAV | 1023 | WO2016081811A1 SEQ ID NO: 29 |
| rAAV | 1024 | WO2016081811A1 SEQ ID NO: 30 |
| rAAV | 1025 | WO2016081811A1 SEQ ID NO: 31 |
| rAAV | 1026 | WO2016081811A1 SEQ ID NO: 32 |
| rAAV | 1027 | WO2016081811A1 SEQ ID NO: 33 |
| rAAV | 1028 | WO2016081811A1 SEQ ID NO: 34 |
| rAAV | 1029 | WO2016081811A1 SEQ ID NO: 35 |
| rAAV | 1030 | WO2016081811A1 SEQ ID NO: 36 |
| rAAV | 1031 | WO2016081811A1 SEQ ID NO: 37 |
| rAAV | 1032 | WO2016081811A1 SEQ ID NO: 38 |
| rAAV | 1033 | WO2016081811A1 SEQ ID NO: 39 |
| rAAV | 1034 | WO2016081811A1 SEQ ID NO: 40 |
| rAAV | 1035 | WO2016081811A1 SEQ ID NO: 41 |
| rAAV | 1036 | WO2016081811A1 SEQ ID NO: 42 |
| rAAV | 1037 | WO2016081811A1 SEQ ID NO: 43 |
| rAAV | 1038 | WO2016081811A1 SEQ ID NO: 44 |
| rAAV | 1039 | WO2016081811A1 SEQ ID NO: 45 |
| rAAV | 1040 | WO2016081811A1 SEQ ID NO: 46 |
| rAAV | 1041 | WO2016081811A1 SEQ ID NO: 47 |
| rAAV | 1042 | WO2016081811A1 SEQ ID NO: 48 |
| rAAV | 1043 | WO2016081811A1 SEQ ID NO: 49 |
| rAAV | 1044 | WO2016081811A1 SEQ ID NO: 50 |
| rAAV | 1045 | WO2016081811A1 SEQ ID NO: 51 |
| rAAV | 1046 | WO2016081811A1 SEQ ID NO: 52 |
| rAAV | 1047 | WO2016081811A1 SEQ ID NO: 53 |
| rAAV | 1048 | WO2016081811A1 SEQ ID NO: 54 |

TABLE 1-continued

Representative AAV Serotypes

| Serotype | SEQ ID NO | Reference Information |
|---|---|---|
| rAAV | 1049 | WO2016081811A1 SEQ ID NO: 55 |
| rAAV | 1050 | WO2016081811A1 SEQ ID NO: 56 |
| rAAV | 1051 | WO2016081811A1 SEQ ID NO: 57 |
| rAAV | 1052 | WO2016081811A1 SEQ ID NO: 58 |
| rAAV | 1053 | WO2016081811A1 SEQ ID NO: 59 |
| rAAV | 1054 | WO2016081811A1 SEQ ID NO: 60 |
| rAAV | 1055 | WO2016081811A1 SEQ ID NO: 61 |
| rAAV | 1056 | WO2016081811A1 SEQ ID NO: 62 |
| rAAV | 1057 | WO2016081811A1 SEQ ID NO: 63 |
| rAAV | 1058 | WO2016081811A1 SEQ ID NO: 64 |
| rAAV | 1059 | WO2016081811A1 SEQ ID NO: 65 |
| rAAV | 1060 | WO2016081811A1 SEQ ID NO: 66 |
| rAAV | 1061 | WO2016081811A1 SEQ ID NO: 67 |
| rAAV | 1062 | WO2016081811A1 SEQ ID NO: 68 |
| rAAV | 1063 | WO2016081811A1 SEQ ID NO: 69 |
| rAAV | 1064 | WO2016081811A1 SEQ ID NO: 70 |
| rAAV | 1065 | WO2016081811A1 SEQ ID NO: 71 |
| rAAV | 1066 | WO2016081811A1 SEQ ID NO: 72 |
| rAAV | 1067 | WO2016081811A1 SEQ ID NO: 73 |
| rAAV | 1068 | WO2016081811A1 SEQ ID NO: 74 |
| rAAV | 1069 | WO2016081811A1 SEQ ID NO: 75 |
| rAAV | 1070 | WO2016081811A1 SEQ ID NO: 76 |
| rAAV | 1071 | WO2016081811A1 SEQ ID NO: 77 |
| rAAV | 1072 | WO2016081811A1 SEQ ID NO: 78 |
| rAAV | 1073 | WO2016081811A1 SEQ ID NO: 79 |
| rAAV | 1074 | WO2016081811A1 SEQ ID NO: 80 |
| rAAV | 1075 | WO2016081811A1 SEQ ID NO: 81 |
| rAAV | 1076 | WO2016081811A1 SEQ ID NO: 82 |
| rAAV | 1077 | WO2016081811A1 SEQ ID NO: 83 |
| rAAV | 1078 | WO2016081811A1 SEQ ID NO: 84 |
| rAAV | 1079 | WO2016081811A1 SEQ ID NO: 85 |
| rAAV | 1080 | WO2016081811A1 SEQ ID NO: 86 |
| rAAV | 1081 | WO2016081811A1 SEQ ID NO: 87 |
| rAAV | 1082 | WO2016081811A1 SEQ ID NO: 88 |
| rAAV | 1083 | WO2016081811A1 SEQ ID NO: 89 |
| rAAV | 1084 | WO2016081811A1 SEQ ID NO: 90 |
| rAAV | 1085 | WO2016081811A1 SEQ ID NO: 91 |
| rAAV | 1086 | WO2016081811A1 SEQ ID NO: 92 |
| rAAV | 1087 | WO2016081811A1 SEQ ID NO: 93 |
| rAAV | 1088 | WO2016081811A1 SEQ ID NO: 94 |
| rAAV | 1089 | WO2016081811A1 SEQ ID NO: 95 |
| rAAV | 1090 | WO2016081811A1 SEQ ID NO: 96 |
| rAAV | 1091 | WO2016081811A1 SEQ ID NO: 97 |
| rAAV | 1092 | WO2016081811A1 SEQ ID NO: 98 |
| rAAV | 1093 | WO2016081811A1 SEQ ID NO: 99 |
| rAAV | 1094 | WO2016081811A1 SEQ ID NO: 100 |
| rAAV | 1095 | WO2016081811A1 SEQ ID NO: 101 |
| rAAV | 1096 | WO2016081811A1 SEQ ID NO: 102 |
| rAAV | 1097 | WO2016081811A1 SEQ ID NO: 103 |
| rAAV | 1098 | WO2016081811A1 SEQ ID NO: 104 |
| rAAV | 1099 | WO2016081811A1 SEQ ID NO: 105 |
| rAAV | 1100 | WO2016081811A1 SEQ ID NO: 106 |
| rAAV | 1101 | WO2016081811A1 SEQ ID NO: 107 |
| rAAV | 1102 | WO2016081811A1 SEQ ID NO: 108 |
| rAAV | 1103 | WO2016081811A1 SEQ ID NO: 109 |
| rAAV | 1104 | WO2016081811A1 SEQ ID NO: 110 |
| rAAV | 1105 | WO2016081811A1 SEQ ID NO: 111 |
| rAAV | 1106 | WO2016081811A1 SEQ ID NO: 112 |
| rAAV | 1107 | WO2016081811A1 SEQ ID NO: 113 |
| rAAV | 1108 | WO2016081811A1 SEQ ID NO: 114 |
| rAAV | 1109 | WO2016081811A1 SEQ ID NO: 115 |
| rAAV | 1110 | WO2016081811A1 SEQ ID NO: 116 |
| rAAV | 1111 | WO2016081811A1 SEQ ID NO: 117 |
| rAAV | 1112 | WO2016081811A1 SEQ ID NO: 118 |
| rAAV | 1113 | WO2016081811A1 SEQ ID NO: 119 |
| rAAV | 1114 | WO2016081811A1 SEQ ID NO: 120 |
| rAAV | 1115 | WO2016081811A1 SEQ ID NO: 121 |
| rAAV | 1116 | WO2016081811A1 SEQ ID NO: 122 |
| rAAV | 1117 | WO2016081811A1 SEQ ID NO: 123 |
| rAAV | 1118 | WO2016081811A1 SEQ ID NO: 124 |
| rAAV | 1119 | WO2016081811A1 SEQ ID NO: 125 |
| rAAV | 1120 | WO2016081811A1 SEQ ID NO: 126 |
| rAAV | 1121 | WO2016081811A1 SEQ ID NO: 127 |
| rAAV | 1122 | WO2016081811A1 SEQ ID NO: 128 |
| AAV8 E532K | 1123 | WO2016081811A1 SEQ ID NO: 133 |
| AAV8 E532K | 1124 | WO2016081811A1 SEQ ID NO: 134 |

TABLE 1-continued

Representative AAV Serotypes

| Serotype | SEQ ID NO | Reference Information |
|---|---|---|
| rAAV4 | 1125 | WO2016115382A1 SEQ ID NO: 2 |
| rAAV4 | 1126 | WO2016115382A1 SEQ ID NO: 3 |
| rAAV4 | 1127 | WO2016115382A1 SEQ ID NO: 4 |
| rAAV4 | 1128 | WO2016115382A1 SEQ ID NO: 5 |
| rAAV4 | 1129 | WO2016115382A1 SEQ ID NO: 6 |
| rAAV4 | 1130 | WO2016115382A1 SEQ ID NO: 7 |
| rAAV4 | 1131 | WO2016115382A1 SEQ ID NO: 8 |
| rAAV4 | 1132 | WO2016115382A1 SEQ ID NO: 9 |
| rAAV4 | 1133 | WO2016115382A1 SEQ ID NO: 10 |
| rAAV4 | 1134 | WO2016115382A1 SEQ ID NO: 11 |
| rAAV4 | 1135 | WO2016115382A1 SEQ ID NO: 12 |
| rAAV4 | 1136 | WO2016115382A1 SEQ ID NO: 13 |
| rAAV4 | 1137 | WO2016115382A1 SEQ ID NO: 14 |
| rAAV4 | 1138 | WO2016115382A1 SEQ ID NO: 15 |
| rAAV4 | 1139 | WO2016115382A1 SEQ ID NO: 16 |
| rAAV4 | 1140 | WO2016115382A1 SEQ ID NO: 17 |
| rAAV4 | 1141 | WO2016115382A1 SEQ ID NO: 18 |
| rAAV4 | 1142 | WO2016115382A1 SEQ ID NO: 19 |
| rAAV4 | 1143 | WO2016115382A1 SEQ ID NO: 20 |
| rAAV4 | 1144 | WO2016115382A1 SEQ ID NO: 21 |
| AAV11 | 1145 | WO2016115382A1 SEQ ID NO: 22 |
| AAV12 | 1146 | WO2016115382A1 SEQ ID NO: 23 |
| rh32 | 1147 | WO2016115382A1 SEQ ID NO: 25 |
| rh33 | 1148 | WO2016115382A1 SEQ ID NO: 26 |
| rh34 | 1149 | WO2016115382A1 SEQ ID NO: 27 |
| rAAV4 | 1150 | WO2016115382A1 SEQ ID NO: 28 |
| rAAV4 | 1151 | WO2016115382A1 SEQ ID NO: 29 |
| rAAV4 | 1152 | WO2016115382A1 SEQ ID NO: 30 |
| rAAV4 | 1153 | WO2016115382A1 SEQ ID NO: 31 |
| rAAV4 | 1154 | WO2016115382A1 SEQ ID NO: 32 |
| rAAV4 | 1155 | WO2016115382A1 SEQ ID NO: 33 |
| AAV2/8 | 1156 | WO2016131981A1 SEQ ID NO: 47 |
| AAV2/8 | 1157 | WO2016131981A1 SEQ ID NO: 48 |
| ancestral AAV | 1158 | WO2016154344A1 SEQ ID NO: 7 |
| ancestral AAV variant C4 | 1159 | WO2016154344A1 SEQ ID NO: 13 |
| ancestral AAV variant C7 | 1160 | WO2016154344A1 SEQ ID NO: 14 |
| ancestral AAV variant G4 | 1161 | WO2016154344A1 SEQ ID NO: 15 |
| consensus amino acid sequence of ancestral AAV variants, C4, C7 and G4 | 1162 | WO2016154344A1 SEQ ID NO: 16 |
| consensus amino acid sequence of ancestral AAV variants, C4 and C7 | 1163 | WO2016154344A1 SEQ ID NO: 17 |
| AAV8 (with a AAV2 phospholipase domain) | 1164 | WO2016150403A1 SEQ ID NO: 13 |
| AAV VR-942n | 1165 | US20160289275A1 SEQ ID NO: 10 |
| AAV5-A (M569V) | 1166 | US20160289275A1 SEQ ID NO: 13 |
| AAV5-A (M569V) | 1167 | US20160289275A1 SEQ ID NO: 14 |
| AAV5-A (Y585V) | 1168 | US20160289275A1 SEQ ID NO: 16 |
| AAV5-A (Y585V) | 1169 | US20160289275A1 SEQ ID NO: 17 |
| AAV5-A (L587T) | 1170 | US20160289275A1 SEQ ID NO: 19 |
| AAV5-A (L587T) | 1171 | US20160289275A1 SEQ ID NO: 20 |
| AAV5-A (Y585V/L587T) | 1172 | US20160289275A1 SEQ ID NO: 22 |
| AAV5-A (Y585V/L587T) | 1173 | US20160289275A1 SEQ ID NO: 23 |
| AAV5-B (D652A) | 1174 | US20160289275A1 SEQ ID NO: 25 |
| AAV5-B (D652A) | 1175 | US20160289275A1 SEQ ID NO: 26 |
| AAV5-B (T362M) | 1176 | US20160289275A1 SEQ ID NO: 28 |
| AAV5-B (T362M) | 1177 | US20160289275A1 SEQ ID NO: 29 |
| AAV5-B (Q359D) | 1178 | US20160289275A1 SEQ ID NO: 31 |
| AAV5-B (Q359D) | 1179 | US20160289275A1 SEQ ID NO: 32 |
| AAV5-B (E350Q) | 1180 | US20160289275A1 SEQ ID NO: 34 |
| AAV5-B (E350Q) | 1181 | US20160289275A1 SEQ ID NO: 35 |
| AAV5-B (P533S) | 1182 | US20160289275A1 SEQ ID NO: 37 |
| AAV5-B (P533S) | 1183 | US20160289275A1 SEQ ID NO: 38 |
| AAV5-B (P533G) | 1184 | US20160289275A1 SEQ ID NO: 40 |
| AAV5-B (P533G) | 1185 | US20160289275A1 SEQ ID NO: 41 |
| AAV5-mutation in loop VII | 1186 | US20160289275A1 SEQ ID NO: 43 |
| AAV5-mutation in loop VII | 1187 | US20160289275A1 SEQ ID NO: 44 |
| AAV8 | 1188 | US20160289275A1 SEQ ID NO: 47 |
| Mut A (LK03/AAV8) | 1189 | WO2016181123A1 SEQ ID NO: 1 |
| Mut B (LK03/AAV5) | 1190 | WO2016181123A1 SEQ ID NO: 2 |
| Mut C (AAV8/AAV3B) | 1191 | WO2016181123A1 SEQ ID NO: 3 |
| Mut D (AAV5/AAV3B) | 1192 | WO2016181123A1 SEQ ID NO: 4 |
| Mut E (AAV8/AAV3B) | 1193 | WO2016181123A1 SEQ ID NO: 5 |
| Mut F (AAV3B/AAV8) | 1194 | WO2016181123A1 SEQ ID NO: 6 |
| AAV44.9 | 1195 | WO2016183297A1 SEQ ID NO: 4 |

TABLE 1-continued

Representative AAV Serotypes

| Serotype | SEQ ID NO | Reference Information |
|---|---|---|
| AAV44.9 | 1196 | WO2016183297A1 SEQ ID NO: 5 |
| AAVrh8 | 1197 | WO2016183297A1 SEQ ID NO: 6 |
| AAV44.9 (S470N) | 1198 | WO2016183297A1 SEQ ID NO: 9 |
| rh74 VP1 | 1199 | US20160375110A1 SEQ ID NO: 1 |
| AAV-LK03 (L125I) | 1200 | WO2017015102A1 SEQ ID NO: 5 |
| AAV3B (S663V + T492V) | 1201 | WO2017015102A1 SEQ ID NO: 6 |
| Anc80 | 1202 | WO2017019994A2 SEQ ID NO: 1 |
| Anc80 | 1203 | WO2017019994A2 SEQ ID NO: 2 |
| Anc81 | 1204 | WO2017019994A2 SEQ ID NO: 3 |
| Anc81 | 1205 | WO2017019994A2 SEQ ID NO: 4 |
| Anc82 | 1206 | WO2017019994A2 SEQ ID NO: 5 |
| Anc82 | 1207 | WO2017019994A2 SEQ ID NO: 6 |
| Anc83 | 1208 | WO2017019994A2 SEQ ID NO: 7 |
| Anc83 | 1209 | WO2017019994A2 SEQ ID NO: 8 |
| Anc84 | 1210 | WO2017019994A2 SEQ ID NO: 9 |
| Anc84 | 1211 | WO2017019994A2 SEQ ID NO: 10 |
| Anc94 | 1212 | WO2017019994A2 SEQ ID NO: 11 |
| Anc94 | 1213 | WO2017019994A2 SEQ ID NO: 12 |
| Anc113 | 1214 | WO2017019994A2 SEQ ID NO: 13 |
| Anc113 | 1215 | WO2017019994A2 SEQ ID NO: 14 |
| Anc126 | 1216 | WO2017019994A2 SEQ ID NO: 15 |
| Anc126 | 1217 | WO2017019994A2 SEQ ID NO: 16 |
| Anc127 | 1218 | WO2017019994A2 SEQ ID NO: 17 |
| Anc127 | 1219 | WO2017019994A2 SEQ ID NO: 18 |
| Anc80L27 | 1220 | WO2017019994A2 SEQ ID NO: 19 |
| Anc80L59 | 1221 | WO2017019994A2 SEQ ID NO: 20 |
| Anc80L60 | 1222 | WO2017019994A2 SEQ ID NO: 21 |
| Anc80L62 | 1223 | WO2017019994A2 SEQ ID NO: 22 |
| Anc80L65 | 1224 | WO2017019994A2 SEQ ID NO: 23 |
| Anc80L33 | 1225 | WO2017019994A2 SEQ ID NO: 24 |
| Anc80L36 | 1226 | WO2017019994A2 SEQ ID NO: 25 |
| Anc80L44 | 1227 | WO2017019994A2 SEQ ID NO: 26 |
| Anc80L1 | 1228 | WO2017019994A2 SEQ ID NO: 35 |
| Anc80L1 | 1229 | WO2017019994A2 SEQ ID NO: 36 |
| AAVrh10 | 1230 | WO2017019994A2 SEQ ID NO: 41 |
| Anc110 | 1231 | WO2017019994A2 SEQ ID NO: 42 |
| Anc110 | 1232 | WO2017019994A2 SEQ ID NO: 43 |
| AAVrh32.33 | 1233 | WO2017019994A2 SEQ ID NO: 45 |
| AAVrh74 | 1234 | WO2017049031A1 SEQ ID NO: 1 |
| AAV2 | 1235 | WO2017053629A2 SEQ ID NO: 49 |
| AAV2 | 1236 | WO2017053629A2 SEQ ID NO: 50 |
| AAV2 | 1237 | WO2017053629A2 SEQ ID NO: 82 |
| Parvo-like virus | 1238 | WO2017070476A2 SEQ ID NO: 1 |
| Parvo-like virus | 1239 | WO2017070476A2 SEQ ID NO: 2 |
| Parvo-like virus | 1240 | WO2017070476A2 SEQ ID NO: 3 |
| Parvo-like virus | 1241 | WO2017070476A2 SEQ ID NO: 4 |
| Parvo-like virus | 1242 | WO2017070476A2 SEQ ID NO: 5 |
| Parvo-like virus | 1243 | WO2017070476A2 SEQ ID NO: 6 |
| AAVrh.10 | 1244 | WO2017070516A1 SEQ ID NO: 7 |
| AAVrh.10 | 1245 | WO2017070516A1 SEQ ID NO: 14 |
| AAV2tYF | 1246 | WO2017070491A1 SEQ ID NO: 1 |
| AAV-SPK | 1247 | WO2017075619A1 SEQ ID NO: 28 |
| AAV2.5 | 1248 | US20170128528A1 SEQ ID NO: 13 |
| AAV1.1 | 1249 | US20170128528A1 SEQ ID NO: 15 |
| AAV6.1 | 1250 | US20170128528A1 SEQ ID NO: 17 |
| AAV6.3.1 | 1251 | US20170128528A1 SEQ ID NO: 18 |
| AAV2i8 | 1252 | US20170128528A1 SEQ ID NO: 28 |
| AAV2i8 | 1253 | US20170128528A1 SEQ ID NO: 29 |
| ttAAV | 1254 | US20170128528A1 SEQ ID NO: 30 |
| ttAAV-S312N | 1255 | US20170128528A1 SEQ ID NO: 32 |
| ttAAV-S312N | 1256 | US20170128528A1 SEQ ID NO: 33 |
| AAV6 (Y705, Y731, and T492) | 1257 | WO2016134337A1 SEQ ID NO: 24 |
| AAV2 | 1258 | WO2016134375A1 SEQ ID NO: 9 |
| AAV2 | 1259 | WO2016134375A1 SEQ ID NO: 10 |

The contents of each of the patents, applications, and/or publications listed in Table 1 are hereby incorporated by reference in their entirety.

In some embodiments, the AAV serotype may be, or may comprise a sequence as described in International Patent Publication WO2015038958, the contents of which are herein incorporated by reference in their entirety, such as, but not limited to, AAV9 (SEQ ID NO: 2 and 11 of WO2015038958 or SEQ ID NO: 135 and 136 herein), PHP.B (SEQ ID NO: 8 and 9 of WO2015038958, herein SEQ ID NO: 3 and 4), G2B-13 (SEQ ID NO: 12 of WO2015038958, herein SEQ ID NO: 5), G2B-26 (SEQ ID NO: 13 of WO2015038958, herein SEQ ID NO: 3), TH1.1-32 (SEQ ID NO: 14 of WO2015038958, herein SEQ ID NO:

6), TH1.1-35 (SEQ ID NO: 15 of WO2015038958, herein SEQ ID NO: 7), or variants thereof. Further, any of the "targeting peptides" or "amino acid inserts" (used herein interchangeably to mean sequences that may be inserted into an AAV capsid sequence to facilitate delivery to CNS tissue) described in WO2015038958, may be inserted into any parent AAV serotype, such as, but not limited to, AAV9 (SEQ ID NO: 135 for the DNA sequence and SEQ ID NO: 136 for the amino acid sequence). In some embodiments, the amino acid insert is inserted between amino acids 586-592 of the parent AAV (e.g., AAV9). In some embodiments, the amino acid insert is inserted between amino acids 588-589 of the parent AAV sequence. The amino acid insert may be, but is not limited to, any of the following amino acid sequences, TLAVPFK (SEQ ID NO: 1 of WO2015038958; herein SEQ ID NO: 1260), KFPVALT (SEQ ID NO: 3 of WO2015038958; herein SEQ ID NO: 1261), LAVPFK (SEQ ID NO: 31 of WO2015038958; herein SEQ ID NO: 1262), AVPFK (SEQ ID NO: 32 of WO2015038958; herein SEQ ID NO: 1263), VPFK (SEQ ID NO: 33 of WO2015038958; herein SEQ ID NO: 1264), TLAVPF (SEQ ID NO: 34 of WO2015038958; herein SEQ ID NO: 1265), TLAVP (SEQ ID NO: 35 of WO2015038958; herein SEQ ID NO: 1266), TLAV (SEQ ID NO: 36 of WO2015038958; herein SEQ ID NO: 1267), SVSKPFL (SEQ ID NO: 28 of WO2015038958; herein SEQ ID NO: 1268), FTLTTPK (SEQ ID NO: 29 of WO2015038958; herein SEQ ID NO: 1269), MNATKNV (SEQ ID NO: 30 of WO2015038958; herein SEQ ID NO: 1270), QSSQTPR (SEQ ID NO: 54 of WO2015038958; herein SEQ ID NO: 1271), ILGTGTS (SEQ ID NO: 55 of WO2015038958; herein SEQ ID NO: 1272), TRTNPEA (SEQ ID NO: 56 of WO2015038958; herein SEQ ID NO: 1273), NGGTSSS (SEQ ID NO: 58 of WO2015038958; herein SEQ ID NO: 1274), or YTLSQGW (SEQ ID NO: 60 of WO2015038958; herein SEQ ID NO: 1275). Non-limiting examples of nucleotide sequences that may encode the amino acid inserts include, but are not limited to, the following, AAGTTTCCTGTGGCGTTGACT (for SEQ ID NO: 3 of WO2015038958; herein SEQ ID NO: 1276), ACTTTGGCGGTGCCTTTTAAG (SEQ ID NO: 24 and 49 of WO2015038958; herein SEQ ID NO: 1277), AGTGTGAGTAAGCCTTTTTTG (SEQ ID NO: 25 of WO2015038958; herein SEQ ID NO: 1278), TTTACGTTGACGACGCCTAAG (SEQ ID NO: 26 of WO2015038958; herein SEQ ID NO: 1279), ATGAATGCTACGAAGAATGTG (SEQ ID NO: 27 of WO2015038958; herein SEQ ID NO: 1280), CAGTCGTCGCAGACGCCTAGG (SEQ ID NO: 48 of WO2015038958; herein SEQ ID NO: 1281), ATTCTGGGGACTGGTACTTCG (SEQ ID NO: 50 and 52 of WO2015038958; herein SEQ ID NO: 1282), ACGCGGACTAATCCTGAGGCT (SEQ ID NO: 51 of WO2015038958; herein SEQ ID NO: 1283), AATGGGGGGACTAGTAGTTCT (SEQ ID NO: 53 of WO2015038958; herein SEQ ID NO: 1284), or TATACTTTGTCGCAGGGTTGG (SEQ ID NO: 59 of WO2015038958; herein SEQ ID NO: 1285).

In some embodiments, the AAV serotype may be, or may comprise a sequence as described in International Patent Publication WO2017100671, the contents of which are herein incorporated by reference in their entirety, such as, but not limited to, AAV9 K449R (SEQ ID NO: 45 of WO2017100671; herein SEQ ID NO: 9), PHP.N (SEQ ID NO: 46 of WO2017100671, herein SEQ ID NO: 2), PHP.S (SEQ ID NO: 47 of WO2017100671, herein SEQ ID NO: 8), or variants thereof. Further, any of the targeting peptides or amino acid inserts described in WO2017100671 may be inserted into any parent AAV serotype, such as, but not limited to, AAV9 (SEQ ID NO: 9 or SEQ ID NO: 136). In some embodiments, the amino acid insert is inserted between amino acids 586-592 of the parent AAV (e.g., AAV9). In some embodiments, the amino acid insert is inserted between amino acids 588-589 of the parent AAV sequence. The amino acid insert may be, but is not limited to, any of the following amino acid sequences, AQTLAVPFKAQ (SEQ ID NO: 1 of WO2017100671; herein SEQ ID NO: 1286), AQSVSKPFLAQ (SEQ ID NO: 2 of WO2017100671; herein SEQ ID NO: 1287), AQFTLTTPKAQ (SEQ ID NO: 3 in the sequence listing of WO2017100671; herein SEQ ID NO: 1288), DGTLAVPFKAQ (SEQ ID NO: 4 in the sequence listing of WO2017100671; herein SEQ ID NO: 1289), ESTLAVPFKAQ (SEQ ID NO: 5 of WO2017100671; herein SEQ ID NO: 1290), GGTLAVPFKAQ (SEQ ID NO: 6 of WO2017100671; herein SEQ ID NO: 1291), AQTLATPFKAQ (SEQ ID NO: 7 and 33 of WO2017100671; herein SEQ ID NO: 1292), ATTLATPFKAQ (SEQ ID NO: 8 of WO2017100671; herein SEQ ID NO: 1293), DGTLATPFKAQ (SEQ ID NO: 9 of WO2017100671; herein SEQ ID NO: 1294), GGTLATPFKAQ (SEQ ID NO: 10 of WO2017100671; herein SEQ ID NO: 1295), SGSLAVPFKAQ (SEQ ID NO: 11 of WO2017100671; herein SEQ ID NO: 1296), AQTLAQPFKAQ (SEQ ID NO: 12 of WO2017100671; herein SEQ ID NO: 1297), AQTLQQPFKAQ (SEQ ID NO: 13 of WO2017100671; herein SEQ ID NO: 1298), AQTLSNPFKAQ (SEQ ID NO: 14 of WO2017100671; herein SEQ ID NO: 1299), AQTLAVPFSNP (SEQ ID NO: 15 of WO2017100671; herein SEQ ID NO: 1300), QGTLAVPFKAQ (SEQ ID NO: 16 of WO2017100671; herein SEQ ID NO: 1301), NQTLAVPFKAQ (SEQ ID NO: 17 of WO2017100671; herein SEQ ID NO: 1302), EGSLAVPFKAQ (SEQ ID NO: 18 of WO2017100671; herein SEQ ID NO: 1303), SGNLAVPFKAQ (SEQ ID NO: 19 of WO2017100671; herein SEQ ID NO: 1304), EGTLAVPFKAQ (SEQ ID NO: 20 of WO2017100671; herein SEQ ID NO: 1305), DSTLAVPFKAQ (SEQ ID NO: 21 in Table 1 of WO2017100671; herein SEQ ID NO: 1306), AVTLAVPFKAQ (SEQ ID NO: 22 of WO2017100671; herein SEQ ID NO: 1307), AQTLSTPFKAQ (SEQ ID NO: 23 of WO2017100671; herein SEQ ID NO: 1308), AQTLPQPFKAQ (SEQ ID NO: 24 and 32 of WO2017100671; herein SEQ ID NO: 1309), AQTLSQPFKAQ (SEQ ID NO: 25 of WO2017100671; herein SEQ ID NO: 1310), AQTLQLPFKAQ (SEQ ID NO: 26 of WO2017100671; herein SEQ ID NO: 1311), AQTLTMPFKAQ (SEQ ID NO: 27, and 34 of WO2017100671 and SEQ ID NO: 35 in the sequence listing of WO2017100671; herein SEQ ID NO: 1312), AQTLTTPFKAQ (SEQ ID NO: 28 of WO2017100671; herein SEQ ID NO: 1313), AQYTLSQGWAQ (SEQ ID NO: 29 of WO2017100671; herein SEQ ID NO: 1314), AQMNATKNVAQ (SEQ ID NO: 30 of WO2017100671; herein SEQ ID NO: 1315), AQVSGGHHSAQ (SEQ ID NO: 31 of WO2017100671; herein SEQ ID NO: 1316), AQTLTAPFKAQ (SEQ ID NO: 35 in Table 1 of WO2017100671; herein SEQ ID NO: 1317), AQTLSKPFKAQ (SEQ ID NO: 36 of WO2017100671; herein SEQ ID NO: 1318), QAVRTSL (SEQ ID NO: 37 of WO2017100671; herein SEQ ID NO: 1319), YTLSQGW (SEQ ID NO: 38 of WO2017100671; herein SEQ ID NO: 1275), LAKERLS (SEQ ID NO: 39 of WO2017100671; herein SEQ ID NO: 1320), TLAVPFK (SEQ ID NO: 40 in the sequence listing of WO2017100671; herein SEQ ID NO: 1260), SVSKPFL (SEQ ID NO: 41 of WO2017100671; herein SEQ ID NO: 1268), FTLTTPK (SEQ ID NO: 42 of WO2017100671; herein SEQ ID NO: 1269), MNSTKNV (SEQ ID NO: 43 of WO2017100671; herein SEQ ID NO: 1321), VSGGHHS (SEQ ID NO: 44 of WO2017100671; herein SEQ ID NO: 1322), SAQTLAVPFKAQAQ (SEQ ID NO: 48 of WO2017100671; herein SEQ ID NO: 1323), SXXXLAVPFKAQAQ (SEQ ID NO: 49 of WO2017100671 wherein X may be any amino acid; herein SEQ ID NO: 1324), SAQXXXVPFKAQAQ (SEQ ID NO: 50 of WO2017100671 wherein X may be any amino acid; herein SEQ ID NO: 1325), SAQTLXXXFKAQAQ (SEQ ID NO: 51 of WO2017100671 wherein X may be any amino acid; herein SEQ ID NO: 1326), SAQTLAVXXXAQAQ (SEQ ID NO: 52 of WO2017100671 wherein X may be any amino acid; herein SEQ ID NO: 1327), SAQTLAVPFXXXAQ (SEQ ID NO: 53 of WO2017100671 wherein X may be any amino acid; herein SEQ ID NO: 1328), TNHQSAQ (SEQ ID NO: 65 of WO2017100671; herein SEQ ID NO: 1329), AQAQTGW (SEQ ID NO: 66 of WO2017100671; herein SEQ ID NO: 1330), DGTLATPFK (SEQ ID NO: 67 of WO2017100671; herein SEQ ID NO: 1331), DGTLATPFKXX (SEQ ID NO: 68 of WO2017100671 wherein X may be any amino acid; herein SEQ ID NO: 1332), LAVPFKAQ (SEQ ID NO: 80 of WO2017100671; herein SEQ ID NO: 1333), VPFKAQ (SEQ ID NO: 81 of WO2017100671; herein SEQ ID NO: 1334), FKAQ (SEQ ID NO: 82 of WO2017100671; herein SEQ ID NO: 1335), AQTLAV (SEQ ID NO: 83 of WO2017100671; herein SEQ ID NO: 1336), AQTLAVPF (SEQ ID NO: 84 of WO2017100671; herein SEQ ID NO: 1337), QAVR (SEQ ID NO: 85 of WO2017100671; herein SEQ ID NO: 1338), AVRT (SEQ ID NO: 86 of WO2017100671; herein SEQ ID NO: 1339), VRTS (SEQ ID NO: 87 of WO2017100671; herein SEQ ID NO: 1340), RTSL (SEQ ID NO: 88 of WO2017100671; herein SEQ ID NO: 1341), QAVRT (SEQ ID NO: 89 of WO2017100671; herein SEQ ID NO: 1342), AVRTS (SEQ ID NO: 90 of WO2017100671; herein SEQ ID NO: 1343), VRTSL (SEQ ID NO: 91 of WO2017100671; herein SEQ ID NO: 1344), QAVRTS (SEQ ID NO: 92 of WO2017100671; herein SEQ ID NO: 1345), or AVRTSL (SEQ ID NO: 93 of WO2017100671; herein SEQ ID NO: 1346).

Non-limiting examples of nucleotide sequences that may encode the amino acid inserts include the following, GATGGGACTTTGGCGGTGCCTTTTAAGGCACAG (SEQ ID NO: 54 of WO2017100671; herein SEQ ID NO: 1347), GATGGGACGTTGGCGGTGCCTTTTAAGGCACAG (SEQ ID NO: 55 of WO2017100671; herein SEQ ID NO: 1348), CAGGCGGTTAGGACGTCTTTG (SEQ ID NO: 56 of WO2017100671; herein SEQ ID NO: 1349), CAGGTCTTCACGGACTCAGACTATCAG (SEQ ID NO: 57 and 78 of WO2017100671; herein SEQ ID NO: 1350), CAAGTAAAACCTCTACAAATGTGGTAAAATCG (SEQ ID NO: 58 of WO2017100671; herein SEQ ID NO: 1351), ACTCATCGACCAATACTTGTACTATCTCTAGAAC (SEQ ID NO: 59 of WO2017100671; herein SEQ ID NO: 1352), GGAAGTATTCCTTGGTTTTGAACCCA (SEQ ID NO: 60 of WO2017100671; herein SEQ ID NO: 1353), GGTCGCGGTTCTTGTTTGTGGAT (SEQ ID NO: 61 of WO2017100671; herein SEQ ID NO: 1354), CGACCTTGAAGCGCATGAACTCCT (SEQ ID NO: 62 of WO2017100671; herein SEQ ID NO: 1355), GTATTCCTTGGTTTTGAACCCAACCGGTCTGCGCCTGTGCMNNMNNMNNMNNMNN MNNMNNTTGGGCACTCTGGTGGTTTGTC (SEQ ID NO: 63 of WO2017100671 wherein N may be A, C, T, or G; herein SEQ ID NO: 1356), GTATTCCTTGGTTTTGAACCCAACCGGTCTGCGCMNNMNNMNNAAAAGGCACCGCC AAAGTTTG (SEQ ID NO: 69 of WO2017100671 wherein N may be A, C, T, or G; herein SEQ ID NO: 1357), GTATTCCTTGGTTTTGAACCCAACCGGTCTGCGCCTGTGCMNNMNNMNNCACCGCC AAAGTTTGGGCACT (SEQ ID NO: 70 of WO2017100671 wherein N may be A, C, T, or G; herein SEQ ID NO: 1358), GTATTCCTTGGTTTTGAACCCAACCGGTCTGCGCCTGTGCCTTAAAMNNMNNMNNC AAAGTTTGGGCACTCTGGTGG (SEQ ID NO: 71 of WO2017100671 wherein N may be A, C, T, or G; herein SEQ ID NO: 1359), GTATTCCTTGGTTTTGAACCCAACCGGTCTGCGCCTGTGCCTTAAAAGGCACMNNMN NMNNNTTGGGCACTCTGGTGGTTTGTG (SEQ ID NO: 72 of WO2017100671 wherein N may be A, C, T, or G; herein SEQ ID NO: 1360), ACTTTGGCGGTGCCTTTTAAG (SEQ ID NO: 74 of WO2017100671; herein SEQ ID NO: 1277), AGTGTGAGTAAGCCTTTTTG (SEQ ID NO: 75 of WO2017100671; herein SEQ ID NO: 1278), TTTACGTTGACGACGCCTAAG (SEQ ID NO: 76 of WO2017100671; herein SEQ ID NO: 1279), TATACTTTGTCGCAGGGTTGG (SEQ ID NO: 77 of WO2017100671; herein SEQ ID NO: 1285), or CTTGCGAAGGAGCGGCTTTCG (SEQ ID NO: 79 of WO2017100671; herein SEQ ID NO: 1361).

In some embodiments, the AAV serotype may be, or may comprise a sequence as described in U.S. Pat. No. 9,624,274, the contents of which are herein incorporated by reference in their entirety, such as, but not limited to, AAV1 (SEQ ID NO: 181 of U.S. Pat. No. 9,624,274), AAV6 (SEQ ID NO: 182 of U.S. Pat. No. 9,624,274), AAV2 (SEQ ID NO: 183 of U.S. Pat. No. 9,624,274), AAV3b (SEQ ID NO: 184 of U.S. Pat. No. 9,624,274), AAV7 (SEQ ID NO: 185 of U.S. Pat. No. 9,624,274), AAV8 (SEQ ID NO: 186 of U.S. Pat. No. 9,624,274), AAV10 (SEQ ID NO: 187 of U.S. Pat. No. 9,624,274), AAV4 (SEQ ID NO: 188 of U.S. Pat. No. 9,624,274), AAV11 (SEQ ID NO: 189 of U.S. Pat. No. 9,624,274), bAAV (SEQ ID NO: 190 of U.S. Pat. No. 9,624,274), AAV5 (SEQ ID NO: 191 of U.S. Pat. No. 9,624,274), GPV (SEQ ID NO: 192 of U.S. Pat. No. 9,624,274; herein SEQ ID NO: 992), B19 (SEQ ID NO: 193 of U.S. Pat. No. 9,624,274; herein SEQ ID NO: 993), MVM (SEQ ID NO: 194 of U.S. Pat. No. 9,624,274; herein SEQ ID NO: 994), FPV (SEQ ID NO: 195 of U.S. Pat. No. 9,624,274; herein SEQ ID NO: 995), CPV (SEQ ID NO: 196 of U.S. Pat. No. 9,624,274; herein SEQ ID NO: 996) or variants thereof. Further, any of the structural protein inserts described in U.S. Pat. No. 9,624,274, may be inserted into, but not limited to, 1-453 and 1-587 of any parent AAV serotype, such as, but not limited to, AAV2 (SEQ ID NO: 183 of U.S. Pat. No. 9,624,274). The amino acid insert may be, but is not limited to, any of the following amino acid sequences, VNLTWSRASG (SEQ ID NO: 50 of U.S. Pat. No. 9,624,274; herein SEQ ID NO: 1362), EFCINHRGYWVCGD (SEQ ID NO:55 of U.S. Pat. No. 9,624,274; herein SEQ ID NO: 1363), EDGQVMDVDLS (SEQ ID NO: 85 of U.S. Pat. No. 9,624,274; herein SEQ ID NO: 1364), EKQRNGTLT (SEQ ID NO: 86 of U.S. Pat. No. 9,624,274; herein SEQ ID NO: 1365), TYQCRVTHPHLPRALMR (SEQ ID NO: 87 of U.S. Pat. No. 9,624,274; herein SEQ ID NO: 1366), RHSTTQPRKTKGSG (SEQ ID NO: 88 of U.S. Pat. No. 9,624,274; herein SEQ ID NO:

1367), DSNPRGVSAYLSR (SEQ ID NO: 89 of U.S. Pat. No. 9,624,274; herein SEQ ID NO: 1368), TITCLWDLAPSK (SEQ ID NO: 90 of U.S. Pat. No. 9,624,274; herein SEQ ID NO: 1369), KTKGSGFFVF (SEQ ID NO: 91 of U.S. Pat. No. 9,624,274; herein SEQ ID NO: 1370), THPHLPRALMRS (SEQ ID NO: 92 of U.S. Pat. No. 9,624,274; herein SEQ ID NO: 1371), GETYQCRVTHPHLPRALMRSTTK (SEQ ID NO: 93 of U.S. Pat. No. 9,624,274; herein SEQ ID NO: 1372), LPRALMRS (SEQ ID NO: 94 of U.S. Pat. No. 9,624,274; herein SEQ ID NO: 1373), INHRGYWV (SEQ ID NO: 95 of U.S. Pat. No. 9,624,274; herein SEQ ID NO: 1374), CDAGSVRTNAPD (SEQ ID NO: 60 of U.S. Pat. No. 9,624,274; herein SEQ ID NO: 1375), AKAVSNLTESRSESLQS (SEQ ID NO: 96 of U.S. Pat. No. 9,624,274; herein SEQ ID NO: 1376), SLTGDEFKKVLET (SEQ ID NO: 97 of U.S. Pat. No. 9,624,274; herein SEQ ID NO: 1377), REAVAYRFEED (SEQ ID NO: 98 of U.S. Pat. No. 9,624,274; herein SEQ ID NO: 1378), INPEIITLDG (SEQ ID NO: 99 of U.S. Pat. No. 9,624,274; herein SEQ ID NO: 1379), DISVTGAPVITATYL (SEQ ID NO: 100 of U.S. Pat. No. 9,624,274; herein SEQ ID NO: 1380), DISVTGAPVITA (SEQ ID NO: 101 of U.S. Pat. No. 9,624,274; herein SEQ ID NO: 1381), PKTVSNLTESSSESVQS (SEQ ID NO: 102 of U.S. Pat. No. 9,624,274; herein SEQ ID NO: 1382), SLMGDEFKAVLET (SEQ ID NO: 103 of U.S. Pat. No. 9,624,274; herein SEQ ID NO: 1383), QHSVAYTFEED (SEQ ID NO: 104 of U.S. Pat. No. 9,624,274; herein SEQ ID NO: 1384), INPEIITRDG (SEQ ID NO: 105 of U.S. Pat. No. 9,624,274; herein SEQ ID NO: 1385), DISLTGDPVITASYL (SEQ ID NO: 106 of U.S. Pat. No. 9,624,274; herein SEQ ID NO: 1386), DISLTGDPVITA (SEQ ID NO: 107 of U.S. Pat. No. 9,624,274; herein SEQ ID NO: 1387), DQSIDFEIDSA (SEQ ID NO: 108 of U.S. Pat. No. 9,624,274; herein SEQ ID NO: 1388), KNVSEDLPLPTFSPTLLGDS (SEQ ID NO: 109 of U.S. Pat. No. 9,624,274; herein SEQ ID NO: 1389), KNVSEDLPLPT (SEQ ID NO: 110 of U.S. Pat. No. 9,624,274; herein SEQ ID NO: 1390), CDSGRVRTDAPD (SEQ ID NO: 111 of U.S. Pat. No. 9,624,274; herein SEQ ID NO: 1391), FPEHLLVDFLQSLS (SEQ ID NO: 112 of U.S. Pat. No. 9,624,274; herein SEQ ID NO: 1392), DAEFRHDSG (SEQ ID NO: 65 of U.S. Pat. No. 9,624,274; herein SEQ ID NO: 1393), HYAAAQWDFGNTMCQL (SEQ ID NO: 113 of U.S. Pat. No. 9,624,274; herein SEQ ID NO: 1394), YAAQWDFGNTMCQ (SEQ ID NO: 114 of U.S. Pat. No. 9,624,274; herein SEQ ID NO: 1395), RSQKEGLHYT (SEQ ID NO: 115 of U.S. Pat. No. 9,624,274; herein SEQ ID NO: 1396), SSRTPSDKPVAHWANPQAE (SEQ ID NO: 116 of U.S. Pat. No. 9,624,274; herein SEQ ID NO: 1397), SRTPSDKPVAHWANP (SEQ ID NO: 117 of U.S. Pat. No. 9,624,274; herein SEQ ID NO: 1398), SSRTPSDKP (SEQ ID NO: 118 of U.S. Pat. No. 9,624,274; herein SEQ ID NO: 1399), NADGNVDYHMNSVP (SEQ ID NO: 119 of U.S. Pat. No. 9,624,274; herein SEQ ID NO: 1400), DGNVDYHMNSV (SEQ ID NO: 120 of U.S. Pat. No. 9,624,274; herein SEQ ID NO: 1401), RSFKEFLQSSLRALRQ (SEQ ID NO: 121 of U.S. Pat. No. 9,624,274; herein SEQ ID NO: 1402); FKEFLQSSLRA (SEQ ID NO: 122 of U.S. Pat. No. 9,624,274; herein SEQ ID NO: 1403), or QMWAPQWGPD (SEQ ID NO: 123 of U.S. Pat. No. 9,624,274; herein SEQ ID NO: 1404).

In some embodiments, the AAV serotype may be, or may have a sequence as described in U.S. Pat. No. 9,475,845, the contents of which are herein incorporated by reference in their entirety, such as, but not limited to, AAV capsid proteins comprising modification of one or more amino acids at amino acid positions 585 to 590 of the native AAV2 capsid protein. Further the modification may result in, but not limited to, the amino acid sequence RGNRQA (SEQ ID NO: 3 of U.S. Pat. No. 9,475,845; herein SEQ ID NO: 1405), SSSTDP (SEQ ID NO: 4 of U.S. Pat. No. 9,475,845; herein SEQ ID NO: 1406), SSNTAP (SEQ ID NO: 5 of U.S. Pat. No. 9,475,845; herein SEQ ID NO: 1407), SNSNLP (SEQ ID NO: 6 of U.S. Pat. No. 9,475,845; herein SEQ ID NO: 1408), SSTTAP (SEQ ID NO: 7 of U.S. Pat. No. 9,475,845; herein SEQ ID NO: 1409), AANTAA (SEQ ID NO: 8 of U.S. Pat. No. 9,475,845; herein SEQ ID NO: 1410), QQNTAP (SEQ ID NO: 9 of U.S. Pat. No. 9,475,845; herein SEQ ID NO: 1411), SAQAQA (SEQ ID NO: 10 of U.S. Pat. No. 9,475,845; herein SEQ ID NO: 1412), QANTGP (SEQ ID NO: 11 of U.S. Pat. No. 9,475,845; herein SEQ ID NO: 1413), NATTAP (SEQ ID NO: 12 of U.S. Pat. No. 9,475,845; herein SEQ ID NO: 1414), SSTAGP (SEQ ID NO: 13 and 20 of U.S. Pat. No. 9,475,845; herein SEQ ID NO: 1415), QQNTAA (SEQ ID NO: 14 of U.S. Pat. No. 9,475,845; herein SEQ ID NO: 1416), PSTAGP (SEQ ID NO: 15 of U.S. Pat. No. 9,475,845; herein SEQ ID NO: 1417), NQNTAP (SEQ ID NO: 16 of U.S. Pat. No. 9,475,845; herein SEQ ID NO: 1418), QAANAP (SEQ ID NO: 17 of U.S. Pat. No. 9,475,845; herein SEQ ID NO: 1419), SIVGLP (SEQ ID NO: 18 of U.S. Pat. No. 9,475,845; herein SEQ ID NO: 1420), AASTAA (SEQ ID NO: 19, and 27 of U.S. Pat. No. 9,475,845; herein SEQ ID NO: 1421), SQNTTA (SEQ ID NO: 21 of U.S. Pat. No. 9,475,845; herein SEQ ID NO: 1422), QQDTAP (SEQ ID NO: 22 of U.S. Pat. No. 9,475,845; herein SEQ ID NO: 1423), QTNTGP (SEQ ID NO: 23 of U.S. Pat. No. 9,475,845; herein SEQ ID NO: 1424), QTNGAP (SEQ ID NO: 24 of U.S. Pat. No. 9,475,845; herein SEQ ID NO: 1425), QQNAAP (SEQ ID NO: 25 of U.S. Pat. No. 9,475,845; herein SEQ ID NO: 1426), or AANTQA (SEQ ID NO: 26 of U.S. Pat. No. 9,475,845; herein SEQ ID NO: 1427). In some embodiments, the amino acid modification is a substitution at amino acid positions 262 through 265 in the native AAV2 capsid protein or the corresponding position in the capsid protein of another AAV with a targeting sequence. The targeting sequence may be, but is not limited to, any of the amino acid sequences NGRAHA (SEQ ID NO: 38 of U.S. Pat. No. 9,475,845; herein SEQ ID NO: 1428), QPEHSST (SEQ ID NO: 39 and 50 of U.S. Pat. No. 9,475,845; herein SEQ ID NO: 1429), VNTANST (SEQ ID NO: 40 of U.S. Pat. No. 9,475,845; herein SEQ ID NO: 1430), HGPMQKS (SEQ ID NO: 41 of U.S. Pat. No. 9,475,845; herein SEQ ID NO: 1431), PHKPPLA (SEQ ID NO: 42 of U.S. Pat. No. 9,475,845; herein SEQ ID NO: 1432), IKNNEMW (SEQ ID NO: 43 of U.S. Pat. No. 9,475,845; herein SEQ ID NO: 1433), RNLDTPM (SEQ ID NO: 44 of U.S. Pat. No. 9,475,845; herein SEQ ID NO: 1434), VDSHRQS (SEQ ID NO: 45 of U.S. Pat. No. 9,475,845; herein SEQ ID NO: 1435), YDSKTKT (SEQ ID NO: 46 of U.S. Pat. No. 9,475,845; herein SEQ ID NO: 1436), SQLPHQK (SEQ ID NO: 47 of U.S. Pat. No. 9,475,845; herein SEQ ID NO: 1437), STMQQNT (SEQ ID NO: 48 of U.S. Pat. No. 9,475,845; herein SEQ ID NO: 1438), TERYMTQ (SEQ ID NO: 49 of U.S. Pat. No. 9,475,845; herein SEQ ID NO: 1439), DASLSTS (SEQ ID NO: 51 of U.S. Pat. No. 9,475,845; herein SEQ ID NO: 1440), DLPNKKT (SEQ ID NO: 52 of U.S. Pat. No. 9,475,845; herein SEQ ID NO: 1441), DLTAARL (SEQ ID NO: 53 of U.S. Pat. No. 9,475,845; herein SEQ ID NO: 1442), EPHQFNY (SEQ ID NO: 54 of U.S. Pat. No. 9,475,845; herein SEQ ID NO: 1443), EPQSNHT (SEQ ID NO: 55 of U.S. Pat. No. 9,475,845; herein SEQ ID NO:

1444), MSSWPSQ (SEQ ID NO: 56 of U.S. Pat. No. 9,475,845; herein SEQ ID NO: 1445), NPKHNAT (SEQ ID NO: 57 of U.S. Pat. No. 9,475,845; herein SEQ ID NO: 1446), PDGMRTT (SEQ ID NO: 58 of U.S. Pat. No. 9,475,845; herein SEQ ID NO: 1447), PNNNKTT (SEQ ID NO: 59 of U.S. Pat. No. 9,475,845; herein SEQ ID NO: 1448), QSTTHDS (SEQ ID NO: 60 of U.S. Pat. No. 9,475,845; herein SEQ ID NO: 1449), TGSKQKQ (SEQ ID NO: 61 of U.S. Pat. No. 9,475,845; herein SEQ ID NO: 1450), SLKHQAL (SEQ ID NO: 62 of U.S. Pat. No. 9,475,845; herein SEQ ID NO: 1451), SPIDGEQ (SEQ ID NO: 63 of U.S. Pat. No. 9,475,845; herein SEQ ID NO: 1452), WIFPWIQL (SEQ ID NO: 64 and 112 of U.S. Pat. No. 9,475,845; herein SEQ ID NO: 1453), CDCRGDCFC (SEQ ID NO: 65 of U.S. Pat. No. 9,475,845; herein SEQ ID NO: 1454), CNGRC (SEQ ID NO: 66 of U.S. Pat. No. 9,475,845; herein SEQ ID NO: 1455), CPRECES (SEQ ID NO: 67 of U.S. Pat. No. 9,475,845; herein SEQ ID NO: 1456), CTTHWGFTLC (SEQ ID NO: 68 and 123 of U.S. Pat. No. 9,475,845; herein SEQ ID NO: 1457), CGRRAGGSC (SEQ ID NO: 69 of U.S. Pat. No. 9,475,845; herein SEQ ID NO: 1458), CKGGRAKDC (SEQ ID NO: 70 of U.S. Pat. No. 9,475,845; herein SEQ ID NO: 1459), CVPELGHEC (SEQ ID NO: 71 and 115 of U.S. Pat. No. 9,475,845; herein SEQ ID NO: 1460), CRRETAWAK (SEQ ID NO: 72 of U.S. Pat. No. 9,475,845; herein SEQ ID NO: 1461), VSWFSHRYSPFAVS (SEQ ID NO: 73 of U.S. Pat. No. 9,475,845; herein SEQ ID NO: 1462), GYRDGYAGPILYN (SEQ ID NO: 74 of U.S. Pat. No. 9,475,845; herein SEQ ID NO: 1463), XXXYXXX (SEQ ID NO: 75 of U.S. Pat. No. 9,475,845; herein SEQ ID NO: 1464), YXNW (SEQ ID NO: 76 of U.S. Pat. No. 9,475,845; herein SEQ ID NO: 1465), RPLPPLP (SEQ ID NO: 77 of U.S. Pat. No. 9,475,845; herein SEQ ID NO: 1466), APPLPPR (SEQ ID NO: 78 of U.S. Pat. No. 9,475,845; herein SEQ ID NO: 1467), DVFYPYPYASGS (SEQ ID NO: 79 of U.S. Pat. No. 9,475,845; herein SEQ ID NO: 1468), MYWYPY (SEQ ID NO: 80 of U.S. Pat. No. 9,475,845; herein SEQ ID NO: 1469), DITWDQLWDLMK (SEQ ID NO: 81 of U.S. Pat. No. 9,475,845; herein SEQ ID NO: 1470), CWDDXWLC (SEQ ID NO: 82 of U.S. Pat. No. 9,475,845; herein SEQ ID NO: 1471), EWCEYLGGYLRCYA (SEQ ID NO: 83 of U.S. Pat. No. 9,475,845; herein SEQ ID NO: 1472), YXCXXGPXTWXCXP (SEQ ID NO: 84 of U.S. Pat. No. 9,475,845; herein SEQ ID NO: 1473), IEGPTLRQWLAARA (SEQ ID NO: 85 of U.S. Pat. No. 9,475,845; herein SEQ ID NO: 1474), LWXXX (SEQ ID NO: 86 of U.S. Pat. No. 9,475,845; herein SEQ ID NO: 1475), XFXXYLW (SEQ ID NO: 87 of U.S. Pat. No. 9,475,845; herein SEQ ID NO: 1476), SSIISHFRWGLCD (SEQ ID NO: 88 of U.S. Pat. No. 9,475,845; herein SEQ ID NO: 1477), MSRPACPPNDKYE (SEQ ID NO: 89 of U.S. Pat. No. 9,475,845; herein SEQ ID NO: 1478), CLRSGRGC (SEQ ID NO: 90 of U.S. Pat. No. 9,475,845; herein SEQ ID NO: 1479), CHWMFSPWC (SEQ ID NO: 91 of U.S. Pat. No. 9,475,845; herein SEQ ID NO: 1480), WXXF (SEQ ID NO: 92 of U.S. Pat. No. 9,475,845; herein SEQ ID NO: 1481), CSSRLDAC (SEQ ID NO: 93 of U.S. Pat. No. 9,475,845; herein SEQ ID NO: 1482), CLPVASC (SEQ ID NO: 94 of U.S. Pat. No. 9,475,845; herein SEQ ID NO: 1483), CGFECVRQCPERC (SEQ ID NO: 95 of U.S. Pat. No. 9,475,845; herein SEQ ID NO: 1484), CVALCREACGEGC (SEQ ID NO: 96 of U.S. Pat. No. 9,475,845; herein SEQ ID NO: 1485), SWCEPGWCR (SEQ ID NO: 97 of U.S. Pat. No. 9,475,845; herein SEQ ID NO: 1486), YSGKWGW (SEQ ID NO: 98 of U.S. Pat. No. 9,475,845; herein SEQ ID NO: 1487), GLSGGRS (SEQ ID NO: 99 of U.S. Pat. No. 9,475,845; herein SEQ ID NO: 1488), LMLPRAD (SEQ ID NO: 100 of U.S. Pat. No. 9,475,845; herein SEQ ID NO: 1489), CSCFRDVCC (SEQ ID NO: 101 of U.S. Pat. No. 9,475,845; herein SEQ ID NO: 1490), CRDVVSVIC (SEQ ID NO: 102 of U.S. Pat. No. 9,475,845; herein SEQ ID NO: 1491), MARSGL (SEQ ID NO: 103 of U.S. Pat. No. 9,475,845; herein SEQ ID NO: 1492), MARAKE (SEQ ID NO: 104 of U.S. Pat. No. 9,475,845; herein SEQ ID NO: 1493), MSRTMS (SEQ ID NO: 105 of U.S. Pat. No. 9,475,845; herein SEQ ID NO: 1494), KCCYSL (SEQ ID NO: 106 of U.S. Pat. No. 9,475,845; herein SEQ ID NO: 1495), MYWGDSHWLQYWYE (SEQ ID NO: 107 of U.S. Pat. No. 9,475,845; herein SEQ ID NO: 1496), MQLPLAT (SEQ ID NO: 108 of U.S. Pat. No. 9,475,845; herein SEQ ID NO: 1497), EWLS (SEQ ID NO: 109 of U.S. Pat. No. 9,475,845; herein SEQ ID NO: 1498), SNEW (SEQ ID NO: 110 of U.S. Pat. No. 9,475,845; herein SEQ ID NO: 1499), TNYL (SEQ ID NO: 111 of U.S. Pat. No. 9,475,845; herein SEQ ID NO: 1500), WDLAWMFRLPVG (SEQ ID NO: 113 of U.S. Pat. No. 9,475,845; herein SEQ ID NO: 1501), CTVALPGGYVRVC (SEQ ID NO: 114 of U.S. Pat. No. 9,475,845; herein SEQ ID NO: 1502), CVAYCIEHHCWTC (SEQ ID NO: 116 of U.S. Pat. No. 9,475,845; herein SEQ ID NO: 1503), CVFAHNYDYLVC (SEQ ID NO: 117 of U.S. Pat. No. 9,475,845; herein SEQ ID NO: 1504), CVFTSNYAFC (SEQ ID NO: 118 of U.S. Pat. No. 9,475,845; herein SEQ ID NO: 1505), VHSPNKK (SEQ ID NO: 119 of U.S. Pat. No. 9,475,845; herein SEQ ID NO: 1506), CRGDGWC (SEQ ID NO: 120 of U.S. Pat. No. 9,475,845; herein SEQ ID NO: 1507), XRGCDX (SEQ ID NO: 121 of U.S. Pat. No. 9,475,845; herein SEQ ID NO: 1508), PXXX (SEQ ID NO: 122 of U.S. Pat. No. 9,475,845; herein SEQ ID NO: 1509), SGKGPRQITAL (SEQ ID NO: 124 of U.S. Pat. No. 9,475,845; herein SEQ ID NO: 1510), AAAAAAAAAXXXXX (SEQ ID NO: 125 of U.S. Pat. No. 9,475,845; herein SEQ ID NO: 1511), VYMSPF (SEQ ID NO: 126 of U.S. Pat. No. 9,475,845; herein SEQ ID NO: 1512), ATWLPPR (SEQ ID NO: 127 of U.S. Pat. No. 9,475,845; herein SEQ ID NO: 1513), HTMYYHHYQHHL (SEQ ID NO: 128 of U.S. Pat. No. 9,475,845; herein SEQ ID NO: 1514), SEVGCRAGPLQWLCEKYFG (SEQ ID NO: 129 of U.S. Pat. No. 9,475,845; herein SEQ ID NO: 1515), CGLLPVGRPDRNVWRWLC (SEQ ID NO: 130 of U.S. Pat. No. 9,475,845; herein SEQ ID NO: 1516), CKGQCDRFKGLPWEC (SEQ ID NO: 131 of U.S. Pat. No. 9,475,845; herein SEQ ID NO: 1517), SGRSA (SEQ ID NO: 132 of U.S. Pat. No. 9,475,845; herein SEQ ID NO: 1518), WGFP (SEQ ID NO: 133 of U.S. Pat. No. 9,475,845; herein SEQ ID NO: 1519), AEPMPHSLNFSQYLWYT (SEQ ID NO: 134 of U.S. Pat. No. 9,475,845; herein SEQ ID NO: 1520), WAYXSP (SEQ ID NO: 135 of U.S. Pat. No. 9,475,845; herein SEQ ID NO: 1521), IELLQAR (SEQ ID NO: 136 of U.S. Pat. No. 9,475,845; herein SEQ ID NO: 1522), AYTKCSRQWRTCMTTH (SEQ ID NO: 137 of U.S. Pat. No. 9,475,845; herein SEQ ID NO: 1523), PQNSKIPGPTFLDPH (SEQ ID NO: 138 of U.S. Pat. No. 9,475,845; herein SEQ ID NO: 1524), SMEPALPDWWWKMFK (SEQ ID NO: 139 of U.S. Pat. No. 9,475,845; herein SEQ ID NO: 1525), ANTPCGPYTHDCPVKR (SEQ ID NO: 140 of U.S. Pat. No. 9,475,845; herein SEQ ID NO: 1526), TACHQHVRMVRP (SEQ ID NO: 141 of U.S. Pat. No. 9,475,845; herein SEQ ID NO: 1527), VPWMEPAYQRFL (SEQ ID NO: 142 of U.S. Pat. No. 9,475,845; herein SEQ ID NO: 1528), DPRATPGS (SEQ ID NO: 143 of U.S. Pat. No. 9,475,845; herein SEQ ID NO: 1529), FRPNRAQDYNTN (SEQ ID NO: 144 of U.S. Pat. No. 9,475,845; herein SEQ ID NO: 1530), CTKNSYLMC (SEQ ID NO: 145 of U.S. Pat. No. 9,475,845; herein SEQ ID NO: 1531), CXXTXXXGXGC (SEQ ID NO: 146 of U.S. Pat. No. 9,475,845; herein SEQ ID NO: 1532), CPIEDRPMC (SEQ ID NO: 147 of U.S. Pat. No. 9,475,845; herein SEQ ID NO: 1533), HEWSYLAPYPWF (SEQ ID NO: 148 of U.S. Pat. No. 9,475,845; herein SEQ ID NO: 1534), MCPKHPLGC (SEQ ID NO: 149 of U.S. Pat. No. 9,475,845; herein SEQ ID NO: 1535), RMWPSSTVNLSAGRR (SEQ ID NO: 150 of U.S. Pat. No. 9,475,845; herein SEQ ID NO: 1536), SAKTAVSQRVWLPSHRGGEP (SEQ ID NO: 151 of U.S. Pat. No. 9,475,845; herein SEQ ID NO: 1537), KSREHVNNSACPSKRITAAL (SEQ ID NO: 152 of U.S. Pat. No. 9,475,845; herein SEQ ID NO: 1538), EGFR (SEQ ID NO: 153 of U.S. Pat. No. 9,475,845; herein SEQ ID NO: 1539), AGLGVR (SEQ ID NO: 154 of U.S. Pat. No. 9,475,845; herein SEQ ID NO: 1540), GTRQGHTMRLGVSDG (SEQ ID NO: 155 of U.S. Pat. No. 9,475,845; herein SEQ ID NO: 1541), IAGLATPGWSHWLAL (SEQ ID NO: 156 of U.S. Pat. No. 9,475,845; herein SEQ ID NO: 1542), SMSIARL (SEQ ID NO: 157 of U.S. Pat. No. 9,475,845; herein SEQ ID NO: 1543), HTFEPGV (SEQ ID NO: 158 of U.S. Pat. No. 9,475,845; herein SEQ ID NO: 1544), NTSLKRISNKRIRRK (SEQ ID NO: 159 of U.S. Pat. No. 9,475,845; herein SEQ ID NO: 1545), LRIKRKRRRKKTRK (SEQ ID NO: 160 of U.S. Pat. No. 9,475,845; herein SEQ ID NO: 1546), GGG, GFS, LWS, EGG, LLV, LSP, LBS, AGG, GRR, GGH, or GTV.

In some embodiments, the AAV serotype may be, or may have a sequence as described in U.S. Patent Application Publication No. US 20160369298, the contents of which are herein incorporated by reference in their entirety, such as, but not limited to, site-specific mutated capsid protein of AAV2 (SEQ ID NO: 97 of US 20160369298; herein SEQ ID NO: 1547) or variants thereof, wherein the specific mutated site is at least one site selected from sites R447, G453, S578, N587, N587+1, S662 of VP1 or fragment thereof.

Further, any of the mutated sequences described in US 20160369298, may be or may have, but not limited to, any of the following sequences: SDSGASN (SEQ ID NO: 1 and SEQ ID NO: 231 of US20160369298; herein SEQ ID NO: 1548), SPSGASN (SEQ ID NO: 2 of US20160369298; herein SEQ ID NO: 1549), SHSGASN (SEQ ID NO: 3 of US20160369298; herein SEQ ID NO: 1550), SRSGASN (SEQ ID NO: 4 of US20160369298; herein SEQ ID NO: 1551), SKSGASN (SEQ ID NO: 5 of US20160369298; herein SEQ ID NO: 1552), SNSGASN (SEQ ID NO: 6 of US20160369298; herein SEQ ID NO: 1553), SGSGASN (SEQ ID NO: 7 of US20160369298; herein SEQ ID NO: 1554), SASGASN (SEQ ID NO: 8, 175, and 221 of US20160369298; herein SEQ ID NO: 1555), SESGTSN (SEQ ID NO: 9 of US20160369298; herein SEQ ID NO: 1556), STTGGSN (SEQ ID NO: 10 of US20160369298; herein SEQ ID NO: 1557), SSAGSTN (SEQ ID NO: 11 of US20160369298; herein SEQ ID NO: 1558), NNDSQA (SEQ ID NO: 12 of US20160369298; herein SEQ ID NO: 1559), NNRNQA (SEQ ID NO: 13 of US20160369298; herein SEQ ID NO: 1560), NNNKQA (SEQ ID NO: 14 of US20160369298; herein SEQ ID NO: 1561), NAKRQA (SEQ ID NO: 15 of US20160369298; herein SEQ ID NO: 1562), NDEHQA (SEQ ID NO: 16 of US20160369298; herein SEQ ID NO: 1563), NTSQKA (SEQ ID NO: 17 of US20160369298; herein SEQ ID NO: 1564), YYLSRTNTPSGTDTQSRLVFSQAGA (SEQ ID NO: 18 of US20160369298; herein SEQ ID NO: 1565), YYLSRTNTDSGTETQSGLDFSQAGA (SEQ ID NO: 19 of US20160369298; herein SEQ ID NO: 1566), YYLSRTNTESGTPTQSALEFSQAGA (SEQ ID NO: 20 of US20160369298; herein SEQ ID NO: 1567), YYLSRTNTHSGTHTQSPLHFSQAGA (SEQ ID NO: 21 of US20160369298; herein SEQ ID NO: 1568), YYLSRTNTSSGTITISHLIFSQAGA (SEQ ID NO: 22 of US20160369298; herein SEQ ID NO: 1569), YYLSRTNTRSGIMTKSSLMFSQAGA (SEQ ID NO: 23 of US20160369298; herein SEQ ID NO: 1570), YYLSRTNTKSGRKTLSNLSFSQAGA (SEQ ID NO: 24 of US20160369298; herein SEQ ID NO: 1571), YYLSRTNDGSGPVTPSKLRFSQRGA (SEQ ID NO: 25 of US20160369298; herein SEQ ID NO: 1572), YYLSRTNAASGHATHSDLKFSQPGA (SEQ ID NO: 26 of US20160369298; herein SEQ ID NO: 1573), YYLSRTNGQAGSLTMSELGFSQVGA (SEQ ID NO: 27 of US20160369298; herein SEQ ID NO: 1574), YYLSRTNSTGGNQTTSQLLFSQLSA (SEQ ID NO: 28 of US20160369298; herein SEQ ID NO: 1575), YFLSRTNNNTGLNTNSTLNFSQGRA (SEQ ID NO: 29 of US20160369298; herein SEQ ID NO: 1576), SKTGADNNNSEYSWTG (SEQ ID NO: 30 of US20160369298; herein SEQ ID NO: 1577), SKTDADNNNSEYSWTG (SEQ ID NO: 31 of US20160369298; herein SEQ ID NO: 1578), SKTEADNNNSEYSWTG (SEQ ID NO: 32 of US20160369298; herein SEQ ID NO: 1579), SKTPADNNNSEYSWTG (SEQ ID NO: 33 of US20160369298; herein SEQ ID NO: 1580), SKTHADNNNSEYSWTG (SEQ ID NO: 34 of US20160369298; herein SEQ ID NO: 1581), SKTQADNNNSEYSWTG (SEQ ID NO: 35 of US20160369298; herein SEQ ID NO: 1582), SKTIADNNNSEYSWTG (SEQ ID NO: 36 of US20160369298; herein SEQ ID NO: 1583), SKTMADNNNSEYSWTG (SEQ ID NO: 37 of US20160369298; herein SEQ ID NO: 1584), SKTRADNNNSEYSWTG (SEQ ID NO: 38 of US20160369298; herein SEQ ID NO: 1585), SKTNADNNNSEYSWTG (SEQ ID NO: 39 of US20160369298; herein SEQ ID NO: 1586), SKTVGRNNNSEYSWTG (SEQ ID NO: 40 of US20160369298; herein SEQ ID NO: 1587), SKTADRNNNSEYSWTG (SEQ ID NO: 41 of US20160369298; herein SEQ ID NO: 1588), SKKLSQNNNSKYSWQG (SEQ ID NO: 42 of US20160369298; herein SEQ ID NO: 1589), SKPTTGNNNSDYSWPG (SEQ ID NO: 43 of US20160369298; herein SEQ ID NO: 1590), STQKNENNNSNYSWPG (SEQ ID NO: 44 of US20160369298; herein SEQ ID NO: 1591), HKDDEGKF (SEQ ID NO: 45 of US20160369298; herein SEQ ID NO: 1592), HKDDNRKF (SEQ ID NO: 46 of US20160369298; herein SEQ ID NO: 1593), HKDDTNKF (SEQ ID NO: 47 of US20160369298; herein SEQ ID NO: 1594), HEDSDKNF (SEQ ID NO: 48 of US20160369298; herein SEQ ID NO: 1595), HRDGADSF (SEQ ID NO: 49 of US20160369298; herein SEQ ID NO: 1596), HGDNKSRF (SEQ ID NO: 50 of US20160369298; herein SEQ ID NO: 1597), KQGSEKTNVDFEEV (SEQ ID NO: 51 of US20160369298; herein SEQ ID NO: 1598), KQGSEKTNVDSEEV (SEQ ID NO: 52 of US20160369298; herein SEQ ID NO: 1599), KQGSEKTNVDVEEV (SEQ ID NO: 53 of US20160369298; herein SEQ ID NO: 1600), KQGSDKTNVDDAGV (SEQ ID NO: 54 of US20160369298; herein SEQ ID NO: 1601), KQGSSKTNVDPREV (SEQ ID NO: 55 of US20160369298; herein SEQ ID NO: 1602), KQGSRKTNVDHKQV (SEQ ID NO: 56 of US20160369298; herein SEQ ID NO: 1603), KQGSKGGNVDTNRV (SEQ ID NO: 57 of US20160369298; herein SEQ ID NO: 1604), KQGSGEANVDNGDV (SEQ ID NO: 58 of US20160369298; herein SEQ ID NO: 1605), KQDAAADNIDYDHV (SEQ ID NO: 59 of US20160369298; herein SEQ ID NO: 1606), KQSGTRSNAAASSV (SEQ ID NO: 60 of US20160369298; herein SEQ ID NO: 1607), KENTNTNDTELTNV (SEQ ID NO: 61 of US20160369298; herein SEQ ID NO: 1608), QRGNNVAATADVNT (SEQ ID NO: 62 of US20160369298; herein SEQ ID NO: 1609), QRGNNEAATADVNT (SEQ ID NO: 63 of US20160369298; herein SEQ ID NO: 1610), QRGNNPAATADVNT (SEQ ID NO: 64 of US20160369298; herein SEQ ID NO: 1611), QRGNNHAATADVNT (SEQ ID NO: 65 of US20160369298; herein SEQ ID NO: 1612), QEENNIAATPGVNT (SEQ ID NO: 66 of US20160369298; herein SEQ ID NO: 1613), QPPNNMAATHEVNT (SEQ ID NO: 67 of US20160369298; herein SEQ ID NO: 1614), QHHNNSAATTIVNT (SEQ ID NO: 68 of US20160369298; herein SEQ ID NO: 1615), QTTNNRAAFNMVET (SEQ ID NO: 69 of US20160369298; herein SEQ ID NO: 1616), QKKNNNAASKKVAT (SEQ ID NO: 70 of US20160369298; herein SEQ ID NO: 1617), QGGNNKAADDAVKT (SEQ ID NO: 71 of US20160369298; herein SEQ ID NO: 1618), QAAKGGAADDAVKT (SEQ ID NO: 72 of US20160369298; herein SEQ ID NO: 1619), QDDRAAAANESVDT (SEQ ID NO: 73 of US20160369298; herein SEQ ID NO: 1620), QQQHDDAAYQRVHT (SEQ ID NO: 74 of US20160369298; herein SEQ ID NO: 1621), QSSSSLAAVSTVQT (SEQ ID NO: 75 of US20160369298; herein SEQ ID NO: 1622), QNNQTTAAAIRNVTT (SEQ ID NO: 76 of US20160369298; herein SEQ ID NO: 1623), NYNKKSDNVDFT (SEQ ID NO: 77 of US20160369298; herein SEQ ID NO: 1624), NYNKKSENVDFT (SEQ ID NO: 78 of US20160369298; herein SEQ ID NO: 1625), NYNKKSLNVDFT (SEQ ID NO: 79 of US20160369298; herein SEQ ID NO: 1626), NYNKKSPNVDFT (SEQ ID NO: 80 of US20160369298; herein SEQ ID NO: 1627), NYSKKSHCVDFT (SEQ ID NO: 81 of US20160369298; herein SEQ ID NO: 1628), NYRKTIYVDFT (SEQ ID NO: 82 of US20160369298; herein SEQ ID NO: 1629), NYKEKKDVHFT (SEQ ID NO: 83 of US20160369298; herein SEQ ID NO: 1630), NYGHRAIVQFT (SEQ ID NO: 84 of US20160369298; herein SEQ ID NO: 1631), NYANHQFVVCT (SEQ ID NO: 85 of US20160369298; herein SEQ ID NO: 1632), NYDDDPTGVLLT (SEQ ID NO: 86 of US20160369298; herein SEQ ID NO: 1633), NYDDPTGVLLT (SEQ ID NO: 87 of US20160369298; herein SEQ ID NO: 1634), NFEQQNSVEWT (SEQ ID NO: 88 of US20160369298; herein SEQ ID NO: 1635), SQSGASN (SEQ ID NO: 89 and SEQ ID NO: 241 of US20160369298; herein SEQ ID NO: 1636), NNGSQA (SEQ ID NO: 90 of US20160369298; herein SEQ ID NO: 1637), YYLSRTNTPSGTTTWSRLQFSQAGA (SEQ ID NO: 91 of US20160369298; herein SEQ ID NO: 1638), SKTSADNNNSEYSWTG (SEQ ID NO: 92 of US20160369298; herein SEQ ID NO: 1639), HKDDEEKF (SEQ ID NO: 93, 209, 214, 219, 224, 234, 239, and 244 of US20160369298; herein SEQ ID NO: 1640), KQGSEKTNVDIEEV (SEQ ID NO: 94 of US20160369298; herein SEQ ID NO: 1641), QRGNNQAATADVNT (SEQ ID NO: 95 of US20160369298; herein SEQ ID NO: 1642), NYNKKSVNVDFT (SEQ ID NO: 96 of US20160369298; herein SEQ ID NO: 1643), SQSGASNYNTPSGTTTQSRLQFSTSADNNNSEYSWTGATKYH (SEQ ID NO: 106 of US20160369298; herein SEQ ID NO: 1644), SASGASNFNSEGGSLTQSSLGFSTDGENNNSDFSWTGATKYH (SEQ ID NO: 107 of US20160369298; herein SEQ ID NO: 1645), SQSGASNYNTPSGTTTQSRLQFSTDGENNNSDFSWTGATKYH (SEQ ID NO: 108 of US20160369298; herein SEQ ID NO: 1646), SASGASNYNTPSGTTTQSRLQFSTSADNNNSEFSWPGATTYH (SEQ ID NO: 109 of US20160369298; herein SEQ ID NO: 1647), SQSGASNFNSEGGSLTQSSLGFSTDGENNNSDFSWTGATKYH (SEQ ID NO: 110 of US20160369298; herein SEQ ID NO: 1648), SASGASNYNTPSGSLTQSSLGFSTDGENNNSDFSWTGATKYH (SEQ ID NO: 111 of US20160369298; herein SEQ ID NO: 1649), SQSGASNYNTPSGTTTQSRLQFSTSADNNNSDFSWTGATKYH (SEQ ID NO: 112 of US20160369298; herein SEQ ID NO: 1650), SGAGASNFNSEGGSLTQSSLGFSTDGENNNSDFSWTGATKYH (SEQ ID NO: 113 of US20160369298; herein SEQ ID NO: 1651), SGAGASN (SEQ ID NO: 176 of US20160369298; herein SEQ ID NO: 1652), NSEGGSLTQSSLGFS (SEQ ID NO: 177, 185, 193 and 202 of US20160369298; herein SEQ ID NO: 1653), TDGENNNSDFS (SEQ ID NO: 178 of US20160369298; herein SEQ ID NO: 1654), SEFSWPGATT (SEQ ID NO: 179 of US20160369298; herein SEQ ID NO: 1655), TSADNNNSDFSWT (SEQ ID NO: 180 of US20160369298; herein SEQ ID NO: 1656), SQSGASNY (SEQ ID NO: 181, 187, and 198 of US20160369298; herein SEQ ID NO: 1657), NTPSGTTTQSRLQFS (SEQ ID NO: 182, 188, 191, and 199 of US20160369298; herein SEQ ID NO: 1658), TSADNNNSEYSWTGATKYH (SEQ ID NO: 183 of US20160369298; herein SEQ ID NO: 1659), SASGASNF (SEQ ID NO: 184 of US20160369298; herein SEQ ID NO: 1660), TDGENNNSDFSWTGATKYH (SEQ ID NO: 186, 189, 194, 197, and 203 of US20160369298; herein SEQ ID NO: 1661), SASGASNY (SEQ ID NO: 190 and SEQ ID NO: 195 of US20160369298; herein SEQ ID NO: 1662), TSADNNNSEFSWPGATTYH (SEQ ID NO: 192 of US20160369298; herein SEQ ID NO: 1663), NTPSGSLTQSSLGFS (SEQ ID NO: 196 of US20160369298; herein SEQ ID NO: 1664), TSADNNNSDFSWTGATKYH (SEQ ID NO: 200 of US20160369298; herein SEQ ID NO: 1665), SGAGASNF (SEQ ID NO: 201 of US20160369298; herein SEQ ID NO: 1666), CTCCAGVVSVVSMRSRVCVNSGC-AGCTDHCVVSRNSGTCVMSACACAA (SEQ ID NO: 204 of US20160369298; herein SEQ ID NO: 1667), CTCCAGAGAGGCAACAGACAAGCAGCTACCGCAGATGTCAACACACAA (SEQ ID NO: 205 of US20160369298; herein SEQ ID NO: 1668), SAAGASN (SEQ ID NO: 206 of US20160369298; herein SEQ ID NO: 1669), YFLSRTNTESGSTTQSTLRFSQAG (SEQ ID NO: 207 of US20160369298; herein SEQ ID NO: 1670), SKTSADNNNSDFS (SEQ ID NO: 208, 228, and 253 of US20160369298; herein SEQ ID NO: 1671), KQGSEKTDVDIDKV (SEQ ID NO: 210 of US20160369298; herein SEQ ID NO: 1672), STAGASN (SEQ ID NO: 211 of US20160369298; herein SEQ ID NO: 1673), YFLSRTNTTSGIETQSTLRFSQAG (SEQ ID NO: 212 and SEQ ID NO: 247 of US20160369298; herein SEQ ID NO: 1674), SKTDGENNNSDFS (SEQ ID NO: 213 and SEQ ID NO: 248 of US20160369298; herein SEQ ID NO: 1675), KQGAAADDVEIDGV (SEQ ID NO: 215 and SEQ ID NO: 250 of US20160369298; herein SEQ ID NO: 1676), SEAGASN (SEQ ID NO: 216 of US20160369298; herein SEQ ID NO: 1677), YYLSRTNTPSGTTTQSRLQFSQAG (SEQ ID NO: 217, 232 and 242 of US20160369298; herein SEQ ID NO: 1678), SKTSADNNNSEYS (SEQ ID NO: 218, 233, 238, and 243 of US20160369298; herein SEQ ID NO: 1679), KQGSEKTNVDIEKV (SEQ ID NO: 220, 225 and 245 of US20160369298; herein SEQ ID NO: 1680), YFLSRTNDASGSDTKSTLLFSQAG (SEQ ID NO: 222 of US20160369298; herein SEQ ID NO: 1681), STTPSENNN-SEYS (SEQ ID NO: 223 of US20160369298; herein SEQ ID NO: 1682), SAAGATN (SEQ ID NO: 226 and SEQ ID NO: 251 of US20160369298; herein SEQ ID NO: 1683), YFLSRTNGEAGSATLSELRFSQAG (SEQ ID NO: 227 of US20160369298; herein SEQ ID NO: 1684), HGDDADRF (SEQ ID NO: 229 and SEQ ID NO: 254 of US20160369298; herein SEQ ID NO: 1685), KQGAEKSDVEVDRV (SEQ ID NO: 230 and SEQ ID NO: 255 of US20160369298; herein SEQ ID NO: 1686), KQDSGGDNIDIDQV (SEQ ID NO: 235 of US20160369298; herein SEQ ID NO: 1687), SDA-GASN (SEQ ID NO: 236 of US20160369298; herein SEQ ID NO: 1688), YFLSRTNTEGGHDTQSTLRFSQAG (SEQ ID NO: 237 of US20160369298; herein SEQ ID NO: 1689), KEDGGGSDVAIDEV (SEQ ID NO: 240 of US20160369298; herein SEQ ID NO: 1690), SNAGASN (SEQ ID NO: 246 of US20160369298; herein SEQ ID NO: 1691), and YFLSRTNGEAGSATLSELRFSQPG (SEQ ID NO: 252 of US20160369298; herein SEQ ID NO: 1692). Non-limiting examples of nucleotide sequences that may encode the amino acid mutated sites include the following, AGCVVMDCAGGARSCASCAAC (SEQ ID NO: 97 of US20160369298; herein SEQ ID NO: 1693), AACRA-CRRSMRSMAGGCA (SEQ ID NO: 98 of US20160369298; herein SEQ ID NO: 1694), CACRRGGACRRCRMSRRSARSTTT (SEQ ID NO: 99 of US20160369298; herein SEQ ID NO: 1695), TATTTCTT-GAGCAGAACAAACRVCVVSRSCGGAMNCVHSAC-GMHSTCAVVSCTTVDS TTTTCTCAGSBCRGSGCG (SEQ ID NO: 100 of US20160369298; herein SEQ ID NO: 1696), TCAAMAMMMAVNSRVCSRSAACAACAACAG-TRASTTCTCGTGGMMAGGA (SEQ ID NO: 101 of US20160369298; herein SEQ ID NO: 1697), AAGSAARR-CRSCRVSRVARVCRATRYCGMSNHCRVMVRSGTC (SEQ ID NO: 102 of US20160369298; herein SEQ ID NO: 1698), CAGVVSVVSMRSRVCVNSGCAGCT-DHCVVSRNSGTCVMSACA (SEQ ID NO: 103 of US20160369298; herein SEQ ID NO: 1699), AACTWCRVSVASMVSVHSDDTGTGSWSTKSACT (SEQ ID NO: 104 of US20160369298; herein SEQ ID NO: 1700), TTGTTGAACATCACCACGTGACGCACGTTC (SEQ ID NO: 256 of US20160369298; herein SEQ ID NO: 1701), TCCCCGTGGTTCTACTACATAATGTGGCCG (SEQ ID NO: 257 of US20160369298; herein SEQ ID NO: 1702), TTCCACACTCCGTTTTGGATAATGTTGAAC (SEQ ID NO: 258 of US20160369298; herein SEQ ID NO: 1703), AGGGACATCCCCAGCTCCATGCTGTGGTCG (SEQ ID NO: 259 of US20160369298; herein SEQ ID NO: 1704), AGGGACAACCCCTCCGACTCGCCCTAATCC (SEQ ID NO: 260 of US20160369298; herein SEQ ID NO: 1705), TCCTAGTAGAAGACACCCTCTCACTGCCCG (SEQ ID NO: 261 of US20160369298; herein SEQ ID NO: 1706), AGTACCATGTACACCCACTCTCCCAGTGCC (SEQ ID NO: 262 of US20160369298; herein SEQ ID NO: 1707), ATATGGACGTTCATGCTGATCACCATACCG (SEQ ID NO: 263 of US20160369298; herein SEQ ID NO: 1708), AGCAGGAGCTCCTTGGCCTCAGCGTGCGAG (SEQ ID NO: 264 of US20160369298; herein SEQ ID NO: 1709), ACAAGCAGCTTCACTATGACAACCACTGAC (SEQ ID NO: 265 of US20160369298; herein SEQ ID NO: 1710), CAGCCTAGGAACTGGCTTCCTGGACCCTGT-TACCGCCAGCAGAGAGTCTCAAMAMM AVNSRV-CSRSAACAACAACAGTRASTTCTCCTGGMMAG-GAGCTACCAAGTACCACCT CAATGGCAGAGACTC-TCTGGTGAATCCCGGACCAGCTATGGCAAGCCAC-RRGGACR RCRMSRRSARSTTTTTTCCTCAGA-GCGGGGTTCTCATCTTTGGGAAGSAARRCRSCRV SRVARVCRATRYCGMSNHCRVMVRSGTCATGATTA-CAGACGAAGAGGAGATCTGGA C (SEQ ID NO: 266 of US20160369298; herein SEQ ID NO: 1711), TGGGACAATGGCGGTCGTCTCTCAGAGTTKTKKT (SEQ ID NO: 267 of US20160369298; herein SEQ ID NO: 1712), AGAGGACCKKTCCTCGATGGTTCATGGTG-GAGTTA (SEQ ID NO: 268 of US20160369298; herein SEQ ID NO: 1713), CCACTTAGGGCCTGGTCGA-TACCGTTCGGTG (SEQ ID NO: 269 of US20160369298; herein SEQ ID NO: 1714), or TCTCGCCC-CAAGAGTAGAAACCCTTCSTTYYG (SEQ ID NO: 270 of US20160369298; herein SEQ ID NO: 1715).

In some embodiments, the AAV serotype may comprise an ocular cell targeting peptide as described in International Patent Publication WO2016134375, the contents of which are herein incorporated by reference in their entirety, such as, but not limited to SEQ ID NO: 9, or SEQ ID NO:10 of WO2016134375. Further, any of the ocular cell targeting peptides or amino acids described in WO2016134375, may be inserted into any parent AAV serotype, such as, but not limited to, AAV2 (SEQ ID NO:8 of WO2016134375; herein SEQ ID NO: 1716), or AAV9 (SEQ ID NO: 11 of WO2016134375; herein SEQ ID NO: 1717). In some embodiments, modifications, such as insertions are made in AAV2 proteins at P34-A35, T138-A139, A139-P140, G453-T454, N587-R588, and/or R588-Q589. In certain embodiments, insertions are made at D384, G385, I560, T561, N562, E563, E564, E565, N704, and/or Y705 of AAV9. The ocular cell targeting peptide may be, but is not limited to, any of the following amino acid sequences, GSTPPPM (SEQ ID NO: 1 of WO2016134375; herein SEQ ID NO: 1718), or GETRAPL (SEQ ID NO: 4 of WO2016134375; herein SEQ ID NO: 1719).

In some embodiments, the AAV serotype may be modified as described in U.S. Patent Application Publication No. US 20170145405, the contents of which are herein incorporated by reference in their entirety. AAV serotypes may include, modified AAV2 (e.g., modifications at Y444F, Y500F, Y730F and/or S662V), modified AAV3 (e.g., modifications at Y705F, Y731F and/or T492V), and modified AAV6 (e.g., modifications at S663V and/or T492V).

In some embodiments, the AAV serotype may be modified as described in the International Publication No. WO2017083722, the contents of which are herein incorporated by reference in their entirety. AAV serotypes may include, AAV1 (Y705+731F+T492V), AAV2 (Y444+500+730F+T491V), AAV3 (Y705+731F), AAV5, AAV 5 (Y436+693+719F), AAV6 (VP3 variant Y705F/Y731F/T492V), AAV8 (Y733F), AAV9, AAV9 (VP3 variant Y731F), and AAV10 (Y733F).

In some embodiments, the AAV serotype may comprise, as described in International Patent Publication No. WO2017015102, the contents of which are herein incorporated by reference in their entirety, an engineered epitope comprising the amino acids SPAKFA (SEQ ID NO: 24 of WO2017015102; herein SEQ ID NO: 1720) or NKDKLN (SEQ ID NO:2 of WO2017015102; herein SEQ ID NO:

1721). The epitope may be inserted in the region of amino acids 665 to 670 based on the numbering of the VP1 capsid of AAV8 (SEQ ID NO: 3 of WO2017015102) and/or residues 664 to 668 of AAV3B (SEQ ID NO: 3).

In some embodiments, the AAV serotype may be, or may have a sequence as described in International Patent Publication No. WO2017058892, the contents of which are herein incorporated by reference in their entirety, such as, but not limited to, AAV variants with capsid proteins that may comprise a substitution at one or more (e.g., 2, 3, 4, 5, 6, or 7) of amino acid residues 262-268, 370-379, 451-459, 472-473, 493-500, 528-534, 547-552, 588-597, 709-710, or 716-722 of AAV1, in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV, or avian AAV. The amino acid substitution(s) may be, but is/are not limited to, any of the amino acid sequences described in WO2017058892. In some embodiments, the AAV may comprise an amino acid substitution at residues 256L, 258K, 259Q, 261S, 263A, 264S, 265T, 266G, 272H, 385S, 386Q, S472R, V473D, N500E 547S, 709A, 710N, 716D, 717N, 718N, 720L, A456T, Q457T, N458Q, K4595, T492S, K493A, S586R, S587G, S588N, T589R and/or 722T of AAV1 (SEQ ID NO: 1 of WO2017058892) in any combination, 244N, 246Q, 248R, 249E, 250I, 251K, 252S, 253G, 254S, 255V, 256D, 263Y, 377E, 378N, 453L, 456R, 532Q, 533P, 535N, 536P, 537G, 538T, 539T, 540A, 541T, 542Y, 543L, 546N, 653V, 654P, 656S, 697Q, 698F, 704D, 705S, 706T, 707G, 708E, 709Y and/or 710R of AAV5 (SEQ ID NO:5 of WO2017058892) in any combination, 248R, 316V, 317Q, 318D, 319S, 443N, 530N, 531S, 532Q 533P, 534A, 535N, 540A, 541 T, 542Y, 543L, 545G, 546N, 697Q, 704D, 706T, 708E, 709Y and/or 710R of AAV5 (SEQ ID NO: 5 of WO2017058892) in any combination, 264S, 266G, 269N, 272H, 457Q, 588S and/or 5891 of AAV6 (SEQ ID NO:6 WO2017058892) in any combination, 457T, 459N, 496G, 499N, 500N, 589Q, 590N and/or 592A of AAV8 (SEQ ID NO: 8 WO2017058892) in any combination, 451I, 452N, 453G, 454S, 455G, 456Q, 457N and/or 458Q of AAV9 (SEQ ID NO: 9 WO2017058892) in any combination.

In some embodiments, the AAV may include a sequence of amino acids at positions 155, 156, and 157 of VP1 or at positions 17, 18, 19, and 20 of VP2, as described in International Publication No. WO 2017066764, the contents of which are herein incorporated by reference in their entirety. The sequences of amino acid may be, but are not limited to, N-S-S, S-X-S, S-S-Y, N-X-S, N-S-Y, S-X-Y, or N-X-Y, where N, X, and Y are, but not limited to, independently, non-serine or non-threonine amino acids, wherein the AAV may be, but is not limited to, AAV1, AAV2, AAV3, AAV4, AAV5, AAV6, AAV7, AAV8, AAV9, AAV10, AAV11, or AAV12. In some embodiments, the AAV may include a deletion of at least one amino acid at position(s) 156, 157, or 158 of VP1 or at positions 19, 20, or 21 of VP2, wherein the AAV may be, but is not limited to AAV1, AAV2, AAV3, AAV4, AAV5, AAV6, AAV7, AAV8, AAV9, AAV10, AAV11, or AAV12.

In some embodiments, the AAV may be a serotype generated by Cre-recombination-based AAV targeted evolution (CREATE) as described by Deverman et al., (Nature Biotechnology 34(2):204-209 (2016)), Chan et al., (Nature Neuroscience 20(8):1172-1179 (2017)), and in International Patent Application Publication Nos. WO2015038958 and WO2017100671, the contents of each of which are herein incorporated by reference in their entirety. In some embodiments, AAV serotypes generated in this manner have improved CNS transduction and/or neuronal and astrocytic tropism, as compared to AAV serotypes not generated in this manner. As non-limiting examples, the AAV serotype may include a targeting peptide such as, but not limited to, PHP.B, PHP.B2, PHP.B3, PHP.A, PHP.S, PHP.N, G2A12, G2A15, G2A3, G2B4, or G2B5. In some embodiments, these AAV serotypes may be derivates of AAV9 (SEQ ID NO: 136) or AAV9 K449R (SEQ ID NO: 9) with an amino acid insert between amino acids 588 and 589. Non-limiting examples of these amino acid inserts include TLAVPFK (PHP.B; SEQ ID NO: 1260), SVSKPFL (PHP.B2; SEQ ID NO: 1268), FTLTTPK (PHP.B3; SEQ ID NO: 1269), YTLSQGW (PHP.A; SEQ ID NO: 1275), QAVRTSL (PHP.S; SEQ ID NO: 1319), LAKERLS (G2A3; SEQ ID NO: 1320), MNSTKNV (G2B4; SEQ ID NO: 1321), VSGGHHS (G2B5; SEQ ID NO: 1322), and/or DGTLAVPFKAQ (PHP.N; SEQ ID NO: 1289).

In some embodiments, the AAV serotype may be as described in Jackson et al (Frontiers in Molecular Neuroscience 9:154 (2016)), the contents of which are herein incorporated by reference in their entirety.

In some embodiments, the AAV serotype is AAV9 (SEQ ID NO: 135 or 136). In some embodiments, the AAV serotype is an AAV9 with a peptide insert.

In some embodiments, the AAV serotype is a K449R AAV9 variant (SEQ ID NO: 9). AAV9 K449R has the same function as wild-type AAV9. In some embodiments, the AAV serotype is an AAV9 K449R with a peptide insert.

In some embodiments, the AAV serotype is PHP.B (e.g., as described in WO2015038958). In some embodiments, the AAV serotype is paired with a synapsin promoter to enhance neuronal transduction, as compared to when more ubiquitous promoters are used (i.e., CBA or CMV).

In some embodiments, the AAV serotype is PHP.N (e.g., as described in WO2017100671).

In some embodiments, the AAV serotype is a serotype comprising the AAVPHP.N (PHP.N) peptide or a variant thereof.

In some embodiments, the AAV serotype is a serotype comprising the AAVPHP.B (PHP.B) peptide or a variant thereof.

In some embodiments, the AAV serotype is a serotype comprising the AAVPHP.A (PHP.A) peptide or a variant thereof.

In some embodiments, the AAV serotype is a serotype comprising the PHP.S peptide or a variant thereof.

In some embodiments, the AAV serotype is a serotype comprising the PHP.B2 peptide or a variant thereof.

In some embodiments, the AAV serotype is a serotype comprising the PHP.B3 peptide or a variant thereof.

In some embodiments, the AAV serotype is a serotype comprising the G2B4 peptide or a variant thereof.

In some embodiments, the AAV serotype is a serotype comprising the G2B5 peptide or a variant thereof.

In some embodiments, the AAV serotype is VOY101 or a variant thereof. In some embodiments, the VOY101 comprises the amino acid sequence of SEQ ID NO: 1. In some embodiments, the capsid sequence comprises the nucleic acid sequence of SEQ ID NO.:1722.

In some embodiments, the AAV serotype is VOY201 or a variant thereof. In some embodiments, the VOY201 comprises the amino acid sequence of SEQ ID NO: 1724. In some embodiments, the capsid sequence comprises the nucleic acid sequence of SEQ ID NO: 1723.

In some embodiments, the AAV capsid allows for blood brain barrier penetration following intravenous administration. Non-limiting examples of such AAV capsids include AAV9, AAV9 K449R, VOY101, VOY201, or AAV capsids comprising a peptide insert such as, but not limited to, AAVPHP.N (PHP.N), AAVPHP.B (PHP.B), PHP.S, G2A3, G2B4, G2B5, G2A12, G2A15, PHP.B2, PHP.B3, or AAVPHP.A (PHP.A).

In some embodiments, the AAV serotype may comprise a capsid amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the those described above. In some embodiments, the AAV serotype comprises a capsid amino acid sequence at least 80% identical to SEQ ID NO: 1, 2, 3, 9, 136, or 1724. In some embodiments, the AAV serotype comprises a capsid amino acid sequence at least 85% identical to SEQ ID NO: 1, 2, 3, 9, 136, or 1724. In some embodiments, the AAV serotype comprises a capsid amino acid sequence at least 90% identical to SEQ ID NO: 1, 2, 3, 9, 136, or 1724. In some embodiments, the AAV serotype comprises a capsid amino acid sequence at least 95% identical to SEQ ID NO: 1, 2, 3, 9, 136, or 1724. In some embodiments, the AAV serotype comprises a capsid amino acid sequence at least 99% identical to SEQ ID NO: 1, 2, 3, 9, 136, or 1724. In some embodiments, the AAV serotype comprises a capsid amino acid of SEQ ID NO: 1, 2, 3, 9, 136, or 1724.

In some embodiments, the AAV serotype may be encoded by a capsid nucleic acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the those described above. In some embodiments, the AAV serotype comprises a capsid nucleic acid sequence at least 80% identical to SEQ ID NO: 4, 135, 1722, or 1723. In some embodiments, the AAV serotype comprises a capsid nucleic acid sequence at least 85% identical to SEQ ID NO: 4, 135, 1722, or 1723. In some embodiments, the AAV serotype comprises a capsid nucleic acid sequence at least 90% identical to SEQ ID NO: 4, 135, 1722, or 1723. In some embodiments, the AAV serotype comprises a capsid nucleic acid sequence at least 95% identical to SEQ ID NO: 4, 135, 1722, or 1723. In some embodiments, the AAV serotype comprises a capsid nucleic acid sequence at least 99% identical to SEQ ID NO: 4, 135, 1722, or 1723. In some embodiments, the AAV serotype comprises a capsid nucleic acid sequence of SEQ ID NO: 4, 135, 1722, or 1723.

In some embodiments, the initiation codon for translation of the AAV VP1 capsid protein may be CTG, TTG, or GTG as described in U.S. Pat. No. 8,163,543, the contents of which are herein incorporated by reference in its entirety.

The present disclosure refers to structural capsid proteins (including VP1, VP2, and VP3), which are encoded by capsid (Cap) genes. These capsid proteins form an outer protein structural shell (i.e. capsid) of a viral vector such as AAV. VP capsid proteins synthesized from Cap polynucleotides generally include a methionine as the first amino acid in the peptide sequence (Met1), which is associated with the start codon (AUG or ATG) in the corresponding Cap nucleotide sequence. However, it is common for a first-methionine (Met1) residue or generally any first amino acid (AA1) to be cleaved off after or during polypeptide synthesis by protein processing enzymes such as Met-aminopeptidases. This "Met/AA-clipping" process often correlates with a corresponding acetylation of the second amino acid in the polypeptide sequence (e.g., alanine, valine, serine, threonine, etc.). Met-clipping commonly occurs with VP1 and VP3 capsid proteins but can also occur with VP2 capsid proteins.

Where the Met/AA-clipping is incomplete, a mixture of one or more (one, two, or three) VP capsid proteins comprising the viral capsid may be produced, some of which may include a Met1/AA1 amino acid (Met+/AA+) and some of which may lack a Met1/AA1 amino acid as a result of Met/AA-clipping (Met−/AA−). For further discussion regarding Met/AA-clipping in capsid proteins, see Jin, et al. Direct Liquid Chromatography/Mass Spectrometry Analysis for Complete Characterization of Recombinant Adeno-Associated Virus Capsid Proteins. *Hum Gene Ther Methods.* 2017 Oct. 28(5):255-267; Hwang, et al. N-Terminal Acetylation of Cellular Proteins Creates Specific Degradation Signals. *Science.* 2010 Feb. 19. 327(5968): 973-977; the contents of which are each incorporated herein by reference in their entirety.

According to the present disclosure, references to capsid proteins are not limited to either clipped (Met−/AA−) or unclipped (Met+/AA+) sequences and may, in context, refer to independent capsid proteins, viral capsids comprised of a mixture of capsid proteins, and/or polynucleotide sequences (or fragments thereof) which encode, describe, produce, or result in capsid proteins of the present disclosure. A direct reference to a "capsid protein" or "capsid polypeptide" (such as VP1, VP2, or VP3) may also comprise VP capsid proteins which include a Met1/AA1 amino acid (Met+/AA+) as well as corresponding VP capsid proteins which lack the Met1/AA1 amino acid as a result of Met/AA-clipping (Met−/AA−).

Further, according to the present disclosure, a reference to a specific SEQ ID NO (whether a protein or nucleic acid) that comprises or encodes, respectively, one or more capsid proteins that include a Met1/AA1 amino acid (Met+/AA+) should be understood to teach the VP capsid proteins that lack the Met1/AA1 amino acid as upon review of the sequence, it is readily apparent any sequence that merely lacks the first listed amino acid (whether or not methionine).

As a non-limiting example, reference to a VP1 polypeptide sequence which is 736 amino acids in length and which includes a "Met1" amino acid (Met+) encoded by the AUG/ATG start codon may also be understood to teach a VP1 polypeptide sequence that is 735 amino acids in length and that does not include the "Met1" amino acid (Met−) of the 736 amino acid Met+ sequence. As a second non-limiting example, reference to a VP1 polypeptide sequence that is 736 amino acids in length and that includes an "AA1" amino acid (AA1+) encoded by any NNN initiator codon may also be understood to teach a VP1 polypeptide sequence that is 735 amino acids in length and that does not include the "AA1" amino acid (AA1−) of the 736 amino acid AA1+ sequence.

References to viral capsids formed from VP capsid proteins (such as reference to specific AAV capsid serotypes) can incorporate VP capsid proteins that include a Met1/AA1 amino acid (Met+/AA1+), corresponding VP capsid proteins that lack the Met1/AA1 amino acid as a result of Met/AA1-clipping (Met−/AA1−), or combinations thereof (Met+/AA1+ and Met−/AA1−).

As a non-limiting example, an AAV capsid serotype can include VP1 (Met+/AA1+), VP1 (Met−/AA1−), or a combination of VP1 (Met+/AA1+) and VP1 (Met−/AA1−). An AAV capsid serotype can also include VP3 (Met+/AA1+), VP3 (Met−/AA1−), or a combination of VP3 (Met+/AA1+)

and VP3 (Met–/AA1–); and can also include similar optional combinations of VP2 (Met+/AA1) and VP2 (Met–/AA1–).

Expression Vector

In some aspects, the AAV particle of the present disclosure serves as an expression vector, which encodes FXN. Expression vectors are not limited to AAV and may be adenovirus, retrovirus, lentivirus, plasmid, vector, or any variant thereof.

In some embodiments, an AAV particle expression vector may comprise, from ITR to ITR recited 5' to 3', an ITR, a promoter, an intron, a nucleic acid sequence encoding FXN, a polyA sequence, and an ITR.

Inverted Terminal Repeats (ITRs)

The AAV particles of the present disclosure comprise a viral genome with at least one ITR region and a payload region, which encodes FXN. As used herein, a "viral genome" or "vector genome" is a polynucleotide comprising at least one inverted terminal ITR and at least one encoded payload. In one embodiment the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes of the disclosure may be comprised of naturally occurring polynucleotide sequences or recombinantly derived polynucleotide sequences.

The ITRs may be derived from the same serotype as the capsid, selected from any of the serotypes listed in Table 1, or a derivative thereof. The ITR may be of a different serotype than the capsid. In some embodiments, the AAV particle has more than one ITR. In some embodiments, the AAV particle has a viral genome comprising two ITRs. In some embodiments, the ITRs are of the same serotype as one another. In some embodiments, the ITRs are of different serotypes. Non-limiting examples include zero, one, or both of the ITRs having the same serotype as the capsid. In some embodiments, both ITRs of the viral genome of the AAV particle are AAV2 ITRs.

Independently, each ITR may be about 100 nucleotides to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In some embodiments, the ITRs are 140-142 nucleotides in length. Non limiting examples of ITR length are 102, 105, 119, 130, 140, 141, 142, or 145 nucleotides in length, and those having at least 95% identity thereto.

In some embodiments, one or more ITRs are AAV2 ITRs or fragments or variants thereof. In some embodiments, both the 5'ITR and 3'ITR are AAV2 ITRs or fragments or variants thereof. In some embodiments, one or more ITRs are 141 nucleotides in length. In some embodiments, both the 5'ITR and 3'ITR are 141 nucleotides in length. In some embodiments, the 5' ITR comprises a sequence at least 95%, at least 99%, or 100% identical to SEQ ID NO: 1811. In some embodiments, the 3' ITR comprises a sequence at least 95%, at least 99%, or 100% identical to SEQ ID NO: 1812. In some embodiments, the 5' ITR comprises a sequence at least 95%, at least 99%, or 100% identical to SEQ ID NO: 1811 and the 3' ITR comprises a sequence at least 95%, at least 99%, or 100% identical to SEQ ID NO: 1812. In some embodiments, the viral genome comprises 5' and 3' ITRs as described above and a payload region encoding frataxin, e.g., encoding SEQ ID NO: 1725 or a variant thereof having at least 90% sequence identity. In some embodiments, the viral genome comprises 5' and 3' ITRs as described above and a payload region encoding frataxin, e.g., a payload region comprising SEQ ID NO: 1824 or a variant thereof having at least 90% sequence identity, e.g. a variant retaining one or more of the functional properties of wild type frataxin.

Promoters

A person skilled in the art may recognize that a target cell may require a specific promoter including but not limited to a promoter that is species specific, inducible, tissue-specific, or cell cycle-specific (Parr et al., Nat. Med. 3:1145-9 (1997); the contents of which are herein incorporated by reference in their entirety).

In some embodiments, delivery of AAV particles to cells of the central nervous system (e.g., parenchyma) comprises a composition wherein the AAV genome further comprises a cell specific promoter region. In some embodiments, delivery comprises a composition wherein the AAV genome further comprises a ubiquitous promoter region.

In some embodiments, the promoter is efficient to drive the expression of a payload or transgene. In some embodiments, the promoter is efficient to drive the expression of FXN.

In some embodiments, the FXN promoter is used in the viral genomes of the AAV particles encoding FXN or a variant thereof. Certain embodiments provide that the FXN promoter is engineered for optimal FXN expression.

In some embodiments, the promoter is a weak promoter that provides expression of a payload, e.g., FXN, for a period of time in targeted tissues such as, but not limited to, nervous system tissues (e.g., CNS tissues). Expression may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years, or 5-10 years. In some embodiments, the promoter is a weak promoter for sustained expression of a payload in nervous tissues.

In some embodiments, the promoter may be a promoter that is less than 1 kb in size The promoter may have a length of 50, 55, 100, 200, 210, 220, 230, 240, 250, 260, 270, 280, 290, 300, 310, 320, 330, 332, 340, 350, 360, 361, 370, 380, 390, 400, 410, 420, 430, 440, 450, 460, 470, 480, 490, 500, 505, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or more than 800 nucleotides. The promoter may have a length between 50-100, 100-150, 150-200, 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800, or 700-800 nucleotides.

In some embodiments, the promoter may be a combination of two or more components such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or more than 800 nucleotides. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800, or 700-800 nucleotides. In some embodiments, the promoter is a combination of a 382-nucleotide CMV-enhancer sequence and a 260-nucleotide CBA-promoter sequence. In some embodiments, the promoter is a combination of a 380-nucleotide CMV-enhancer sequence and a 260-nucleotide CBA-promoter sequence.

In some embodiments, the vector genome comprises at least one element to enhance the target specificity and expression of FXN (See, e.g., Powell et al. Viral Expression Cassette Elements to Enhance Transgene Target Specificity and Expression in Gene Therapy, 2015; the contents of which are herein incorporated by reference in their entirety). Non-limiting examples of elements to enhance expression include promoters, endogenous miRNAs, post-transcriptional regulatory elements (PREs), polyadenylation (PolyA) signal sequences, upstream enhancers (USEs), CMV enhancers, and/or introns. In certain embodiments, the element used to enhance the target specificity and/or expression of FXN is referred to as an "enhancer" or "enhancer sequence." In some embodiments, a promoter may comprise an enhancer sequence. In some embodiments, an enhancer may be a separate component of the viral genome than the promoter. In some embodiments, an enhancer may be 5' to a promoter sequence in a viral genome. In some embodiments, an enhancer may be 3' to a promoter sequence in a viral genome. In some embodiments, an enhancer comprises or consists of SEQ ID NO: 1777.

As used herein, an "intron" or "intron sequence" encompasses a full length intron or a fragment thereof. As used herein, an "exon" or "exon sequence" encompasses a full length exon or a fragment thereof. In some embodiments, an enhancer may comprise at least one intron or exon sequence. In some embodiments, an enhancer may comprise at least one intron sequence. In some embodiments, an enhancer may comprise at least one exon sequence. In some embodiments, an enhancer comprises one intron sequence and one exon sequence. In some embodiments, an enhancer sequence comprises two intron sequences. In some embodiments, an enhancer sequence comprises two exon sequences. In some embodiments, an enhancer sequence comprises two intron sequences and two exon sequences. In some embodiments, an enhancer comprises SEQ ID NO: 1818. In some embodiments, an enhancer may comprise two intron sequences and two exon sequences. In some embodiments, an enhancer may comprise an ie1 exon (e.g., exon 1), an ie1 intron (e.g., intron 1), a human beta-globin intron (e.g., intron 2) and a human beta-globin exon (e.g., exon 3). In some embodiments, an enhancer may comprise from 5' to 3' SEQ ID NO: 1817, 1819, 1820, 1821. In some embodiments, an enhancer may comprise SEQ ID NO: 1816.

Promoters that promote expression in most tissues include, but are not limited to, human elongation factor 1α-subunit (EF1α), immediate-early cytomegalovirus (CMV), chicken β-actin (CBA) and its derivative CAG, the β glucuronidase (GUSB), or ubiquitin C (UBC). Tissue-specific expression elements can be used to restrict expression to certain cell types such as, but not limited to, nervous system promoters which can be used to restrict expression to neurons, astrocytes, or oligodendrocytes. Non-limiting examples of tissue-specific expression elements for neurons include neuron-specific enolase (NSE), platelet-derived growth factor (PDGF), platelet-derived growth factor B-chain (PDGF-β), synapsin (Syn), methyl-CpG binding protein 2 (MeCP2), CaMKII, mGluR2, NFL, NFH, nβ2, PPE, Enk, and EAAT2 promoters. Non-limiting examples of tissue-specific expression elements for astrocytes include the glial fibrillary acidic protein (GFAP) and EAAT2 promoters. A non-limiting example of a tissue-specific expression element for oligodendrocytes include the myelin basic protein (MBP) promoter.

In some embodiments, the vector genome comprises a ubiquitous promoter. Non-limiting examples of ubiquitous promoters include H1, U6, CMV, CBA (including derivatives CAG, CBh, etc.), EF-1α, PGK, UBC, GUSB (hGBp), and UCOE (promoter of HNRPA2B1-CBX3). Yu et al. (Molecular Pain 2011, 7:63; the contents of which are herein incorporated by reference in their entirety) evaluated the expression of eGFP under the CAG, EFIα, PGK, and UBC promoters in rat DRG cells and primary DRG cells using lentiviral vectors and found that UBC showed weaker expression than the other 3 promoters and there was only 10-12% glia expression seen for all promoters. Soderblom et al. (E. Neuro 2015; the contents of which are herein incorporated by reference in their entirety) studied the expression of eGFP in AAV8 with CMV and UBC promoters and AAV2 with the CMV promoter after injection in the motor cortex. Intranasal administration of a plasmid containing a UBC or EFIα promoter showed a sustained airway expression greater than the expression with the CMV promoter (See, e.g., Gill et al., Gene Therapy 2001, Vol. 8, 1539-1546; the contents of which are herein incorporated by reference in their entirety). Husain et al. (Gene Therapy 2009; the contents of which are herein incorporated by reference in their entirety) evaluated a HβH construct with a hGUSB promoter, a HSV-1LAT promoter and a NSE promoter and found that the HβH construct showed weaker expression than NSE in mice brain. Passini and Wolfe (J. Virol. 2001, 12382-12392, the contents of which are herein incorporated by reference in their entirety) evaluated the long term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in their entirety) when NF-L and NF-H promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650-nucleotide promoter and NFH is a 920-nucleotide promoter, which are both absent in the liver but NFH is abundant in the sensory proprioceptive neurons, brain, and spinal cord and NFH is present in the heart. Scn8a is a 470-nucleotide promoter which expresses throughout the DRG, spinal cord and brain with particularly high expression seen in the hippocampal neurons and cerebellar Purkinje cells, cortex, thalamus, and hypothalamus (See e.g., Drews et al. 2007 and Raymond et al. 2004; the contents of each of which are herein incorporated by reference in their entireties).

In some embodiments, the vector genome comprises a UBC promoter. The UBC promoter may have a size of 300-350 nucleotides. In some embodiments, the UBC promoter is 332 nucleotides in length.

In some embodiments, the vector genome comprises a GUSB promoter. The GUSB promoter may have a size of 350-400 nucleotides. In some embodiments, the GUSB promoter is 378 nucleotides in length. In some embodiments, the construct may be AAV-promoter-CMV/globin intron-FXN-RBG, where the AAV may be self-complementary and the AAV may be an AAV6, AAVrh10, or AAVDJ serotype.

In some embodiments, the vector genome comprises a NFL promoter. The NFL promoter may have a size of 600-700 nucleotides. In some embodiments, the NFL promoter is 650 nucleotides in length.

In some embodiments, the vector genome comprises a NFH promoter. The NFH promoter may have a size of 900-950 nucleotides. In some embodiments, the NFH promoter is 920 nucleotides in length.

In some embodiments, the vector genome comprises a scn8a promoter. The scn8a promoter may have a size of 450-500 nucleotides. In some embodiments, the scn8a promoter is 470 nucleotides in length.

In some embodiments, the vector genome comprises a FXN promoter.

In some embodiments, the vector genome comprises a PGK promoter.

In some embodiments, the vector genome comprises a CBA promoter.

In some embodiments, the vector genome comprises a CMV promoter.

In some embodiments, the vector genome comprises a H1 promoter.

In some embodiments, the vector genome comprises a U6 promoter.

In some embodiments, the vector genome comprises a liver or a skeletal muscle promoter. Non-limiting examples of liver promoters include hAAT and TBG. Non-limiting examples of skeletal muscle promoters include Desmin, MCK, and C5-12.

In some embodiments, the AAV vector comprises an enhancer element, a promoter, and/or a 5'UTR intron. The enhancer may be, but is not limited to, a CMV enhancer; the promoter may be, but is not limited to, a CMV, CBA, FXN, UBC, GUSB, NSE, Synapsin, MeCP2, or GFAP promoter; and the 5'UTR/intron may be, but is not limited to, SV40, and CBA-MVM. In some embodiments, the enhancer, promoter, and/or intron used in combination may be: (1) CMV enhancer, CMV promoter, SV40 5'UTR intron; (2) CMV enhancer, CBA promoter, SV40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter; (9) GFAP promoter; (10) H1 promoter; and/or (11) U6 promoter.

In some embodiments, the AAV vector has an engineered promoter.

In some embodiments, the AAV vector comprises a promoter comprising a sequence having at least 90%, at least 95%, at least 99%, or 100% sequence identity to a sequence selected from the group consisting of SEQ ID NO: 1734-1777. In some embodiments, a promoter is or is derived from a CMV promoter and comprises a sequence having at least 90%, at least 95%, at least 99%, or 100% sequence identity to a sequence selected from the group consisting of SEQ ID NO: 1743-1751, 1767, 1772-1774, and 1777. In some embodiments, a promoter is or is derived from a CBA promoter and comprises a sequence having at least 90%, at least 95%, at least 99%, or 100% sequence identity to a sequence selected from the group consisting of SEQ ID NO: 1734-1742, 1760-1766, 1768, and 1775-1776. In some embodiments, a promoter is or is derived from a FXN promoter and comprises a sequence having at least 90%, at least 95%, at least 99%, or 100% sequence identity to a sequence selected from the group consisting of SEQ ID NO: 1752-1759 and 1769-1770.

In some embodiments, a promoter comprises a sequence having at least 90%, at least 95%, at least 99%, or 100% sequence identity to SEQ ID NO: 1738. In some embodiments, the promoter is SEQ ID NO: 1738. In some embodiments, an AAV vector genome comprises a promoter sequence having at least 90% sequence identity to SEQ ID NO: 1738 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1738 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1738 and a payload region encoding a frataxin polypeptide having an amino acid sequence of SEQ ID NO: 1725 (e.g., a payload region comprising SEQ ID NO: 1824) and/or further comprising one or more sequences, or a 95% identical variant thereof, as provided in Tables 5-11. In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1738. In some embodiments, the promoter is SEQ ID NO: 1740. In some embodiments, an AAV vector genome comprises a promoter sequence having at least 90% sequence identity to SEQ ID NO: 1740 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1740 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1740 and a payload region encoding a frataxin polypeptide having an amino acid sequence of SEQ ID NO: 1725 (e.g., a payload region comprising SEQ ID NO: 1824) and/or further comprising one or more sequences, or a 95% identical variant thereof, as provided in Tables 5-11. In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1742. In some embodiments, the promoter is SEQ ID NO: 1742. In some embodiments, an AAV vector genome comprises a promoter sequence having at least 90% sequence identity to SEQ ID NO: 1742 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1742 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1742 and a payload region encoding a frataxin polypeptide having an amino acid sequence of SEQ ID NO: 1725 (e.g., a payload region comprising SEQ ID NO: 1824) and/or further comprising one or more sequences, or a 95% identical variant thereof, as provided in Tables 5-11. In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1750. In some embodiments, the promoter is SEQ ID NO: 1750. In some embodiments, an AAV vector genome comprises a promoter sequence having at least 90% sequence identity to SEQ ID NO: 1750 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1750 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1750 and a payload region encoding a frataxin polypeptide having an amino acid sequence of SEQ ID NO: 1725 (e.g., a payload region comprising SEQ ID NO: 1824) and/or further comprising one or more sequences, or a 95% identical variant thereof, as provided in Tables 5-11 In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, the viral genome comprises an enhancer, for example an immediate-early "ie" enhancer or a CMV/globin enhancer. In some embodiments, the enhancer comprises ie1 exon 1 and ie1 intron 1 or a fragment thereof. In some embodiments, the enhancer comprises an ie1 exon 1, an ie1 intron 1 or fragment thereof, a human beta-globin intron 2, and a human beta-globin exon 3. In some embodiments, the enhancer comprises a sequence at least 90%, at least 95%, at least 99%, or 100% identical to a sequence as given by any of SEQ ID NOs: 1815-1821. In some embodiments, the enhancer comprises a sequence at least 90%, at least 95%, at least 99%, or 100% identical to a sequence as given by SEQ ID NO: 1816. In some embodiments, the viral genome comprises an enhancer as described above and a payload region encoding frataxin, e.g., encoding SEQ ID NO: 1725 or a variant thereof having at least 90% sequence identity thereto, or comprising the nucleic acid sequence SEQ ID NO: 1824 or a variant having at least 90% sequence identity thereto.

Introns

In some embodiments, the vector genome comprises at least one intron or a fragment or derivative thereof. In some embodiments, the at least one intron may enhance expression of FXN (See e.g., Powell et al. Viral Expression Cassette Elements to Enhance Transgene Target Specificity and Expression in Gene Therapy, 2015; the contents of which are herein incorporated by reference in their entirety). Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps), and hybrid adenovirus splice donor/IgG splice acceptor (230 bps).

In some embodiments, the intron may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 nucleotides. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500 nucleotides.

In some embodiments, the AAV vector may comprise an SV40 intron or fragment or variant thereof. In some embodiments, the promoter may be CMV. In some embodiments, the promoter may be CBA. In some embodiments, the promoter may be H1.

In some embodiments, the AAV vector may comprise one or more beta-globin introns or a fragment or variant thereof. In some embodiments, the intron comprises one or more human beta-globin sequences (e.g., including fragments/variants thereof).

In some embodiments, the intron comprises a sequence at least 90%, at least 95%, at least 99%, or 100% identical to a sequence as given by any of SEQ ID NO: 1815-1821. In some embodiments, the viral genome comprises an intron as described above and a payload region encoding frataxin, e.g., encoding SEQ ID NO: 1725 or a variant thereof having at least 90% sequence identity thereto, or comprising the nucleic acid sequence SEQ ID NO: 1824 or a variant having at least 90% sequence identity thereto. In some embodiments, the promoter may be CMV. In some embodiments, the promoter may be CBA. In some embodiments, the promoter may be H1.

In some embodiments, the encoded FXN may be located downstream of an intron in an expression vector such as, but not limited to, SV40 intron or beta globin intron or others known in the art. Further, the encoded FXN may also be located upstream of the polyadenylation sequence in an expression vector. In some embodiments, the encoded FXN may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides downstream from the promoter with an intron and/or upstream of the polyadenylation sequence in an expression vector. In some embodiments, the encoded FXN may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30, or 25-30 nucleotides downstream from the intron and/or upstream of the polyadenylation sequence in an expression vector. In some embodiments, the encoded FXN may be located within the first 1%, 2%, 3%, 4%, 5%, 6%, 7%, 8%, 9%, 10%, 15%, 20%, 25%, or more than 25% of the nucleotides downstream from the intron and/or upstream of the polyadenylation sequence in an expression vector. In some embodiments, the encoded FXN may be located within the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% of the sequence downstream from the intron and/or upstream of the polyadenylation sequence in an expression vector.

In certain embodiments, the intron sequence is not an enhancer sequence. In certain embodiments, the intron sequence is not a sub-component of a promoter sequence.

Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genomes of the AAV particles of the disclosure to enhance expression in hepatic cell lines or liver.

While not wishing to be bound by theory, wild-type 5' untranslated regions (UTRs) include features that play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In some embodiments, the 5'UTR in the viral genome includes a Kozak sequence.

In some embodiments, the 5'UTR in the viral genome does not include a Kozak sequence.

While not wishing to be bound by theory, wild-type 3' UTRs are known to have stretches of adenosines and uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in their entirety): Class I AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA (U/A)(U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In some embodiments, the 3' UTR of the viral genome may include an oligo(dT) sequence for templated addition of a poly-A tail.

Any UTR from any gene known in the art may be incorporated into the viral genome of the AAV particle. These UTRs, or portions thereof, may be placed in the same orientation as in the gene from which they were selected or they may be altered in orientation or location. In some embodiments, the UTR used in the viral genome of the AAV particle may be inverted, shortened, lengthened, or made with one or more other 5' UTRs or 3' UTRs known in the art. As used herein, the term "altered," as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In some embodiments, the viral genome of the AAV particle comprises at least one artificial UTR, which is not a variant of a wild type UTR.

In some embodiments, the viral genome of the AAV particle comprises UTRs which have been selected from a family of transcripts whose proteins share a common function, structure, feature, or property.

miRNA Target Sites

In some embodiments, the viral genome may include at least one miRNA binding site. microRNAs (or miRNAs or miRs) are 19-25 nucleotide noncoding RNAs that bind to the sites of nucleic acid targets and down-regulate gene expression either by reducing nucleic acid molecule stability or by inhibiting translation. In some embodiments, the 3' UTR of the viral genome may be engineered to include at least one miRNA binding site.

In some embodiments, the viral genome comprises at least one sequence encoding a miRNA target site to reduce the expression of the transgene in a specific tissue. MiRNAs and their targeted tissues are well known in the art. In some embodiments, a miR-122 miRNA target site (miR-122TS), or tandem copies of the same, may be encoded in the viral genome to reduce the expression of the viral genome in the liver where miR-122 is abundantly expressed.

In some embodiments, the viral genome comprises at least one miR122 binding site. In some embodiments, the miR122 binding site comprises a sequence having at least 90%, at least 95%, at least 99%, or 100% identical to SEQ ID NO: 1827. In some embodiments, the AAV vector genome comprises three copies of a miR122 binding site, e.g., three copies of SEQ ID NO: 1827 or a variant thereof having at least 90% sequence identity. In some embodiments, the miR122 binding site series comprises a sequence having at least 90%, at least 95%, at least 99%, or 100% identical to SEQ ID NO: 1826. In some embodiments, the viral genome comprises one, two, or three miR122 binding sites as described above and a payload region encoding frataxin, e.g., encoding SEQ ID NO: 1725 or a variant thereof having at least 90% sequence identity thereto, or comprising the nucleic acid sequence SEQ ID NO: 1824 or a variant having at least 90% sequence identity thereto. In some embodiments, the viral genome comprises three miR122 binding sites as described above and a payload region encoding frataxin, e.g., encoding SEQ ID NO: 1725 or a variant thereof having at least 90% sequence identity thereto, or comprising the nucleic acid sequence SEQ ID NO: 1824 or a variant having at least 90% sequence identity thereto.

Backbone

In certain embodiments, a cis-element such as a vector backbone is incorporated into the viral particle encoding FXN. The backbone sequence may regulate transcription during viral production. The backbone sequence may contribute to the stability of FXN expression. The backbone sequence may contribute to the level of expression of FXN that may be cloned into pAAVsc or pcDNA3.1 vector backbones.

Polyadenylation Sequence

In some embodiments, the viral genome of the AAV particles of the present disclosure comprises at least one polyadenylation sequence. The viral genome of the AAV particle may comprise a polyadenylation sequence between the 3' end of the payload coding sequence and the 5' end of the 3'UTR.

In some embodiments, the polyadenylation sequence or "polyA sequence" may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides in length.

In some embodiments, the polyadenylation sequence is 50-100 nucleotides in length.

In some embodiments, the polyadenylation sequence is 50-150 nucleotides in length.

In some embodiments, the polyadenylation sequence is 50-160 nucleotides in length.

In some embodiments, the polyadenylation sequence is 50-200 nucleotides in length.

In some embodiments, the polyadenylation sequence is 60-100 nucleotides in length.

In some embodiments, the polyadenylation sequence is 60-150 nucleotides in length.

In some embodiments, the polyadenylation sequence is 60-160 nucleotides in length.

In some embodiments, the polyadenylation sequence is 60-200 nucleotides in length.

In some embodiments, the polyadenylation sequence is 70-100 nucleotides in length.

In some embodiments, the polyadenylation sequence is 70-150 nucleotides in length.

In some embodiments, the polyadenylation sequence is 70-160 nucleotides in length.

In some embodiments, the polyadenylation sequence is 70-200 nucleotides in length.

In some embodiments, the polyadenylation sequence is 80-100 nucleotides in length.

In some embodiments, the polyadenylation sequence is 80-150 nucleotides in length.

In some embodiments, the polyadenylation sequence is 80-160 nucleotides in length.

In some embodiments, the polyadenylation sequence is 80-200 nucleotides in length.

In some embodiments, the polyadenylation sequence is 90-100 nucleotides in length.

In some embodiments, the polyadenylation sequence is 90-150 nucleotides in length.

In some embodiments, the polyadenylation sequence is 90-160 nucleotides in length.

In some embodiments, the polyadenylation sequence is 90-200 nucleotides in length.

In some embodiments, the encoded FXN may be located upstream of the polyadenylation sequence in an expression vector. Further, the encoded FXN may be located downstream of a promoter such as, but not limited to, CMV, U6, CBA, or a CBA promoter with a SV40 intron in an expression vector, or a fragment thereof (e.g., one disclosed herein). In some embodiments, the encoded FXN may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides downstream from the promoter and/or upstream of the polyadenylation sequence in an expression vector. In some embodiments, the encoded FXN may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30, or 25-30 nucleotides downstream from the promoter and/or upstream of the polyadenylation sequence in an expression vector. In some embodiments, the encoded FXN may be located within the first 1%, 2%, 3%, 4%, 5%, 6%, 7%, 8%, 9%, 10%, 15%, 20%, 25%, or more than 25% of the nucleotides downstream from the promoter and/or upstream of the polyadenylation sequence in an expression vector. In some embodiments, the encoded FXN may be located within the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In some embodiments, the viral genome comprises a human growth hormone (hGH) polyA sequence. In some embodiments, the viral genome comprises a polyA sequence at least 90%, at least 95%, at least 99%, or 100% identical to SEQ ID NO: 1828. In some embodiments, the viral genome comprises an hGH polyA as described above and a payload region encoding frataxin, e.g., encoding SEQ ID NO: 1725 or a variant thereof having at least 90% sequence identity thereto, or comprising the nucleic acid sequence SEQ ID NO: 1824 or a variant having at least 90% sequence identity thereto.

Filler Sequence

In some embodiments, the viral genome comprises one or more filler sequences. The filler sequence may be a wild-type sequence or an engineered sequence. A filler sequence may be a variant of a wild-type sequence. In one embodiment, a filler sequence is a derivative of human albumin.

In some embodiments, the viral genome comprises one or more filler sequences in order to have the length of the viral genome be the optimal size for packaging. In some embodiments, the viral genome comprises at least one filler sequence in order to have the length of the viral genome be about 2.3 kb. In some embodiments, the viral genome comprises at least one filler sequence in order to have the length of the viral genome be about 4.6 kb.

In some embodiments, the viral genome is a single stranded (ss) viral genome and comprises one or more filler sequences that, independently or together, have a length about between 0.1 kb-3.8 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, or 3.8 kb. In some embodiments, the total length filler sequence in the vector genome is 3.1 kb. In some embodiments, the total length filler sequence in the vector genome is 2.7 kb. In some embodiments, the total length filler sequence in the vector genome is 0.8 kb. In some embodiments, the total length filler sequence in the vector genome is 0.4 kb. In some embodiments, the length of each filler sequence in the vector genome is 0.8 kb. In some embodiments, the length of each filler sequence in the vector genome is 0.4 kb.

In some embodiments, the viral genome is a self-complementary (sc) viral genome and comprises one or more filler sequences that, independently or together, have a length about between 0.1 kb-1.5 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, or 1.5 kb. In some embodiments, the total length filler sequence in the vector genome is 0.8 kb. In some embodiments, the total length filler sequence in the vector genome is 0.4 kb. In some embodiments, the length of each filler sequence in the vector genome is 0.8 kb. In some embodiments, the length of each filler sequence in the vector genome is 0.4 kb.

In some embodiments, the viral genome comprises any portion of a filler sequence. The viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of a filler sequence.

In some embodiments, the viral genome is a single stranded (ss) viral genome and comprises one or more filler sequences in order to have the length of the viral genome be about 4.6 kb. In some embodiments, the viral genome comprises at least one filler sequence and the filler sequence is located 3' to the 5' ITR sequence. In some embodiments, the viral genome comprises at least one filler sequence and the filler sequence is located 5' to a promoter sequence. In some embodiments, the viral genome comprises at least one filler sequence and the filler sequence is located 3' to the polyadenylation signal sequence. In some embodiments, the viral genome comprises at least one filler sequence and the filler sequence is located 5' to the 3' ITR sequence. In some embodiments, the viral genome comprises at least one filler sequence, and the filler sequence is located between two intron sequences. In some embodiments, the viral genome comprises at least one filler sequence, and the filler sequence is located within an intron sequence. In some embodiments, the viral genome comprises two filler sequences, and the first filler sequence is located 3' to the 5' ITR sequence and the second filler sequence is located 3' to the polyadenylation signal sequence. In some embodiments, the viral genome comprises two filler sequences, and the first filler sequence is located 5' to a promoter sequence and the second filler sequence is located 3' to the polyadenylation signal sequence. In some embodiments, the viral genome comprises two filler sequences, and the first filler sequence is located 3' to the 5' ITR sequence and the second filler sequence is located 5' to the 5' ITR sequence.

In some embodiments, the viral genome is a self-complementary (sc) viral genome and comprises one or more filler sequences in order to have the length of the viral genome be about 2.3 kb. In some embodiments, the viral genome comprises at least one filler sequence and the filler sequence is located 3' to the 5' ITR sequence. In some embodiments, the viral genome comprises at least one filler sequence and the filler sequence is located 5' to a promoter sequence. In some embodiments, the viral genome comprises at least one filler sequence and the filler sequence is located 3' to the polyadenylation signal sequence. In some embodiments, the viral genome comprises at least one filler sequence and the filler sequence is located 5' to the 3' ITR sequence. In some embodiments, the viral genome comprises at least one filler sequence, and the filler sequence is located between two intron sequences. As a non-limiting example, the viral genome comprises at least one filler sequence, and the filler sequence is located within an intron sequence. In some embodiments, the viral genome comprises two filler sequences, and the first filler sequence is located 3' to the 5' ITR sequence and the second filler sequence is located 3' to the polyadenylation signal sequence. In some embodiments, the viral genome comprises two filler sequences, and the first filler sequence is located 5' to a promoter sequence and the second filler sequence is located 3' to the polyadenylation signal sequence. In some embodiments, the viral genome comprises two filler sequences, and the first filler sequence is located 3' to the 5' ITR sequence and the second filler sequence is located 5' to the 5' ITR sequence.

In some embodiments, the viral genome may comprise one or more filler sequences between one of more regions of the viral genome. In some embodiments, the filler region may be located before a region such as, but not limited to, a payload region, an inverted terminal repeat (ITR), a promoter region, an intron region, an enhancer region, a polyadenylation signal sequence region, and/or an exon region. In some embodiments, the filler region may be located after a region such as, but not limited to, a payload region, an inverted terminal repeat (ITR), a promoter region, an intron region, an enhancer region, a polyadenylation signal sequence region, and/or an exon region. In some embodiments, the filler region may be located before and after a region such as, but not limited to, a payload region, an inverted terminal repeat (ITR), a promoter region, an intron region, an enhancer region, a polyadenylation signal sequence region, and/or an exon region.

In some embodiments, the viral genome may comprise one or more filler sequences that bifurcate(s) at least one region of the viral genome. The bifurcated region of the viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of the of the region to the 5' of the filler sequence region. In some embodiments, the filler sequence may bifurcate at least one region so that 10% of the region is located 5' to the filler sequence and 90% of the region is located 3' to the filler sequence. In some embodiments, the filler sequence may bifurcate at least one region so that 20% of the region is located 5' to the filler sequence and 80% of the region is located 3' to the filler sequence. In some embodiments, the filler sequence may bifurcate at least one region so that 30% of the region is located 5' to the filler sequence and 70% of the region is located 3' to the filler sequence. In some embodiments, the filler sequence may bifurcate at least one region so that 40% of the region is located 5' to the filler sequence and 60% of the region is located 3' to the filler sequence. In some embodiments, the filler sequence may bifurcate at least one region so that 50% of the region is located 5' to the filler sequence and 50% of the region is located 3' to the filler sequence. In some embodiments, the filler sequence may bifurcate at least one region so that 60% of the region is located 5' to the filler sequence and 40% of the region is located 3' to the filler sequence. In some embodiments, the filler sequence may bifurcate at least one region so that 70% of the region is located 5' to the filler sequence and 30% of the region is located 3' to the filler sequence. In some embodiments, the filler sequence may bifurcate at least one region so that 80% of the region is located 5' to the filler sequence and 20% of the region is located 3' to the filler sequence. In some embodiments, the filler sequence may bifurcate at least one region so that 90% of the region is located 5' to the filler sequence and 10% of the region is located 3' to the filler sequence.

In some embodiments, the viral genome comprises a filler sequence after the 5' ITR.

In some embodiments, the viral genome comprises a filler sequence after the promoter region. In some embodiments, the viral genome comprises a filler sequence after the payload region. In some embodiments, the viral genome comprises a filler sequence after the intron region. In some embodiments, the viral genome comprises a filler sequence after the enhancer region. In some embodiments, the viral genome comprises a filler sequence after the polyadenylation signal sequence region. In some embodiments, the viral genome comprises a filler sequence after the exon region.

In some embodiments, the viral genome comprises a filler sequence before the promoter region. In some embodiments, the viral genome comprises a filler sequence before the payload region. In some embodiments, the viral genome comprises a filler sequence before the intron region. In some embodiments, the viral genome comprises a filler sequence before the enhancer region. In some embodiments, the viral genome comprises a filler sequence before the polyadenylation signal sequence region. In some embodiments, the viral genome comprises a filler sequence before the exon region.

In some embodiments, the viral genome comprises a filler sequence before the 3' ITR.

In some embodiments, a filler sequence may be located between two regions, such as, but not limited to, the 5' ITR and the promoter region. In some embodiments, a filler sequence may be located between two regions, such as, but not limited to, the 5' ITR and the payload region. In some embodiments, a filler sequence may be located between two regions, such as, but not limited to, the 5' ITR and the intron region. In some embodiments, a filler sequence may be located between two regions, such as, but not limited to, the 5' ITR and the enhancer region. In some embodiments, a filler sequence may be located between two regions, such as, but not limited to, the 5' ITR and the polyadenylation signal sequence region.

In some embodiments, a filler sequence may be located between two regions, such as, but not limited to, the 5' ITR and the exon region.

In some embodiments, a filler sequence may be located between two regions, such as, but not limited to, the promoter region and the payload region. In some embodiments, a filler sequence may be located between two regions, such as, but not limited to, the promoter region and the intron region. In some embodiments, a filler sequence may be located between two regions, such as, but not limited to, the promoter region and the enhancer region. In some embodiments, a filler sequence may be located between two regions, such as, but not limited to, the promoter region and the polyadenylation signal sequence region. In some embodiments, a filler sequence may be located between two regions, such as, but not limited to, the promoter region and the exon region. In some embodiments, a filler sequence may be located between two regions, such as, but not limited to, the promoter region and the 3' ITR.

In some embodiments, a filler sequence may be located between two regions, such as, but not limited to, the payload region and the intron region. In some embodiments, a filler sequence may be located between two regions, such as, but not limited to, the payload region and the enhancer region. In some embodiments, a filler sequence may be located between two regions, such as, but not limited to, the payload region and the polyadenylation signal sequence region. In some embodiments, a filler sequence may be located between two regions, such as, but not limited to, the payload region and the exon region.

In some embodiments, a filler sequence may be located between two regions, such as, but not limited to, the payload region and the 3' ITR.

Self-Complementary and Single Strand Vectors

In some embodiments, the AAV vector used in the present disclosure is a single strand vector (ssAAV).

In some embodiments, the AAV vectors may be self-complementary AAV vectors (scAAVs). See, e.g., U.S. Pat. No. 7,465,583. scAAV vectors contain both DNA strands that anneal together to form double stranded DNA. By skipping second strand synthesis, scAAVs allow for rapid expression in the cell.

In some embodiments, the AAV vector used in the present disclosure is a scAAV.

Methods for producing and/or modifying AAV vectors are disclosed in the art such as pseudotyped AAV vectors (International Patent Publication Nos. WO200028004;

WO200123001; WO2004112727; WO 2005005610 and WO 2005072364, the content of each of which are incorporated herein by reference in their entirety).

Genome Size

In some embodiments, the viral genome of the AAV particles of the present disclosure may be single or double stranded. The size of the vector genome may be small, medium, large or the maximum size.

In some embodiments, the vector genome, which comprises a nucleic acid sequence encoding FXN described herein, may be a small single stranded vector genome. A small single stranded vector genome may be about 2.7 kb to about 3.5 kb in size such as about 2.7, about 2.8, about 2.9, about 3.0, about 3.1, about 3.2, about 3.3, about 3.4, or about 3.5 kb in size. In some embodiments, the small single stranded vector genome may be 3.2 kb in size.

In some embodiments, the vector genome, which comprises a nucleic acid sequence encoding FXN described herein, may be a small double stranded vector genome. A small double stranded vector genome may be about 1.3 to about 1.7 kb in size such as about 1.3, about 1.4, about 1.5, about 1.6, or about 1.7 kb in size. In some embodiments, the small double stranded vector genome may be 1.6 kb in size.

In some embodiments, the vector genome, which comprises a nucleic acid sequence encoding FXN described herein, may be a medium single stranded vector genome. A medium single stranded vector genome may be about 3.6 to about 4.3 kb in size such as about 3.6, about 3.7, about 3.8, about 3.9, about 4.0, about 4.1, about 4.2, or about 4.3 kb in size. In some embodiments, the medium single stranded vector genome may be 4.0 kb in size.

In some embodiments, the vector genome, which comprises a nucleic acid sequence encoding FXN described herein, may be a medium double stranded vector genome. A medium double stranded vector genome may be about 1.8 to about 2.1 kb in size such as about 1.8, about 1.9, about 2.0, or about 2.1 kb in size. In some embodiments, the medium double stranded vector genome may be 2.0 kb in size. Additionally, the vector genome may comprise a promoter and a polyA tail.

In one embodiment, the vector genome which comprises a nucleic acid sequence encoding FXN described herein may be a large single stranded vector genome. A large single stranded vector genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded vector genome may be 4.7 kb in size. As another non-limiting example, the large single stranded vector genome may be 4.8 kb in size. As yet another non-limiting example, the large single stranded vector genome may be 6.0 kb in size.

In one embodiment, the vector genome which comprises a nucleic acid sequence encoding FXN described herein may be a large double stranded vector genome. A large double stranded vector genome may be 2.2 to 3.0 kb in size such as about 2.2, 2.3, 2.4, 2.5, 2.6, 2.7, 2.8, 2.9 and 3.0 kb in size. As a non-limiting example, the large double stranded vector genome may be 2.4 kb in size.

Payloads

In some embodiments, the disclosure herein provides constructs that allow for improved expression of FXN delivered by gene therapy vectors.

In some aspects, the present disclosure relates to compositions containing or comprising nucleic acid sequence(s) encoding frataxin (FXN) or functional fragment(s) thereof and methods of administering these compositions in vitro or in vivo in humans and/or animal models of disease.

AAV particles of the present disclosure may comprise a nucleic acid sequence encoding at least one "payload." As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide or multi-polypeptide, e.g., FXN or a variant thereof. The payload may comprise any nucleic acid known in the art that is useful for the expression (by supplementation of the protein product or gene replacement using a modulatory nucleic acid) of FXN in a target cell transduced or contacted with the AAV particle carrying the payload.

The payload construct may comprise a combination of coding and non-coding nucleic acid sequences.

Any segment, fragment, or the entirety of the viral genome and therein, the payload construct, may be codon optimized.

In some embodiments, the nucleic acid sequence of the AAV particle may be a payload construct comprising at least one portion encoding FXN.

In some embodiments, the payload construct encodes more than one payload. As a non-limiting example, a payload construct encoding more than one payload may be replicated and packaged into a viral particle. A target cell transduced with a viral particle comprising more than one payload may express each of the payloads in a single cell.

In some embodiments, the payload construct may encode a coding or non-coding RNA. In certain embodiments, the adeno-associated viral vector particle further comprises at least one cis-element selected from the group consisting of a Kozak sequence, a backbone sequence, and an intron sequence.

In some embodiments, the payload is a polypeptide which may be a peptide or protein. A protein encoded by the payload construct may comprise a secreted protein, an intracellular protein, an extracellular protein, and/or a membrane protein. The encoded proteins may be structural or functional. Proteins encoded by the payload construct include, but are not limited to, mammalian proteins. In certain embodiments, the AAV particle contains a viral genome that encodes FXN or a variant thereof. The AAV particles encoding a payload may be useful in the fields of human disease, veterinary applications, and a variety of in vivo and in vitro settings.

In some embodiments, a payload may comprise polypeptides that serve as marker proteins to assess cell transformation and expression, fusion proteins, polypeptides having a desired biological activity, gene products that can complement a genetic defect, RNA molecules, transcription factors, and other gene products that are of interest in regulation and/or expression. In some embodiments, a payload may comprise nucleotide sequences that provide a desired effect or regulatory function (e.g., transposons, transcription factors).

The encoded payload may comprise a gene therapy product. A gene therapy product may include, but is not limited to, a polypeptide, RNA molecule, or other gene product that, when expressed in a target cell, provides a desired therapeutic effect. In some embodiments, a gene therapy product may comprise a substitute for a non-functional gene or a gene that is absent, expressed in insufficient amounts, or mutated. In some embodiments, a gene therapy product may comprise a substitute for a non-functional protein or polypeptide or a protein or polypeptide that is absent, expressed in insufficient amounts, misfolded, degraded too rapidly, or mutated. For example, a gene therapy product may comprise a FXN polypeptide or a polynucleotide encoding a FXN polypeptide to treat FXN deficiency or FA.

In some embodiments, the payload encodes a messenger RNA (mRNA). As used herein, the term "messenger RNA" (mRNA) refers to any polynucleotide that encodes a polypeptide of interest and that is capable of being translated to produce the encoded polypeptide of interest in vitro, in vivo, in situ, or ex vivo. Certain embodiments provide the mRNA as encoding FXN or a variant thereof.

The components of an mRNA include, but are not limited to, a coding region, a 5'-UTR (untranslated region), a 3'-UTR, a 5'-cap and a poly-A tail. In some embodiments, the encoded mRNA or any portion of the AAV genome may be codon optimized.

In some embodiments, the protein or polypeptide encoded by the payload construct encoding FXN or a variant thereof is between about 50 and about 4500 amino acid residues in length (hereinafter in this context, "X amino acids in length" refers to X amino acid residues). In some embodiments, the protein or polypeptide encoded is between 50-2000 amino acids in length. In some embodiments, the protein or polypeptide encoded is between 50-1000 amino acids in length. In some embodiments, the protein or polypeptide encoded is between 50-1500 amino acids in length. In some embodiments, the protein or polypeptide encoded is between 50-1000 amino acids in length. In some embodiments, the protein or polypeptide encoded is between 50-800 amino acids in length. In some embodiments, the protein or polypeptide encoded is between 50-600 amino acids in length. In some embodiments, the protein or polypeptide encoded is between 50-400 amino acids in length. In some embodiments, the protein or polypeptide encoded is between 50-200 amino acids in length. In some embodiments, the protein or polypeptide encoded is between 50-100 amino acids in length.

A payload construct encoding a payload may comprise or encode a selectable marker. A selectable marker may comprise a gene sequence or a protein or polypeptide encoded by a gene sequence expressed in a host cell that allows for the identification, selection, and/or purification of the host cell from a population of cells that may or may not express the selectable marker. In some embodiments, the selectable marker provides resistance to survive a selection process that would otherwise kill the host cell, such as treatment with an antibiotic. In some embodiments, an antibiotic selectable marker may comprise one or more antibiotic resistance factors, including but not limited to neomycin resistance (e.g., neo), hygromycin resistance, kanamycin resistance, and/or puromycin resistance.

In some embodiments, any nucleic acid sequence encoding a protein or polypeptide can be used as a selectable marker comprising recognition by a specific antibody.

In some embodiments, a payload construct encoding a payload may comprise a selectable marker including, but not limited to, β-lactamase, luciferase, β-galactosidase, or any other reporter gene as that term is understood in the art, including cell-surface markers, such as CD4 or the truncated nerve growth factor (NGFR) (for GFP, see WO 96/23810; Heim et al., *Current Biology* 2:178-182 (1996); Heim et al., *Proc. Natl. Acad. Sci. USA* (1995); or Heim et al., *Science* 373:663-664 (1995); for β-lactamase, see WO 96/30540); the contents of each of which are herein incorporated by reference in their entirety.

In some embodiments, a payload construct encoding a selectable marker may comprise a fluorescent protein. A fluorescent protein as herein described may comprise any fluorescent marker including but not limited to green, yellow, and/or red fluorescent protein (GFP, YFP, and/or RFP). In some embodiments, a payload construct encoding a selectable marker may comprise a human influenza hemagglutinin (HA) tag.

In certain embodiments, a nucleic acid for expression of a payload in a target cell will be incorporated into the viral genome and located between two ITR sequences.

Payload: Frataxin

In some embodiments, the payload is a frataxin protein. As used herein, the term "frataxin protein" or "FXN protein" is used interchangeably with "frataxin polypeptide" or "FXN polypeptide" and encompasses wild-type FXN as well as functional variants thereof. A functional variant is a variant that retains some or all of the activity of its wild-type counterpart, so as to achieve a desired therapeutic effect. For example, in some embodiments, a functional variant is effective to be used in gene therapy to treat a disorder or condition, for example, FXN deficiency or FA. Unless indicated otherwise, a variant of FXN as described herein (e.g., in the context of the constructs, vectors, genomes, methods, kits, compositions, etc. of the disclosure) is a functional variant.

Friedreich's ataxia (FA) is an autosomal recessive disorder that occurs when the frataxin (FXN) gene contains amplified intronic GAA repeats (an example of trinucleotide repeat expansion). See Parkinson et al., *Journal of Neurochemistry*, 2013, 126 (Suppl. 1), 103-117, the contents of which are herein incorporated by reference in their entirety. GAA repeat expansion within the gene causes FXN protein levels to be reduced. FXN is an iron-binding protein responsible for forming iron-sulfur clusters. One result of FXN protein deficiency is mitochondrial iron overload which can cause damage to many proteins. See Nageshwaran and Festenstein, *Frontiers in Neurology*, Vol. 6, Art. 262 (2015), the content of which is herein incorporated by reference in its entirety. The FXN gene is located on chromosome 9. See Sandi et al., *Frontiers in Genetics*, Vol. 5, Art. 165 (June 2014), the contents of which are herein incorporated by reference in their entirety.

The mutant gene contains expanded GAA triplet repeats in the first intron, and in a few instances, point mutations have been detected. Because the defect is located in an intron (which is removed from the mRNA transcript between transcription and translation), this mutation does not result in the production of abnormal FXN proteins. See Nageshwaran and Festenstein, *Frontiers in Neurology*, Vol. 6, Art. 262 (2015). Instead, the mutation causes gene silencing (i.e., the mutation decreases the transcription of the gene) through induction of a heterochromatin structure in a manner similar to position-effect variegation. Besides reducing expression of FXN protein, long tracts of GAA repeats induce chromosome breaks in in vivo yeast studies.

Low levels of FXN protein lead to insufficient biosynthesis of iron-sulfur clusters that are required for mitochondrial electron transport and assembly of functional aconitase and dysregulated iron metabolism of the entire cell. See Nageshwaran and Festenstein, *Frontiers in Neurology*, Vol. 6, Art. 262 (2015). In normal individuals, the FXN gene encodes a mitochondrial matrix FXN protein. This globular protein consists of two α helices and seven β strands and is highly conserved, occurring in all eukaryotes and some prokaryotes. FXN protein has a variety of known functions; most notably, it assists iron-sulfur protein synthesis in the electron transport chain to ultimately generate adenosine triphosphate (ATP), the energy currency necessary to carry out metabolic functions in cells. FXN protein also regulates iron transfer in the mitochondria in order to provide a proper amount of reactive oxygen species (ROS) to maintain normal processes. Without FXN protein, the energy in the mitochondria fails, and excess iron causes extra ROS to be created, leading to further cell damage.

Other disorders of the central nervous system may ultimately be found to be related to aberrant expression or a deficiency in the quantity or function of FXN protein. Such disorders may include, but are not limited to, neurological or neuromuscular disorders such as Alzheimer's disease, Huntington's disease, autism, Parkinson's disease, and spinal muscular atrophy, or other neurological or neuromuscular diseases, disorders, or conditions described herein.

As used herein, "associated with decreased frataxin protein levels" or "associated with decreased expression" means that one or more symptoms of the disease are caused by lower-than-normal frataxin protein levels in a target tissue or in a biofluid such as blood. A disease or condition associated with decreased frataxin protein levels or expression may be a disorder of the central nervous system. Such a disease or condition may be a neuromuscular or a neurological disorder or condition. For example, a disease associated with decreased frataxin protein levels may be FA, or may be another neurological or neuromuscular disorder described herein.

The present disclosure addresses the need for new technologies by providing FXN related treatment deliverable by AAV-based compositions and complexes for the treatment of FA.

While delivery is exemplified in the AAV context, other viral vectors, non-viral vectors, nanoparticles, or liposomes may be similarly used to deliver the therapeutic FXN and include, but are not limited to, vector genomes of any of the AAV serotypes or other viral delivery vehicles or lentivirus, etc. The observations and teachings extend to any macromolecular structure, including modified cells, introduced into the CNS in the manner as described herein.

Given in Table 2 are the sequence identifiers of representative polynucleotide and polypeptide sequences for frataxin that may be used in the viral genomes disclosed herein and which may constitute a frataxin payload. Functional variants, e.g., those retaining at least about 90% or at least 95% sequence identity to a sequence shown in Table 2, may also be used. Codon-optimized and other variants that encode the same or essentially the same FXN amino acid sequence (e.g., those having at least about 90% amino acid sequence identity) may also be used.

TABLE 2

Representative Frataxin Sequences

| SEQ ID NO: | Type | Species | Description |
|---|---|---|---|
| 1725 | PRT | Homo sapiens | NP_000135.2 |
| 1726 | PRT | Homo sapiens | NP_852090.1 |
| 1727 | PRT | Homo sapiens | NP_001155178.1 |
| 1728 | DNA | Homo sapiens | NM_000144.4 encodes NP_000135.2 |
| 1729 | DNA | Homo sapiens | NM_181425.2 encodes NP_852090.1 |
| 1730 | DNA | Homo sapiens | NM_001161706.1 encodes NP_001155178.1 |
| 1731 | PRT | Macaca fascicularis | A0A2K5VX49 (UniProt) |
| 1732 | PRT | Macaca fascicularis | NP_001271967.1 |
| 1733 | PRT | Macaca mulatta | NP_001247670.1 |

In some embodiments, the viral genome comprises a payload region encoding a frataxin protein. The encoded frataxin may be derived from any species, such as, but not limited to human, non-human primate, or rodent.

In some embodiments, the viral genome comprises a payload region encoding a human (Homo sapiens) frataxin, or a variant thereof.

Various embodiments of the disclosure herein provide an adeno-associated viral (AAV) particle comprising a viral genome, the viral genome comprising at least one inverted terminal repeat region and a nucleic acid sequence encoding a polypeptide having at least 90% sequence identity to a human frataxin (hFXN) sequence of SEQ ID NO: 1725, 1726, and/or 1727, or a variant thereof.

In some embodiments, the AAV viral genome comprises at least one inverted terminal repeat region and a nucleic acid sequence encoding a polypeptide having at least 90% sequence identity to SEQ ID NO: 1725. In some embodiments, the AAV viral genome comprises at least one inverted terminal repeat region and a nucleic acid sequence encoding a polypeptide having at least 95% sequence identity to SEQ ID NO: 1725. In some embodiments, the AAV viral genome comprises at least one inverted terminal repeat region and a nucleic acid sequence encoding a polypeptide having at least 98% sequence identity to SEQ ID NO: 1725. In some embodiments, the AAV viral genome comprises at least one inverted terminal repeat region and a nucleic acid sequence encoding a polypeptide having at least 99% sequence identity to SEQ ID NO: 1725. In some embodiments, the AAV viral genome comprises at least one inverted terminal repeat region and a nucleic acid sequence encoding SEQ ID NO: 1725.

In some embodiments, the AAV viral genome comprises at least one inverted terminal repeat region and a nucleic acid sequence having at least 90% sequence identity to SEQ ID NO: 1728 or a fragment thereof. In some embodiments, the AAV viral genome comprises at least one inverted terminal repeat region and a nucleic acid sequence having at least 95% sequence identity to SEQ ID NO: 1728 or a fragment thereof. In some embodiments, the AAV viral genome comprises at least one inverted terminal repeat region and a nucleic acid sequence having at least 98% sequence identity to SEQ ID NO: 1728 or a fragment thereof. In some embodiments, the AAV viral genome comprises at least one inverted terminal repeat region and a nucleic acid sequence having at least 99% sequence identity to SEQ ID NO: 1728 or a fragment thereof. In some embodiments, the AAV viral genome comprises at least one inverted terminal repeat region and a nucleic acid sequence of SEQ ID NO: 1728 or a fragment thereof. In some embodiments, the fragment of SEQ ID NO: 1728 comprises nucleotides 221-853 of SEQ ID NO: 1728.

In some embodiments, the AAV viral genome comprises at least one inverted terminal repeat region and a nucleic acid sequence having at least 90% sequence identity to SEQ ID NO: 1823 or a fragment thereof. In some embodiments, the AAV viral genome comprises at least one inverted terminal repeat region and a nucleic acid sequence having at least 95% sequence identity to SEQ ID NO: 1823 or a fragment thereof. In some embodiments, the AAV viral genome comprises at least one inverted terminal repeat region and a nucleic acid sequence having at least 98% sequence identity to SEQ ID NO: 1823 or a fragment thereof. In some embodiments, the AAV viral genome comprises at least one inverted terminal repeat region and a nucleic acid sequence having at least 99% sequence identity to SEQ ID NO: 1823 or a fragment thereof. In some embodiments, the AAV viral genome comprises at least one inverted terminal repeat region and a nucleic acid sequence of SEQ ID NO: 1823 or a fragment thereof. In some embodiments, the nucleic acid sequence further comprises a stop codon.

In some embodiments, the AAV viral genome comprises at least one inverted terminal repeat region and a nucleic acid sequence having at least 90% sequence identity to SEQ ID NO: 1824 or a fragment thereof. In some embodiments, the AAV viral genome comprises at least one inverted terminal repeat region and a nucleic acid sequence having at least 95% sequence identity to SEQ ID NO: 1824 or a fragment thereof. In some embodiments, the AAV viral genome comprises at least one inverted terminal repeat region and a nucleic acid sequence having at least 98% sequence identity to SEQ ID NO: 1824 or a fragment thereof. In some embodiments, the AAV viral genome comprises at least one inverted terminal repeat region and a nucleic acid sequence having at least 99% sequence identity to SEQ ID NO: 1824 or a fragment thereof. In some embodiments, the AAV viral genome comprises at least one inverted terminal repeat region and a nucleic acid sequence of SEQ ID NO: 1824 or a fragment thereof.

In some embodiments, the FXN polypeptide is derived from a FXN sequence of a non-human primate, such as the cynomolgus monkey, *Macaca fascicularis* (cynoFXN). Certain embodiments provide the FXN polypeptide as a humanized version of a *Macaca fascicularis* (HcynoFXN) sequence. In some embodiments, the FXN polypeptide sequence has at least about 90% sequence identity with the art-accepted canonical human FXN amino acid sequence of SEQ ID NO: 1725, which may be encoded by the nucleic acid sequence of SEQ ID NO: 1728. In some embodiments, the FXN polypeptide sequence has at least about 90% sequence identity with the art-accepted canonical human FXN amino acid sequence of SEQ ID NO: 1726, which is encoded by the nucleic acid sequence of SEQ ID NO: 1729. In some embodiments, the FXN polypeptide sequence has at least about 90% sequence identity with the art-accepted canonical human FXN amino acid sequence of SEQ ID NO: 1727, which is encoded by the nucleic acid sequence of SEQ ID NO: 1730.

In some embodiments, the viral genome comprises a payload region encoding a cynomolgus or crab-eating (long-tailed) macaque (*Macaca fascicularis*) frataxin, or a variant thereof.

In some embodiments, the viral genome comprises a payload region encoding a rhesus macaque (*Macaca mulatta*) frataxin, or a variant thereof.

In some embodiments, the AAV viral genome comprises at least one inverted terminal repeat region and a nucleic acid sequence having at least 90% sequence identity to SEQ ID NO: 1822 or a fragment thereof. In some embodiments, the AAV viral genome comprises at least one inverted terminal repeat region and a nucleic acid sequence having at least 95% sequence identity to SEQ ID NO: 1822 or a fragment thereof. In some embodiments, the AAV viral genome comprises at least one inverted terminal repeat region and a nucleic acid sequence having at least 98% sequence identity to SEQ ID NO: 1822 or a fragment thereof. In some embodiments, the AAV viral genome comprises at least one inverted terminal repeat region and a nucleic acid sequence having at least 99% sequence identity to SEQ ID NO: 1822 or a fragment thereof. In some embodiments, the AAV viral genome comprises at least one inverted terminal repeat region and a nucleic acid sequence of SEQ ID NO: 1822 or a fragment thereof.

In some embodiments, the frataxin polypeptide may comprise an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the those described above.

In some embodiments, the frataxin polypeptide may be encoded by a nucleic acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the those described above.

Viral Genome: Promoters

In some embodiments, the payload region of the viral genome comprises an element to enhance or modulate payload expression, such as, but not limited to, a promoter. The promoter may be a wild-type or engineered promoter, or a combination thereof. In some embodiments, the viral genome comprises at least one promoter. In some embodiments, the viral genome comprises more than one promoter.

In some embodiments, the promoter is a wild-type frataxin promoter, or a derivative (e.g., a truncation or variant) thereof. Suitable derivatives of a wild-type frataxin promoter are those that are functional, e.g., are effective to express a payload in at least a minimally-detectable level.

In some embodiments, the promoter is an engineered frataxin promoter. Included herein are shorter variants of frataxin promoters. A frataxin promoter may be 200-1400 nt in length, or any length in between. In some embodiments, a frataxin promoter variant may be 223, 363, 534, 747, 906, 1060, 1226, or 1353 nucleotides in length. A frataxin promoter variant may be shorter than a wild-type frataxin promoter sequence due to deletions in any region of the promoter sequence, such as, but not limited to, the 5' end of the promoter sequence, the 3' end of the promoter sequence, or within the promoter sequence.

In some embodiments, the promoter is a combination of one or more of any of the promoters described herein. In some embodiments, the promoter is used with an enhancer sequence. In some embodiments, the enhancer sequence may be derived from a cytomegalovirus immediate early gene (CMVie). In some embodiments, the enhancer may be located upstream (5') to the promoter. In some embodiments, the enhancer comprises SEQ ID NO: 1777.

In some embodiments, the promoter is a CBA promoter, or a derivative (e.g., a truncation or variant) thereof. It is to be understood that suitable derivatives of a CBA promoter are functional, e.g., are effective to express a payload.

In some embodiments, a CBA promoter comprises a CMVie enhancer, a backbone sequence, and a CB promoter sequence, when recited 5' to 3'. Each of the three components (CMVie enhancer, backbone, and CB sequences) may be of differing lengths among variants.

In some embodiments, a CBA promoter comprises a backbone sequence and a CB promoter sequence, when recited 5' to 3'.

In some embodiments, a CBA promoter comprises a CB promoter sequence.

In some embodiments, a CBA promoter may be 100-700 nt in length, or any length in between. In some embodiments, CBA promoter variants may be 100, 180, 260, 270, 332, 412, 492, or 572 nucleotides in length. A CBA promoter variant may be shorter than a wild-type CBA promoter sequence due to deletions in any region of the enhancer, backbone, or promoter sequence, such as, but not limited to, the 5' end of the promoter sequence, the 3' end of the promoter sequence or within the promoter sequence.

In some embodiments, the promoter is a CMV promoter, or a derivative (e.g., a truncation or variant) thereof. It is to be understood that suitable derivatives of a CMV promoter are functional, e.g., are effective to express a payload. A CMV promoter may comprise a CMV enhancer and a CMV promoter sequence, or only a CMV promoter sequence. The CMV enhancer and CMV promoter sequences may be of differing lengths between promoter variants.

In some embodiments, a CMV promoter may be 50-700 nt in length, or any length in between. In some embodiments, CMV promoter variants may be 55, 109, 163, 217, 289, 361, 433, or 505 nucleotides in length. A CMV promoter variant may be shorter than a wild-type CMV promoter sequence due to deletions in any region of the enhancer or promoter sequence, such as, but not limited to, the 5' end of the promoter sequence, the 3' end of the promoter sequence, or within the promoter sequence.

In some embodiments, the promoter is a deletion variant of a parent promoter sequence, wherein one or more nucleotides has been removed from the parent sequence.

In some embodiments, the promoter is an insertion variant of a parent promoter sequence, wherein one or more nucleotides is added to the parent sequence.

In some embodiments, the promoter comprises one or more mutations as compared to a parent promoter sequence.

In some embodiments, the promoter is modified in one or more ways (e.g., deletion, mutation, and/or insertion) to create a promoter variant.

In some embodiments, a promoter may comprise a sequence, fragment, or variant thereof, of any of the sequences in Table 3. For example, a promoter may comprise a sequence having at least 90%, at least 95%, at least 99%, or 100% sequence identity to a sequence selected from the group consisting of SEQ ID NO: 1734-1777, e.g., a sequence having the specified percent identity and providing some or all of the same function as the sequence selected from the group consisting of SEQ ID NO: 1734-1777. In some embodiments, a promoter is or is derived from a CMV promoter and comprises a sequence having at least 90%, at least 95%, at least 99%, or 100% sequence identity to a sequence selected from the group consisting of SEQ ID NO: 1743-1751, 1767, 1772-1772 and 1777. In some embodiments, a promoter is or is derived from a CBA promoter and comprises a sequence having at least 90%, at least 95%, at least 99%, or 100% sequence identity to a sequence selected from the group consisting of SEQ ID NO: 1734-1742, 1760-1766, 1768, and 1775-1776. In some embodiments, a promoter is or is derived from a FXN promoter and comprises a sequence having at least 90%, at least 95%, at least 99%, or 100% sequence identity to a sequence selected from the group consisting of SEQ ID NO: 1752-1759 and 1769-1770.

In some embodiments, a promoter may comprise a combination of more than one sequence of any of those listed in Table 3. In some embodiments, a promoter sequence may further comprise at least one of the intron/exon sequences as given in Table 6.

In some embodiments, a promoter comprises a sequence having at least 90%, at least 95%, at least 99%, or 100% sequence identity to SEQ ID NO: 1738. In some embodiments, the promoter is SEQ ID NO: 1738. In some embodiments, an AAV vector genome comprises a promoter sequence having at least 90% sequence identity to SEQ ID NO: 1738 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1738 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1738 and a payload region encoding a frataxin polypeptide having an amino acid sequence of SEQ ID NO: 1725 (e.g., a payload region comprising SEQ ID NO: 1824). In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1740. In some embodiments, the promoter is SEQ ID NO: 1740. In some embodiments, an AAV vector genome comprises a promoter sequence having at least 90% sequence identity to SEQ ID NO: 1740 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1740 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1740 and a payload region encoding a frataxin polypeptide having an amino acid sequence of SEQ ID NO: 1725 (e.g., a payload region comprising SEQ ID NO: 1824). In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1742. In some embodiments, the promoter is SEQ ID NO: 1742. In some embodiments, an AAV vector genome comprises a promoter sequence having at least 90% sequence identity to SEQ ID NO: 1742 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1742 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1742 and a payload region encoding a frataxin polypeptide having an amino acid sequence of SEQ ID NO: 1725 (e.g., a payload region comprising SEQ ID NO: 1824).

In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1750. In some embodiments, the promoter is SEQ ID NO: 1750. In some embodiments, an AAV vector genome comprises a promoter sequence having at least 90% sequence identity to SEQ ID NO: 1750 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1750 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1750 and a payload region encoding a frataxin polypeptide having an amino acid sequence of SEQ ID NO: 1725 (e.g., a payload region comprising SEQ ID NO: 1824). In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter used in a viral genome disclosed herein comprises any one of the promoter sequences in Table 3. In Table 3, CMV stands for "cytomegalovirus;" CBA stands for "chicken β-actin," which may have a CMV IE ("immediate early") enhancer region and a promoter region; CAG stands for CMV enhancer, CBA promoter, and rabbit beta-globin splice acceptor site; FXN stands for "Frataxin;" and mCBA stands for a variant of the CBA promoter that was generated using PCR.

TABLE 3

Representative Promoters

| Promoter Name | Starting Promoter | Length of Promoter | SEQ ID NO of Promoter |
|---|---|---|---|
| CBA | CBA | 652 | 1734 |
| CBA-D1 | CBA | 572 | 1735 |
| CBA-D2 | CBA | 492 | 1736 |
| CBA-D3 | CBA | 412 | 1737 |
| CBA-D4 | CBA | 332 | 1738 |
| CBA-D5 | CBA | 270 | 1739 |
| CBA-D6 | CBA | 260 | 1740 |
| CBA-D7 | CBA | 180 | 1741 |
| CBA-D8 | CBA | 100 | 1742 |
| CMV | CMV | 588 | 1743 |
| CMV-D1 | CMV | 505 | 1744 |
| CMV-D2 | CMV | 433 | 1745 |
| CMV-D3 | CMV | 361 | 1746 |
| CMV-D4 | CMV | 289 | 1747 |
| CMV-D5 | CMV | 217 | 1748 |
| CMV-D6 | CMV | 163 | 1749 |
| CMV-D7 | CMV | 109 | 1750 |
| CMV-D8 | CMV | 55 | 1751 |
| FXNpro223 | FXN | 223 | 1752 |
| FXNpro363 | FXN | 363 | 1753 |
| FXNpro534 | FXN | 534 | 1754 |

TABLE 3-continued

Representative Promoters

| Promoter Name | Starting Promoter | Length of Promoter | SEQ ID NO of Promoter |
|---|---|---|---|
| FXNpro907 | FXN | 907 | 1755 |
| FXNpro1060 | FXN | 1060 | 1756 |
| FXNpro1226 | FXN | 1226 | 1757 |
| FXNpro1353 | FXN | 1353 | 1758 |
| FXNproN1336 | FXN | 1336 | 1759 |
| mCBA | mCBA | 610 | 1760 |
| mCBA-D1 | mCBA | 526 | 1761 |
| mCBA-D2 | mCBA | 441 | 1762 |
| mCBA-D3 | mCBA | 366 | 1763 |
| mCBA-D4 | mCBA | 286 | 1764 |
| mCBA-D5 | mCBA | 224 | 1765 |
| mCBA-D6 | mCBA | 214 | 1766 |
| CMV-80 | CMV | 80 | 1767 |
| CBA-90 | CBA | 90 | 1768 |
| FXN-150 | FXN | 150 | 1769 |
| FXN-200 | FXN | 198 | 1770 |
| CAG | CAG | 1715 | 1771 |
| CMV-205 | CMV | 205 | 1772 |
| CMV-299 | CMV | 299 | 1773 |
| CMV-380 | CMV | 380 | 1774 |
| CBAmin | CBA | 283 | 1775 |
| CBA-654 | CBA | 654 | 1776 |
| CMV Enhancer | CMV | 383 | 1777 |

In some embodiments, a promoter is used to modulate frataxin expression in a target cell. In certain embodiments, a promoter may be used to increase frataxin expression in a target cell to a level greater than that of normal endogenous frataxin expression. In certain embodiments, a promoter may be used to induce frataxin expression in a target cell to a level close to or equivalent to that of normal endogenous frataxin expression.

In some embodiments, a junction sequence may be used in combination with a promoter described herein such as, but not limited to, those listed in Table 3. In certain embodiments, the junction sequence may be located 5' to the promoter in the viral genome. In certain embodiments, the junction sequence may be located 3' to the promoter in the viral genome. In certain embodiments, the viral genome may include more than one junction sequence. As a non-limiting example, the viral genome may comprise a junction sequence on the 5' end of the promoter and on the 3' end of the promoter. The junction sequence may be the same sequence, two different sequences or a sequence split on either side of the promoter sequence. In certain embodiments, the junction sequence comprises SEQ ID NO: 1813. In certain embodiments, the junction sequence comprises SEQ ID NO: 1814.

In some embodiments, a promoter is used to enhance frataxin expression in a target cell (e.g., nervous system or cardiac tissue). Frataxin expression may be increased by 0.01 to 100 (0.01-100×) times endogenous frataxin expression for that target cell. In some embodiments, a promoter is used to maintain frataxin expression in a target cell at 0.5-3× (e.g., 0.5-1×, 1-1.5×, 1.5-2×, 2-2.5×, 2.5-3×) endogenous frataxin (i.e., normal human levels or approximately 5.5-32.8 ng/mg protein).

In some embodiments, a promoter, e.g., a promoter in Table 3, is used in an AAV vector genome further comprising a sequence encoding a frataxin polypeptide sequence, e.g., a human frataxin polypeptide sequence. In some embodiments, the promoter comprises a sequence having at least 90%, at least 95%, at least 99%, or 100% sequence identity to SEQ ID NO: 1742. In some embodiments, the promoter is SEQ ID NO: 1742. In some embodiments, an AAV vector genome comprises a promoter sequence having at least 90% sequence identity to SEQ ID NO: 1742 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1742 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1742 and a payload region encoding a frataxin polypeptide having an amino acid sequence of SEQ ID NO: 1725 (e.g., a payload region comprising SEQ ID NO: 1824) and/or further comprising one or more sequences, or a 95% identical variant thereof, as provided in Tables 5-11. In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1750. In some embodiments, the promoter is SEQ ID NO: 1750. In some embodiments, an AAV vector genome comprises a promoter sequence having at least 90% sequence identity to SEQ ID NO: 1750 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1750 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1750 and a payload region encoding a frataxin polypeptide having an amino acid sequence of SEQ ID NO: 1725 (e.g., a payload region comprising SEQ ID NO: 1824) and/or further comprising one or more sequences, or a 95% identical variant thereof, as provided in Tables 5-11. In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1738. In some embodiments, the promoter is SEQ ID NO: 1738. In some embodiments, an AAV vector genome comprises a promoter sequence having at least 90% sequence identity to SEQ ID NO: 1738 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1738 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1738 and a payload region encoding a frataxin polypeptide having an amino acid sequence of SEQ ID NO: 1725 (e.g., a payload region comprising SEQ ID NO: 1824) and/or further comprising one or more sequences, or a 95% identical variant thereof, as provided in Tables 5-11. In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In some embodiments, a promoter comprises a sequence having at least 90%, at least 95%, at least 99%, or 100% sequence identity to SEQ ID NO: 1740. In some embodiments, the promoter is SEQ ID NO: 1740. In some embodiments, an AAV vector genome comprises a promoter sequence having at least 90% sequence identity to SEQ ID NO: 1740 and a payload region encoding a frataxin polypeptide having an amino acid sequence at least 90% identical to SEQ ID NO: 1725 (e.g., a payload region comprising a nucleic acid sequence at least 90% identical to SEQ ID NO: 1824). In some embodiments, an AAV vector genome comprises a promoter sequence having at least 95% sequence identity to SEQ ID NO: 1740 and a payload region encoding a frataxin polypeptide having an amino acid sequence at least 95% identical to SEQ ID NO: 1725 (e.g., a payload region comprising a nucleic acid sequence at least 95% identical to SEQ ID NO: 1824). In some embodiments, an AAV vector genome comprises the promoter sequence of SEQ ID NO: 1740 and a payload region encoding a frataxin polypeptide having an amino acid sequence of SEQ ID NO: 1725 (e.g., a payload region comprising SEQ ID NO: 1824) and/or further comprising one or more sequences, or a 95% identical variant thereof, as provided in Tables 5-11. In some embodiments, the frataxin polypeptide is encoded by a nucleic acid sequence comprising SEQ ID NO: 1728 or a fragment thereof, optionally nucleotides 221-853 of SEQ ID NO: 1728. In some embodiments, the frataxin polypeptide is encoded by a nucleic acid sequence comprising SEQ ID NO: 1822, 1823, or 1824.

In various embodiments, any of the promoters disclosed herein, e.g., a promoter from Table 3 or a promoter having 90% or greater homology thereto, may be paired in an AAV viral vector genome with one or more of the components disclosed in Table 5-11 or component(s) having 90% or greater homology thereto, alone or in combination with additional sequences, e.g., filler sequence(s). In some embodiments, the AAV vector genome may comprise multiple copies (e.g., two, three, or more copies) of one or more viral genome components described herein. In some embodiments, the viral genome comprises two miR binding sites (e.g., two miR122 binding sites). In some embodiments, the viral genome comprises three miR binding sites (e.g., three miR122 binding sites). In some embodiments, the viral genome comprises any of the promoters disclosed herein, e.g., a promoter from Table 3 or a promoter having 90% or greater homology thereto, along with one or more components provided in any of Tables 5-11 or otherwise described herein, in the 5' to 3' order shown in any of Tables 4, 12, 13, 14, 15, 16, or 17. In some embodiments, the viral genome comprises a promoter provided in Table 3 along with one or more components provided in any of Tables 5-11 or otherwise described herein, in the 5' to 3' order shown in any of Tables 4, 12, 13, 14, 15, 16, or 17. In some embodiments, the viral genome comprises all components and the 5' to 3' order shown in any of Tables 4, 12, 13, 14, 15, 16, or 17.

For example, a promoter comprising SEQ ID NO: 1742, or having 90% or greater homology thereto, may be paired with any of the components in Tables 5-11 (or component(s) having 90% or greater homology thereto) in an AAV vector genome, e.g., with the promoter positioned between the 5' ITR sequence and the ie1 exon 1 (e.g., directly contacting the two other components or separated by one or more non-coding sequences). In some embodiments, the viral genome comprises three miR122 binding sites. In some embodiments, the viral genome further comprises a payload region, e.g., one encoding a frataxin protein.

In another example, a promoter comprising SEQ ID NO: 1750, or having 90% or greater homology thereto, may be paired with any of the components in Tables 5-11 (or component(s) having 90% or greater homology thereto) in an AAV vector genome, e.g., with the promoter positioned between the 5' ITR sequence and the ie1 exon 1 (e.g., directly contacting the two other components or separated by one or more non-coding sequences). In some embodiments, the viral genome comprises three miR122 binding sites. In some embodiments, the viral genome further comprises a payload region, e.g., one encoding a frataxin protein.

For example, a promoter comprising SEQ ID NO: 1738, or having 90% or greater homology thereto, may be paired with any of the components in Tables 5-11 (or component(s) having 90% or greater homology thereto) in an AAV vector genome, e.g., with the promoter positioned between the 5' ITR sequence and the ie1 exon 1 (e.g., directly contacting the two other components or separated by one or more non-coding sequences). In some embodiments, the viral genome comprises three miR122 binding sites. In some embodiments, the viral genome further comprises a payload region, e.g., one encoding a frataxin protein.

In another example, a promoter comprising SEQ ID NO: 1740, or having 90% or greater homology thereto, may be paired with any of the components in Tables 5-11 (or component(s) having 90% or greater homology thereto) in an AAV vector genome, e.g., with the promoter positioned between the 5' ITR sequence and the ie1 exon 1 (e.g., directly contacting the two other components or separated by one or more non-coding sequences). In some embodiments, the viral genome comprises three miR122 binding sites. In some embodiments, the viral genome further comprises a payload region, e.g., one encoding a frataxin protein.

In some embodiments, the promoter is or is derived from a CBA promoter. The CBA promoter may drive expression of a payload in various tissues in a subject. As a non-limiting example, expression of FXN using a CBA promoter (promoter provided as SEQ ID NO: 1776 and ITR to ITR provided as SEQ ID NO: 1778) is shown in Example 4, including Tables 16-28, of co-owned International Patent Application No. PCT/US2019/032387, the contents of which are herein incorporated by reference in their entirety. Expression of FXN in mice after IV injection is shown in Table 16 of co-owned International Patent Application No. PCT/US2019/032387, where expression is seen in the cortex, lumbar spinal cord, lumbar dorsal root ganglia, trigeminal ganglion, heart and liver with VOY101 particles with a CBA promoter. The expression of FXN in NHP after IV injection is shown in Table 18 of co-owned International Patent Application No. PCT/US2019/032387, where expression is seen in the brainstem, cervical spinal cord, thoracic spinal cord, lumbar spinal cord, cervical DRG, thoracic DRG, lumbar/sacral DRG, heart ventricle, heart atrium, liver, soleus, and jejunum with VOY101 particles with a CBA promoter. The expression of FXN in NHP after IV injection at different doses ($6.3 \times 10^{11}$ VG/kg, $2 \times 10^{12}$ VG/kg, or $2 \times 10^{13}$ VG/kg) is shown in Table 19 of co-owned International Patent Application No. PCT/US2019/032387, where expression is seen in the brainstem, cerebellum, cervical spinal cord, thoracic spinal cord, lumbar spinal cord, cervical DRG, thoracic DRG, lumbar/sacral DRG, heart ventricle, heart atrium, liver, kidney, lung, soleus and/or spleen with VOY201 particles with a CBA promoter. The expression of FXN in NHP after IV injection at different doses ($6.7 \times 10^{12}$ VG/kg, or $4.89 \times 10^{13}$ VG/kg) is shown in Table 20 of co-owned International Patent Application No. PCT/US2019/032387, where expression is seen in the brainstem, cerebellum, cortex, cervical spinal cord, thoracic spinal cord, lumbar spinal cord, cervical DRG, thoracic DRG, lumbar/sacral DRG, heart ventricle, heart atrium, liver, kidney, soleus, sympathetic thoracic chain ganglia, and/or adrenal gland with VOY101 particles with a CBA promoter. Distribution of the vector genome after IV injection in mice is shown in Table 17 of co-owned International Patent Application No. PCT/US2019/032387, where distribution is seen in the cortex, lumbar spinal cord, thoracic dorsal root ganglia, trigeminal ganglion, heart and liver with VOY101 and AAV9 particles with a CBA promoter. Distribution of the vector genome after IV injection in NHP is shown in Table 18 of co-owned International Patent Application No. PCT/US2019/032387, where distribution is seen in the Frontal Cortex, Striatum, Brainstem, Cerebellum, Cervical Spinal Cord, Thoracic Spinal Cord, Cervical Dorsal Root Ganglia, Thoracic Dorsal Root Ganglia, Lumbar/Sacral Dorsal Root Ganglia, Heart Ventricle, Heart Atrium, Liver, Kidney, Lung, Soleus, Jejunum, and Spleen with VOY101 particles with a CBA promoter. Distribution of the vector genome in NHP after IV injection at different doses ($6.3 \times 10^{11}$ VG/kg, $2 \times 10^{12}$ VG/kg, or $2 \times 10^{13}$ VG/kg) is shown in Table 19 of co-owned International Patent Application No. PCT/US2019/032387, where distribution is seen in the frontal cortex, striatum, brainstem, cerebellum, cervical spinal cord, thoracic spinal cord, lumbar spinal cord, cervical DRG, thoracic DRG, lumbar/sacral DRG, heart ventricle, heart atrium, liver, kidney, lung, soleus, jejunum, and/or spleen with VOY201 particles with a CBA promoter. Distribution of the vector genome in NHP after IV injection at different doses ($6.7 \times 10^{12}$ VG/kg, or $4.89 \times 10^{13}$ VG/kg) is shown in Table 20 of co-owned International Patent Application No. PCT/US2019/032387, where distribution is seen in the motor cortex, sensorimotor cortex, striatum, brainstem, cerebellar cortex, cervical spinal cord, thoracic spinal cord, lumbar spinal cord, thoracic spinal cord, cervical DRG, thoracic DRG, lumbar/sacral DRG, heart ventricle, heart atrium, liver, kidney, soleus, jejunum, spleen, sympathetic thoracic chain ganglia, and/or adrenal with VOY101 particles with a CBA promoter.

In some embodiments, the promoter is or is derived from a promoter which includes a CMVie enhancer, a CBA, a CMV, a frataxin promoter, a truncated CBA and/or a truncated CMV promoter. The promoter may drive expression of a payload in various tissues in a subject. As a non-limiting example, a mouse model of Friedreich's Ataxia for evaluating the in vivo distribution, expression and efficacy of IV dosing of VOY101 particles with FXN, as shown in Example 5 of co-owned International Patent Application No. PCT/US2019/032387, the contents of which are herein incorporated by reference in their entirety, may be used. In certain embodiments, promoters such as, but not limited to those in Table 3, may be evaluated for driving expression of FXN in mice as outlined in Example 5 of co-owned International Patent Application No. PCT/US2019/032387. As another non-limiting example, a NHP model of Friedreich's Ataxia for evaluating the in vivo distribution and expression of IV dosing of VOY101 particles with FXN is shown in Example 5 of co-owned International Patent Application No. PCT/US2019/032387, the contents of which are herein incorporated by reference in their entirety. In certain embodiments, promoters such as, but not limited to those in Table 3, may be evaluated for driving expression of FXN in NHP as outlined in in Example 5 of co-owned International Patent Application No. PCT/US2019/032387.

In some embodiments, the promoter is or is derived from a CBA promoter which may drive expression of a payload in various tissues in a subject. As a non-limiting example, expression of FXN using a CBA promoter (promoter provided as SEQ ID NO: 1776 and ITR to ITR provided as SEQ ID NO: 1778) is shown in Example 14, including Tables 33-34, of co-owned International Patent Application No. PCT/US2019/032387, the contents of which are herein incorporated by reference in their entirety. Expression of FXN in mice after IV injection is shown in Table 33 of co-owned International Patent Application No. PCT/US2019/032387, where expression is seen in the cortex, striatum, hippocampus, brainstem, thoracic spinal cord, thoracic DRG, heart and/or liver with VOY101, VOY801 and/or VOY1101 particles with a CBA promoter. Distribution of the vector genome after IV injection in mice is shown in Table 34 of co-owned International Patent Application No. PCT/US2019/032387, where distribution is seen in the cortex, striatum, hippocampus, brainstem, thoracic spinal cord, heart and liver with VOY101, VOY801, and/or VOY1101 particles with a CBA promoter. As another non-limiting example, expression of FXN using a CBA promoter (promoter provided as SEQ ID NO: 1776 and ITR to ITR provided as SEQ ID NO: 1778) in a VOY701 and VOY101 capsid is shown in Example 14, including Tables 35-36, of co-owned Provisional Patent Application No. 62/839,889, the contents of which are herein incorporated by reference in their entirety. Expression of FXN in mice after IV injection is shown in Table 35 of co-owned Provisional Patent Application No. 62/839,889, where expression is seen in the cortex, striatum, hippocampus, brainstem, thoracic spinal cord, and/or liver with VOY701 and/or VOY101 particles with a CBA promoter. Distribution of the vector genome after IV injection in mice is shown in Table 36 of co-owned Provisional Patent Application No. 62/839,889, where distribution is seen in the cortex, striatum, hippocampus, brainstem, thoracic spinal cord, and/or liver with VOY701 and/or VOY101 particles with a CBA promoter.

In some embodiments, the AAV particles described herein comprise a viral genome with a payload region encoding a frataxin protein. The viral genome may be engineered to optimize frataxin expression in a target cell.

Viral Genome: ITR to ITR Sequences Including a Frataxin Payload

Any of the components described herein may be used to design and optimize the ITR to ITR sequence of the viral genome for desired frataxin expression. A viral genome may comprise any number of components, such as, but not limited to, one or more of an ITR, an enhancer, a promoter, an intron, a UTR, a payload region, a tag or selectable marker, a miR binding or target site, a backbone region, a polyA sequence, and/or a filler sequence. Each of these components may be present zero, one, two, or more than two times in a given viral genome.

Each of the ITR, promoter, enhancer, intron, exon, payload, tag, miR binding site, polyA, and/or filler components may be selected, independently and in any combination, from the sequences provided in Tables 3 and 5-11.

In some embodiments, the AAV viral genome comprises a 5' ITR, an enhancer, an intron, a payload region, an optional tag, up to three miR binding sites, a polyA sequence, an optional filler sequence, and a 3' ITR. In some embodiments, the 5' ITR is an AAV2 ITR. In some embodiments, the 5' ITR comprises a sequence at least 90%, at least 95%, at least 99%, or 100% identical to SEQ ID NO: 1811. In some embodiments, the enhancer comprises ie1 exon 1 and ie1 intron 1 or a fragment thereof. In some embodiments, the enhancer comprises a sequence at least 90%, at least 95%, at least 99%, or 100% identical to SEQ ID NOs: 1817 and/or 1819. In some embodiments, the enhancer comprises one or more human beta-globin sequences, e.g., a sequence at least 90%, at least 95%, at least 99%, or 100% identical to SEQ ID NOs: 1816, 1820 and/or 1821. In some embodiments, the enhancer comprises SEQ ID NO: 1817, 1819, 1820, and 1821. In some embodiments, the enhancer comprises SEQ ID NO: 1816.

In some embodiments, the payload region comprises a nucleic acid sequence encoding a polypeptide having at least 90%, at least 95%, at least 99%, or 100% sequence identity to SEQ ID NO: 1725, 1726, 1727, 1731, 1732, or 1733, e.g., having at least 90%, at least 95%, at least 99%, or 100% sequence identity to SEQ ID NO: 1725. In some embodiments, the payload region comprises a nucleic acid sequence having at least 90%, at least 95%, at least 99%, or 100% sequence identity to SEQ ID NO: 1728, 1729, 1730, or a fragment thereof. In some embodiments, the fragment of SEQ ID NO: 1728 comprises nucleotides 221-853 of SEQ ID NO: 1728. In some embodiments, the frataxin polypeptide is encoded by a nucleic acid sequence comprising SEQ ID NO: 1822, 1823, or 1824. In some embodiments, the tag is absent. In some embodiments, the tag is present and is a human influenza hemagglutinin HA tag. In some embodiments, the HA tag comprises SEQ ID NO: 1825. In some embodiments, the miR binding site is absent. In some embodiments, at least one miR binding site is present and comprises a miR122 binding site. In some embodiments, the miR122 binding site comprises a sequence having at least 90%, at least 95%, at least 99%, or 100% identical to SEQ ID NO: 1827. In some embodiments, the AAV vector genome comprises three copies of a miR122 binding site, e.g., three copies of SEQ ID NO: 1827 or a variant thereof having at least 90% sequence identity. In some embodiments, the miR binding site series, comprising three copies of a miR122 binding site comprises SEQ ID NO: 1826. In some embodiments, the viral genome comprises a human growth hormone polyA sequence. In some embodiments, the viral genome comprises a polyA sequence comprising at least 90%, at least 95%, at least 99%, or 100% identical to SEQ ID NO: 1828. In some embodiments, the AAV viral genome further comprises a filler sequence, e.g., an albumin filler sequence. In some embodiments, the filler sequence comprises any of those given by SEQ ID NO: 1829-1842. In some embodiments, the 3' ITR is an AAV2 ITR. In some embodiments, the 3' ITR comprises a sequence at least 90%, at least 95%, at least 99%, or 100% identical to SEQ ID NO: 1812.

In certain embodiments, the AAV particle comprises at least one cis-element including, but not limited to, a Kozak sequence, a backbone sequence, and/or an intron sequence.

Certain embodiments provide that the AAV particle further comprises a promoter region. For example, the promoter may include one from any of the CBA, CMV, FXN, and/or SV40 genes, or variants thereof. Non-limiting examples of ITR to ITR sequences of AAV particles comprising a viral genome with a payload region encoding a frataxin protein are described in Table 4.

In Table 4, cFXN indicates cynomolgus monkey (*Macaca fascicularis*) frataxin, hFXN indicates human (*Homo sapiens*) frataxin, hβglobin indicates human beta-globin, HA indicates human influenza hemagglutinin HA tag, hGH indicates human growth hormone. Alb indicates albumin. The number after alb indicates the length of albumin filler. miR-122 BS is a miR-122 binding site. The "−" sign indicates that the construct is without the component or sequence. The "+" sign indicates that the construct has the component or sequence.

the viral genome comprises a sequence that has at least 85% identity to any of SEQ ID NO: 1778-1810. In some embodiments, the viral genome comprises a sequence that has at least 90% identity to any of SEQ ID NO: 1778-1810. In some embodiments, the viral genome comprises a sequence that has at least 95% identity to any of SEQ ID NO: 1778-1810. In some embodiments, the viral genome comprises a sequence that has at least 99% identity to any of SEQ ID NO: 1778-1810.

In some embodiments, the viral genome comprises a sequence that has at least 95% sequence identity to SEQ ID NO: 1797. In some embodiments the viral genome comprises SEQ ID NO: 1797. In some embodiments, the viral genome comprises a sequence that has at least 95% sequence identity to SEQ ID NO: 1801. In some embodiments the viral genome comprises SEQ ID NO: 1801. In some embodiments, the viral genome comprises a sequence

TABLE 4

Representative ITR to ITR sequences

| Construct Name | 5'ITR | Promoter | Intron | Payload | Tag | miR-122 BS (3x) | Poly(A) | Filler | 3'ITR | SEQ ID NO |
|---|---|---|---|---|---|---|---|---|---|---|
| cFXN1  | + | CBA       | hβglobin | cFXN | HA | − | hGH | —      | + | 1778 |
| cFXN2  | + | CBA       | hβglobin | cFXN | HA | + | hGH | —      | + | 1779 |
| cFXN3  | + | CBA-D4    | hβglobin | cFXN | HA | + | hGH | —      | + | 1780 |
| cFXN4  | + | CBA-D6    | hβglobin | cFXN | HA | + | hGH | —      | + | 1781 |
| cFXN5  | + | CBA-D6    | hβglobin | cFXN | HA | + | hGH | Alb450 | + | 1782 |
| cFXN6  | + | CBA-D8    | hβglobin | cFXN | HA | + | hGH | —      | + | 1783 |
| cFXN7  | + | CBA-D8    | hβglobin | cFXN | HA | + | hGH | Alb450 | + | 1784 |
| cFXN8  | + | mCBA      | hβglobin | cFXN | HA | + | hGH | —      | + | 1785 |
| cFXN9  | + | mCBA-D1   | hβglobin | cFXN | HA | + | hGH | —      | + | 1786 |
| cFXN10 | + | mCBA-D2   | hβglobin | cFXN | HA | + | hGH | —      | + | 1787 |
| cFXN11 | + | CMV       | hβglobin | cFXN | HA | − | hGH | —      | + | 1788 |
| cFXN12 | + | CMV       | hβglobin | cFXN | HA | + | hGH | —      | + | 1789 |
| cFXN13 | + | CMV-D1    | hβglobin | cFXN | HA | + | hGH | —      | + | 1790 |
| cFXN14 | + | CMV-D3    | hβglobin | cFXN | HA | + | hGH | —      | + | 1791 |
| cFXN15 | + | CMV-D7    | hβglobin | cFXN | HA | + | hGH | —      | + | 1792 |
| cFXN16 | + | CMV-D7    | hβglobin | cFXN | HA | + | hGH | Alb450 | + | 1793 |
| cFXN17 | + | FXNpro534 | hβglobin | cFXN | HA | + | hGH | —      | + | 1794 |
| cFXN18 | + | FXNpro1060| hβglobin | cFXN | HA | + | hGH | —      | + | 1795 |
| hFXN1  | + | CBA       | hβglobin | hFXN | HA | + | hGH | —      | + | 1796 |
| hFXN2  | + | CBA-D8    | hβglobin | hFXN | — | + | hGH | Alb2266| + | 1797 |
| hFXN3  | + | CBA-D8    | hβglobin | hFXN | — | − | hGH | Alb2335| + | 1798 |
| hFXN4  | + | CMV       | hβglobin | hFXN | — | + | hGH | Alb1785| + | 1799 |
| hFXN5  | + | CMV       | hβglobin | hFXN | — | − | hGH | Alb1856| + | 1800 |
| hFXN6  | + | CMV-D7    | hβglobin | hFXN | — | + | hGH | Alb2264| + | 1801 |
| hFXN7  | + | CMV-D7    | hβglobin | hFXN | — | − | hGH | Alb2335| + | 1802 |
| hFXN8  | + | FXNpro1060| hβglobin | hFXN | — | + | hGH | Alb1313| + | 1803 |
| hFXN9  | + | FXNpro1060| hβglobin | hFXN | — | − | hGH | Alb1384| + | 1804 |
| hFXN10 | + | CAG       | intron   | hFXN | — | + | hGH | Alb570 | + | 1805 |
| hFXN11 | + | CMV-D1    | hβglobin | hFXN | — | + | hGH | Alb1870| + | 1806 |
| hFXN12 | + | CMV-D3    | hβglobin | hFXN | — | + | hGH | Alb2014| + | 1807 |
| hFXN13 | + | CBA-D4    | hβglobin | hFXN | — | + | hGH | Alb2034| + | 1808 |
| hFXN14 | + | CBA-D6    | hβglobin | hFXN | — | + | hGH | Alb2106| + | 1809 |
| hFXN15 | + | CMV/CBA   | hβglobin | hFXN | — | + | hGH | Alb1790| + | 1810 |

In some embodiments, the AAV particle comprises a viral genome which comprises a sequence which has a percent identity to any of SEQ ID NOs: 1778-1810. The viral genome may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or 100% identity to any of SEQ ID NOs: 1778-1810. The viral genome may have 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% identity to any of SEQ ID NOs: 1778-1810. In some embodiments, the viral genome comprises a sequence that has at least 80% identity to any of SEQ ID NO: 1778-1810. In some embodiments, that has at least 95% sequence identity to SEQ ID NO: 1808. In some embodiments the viral genome comprises SEQ ID NO: 1808. In some embodiments, the viral genome comprises a sequence that has at least 95% sequence identity to SEQ ID NO: 1809. In some embodiments the viral genome comprises SEQ ID NO: 1809. In some embodiments, the viral genome of the AAV particles of the present disclosure may comprise any combination of the sequence regions described in Tables 2-11, or otherwise described herein, encapsulated in any of the capsids listed in Table 1 or described herein.

In some embodiments, the AAV particle viral genome may comprise at least one sequence region as described in Tables 2-11. The regions may be located before or after any of the other sequence regions described herein. Viral genomes may further comprise more than one copy of one or more sequence regions as described in Tables 2-11.

Viral Genome: Inverted Terminal Repeat (ITRs)

In some embodiments, the AAV particle viral genome may comprise at least one inverted terminal repeat (ITR) region. The ITR region(s) may, independently, have a length such as, but not limited to, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, and 175 nucleotides. The length of the ITR region for the viral genome may be 75-80, 75-85, 75-100, 80-85, 80-90, 80-105, 85-90, 85-95, 85-110, 90-95, 90-100, 90-115, 95-100, 95-105, 95-120, 100-105, 100-110, 100-125, 105-110, 105-115, 105-130, 110-115, 110-120, 110-135, 115-120, 115-125, 115-140, 120-125, 120-130, 120-145, 125-130, 125-135, 125-150, 130-135, 130-140, 130-155, 135-140, 135-145, 135-160, 140-145, 140-150, 140-165, 145-150, 145-155, 145-170, 150-155, 150-160, 150-175, 155-160, 155-165, 160-165, 160-170, 165-170, 165-175, and 170-175 nucleotides. As a non-limiting example, the viral genome comprises a 5' ITR that is about 141 nucleotides in length. As a non-limiting example, the viral genome comprises a 5' ITR that is about 130 nucleotides in length. As a non-limiting example, the viral genome comprises a 5' ITR that is about 119 nucleotides in length. As a non-limiting example, the viral genome comprises a 3' ITR that is about 141 nucleotides in length. As a non-limiting example, the viral genome comprises a 3' ITR that is about 130 nucleotides in length. As a non-limiting example, the viral genome comprises a 3' ITR that is about 119 nucleotides in length. As a non-limiting example, the 5' ITR and the 3' ITR may comprise the same length and/or the same sequence. In another non-limiting example, the 5' ITR and the 3' ITR are different in length and/or in sequence.

In some embodiments, the AAV particle viral genome comprises at least one inverted terminal repeat sequence region. Non-limiting examples of ITR sequence regions are described in Table 5.

TABLE 5

Representative Inverted Terminal Repeat (ITR) Sequence Regions

| Sequence Region Name | Sequence Length | SEQ ID NO |
|---|---|---|
| ITR1 | 141 | 1811 |
| ITR2 | 141 | 1812 |

In some embodiments, the AAV particle viral genome may have an ITR that comprises ITR1. In some embodiments, the AAV particle viral genome may have an ITR that comprises ITR2. In some embodiments, the AAV particle viral genome may have two ITRs. As a non-limiting example, the two ITRs may be ITR1 and ITR2.

Viral Genome: Intron and Exon Sequences of the Payload Region

In some embodiments, the AAV particle viral genome comprises at least one intron and/or exon sequence region. Non-limiting examples of intron and exon sequence regions are described in Table 6.

TABLE 6

Representative Intron and Exon Sequence Regions

| Sequence Region Name | Sequence Length | SEQ ID NO |
|---|---|---|
| intron | 1016 | 1815 |
| hBglobin intron/exon | 566 | 1816 |
| ie1 exon 1 | 134 | 1817 |
| CMV/globin intron | 379 | 1818 |
| ie1 intron 1 (partial) | 32 | 1819 |
| hBglobin intron 2 | 347 | 1820 |
| hBglobin exon 3 | 53 | 1821 |

In some embodiments, the AAV particle viral genome may comprise at least one intron sequence region. The intron sequence region(s) may, independently, have a length such as, but not limited to, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, and more than 350 nucleotides. The length of the intron sequence region for the viral genome may be 25-35, 25-50, 35-45, 45-55, 50-75, 55-65, 65-75, 75-85, 75-100, 85-95, 95-105, 100-125, 105-115, 115-125, 125-135, 125-150, 135-145, 145-155, 150-175, 155-165, 165-175, 175-185, 175-200, 185-195, 195-205, 200-225, 205-215, 215-225, 225-235, 225-250, 235-245, 245-255, 250-275, 255-265, 265-275, 275-285, 275-300, 285-295, 295-305, 300-325, 305-315, 315-325, 325-335, 325-350, and 335-345 nucleotides. As a non-limiting example, the viral genome comprises an intron sequence region that is about 32 nucleotides in length. As a non-limiting example, the viral genome comprises an intron sequence region that is about 53 nucleotides in length. As a non-limiting example, the viral genome comprises an intron sequence region that is about 134 nucleotides in length. As a non-limiting example, the viral genome comprises an intron sequence region that is about 347 nucleotides in length. As a non-limiting example, the viral genome comprises an intron sequence region that is about 379 nucleotides in length. As a non-limiting example, the viral genome comprises an intron sequence region that is about 566 nucleotides in length. As a non-limiting example, the viral genome comprises an intron sequence region that is about 1016 nucleotides in length. As a non-limiting example, the viral genome comprises an intron sequence region that is more than about 1016 nucleotides in length.

In some embodiments, the AAV particle viral genome comprises two intron sequence regions. In some embodiments, the AAV particle viral genome comprises three intron sequence regions. In some embodiments, the AAV particle viral genome comprises more than three intron sequence regions.

In some embodiments, the AAV particle viral genome may comprise at least one exon sequence region. The exon sequence region(s) may, independently, have a length such as, but not limited to, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, and more than 350 nucleotides. The length of the exon sequence region for the viral genome may be 25-35, 25-50, 35-45, 45-55, 50-75, 55-65, 65-75, 75-85, 75-100, 85-95, 95-105, 100-125, 105-115, 115-125, 125-135, 125-150, 135-145, 145-155, 150-175, 155-165, 165-175, 175-185, 175-200, 185-195, 195-205, 200-225, 205-215, 215-225, 225-235, 225-250, 235-245, 245-255, 250-275, 255-265, 265-275, 275-285, 275-300, 285-295, 295-305, 300-325, 305-315, 315-325, 325-335, 325-350, and 335-345 nucleotides. As a non-limiting example, the viral genome comprises an exon region that is about 32 nucleotides in length. As a non-limiting example, the viral genome comprises an exon sequence region that is about 53 nucleotides in length. As a non-limiting example, the viral genome comprises an exon sequence region that is about 134 nucleotides in length. As a non-limiting example, the viral genome comprises an exon sequence region that is about 347 nucleotides in length. As a non-limiting example, the viral genome comprises an exon sequence region that is about 379 nucleotides in length. As a non-limiting example, the viral genome comprises an exon sequence region that is about 566 nucleotides in length. As a non-limiting example, the viral genome comprises an exon sequence region that is about 1016 nucleotides in length. As a non-limiting example, the viral genome comprises an exon sequence region that is more than about 1016 nucleotides in length.

In some embodiments, the AAV particle viral genome comprises two exon sequence regions. In some embodiments, the AAV particle viral genome comprises three exon sequence regions. In some embodiments, the AAV particle viral genome comprises more than three exon sequence regions.

In some embodiments, the AAV particle viral genome comprises a hybrid intron/exon sequence region comprising at least one intron and at least one exon. In some embodiments, the hybrid intron/exon sequence region comprises one intron and one exon. In some embodiments, the hybrid intron/exon sequence region comprises two introns and two exons. In some embodiments, an intron or exon sequence may comprise a full length intron or exon. In some embodiments, an intron or exon sequence may comprise a fragment or variant of an intron or exon sequence.

The hybrid intron/exon sequence region(s) may, independently, have a length such as, but not limited to, 15-100, 100-200, 200-300, 300-400, 400-500, 500-600, 600-700, 700-800, 800-900, 900-1000, 1000-1100, 1100-1200, and more than 1200 nucleotides. As a non-limiting example, the viral genome comprises a hybrid intron/exon sequence region that is about 379 nucleotides in length. As a non-limiting example, the viral genome comprises a hybrid intron/exon sequence region that is about 566 nucleotides in length. As a non-limiting example, the viral genome comprises a hybrid intron/exon region that is about 379 nucleotides in length.

In some embodiments, the intron/exon sequence region is an enhancer sequence. In some embodiments, the intron/exon sequence region is not an enhancer sequence.

In some embodiments, the intron/exon sequence region is a component of a promoter sequence. In some embodiments, the intron/exon sequence region is not a component of a promoter sequence.

Viral Genome: Frataxin Payloads

In some embodiments, the payload may comprise any of the sequences given in Table 7.

TABLE 7

Representative Frataxin payload sequences

| Sequence Region Name | Sequence Length | SEQ ID NO |
|---|---|---|
| cFXN | 630 | 1822 |
| hFXN | 630 | 1823 |
| hFXN + stop | 633 | 1824 |

In some embodiments, the payload sequence encodes a frataxin protein derived from cynomolgus monkey (*Macaca fascicularis*), or a variant thereof. In some embodiments, the payload sequence encodes a frataxin protein derived from cynomolgus monkey (*Macaca fascicularis*), but differing by at least one amino acid. In some embodiments, the payload sequence encodes a frataxin protein derived from cynomolgus monkey (*Macaca fascicularis*), but differing from wild-type by at least one amino acid. In some embodiments, the payload sequence encodes a frataxin protein derived from cynomolgus monkey (*Macaca fascicularis*), but differing from wild-type by at least two amino acids.

In some embodiments, the payload sequence encodes a frataxin protein derived from human (*Homo sapiens*), or a variant thereof. In some embodiments, the payload sequence comprises a stop codon.

Viral Genome: Tag Sequences

In some embodiments, the AAV particle viral genome may comprise at least one tag sequence region. As used herein, the term "tag" indicates a polynucleotide sequence appended to the payload, that once expressed may be used to identify the expressed payload. Alternatively, the term "tag" may indicate a polynucleotide sequence appended to the payload that signals for retention of the expressed payload in a particular region of the cell (e.g., endoplasmic reticulum). The tag sequence region(s) may, independently, have a length such as, but not limited to, 10, 11, 12, 13, 14, 15, 16, 17, 18, 19, 20, 21, 22, 23, 24, 25, 26, 27, 28, 29, 30 or more than 30 nucleotides. The length of the tag sequence region in the viral genome may be 10-15, 15-20, 20-25, 25-30, or more than 30 nucleotides. As a non-limiting example, the viral genome comprises a tag sequence region that is about 27 nucleotides in length.

In some embodiments, the AAV particle viral genome comprises at least one tag sequence region. A non-limiting example of tag sequence region is shown in Table 8.

TABLE 8

Representative Tag Sequence Region

| Sequence Region Name | Sequence Length | SEQ ID NO |
|---|---|---|
| HA | 27 | 1825 |

In some embodiments, the AAV particle viral genome comprises one tag sequence region. In some embodiments, the tag sequence region is a Human influenza hemagglutinin (HA) tag.

In some embodiments, the AAV particle viral genome comprises more than one tag sequence region. In one embodiment, the AAV particle viral genome comprises two tag sequence regions. In one embodiment, the AAV particle viral genome comprises three tag sequence regions. In one embodiment, the AAV particle viral genome comprises more than three tag sequence regions.

Viral Genome: microRNA (i.e., miR) Binding Sites

In some embodiments, the AAV particle viral genome may comprise at least one miR binding site. Non-limiting examples of miR-binding site sequence regions are shown in Table 9.

TABLE 9

Representative miR Binding Site Sequence Regions

| Sequence Region Name | Sequence Length | SEQ ID NO |
|---|---|---|
| miR binding site series | 71 | 1826 |
| Single miR binding site | 23 | 1827 |

In some embodiments, the AAV particle viral genome comprises a single miR binding site sequence. As a non-limiting example, the miR-binding site sequence may be a miR-122 binding site.

In some embodiments, the viral genome may comprise more than one miR binding site sequence. As non-limiting examples, the viral genome may comprise two, three, four, or five miR binding site sequences.

In some embodiments, the viral genome may comprise a miR binding site series (SEQ ID NO: 1826), comprising three single miR binding site sequences (SEQ ID NO: 1827).

The miR binding site sequence region may have a length such as, but not limited to, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 nucleotides.

Viral Genome: polyA Signals

In some embodiments, the AAV particle viral genome may comprise at least one polyadenylation (polyA) sequence region. The polyadenylation sequence region(s) may, independently, have a length such as, but not limited to, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, and 600 nucleotides. The length of the polyadenylation sequence region for the viral genome may be 4-10, 10-20, 10-50, 20-30, 30-40, 40-50, 50-60, 50-100, 60-70, 70-80, 80-90, 90-100, 100-110, 100-150, 110-120, 120-130, 130-140, 140-150, 150-160, 150-200, 160-170, 170-180, 180-190, 190-200, 200-210, 200-250, 210-220, 220-230, 230-240, 240-250, 250-260, 250-300, 260-270, 270-280, 280-290, 290-300, 300-310, 300-350, 310-320, 320-330, 330-340, 340-350, 350-360, 350-400, 360-370, 370-380, 380-390, 390-400, 400-410, 400-450, 410-420, 420-430, 430-440, 440-450, 450-460, 450-

500, 460-470, 470-480, 480-490, 490-500, 500-510, 500-550, 510-520, 520-530, 530-540, 540-550, 550-560, 550-600, 560-570, 570-580, 580-590, and 590-600 nucleotides. In some embodiments, the viral genome comprises a polyadenylation sequence region that is about 477 nucleotides in length.

In some embodiments, the AAV particle viral genome comprises at least one polyA sequence region. A non-limiting example of a polyA sequence region is described in Table 10.

TABLE 10

Representative PolyA Sequence Region

| Sequence Region Name | Sequence Length | SEQ ID NO |
|---|---|---|
| hGHpA | 477 | 1828 |

In some embodiments, the AAV particle viral genome comprises one polyA sequence region. As a non-limiting example, the polyA sequence comprises a human growth hormone polyadenylation sequence.

In one embodiment, the AAV particle viral genome comprises more than one polyA sequence region.

Viral Genome: Filler (or Sniffer) Sequences

In one embodiment, the AAV particle viral genome may comprise at least one or multiple filler sequence regions. The filler region(s) may, independently, have a length such as, but not limited to, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3161, 3162, 3163, 3164, 3165, 3166, 3167, 3168, 3169, 3170, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, and 3250 nucleotides. The length of any filler region for the viral genome may be 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2050, 2050-2100, 2100-2150, 2150-2200, 2200-2250, 2250-2300, 2300-2350, 2350-2400, 2400-2450, 2450-2500, 2500-2550, 2550-2600, 2600-2650, 2650-2700, 2700-2750, 2750-2800, 2800-2850, 2850-2900, 2900-2950, 2950-3000, 3000-3050, 3050-3100, 3100-3150, 3150-3200, and 3200-3250 nucleotides. As a non-limiting example, the viral genome comprises a filler region that is about 450 nucleotides in length. As a non-limiting example, the viral genome comprises a filler region that is about 570 nucleotides in length. As a non-limiting example, the viral genome comprises a filler region that is about 1313 nucleotides in length. As a non-limiting example, the viral genome comprises a filler region that is about 1384 nucleotides in length. As a non-limiting example, the viral genome comprises a filler region that is about 1785 nucleotides in length. As a non-limiting example, the viral genome comprises a filler region that is about 1790 nucleotides in length. As a non-limiting example, the viral genome comprises a filler region that is about 1856 nucleotides in length. As a non-limiting example, the viral genome comprises a filler region that is about 1868 nucleotides in length. As a non-limiting example, the viral genome comprises a filler region that is about 1870 nucleotides in length. As a non-limiting example, the viral genome comprises a filler region that is about 2012 nucleotides in length. As a non-limiting example, the viral genome comprises a filler region that is about 2014 nucleotides in length. As a non-limiting example, the viral genome comprises a filler region that is about 2034 nucleotides in length. As a non-limiting example, the viral genome comprises a filler region that is about 2106 nucleotides in length. As a non-limiting example, the viral genome comprises a filler region that is about 2264 nucleotides in length. As a non-limiting example, the viral genome comprises a filler region that is about 2266 nucleotides in length. As a non-limiting example, the viral genome comprises a filler region that is about 2335 nucleotides in length.

In some embodiments, the AAV particle viral genome comprises at least one filler sequence region. Non-limiting examples of filler sequence regions are described in Table 11.

TABLE 11

Representative Filler Sequence Regions

| Sequence Region Name | Sequence Length | SEQ ID NO |
|---|---|---|
| Alb450 | 450 | 1829 |
| Alb570 | 570 | 1830 |
| Alb1313 | 1313 | 1831 |
| Alb1384 | 1384 | 1832 |
| Alb1785 | 1785 | 1833 |
| Alb1790 | 1790 | 1834 |
| Alb1856 | 1856 | 1835 |
| Alb1870 | 1870 | 1836 |
| Alb2014 | 2014 | 1837 |
| Alb2034 | 2034 | 1838 |
| Alb2106 | 2106 | 1839 |
| Alb2264 | 2264 | 1840 |
| Alb2266 | 2266 | 1841 |
| Alb2335 | 2335 | 1842 |

In some embodiments, the AAV particle viral genome comprises a filler sequence region comprising a human albumin sequence. In some embodiments, the AAV particle viral genome comprises filler sequence region Alb450. In some embodiments, the AAV particle viral genome comprises filler sequence region Alb570. In some embodiments, the AAV particle viral genome comprises filler sequence region Alb1313. In some embodiments, the AAV particle viral genome comprises filler sequence region Alb1384. In some embodiments, the AAV particle viral genome comprises filler sequence region Alb1785. In some embodiments, the AAV particle viral genome comprises filler sequence region Alb1790. In some embodiments, the AAV particle viral genome comprises filler sequence region Alb1856. In some embodiments, the AAV particle viral genome comprises filler sequence region Alb1870. In some embodiments, the AAV particle viral genome comprises filler sequence region Alb2014. In some embodiments, the AAV particle viral genome comprises filler sequence region Alb2034. In some embodiments, the AAV particle viral genome comprises filler sequence region Alb2106. In some embodiments, the AAV particle viral genome comprises filler sequence region Alb2264. In some embodiments, the AAV particle viral genome comprises filler sequence region Alb2266. In some embodiments, the AAV particle viral genome comprises filler sequence region Alb2335.

Viral Genome: Junction Sequences

In some embodiments, a junction sequence may be used in combination with any of the viral genome components described herein such as, but not limited to, those listed in Tables 5-11. In certain embodiments, the junction sequence may be located 5' to the viral genome component (e.g., promoter, enhancer, intron/exon, miR binding site, tag, polyA) within the viral genome. In certain embodiments, the junction sequence may be located 3' to the viral genome component (e.g., promoter, enhancer, intron/exon, miR binding site, tag, polyA) within the viral genome. In certain embodiments, the viral genome may include more than one junction sequence. As a non-limiting example, the viral genome may comprise a junction sequence on the 5' end of the viral genome component and on the 3' end of the viral genome component. The junction sequence may be the same sequence, two different sequences or a sequence split on either side of the viral genome component. In certain embodiments, the junction sequence comprises SEQ ID NO: 1813. In certain embodiments, the junction sequence comprises SEQ ID NO: 1814.

Viral Genome: ITR to ITR Modularity

In some embodiments, the ITR to ITR sequence of the viral genome may comprise any of the sequences given in Tables 12-17.

TABLE 12

Representative Sequence Regions of ITR to ITR Sequences

| | cFXN1 | cFXN2 | cFXN3 | cFXN4 | cFXN5 | cFXN6 |
|---|---|---|---|---|---|---|
| ITR to ITR | 1778 | 1779 | 1780 | 1781 | 1782 | 1783 |
| 5'ITR | 1811 | 1811 | 1811 | 1811 | 1811 | 1811 |
| Promoter | 1776 | 1776 | 1738 | 1740 | 1740 | 1742 |
| Junction | | | 1813 | 1813 | 1813 | 1813 |
| Intron/Exon | 1816 | 1816 | 1816 | 1816 | 1816 | 1816 |
| Intron/Exon components | 1817, 1819, 1820, 1821 | 1817, 1819, 1820, 1821 | 1817, 1819, 1820, 1821 | 1817, 1819, 1820, 1821 | 1817, 1819, 1820, 1821 | 1817, 1819, 1820, 1821 |
| FXN Payload | 1822 | 1822 | 1822 | 1822 | 1822 | 1822 |
| Tag | 1825 | 1825 | 1825 | 1825 | 1825 | 1825 |
| miR122 BS (3x) | | 1826 | 1826 | 1826 | 1826 | 1826 |
| miR122 BS (3x) | | 1827 | 1827 | 1827 | 1827 | 1827 |
| Poly(A) | 1828 | 1828 | 1828 | 1828 | 1828 | 1828 |
| Filler | | | | | 1829 | |
| 3'ITR | 1812 | 1812 | 1812 | 1812 | 1812 | 1812 |

In some embodiments, the AAV particle genome comprises SEQ ID NO: 1778 (cFXN1), which comprises a 5' inverted terminal repeat (ITR) sequence region and a 3' ITR sequence region, a CBA promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, and a human growth hormone polyadenylation sequence.

In some embodiments, the AAV particle genome comprises SEQ ID NO: 1779 (cFXN2), which comprises a 5' inverted terminal repeat (ITR) sequence region and a 3' ITR sequence region, a CBA promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1780 (cFXN3), which comprises a 5' inverted terminal repeat (ITR) sequence region and a 3' ITR sequence region, a CBA-D4 promoter region, a junction sequence, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1781 (cFXN4), which comprises a 5' inverted terminal repeat (ITR) sequence region and a 3' ITR sequence region, a CBA-D6 promoter region, a junction sequence, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1782 (cFXN5), which comprises a 5' inverted terminal repeat (ITR) sequence region and a 3' ITR sequence region, a CBA-D6 promoter region, a junction sequence, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, a human growth hormone polyadenylation sequence, and an albumin filler sequence.

In some embodiments, the AAV particle genome comprises SEQ ID NO: 1783 (cFXN6), which comprises a 5' inverted terminal repeat (ITR) sequence region and a 3' ITR sequence region, a CBA-D8 promoter region, a junction sequence, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

TABLE 13

Representative Sequence Regions of ITR to ITR Sequences

|  | cFXN7 | cFXN8 | cFXN9 | cFXN10 | cFXN11 | cFXN12 |
|---|---|---|---|---|---|---|
| ITR to ITR | 1784 | 1785 | 1786 | 1787 | 1788 | 1789 |
| 5'ITR | 1811 | 1811 | 1811 | 1811 | 1811 | 1811 |
| Enhancer |  |  |  |  | 1777 | 1777 |
| Promoter | 1742 | 1760 | 1761 | 1762 | 1772 | 1772 |
| Junction | 1813 | 1814 | 1813 | 1813 |  |  |
| Intron/Exon | 1816 | 1816 | 1816 | 1816 | 1816 | 1816 |
| Intron/Exon components | 1817, 1819, 1820, 1821 | 1817, 1819, 1820, 1821 | 1817, 1819, 1820, 1821 | 1817, 1819, 1820, 1821 | 1817, 1819, 1820, 1821 | 1817, 1819, 1820, 1821 |
| FXN Payload | 1822 | 1822 | 1822 | 1822 | 1822 | 1822 |
| Tag | 1825 | 1825 | 1825 | 1825 | 1825 | 1825 |
| miR122 BS (3x) | 1826 | 1826 | 1826 | 1826 |  | 1826 |
| miR122 BS (3x) | 1827 | 1827 | 1827 | 1827 |  | 1827 |
| Poly(A) | 1828 | 1828 | 1828 | 1828 | 1828 | 1828 |
| Filler | 1829 |  |  |  |  |  |
| 3'TTR | 1812 | 1812 | 1812 | 1812 | 1812 | 1812 |

In some embodiments, the AAV particle genome comprises SEQ ID NO: 1784 (cFXN7), which comprises a 5' inverted terminal repeat (ITR) sequence region and a 3' ITR sequence region, a CBA-D8 promoter region, a junction sequence, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, a human growth hormone polyadenylation sequence, and an albumin filler sequence.

In some embodiments, the AAV particle genome comprises SEQ ID NO: 1785 (cFXN8), which comprises a 5' inverted terminal repeat (ITR) sequence region and a 3' ITR sequence region, an mCBA promoter region, a junction sequence, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1786 (cFXN9), which comprises a 5' inverted terminal repeat (ITR) sequence region and a 3' ITR sequence region, an mCBA-D1 promoter region, a junction sequence, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1787 (cFXN10), which comprises a 5' inverted terminal repeat (ITR) sequence region and a 3' ITR sequence region, an mCBA-D2 promoter region, a junction sequence, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1788 (cFXN11), which comprises a 5' inverted terminal repeat (ITR) sequence region and a 3' ITR sequence region, a CMV enhancer and promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, and a human growth hormone polyadenylation sequence.

In some embodiments, the AAV particle genome comprises SEQ ID NO: 1789 (cFXN12), which comprises a 5' inverted terminal repeat (ITR) sequence region and a 3' ITR sequence region, a CMV enhancer and promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

TABLE 14

Representative Sequence Regions of ITR to ITR Sequences

|  | cFXN13 | cFXN14 | cFXN15 | cFXN16 | cFXN17 | cFXN18 |
|---|---|---|---|---|---|---|
| ITR to ITR | 1790 | 1791 | 1792 | 1793 | 1794 | 1795 |
| 5'ITR | 1811 | 1811 | 1811 | 1811 | 1811 | 1811 |
| Promoter | 1744 | 1746 | 1750 | 1750 | 1754 | 1756 |
| Intron/Exon | 1816 | 1816 | 1816 | 1816 | 1816 | 1816 |
| Intron/Exon components | 1817, 1819, 1820, 1821 | 1817, 1819, 1820, 1821 | 1817, 1819, 1820, 1821 | 1817, 1819, 1820, 1821 | 1817, 1819, 1820, 1821 | 1817, 1819, 1820, 1821 |
| FXN Payload | 1822 | 1822 | 1822 | 1822 | 1822 | 1822 |
| Tag | 1825 | 1825 | 1825 | 1825 | 1825 | 1825 |
| miR122 BS (3x) | 1826 | 1826 | 1826 | 1826 | 1826 | 1826 |

TABLE 14-continued

Representative Sequence Regions of ITR to ITR Sequences

|  | cFXN13 | cFXN14 | cFXN15 | cFXN16 | cFXN17 | cFXN18 |
|---|---|---|---|---|---|---|
| miR122 BS | 1827 (3x) | 1827 (3x) | 1827 (3x) | 1827 (3x) | 1827 (3x) | 1827 (3x) |
| Poly(A) | 1828 | 1828 | 1828 | 1828 | 1828 | 1828 |
| Filler |  |  |  | 1829 |  |  |
| 3'TTR | 1812 | 1812 | 1812 | 1812 | 1812 | 1812 |

In some embodiments, the AAV particle genome comprises SEQ ID NO: 1790 (cFXN13), which comprises a 5' inverted terminal repeat (ITR) sequence region and a 3' ITR sequence region, a CMV-D1 promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1791 (cFXN14), which comprises a 5' inverted terminal repeat (ITR) sequence region and a 3' ITR sequence region, a CMV-D3 promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1792 (cFXN15), which comprises a 5' inverted terminal repeat (ITR) sequence region and a 3' ITR sequence region, a CMV-D7 promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1793 (cFXN16), which comprises a 5' inverted terminal repeat (ITR) sequence region and a 3' ITR sequence region, a CMV-D7 promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, a human growth hormone polyadenylation sequence and an albumin filler sequence.

In some embodiments, the AAV particle genome comprises SEQ ID NO: 1794 (cFXN17), which comprises a 5' inverted terminal repeat (ITR) sequence region and a 3' ITR sequence region, a frataxin promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1795 (cFXN18), which comprises a 5' inverted terminal repeat (ITR) sequence region and a 3' ITR sequence region, a frataxin promoter region, a human beta globin intron/exon region comprising an ie1 exon 1 region, an ie1 intron 1 region, a human beta-globin intron region, a human beta-globin exon region, a cynomolgus frataxin payload sequence, an HA tag sequence, a miR binding site series comprising three repeats of single miR122 binding site sequences, and a human growth hormone polyadenylation sequence.

TABLE 15

Representative Sequence Regions of ITR to ITR Sequences

|  | hFXN1 | hFXN2 | hFXN3 | hFXN4 | hFXN5 |
|---|---|---|---|---|---|
| ITR to ITR | 1796 | 1797 | 1798 | 1799 | 1800 |
| 5'TTR | 1811 | 1811 | 1811 | 1811 | 1811 |
| Enhancer |  |  |  | 1777 | 1777 |
| Promoter | 1776 | 1742 | 1742 | 1772 | 1772 |
| Junction |  | 1813 | 1813 |  |  |
| Intron/Exon | 1816 | 1816 | 1816 | 1816 | 1816 |
| Intron/Exon components | 1817, 1819, 1820, 1821 | 1817, 1819, 1820, 1821 | 1817, 1819, 1820, 1821 | 1817, 1819, 1820, 1821 | 1817, 1819, 1820, 1821 |
| FXN Payload | 1823 | 1824 | 1824 | 1824 | 1824 |
| Tag | 1825 |  |  |  |  |
| miR122 BS (3x) | 1826 | 1826 |  | 1826 |  |
| miR122 BS | 1827 (3x) | 1827 (3x) |  | 1827 (3x) |  |
| Poly(A) | 1828 | 1828 | 1828 | 1828 | 1828 |
| Filler |  | 1841 | 1842 | 1833 | 1835 |
| 3'TTR | 1812 | 1812 | 1812 | 1812 | 1812 |

In some embodiments, the AAV particle genome comprises SEQ ID NO: 1796 (hFXN1), which comprises a 5' inverted terminal repeat (ITR) sequence region and a 3' ITR sequence region, a CBA promoter region, a human beta globin intron/exon region comprising an ie1 exon 1 region, an ie1 intron 1 region, a human beta-globin intron region, a human beta-globin exon region, a human frataxin payload sequence, an HA tag sequence, a miR binding site series comprising three repeats of single miR122 binding site sequences, and a human growth hormone polyadenylation sequence.

In some embodiments, the AAV particle genome comprises SEQ ID NO: 1797 (hFXN2), which comprises a 5' inverted terminal repeat (ITR) sequence region and a 3' ITR sequence region, a CBA-D8 promoter region, a junction sequence, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence.

In some embodiments, the AAV particle genome comprises SEQ ID NO: 1798 (hFXN3), which comprises a 5' inverted terminal repeat (ITR) sequence region and a 3' ITR sequence region, a CBA-D8 promoter region, a junction sequence, a human beta globin intron/exon region comprising an ie1 exon 1 region, an ie1 intron 1 region, a human beta-globin intron region, a human beta-globin exon region, a human frataxin payload sequence, a human growth hormone polyadenylation sequence, and an albumin filler sequence.

In some embodiments, the AAV particle genome comprises SEQ ID NO: 1799 (hFXN4), which comprises a 5' inverted terminal repeat (ITR) sequence region and a 3' ITR sequence region, a CMV enhancer and promoter region, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence.

In some embodiments, the AAV particle genome comprises SEQ ID NO: 1800 (hFXN5), which comprises a 5' inverted terminal repeat (ITR) sequence region and a 3' ITR sequence region, a CMV enhancer and promoter region, a human beta globin intron/exon region comprising an ie1 exon 1 region, an ie1 intron 1 region, a human beta-globin intron region, a human beta-globin exon region, a human frataxin payload sequence, a human growth hormone polyadenylation sequence, and an albumin filler sequence.

TABLE 16

Representative Sequence Regions of ITR to ITR Sequences

| | hFXN6 | hFXN7 | hFXN8 | hFXN9 | hFXN10 |
|---|---|---|---|---|---|
| ITR to ITR | 1801 | 1802 | 1803 | 1804 | 1805 |
| 5'ITR | 1811 | 1811 | 1811 | 1811 | 1811 |
| Promoter | 1750 | 1750 | 1756 | 1756 | 1771 |
| Promoter components | | | | | 1773, 1775 |
| Intron/Exon | 1816 | 1816 | 1816 | 1816 | 1815 |
| Intron/Exon components | 1817, 1819, 1820, 1821 | 1817, 1819, 1820, 1821 | 1817, 1819, 1820, 1821 | 1817, 1819, 1820, 1821 | |
| FXN Payload | 1824 | 1824 | 1824 | 1824 | 1824 |
| miR122 BS (3x) | 1826 | | 1826 | | 1826 |
| miR122 BS (3x) | 1827 | | 1827 | | 1827 |
| Poly(A) | 1828 | 1828 | 1828 | 1828 | 1828 |
| Filler | 1840 | 1842 | 1831 | 1832 | 1830 |
| 3'ITR | 1812 | 1812 | 1812 | 1812 | 1812 |

In some embodiments, the AAV particle genome comprises SEQ ID NO: 1801 (hFXN6), which comprises a 5' inverted terminal repeat (ITR) sequence region and a 3' ITR sequence region, a CMV-D7 promoter region, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence.

In some embodiments, the AAV particle genome comprises SEQ ID NO: 1802 (hFXN7), which comprises a 5' inverted terminal repeat (ITR) sequence region and a 3' ITR sequence region, a CMV-D7 promoter region, a human beta globin intron/exon region comprising an ie1 exon 1 region, an ie1 intron 1 region, a human beta-globin intron region, a human beta-globin exon region, a human frataxin payload sequence, a human growth hormone polyadenylation sequence, and an albumin filler sequence.

In some embodiments, the AAV particle genome comprises SEQ ID NO: 1803 (hFXN8), which comprises a 5' inverted terminal repeat (ITR) sequence region and a 3' ITR sequence region, a frataxin promoter region, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence.

In some embodiments, the AAV particle genome comprises SEQ ID NO: 1804 (hFXN9), which comprises a 5' inverted terminal repeat (ITR) sequence region and a 3' ITR sequence region, a frataxin promoter region, a human beta globin intron/exon region comprising an ie1 exon 1 region, an ie1 intron 1 region, a human beta-globin intron region, a human beta-globin exon region, a human frataxin payload sequence, a human growth hormone polyadenylation sequence, and an albumin filler sequence.

In some embodiments, the AAV particle genome comprises SEQ ID NO: 1805 (hFXN10), which comprises a 5' inverted terminal repeat (ITR) sequence region and a 3' ITR sequence region, a CAG promoter region comprising a CMV promoter region and a CBA promoter region, an intron, a human frataxin payload sequence, a miR binding site series comprising three repeats of single miR122 binding site sequences, a human growth hormone polyadenylation sequence, and an albumin filler sequence.

TABLE 17

Representative Sequence Regions of ITR to ITR Sequences

| | hFXN11 | hFXN12 | hFXN13 | hFXN14 | hFXN15 |
|---|---|---|---|---|---|
| ITR to ITR | 1806 | 1807 | 1808 | 1809 | 1810 |
| 5'ITR | 1811 | 1811 | 1811 | 1811 | 1811 |
| Promoter | 1744 | 1746 | 1738 | 1740 | 1774 |
| Promoter components | | | | | 1740 |
| Junction | | | 1813 | | |
| Intron/Exon | 1816 | 1816 | 1816 | 1816 | 1816 |
| Intron/Exon components | 1817, 1819, 1820, 1821 | 1817, 1819, 1820, 1821 | 1817, 1819, 1820, 1821 | 1817, 1819, 1820, 1821 | 1817, 1819, 1820, 1821 |
| FXN Payload | 1824 | 1824 | 1824 | 1824 | 1824 |
| miR122 BS (3x) | 1826 | 1826 | 1826 | 1826 | 1826 |
| miR122 BS (3x) | 1827 | 1827 | 1827 | 1827 | 1827 |
| Poly(A) | 1828 | 1828 | 1828 | 1828 | 1828 |
| Filler | 1836 | 1837 | 1838 | 1839 | 1834 |
| 3'ITR | 1812 | 1812 | 1812 | 1812 | 1812 |

In some embodiments, the AAV particle genome comprises SEQ ID NO: 1806 (hFXN11), which comprises a 5' inverted terminal repeat (ITR) sequence region and a 3' ITR sequence region, a CMV-D1 promoter region, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence.

In some embodiments, the AAV particle genome comprises SEQ ID NO: 1807 (hFXN12), which comprises a 5' inverted terminal repeat (ITR) sequence region and a 3' ITR sequence region, a CMV-D3 promoter region, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence.

In some embodiments, the AAV particle genome comprises SEQ ID NO: 1808 (hFXN13), which comprises a 5' inverted terminal repeat (ITR) sequence region and a 3' ITR sequence region, a CBA-D4 promoter region, a junction sequence, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence.

In some embodiments, the AAV particle genome comprises SEQ ID NO: 1809 (hFXN14), which comprises a 5' inverted terminal repeat (ITR) sequence region and a 3' ITR sequence region, a CBA-D6 promoter region, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence.

In some embodiments, the AAV particle genome comprises SEQ ID NO: 1810 (hFXN15), which comprises a 5' inverted terminal repeat (ITR) sequence region and a 3' ITR sequence region, a promoter region comprising a CMV region and a CBA region, a human beta globin intron/exon region comprising an ie1 exon 1 region, an ie1 intron 1 region, a human beta-globin intron region, a human beta-globin exon region, a human frataxin payload sequence, a miR binding site series comprising three repeats of single miR122 binding site sequences, a human growth hormone polyadenylation sequence, and an albumin filler sequence. Certain embodiments provide the viral genome as packaged in a capsid having a serotype selected from Table 1. For example, the capsid serotype may be selected from the group consisting of VOY101, VOY102, AAVPHP.B, AAVPHP.N, AAV1, AAV2, AAV3, AAV4, AAV5, AAV6, AAV7, AAV8, AAV9, AAV9.47, AAV9(hu14), AAV9 K449R, AAV10, AAV11, AAV12, AAVrh8, AAVrh10, AAVDJ, and AAVDJ8, or any variant thereof. In some embodiments, the capsid serotype is AAVPHP.B, AAV9, AAV6, AAVrh10, and/or AAVDJ.

In some embodiments a viral genome as provided in any of Tables 4, 12, 13, 14, 15, 16, or 17 is packaged into an AAV capsid to generate an AAV particle. In some embodiments, the AAV particle comprises a viral genome comprising SEQ ID NO: 1797 and a VOY101 capsid. In some embodiments, the AAV particle comprises a viral genome comprising SEQ ID NO: 1797 and a VOY201 capsid. In some embodiments, the AAV particle comprises a viral genome comprising SEQ ID NO: 1797 and an AAV9 capsid. In some embodiments, the AAV particle comprises a viral genome comprising SEQ ID NO: 1797 and an AAV9 K449R capsid. In some embodiments, the AAV particle comprises a viral genome comprising SEQ ID NO: 1797 and an AAVPHP.B capsid. In some embodiments, the AAV particle comprises a viral genome comprising SEQ ID NO: 1797 and an AAVPHP.N capsid. In some embodiments, the AAV particle comprises a viral genome comprising SEQ ID NO: 1797 and a capsid comprising SEQ ID NO: 1. In some embodiments, the AAV particle comprises a viral genome comprising SEQ ID NO: 1797 and a capsid encoded by a nucleic acid sequence comprising SEQ ID NO: 1722. In some embodiments, the AAV particle comprises a viral genome comprising SEQ ID NO: 1797 and a capsid comprising SEQ ID NO: 1724. In some embodiments, the AAV particle comprises a viral genome comprising SEQ ID NO: 1797 and a capsid encoded by a nucleic acid sequence comprising SEQ ID NO: 1723. In some embodiments, the AAV particle comprises a viral genome comprising SEQ ID NO: 1797 and a capsid comprising SEQ ID NO: 136. In some embodiments, the AAV particle comprises a viral genome comprising SEQ ID NO: 1797 and a capsid encoded by a nucleic acid sequence comprising SEQ ID NO: 135. In some embodiments, the AAV particle comprises a viral genome comprising SEQ ID NO: 1797 and a capsid comprising SEQ ID NO: 3. In some embodiments, the AAV particle comprises a viral genome comprising SEQ ID NO: 1797 and a capsid encoded by a nucleic acid sequence comprising SEQ ID NO: 4. In some embodiments, the AAV particle comprises a viral genome comprising SEQ ID NO: 1797 and a capsid comprising SEQ ID NO: 2. In some embodiments, the AAV particle comprises a viral genome comprising SEQ ID NO: 1797 and a capsid comprising SEQ ID NO: 9.

In some embodiments, the AAV particle comprises a viral genome comprising SEQ ID NO: 1801 and a VOY101 capsid. In some embodiments, the AAV particle comprises a viral genome comprising SEQ ID NO: 1801 and a VOY201 capsid. In some embodiments, the AAV particle comprises a viral genome comprising SEQ ID NO: 1801 and an AAV9 capsid. In some embodiments, the AAV particle comprises a viral genome comprising SEQ ID NO: 1801 and an AAV9 K449R capsid. In some embodiments, the AAV particle comprises a viral genome comprising SEQ ID NO: 1801 and an AAVPHP.B capsid. In some embodiments, the AAV particle comprises a viral genome comprising SEQ ID NO: 1801 and an AAVPHP.N capsid. In some embodiments, the AAV particle comprises a viral genome comprising SEQ ID NO: 1801 and a capsid comprising SEQ ID NO: 1. In some embodiments, the AAV particle comprises a viral genome comprising SEQ ID NO: 1801 and a capsid encoded by a nucleic acid sequence comprising SEQ ID NO: 1722. In some embodiments, the AAV particle comprises a viral genome comprising SEQ ID NO: 1801 and a capsid comprising SEQ ID NO: 1724. In some embodiments, the AAV particle comprises a viral genome comprising SEQ ID NO: 1801 and a capsid encoded by a nucleic acid sequence comprising SEQ ID NO: 1723. In some embodiments, the AAV particle comprises a viral genome comprising SEQ ID NO: 1801 and a capsid comprising SEQ ID NO: 136. In some embodiments, the AAV particle comprises a viral genome comprising SEQ ID NO: 1801 and a capsid encoded by a nucleic acid sequence comprising SEQ ID NO: 135. In some embodiments, the AAV particle comprises a viral genome comprising SEQ ID NO: 1801 and a capsid comprising SEQ ID NO: 3. In some embodiments, the AAV particle comprises a viral genome comprising SEQ ID NO: 1801 and a capsid encoded by a nucleic acid sequence comprising SEQ ID NO: 4. In some embodiments, the AAV particle comprises a viral genome comprising SEQ ID NO: 1801 and a capsid comprising SEQ ID NO: 2. In some embodiments, the AAV particle comprises a viral genome comprising SEQ ID NO: 1801 and a capsid comprising SEQ ID NO: 9.

In some embodiments, the AAV particle comprises a viral genome comprising SEQ ID NO: 1808 and a VOY101 capsid. In some embodiments, the AAV particle comprises a viral genome comprising SEQ ID NO: 1808 and a VOY201 capsid. In some embodiments, the AAV particle comprises a viral genome comprising SEQ ID NO: 1808 and an AAV9 capsid. In some embodiments, the AAV particle comprises a viral genome comprising SEQ ID NO: 1808 and an AAV9 K449R capsid. In some embodiments, the AAV particle comprises a viral genome comprising SEQ ID NO: 1808 and an AAVPHP.B capsid. In some embodiments, the AAV particle comprises a viral genome comprising SEQ ID NO: 1808 and an AAVPHP.N capsid. In some embodiments, the AAV particle comprises a viral genome comprising SEQ ID NO: 1808 and a capsid comprising SEQ ID NO: 1. In some embodiments, the AAV particle comprises a viral genome comprising SEQ ID NO: 1808 and a capsid encoded by a nucleic acid sequence comprising SEQ ID NO: 1722. In some embodiments, the AAV particle comprises a viral genome comprising SEQ ID NO: 1808 and a capsid comprising SEQ ID NO: 1724. In some embodiments, the AAV particle comprises a viral genome comprising SEQ ID NO: 1808 and a capsid encoded by a nucleic acid sequence comprising SEQ ID NO: 1723. In some embodiments, the AAV particle comprises a viral genome comprising SEQ ID NO: 1808 and a capsid comprising SEQ ID NO: 136. In some embodiments, the AAV particle comprises a viral genome comprising SEQ ID NO: 1808 and a capsid encoded by a nucleic acid sequence comprising SEQ ID NO: 135. In some embodiments, the AAV particle comprises a viral genome comprising SEQ ID NO: 1808 and a capsid comprising SEQ ID NO: 3. In some embodiments, the AAV particle comprises a viral genome comprising SEQ ID NO: 1808 and a capsid encoded by a nucleic acid sequence comprising SEQ ID NO: 4. In some embodiments, the AAV particle comprises a viral genome comprising SEQ ID NO: 1808 and a capsid comprising SEQ ID NO: 2. In some embodiments, the AAV particle comprises a viral genome comprising SEQ ID NO: 1808 and a capsid comprising SEQ ID NO: 9.

In some embodiments, the AAV particle comprises a viral genome comprising SEQ ID NO: 1809 and a VOY101 capsid. In some embodiments, the AAV particle comprises a viral genome comprising SEQ ID NO: 1809 and a VOY201 capsid. In some embodiments, the AAV particle comprises a viral genome comprising SEQ ID NO: 1809 and an AAV9 capsid. In some embodiments, the AAV particle comprises a viral genome comprising SEQ ID NO: 1809 and an AAV9 K449R capsid. In some embodiments, the AAV particle comprises a viral genome comprising SEQ ID NO: 1809 and an AAVPHP.B capsid. In some embodiments, the AAV particle comprises a viral genome comprising SEQ ID NO: 1809 and an AAVPHP.N capsid. In some embodiments, the AAV particle comprises a viral genome comprising SEQ ID NO: 1809 and a capsid comprising SEQ ID NO: 1. In some embodiments, the AAV particle comprises a viral genome comprising SEQ ID NO: 1809 and a capsid encoded by a nucleic acid sequence comprising SEQ ID NO: 1722. In some embodiments, the AAV particle comprises a viral genome comprising SEQ ID NO: 1809 and a capsid comprising SEQ ID NO: 1724. In some embodiments, the AAV particle comprises a viral genome comprising SEQ ID NO: 1809 and a capsid encoded by a nucleic acid sequence comprising SEQ ID NO: 1723. In some embodiments, the AAV particle comprises a viral genome comprising SEQ ID NO: 1809 and a capsid comprising SEQ ID NO: 136. In some embodiments, the AAV particle comprises a viral genome comprising SEQ ID NO: 1809 and a capsid encoded by a nucleic acid sequence comprising SEQ ID NO: 135. In some embodiments, the AAV particle comprises a viral genome comprising SEQ ID NO: 1809 and a capsid comprising SEQ ID NO: 3. In some embodiments, the AAV particle comprises a viral genome comprising SEQ ID NO: 1809 and a capsid encoded by a nucleic acid sequence comprising SEQ ID NO: 4. In some embodiments, the AAV particle comprises a viral genome comprising SEQ ID NO: 1809 and a capsid comprising SEQ ID NO: 2. In some embodiments, the AAV particle comprises a viral genome comprising SEQ ID NO: 1809 and a capsid comprising SEQ ID NO: 9.

In some embodiments, AAV particles comprising a viral genome as given in any of Tables 4, 12, 13, 14, 15, 16, or 17 and a capsid are formulated in a solution suitable for administration, e.g., a formulation comprising one or more salt and one or more surfactant. In some embodiments, the formulation comprises one or more of sodium chloride, sodium phosphate, potassium chloride, potassium phosphate, and pluronic F-68, at a pH of about 7-8. In some embodiments, the formulation comprises 192 mM sodium chloride, 10 mM sodium phosphate (dibasic), 2.7 mM potassium chloride, 2 mM potassium phosphate (monobasic) and 0.001% pluronic F-68 (v/v), at pH 7.4 (Formulation 1 in the present disclosure). In some embodiments, AAV particles comprising a viral genome comprising SEQ ID NO: 1797 and a VOY101 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a VOY201 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and an AAV9 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and an AAV9 K449R capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and an AAVPHP.B capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and an AAVPHP.N capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid comprising SEQ ID NO: 1 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid encoded by a nucleic acid sequence comprising SEQ ID NO: 1722 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid comprising SEQ ID NO: 1724 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid encoded by a nucleic acid sequence comprising SEQ ID NO: 1723 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid comprising SEQ ID NO: 136 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid encoded by a nucleic acid sequence comprising SEQ ID NO: 135 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid comprising SEQ ID NO: 3 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid encoded by a nucleic acid sequence comprising SEQ ID NO: 4 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid comprising SEQ ID NO: 2 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1797 and a capsid comprising SEQ ID NO: 9 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4.

In some embodiments, AAV particles comprising a viral genome comprising SEQ ID NO: 1801 and a VOY101 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a VOY201 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and an AAV9 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and an AAV9 K449R capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and an AAVPHP.B capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and an AAVPHP.N capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid comprising SEQ ID NO: 1 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid encoded by a nucleic acid sequence comprising SEQ ID NO: 1722 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid comprising SEQ ID NO: 1724 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid encoded by a nucleic acid sequence comprising SEQ ID NO: 1723 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid comprising SEQ ID NO: 136 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid encoded by a nucleic acid sequence comprising SEQ ID NO: 135 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid comprising SEQ ID NO: 3 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid encoded by a nucleic acid sequence comprising SEQ ID NO: 4 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid comprising SEQ ID NO: 2 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1801 and a capsid comprising SEQ ID NO: 9 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4.

In some embodiments, AAV particles comprising a viral genome comprising SEQ ID NO: 1808 and a VOY101 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a VOY201 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and an AAV9 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and an AAV9 K449R capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and an AAVPHP.B capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and an AAVPHP.N capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid comprising SEQ ID NO: 1 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid encoded by a nucleic acid sequence comprising SEQ ID NO: 1722 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid comprising SEQ ID NO: 1724 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid encoded by a nucleic acid sequence comprising SEQ ID NO: 1723 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid comprising SEQ ID NO: 136 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid encoded by a nucleic acid sequence comprising SEQ ID NO: 135 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid comprising SEQ ID NO: 3 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid encoded by a nucleic acid sequence comprising SEQ ID NO: 4 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid comprising SEQ ID NO: 2 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1808 and a capsid comprising SEQ ID NO: 9 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4.

In some embodiments, AAV particles comprising a viral genome comprising SEQ ID NO: 1809 and a VOY101 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a VOY201 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and an AAV9 capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and an AAV9 K449R capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and an AAVPHP.B capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and an AAVPHP.N capsid are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid comprising SEQ ID NO: 1 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid encoded by a nucleic acid sequence comprising SEQ ID NO: 1722 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid comprising SEQ ID NO: 1724 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid encoded by a nucleic acid sequence comprising SEQ ID NO: 1723 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid comprising SEQ ID NO: 136 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid encoded by a nucleic acid sequence comprising SEQ ID NO: 135 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid comprising SEQ ID NO: 3 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid encoded by a nucleic acid sequence comprising SEQ ID NO: 4 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid comprising SEQ ID NO: 2 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. In some embodiments, AAV particles comprising a viral genome comprising SEQ ID NO: 1809 and a capsid comprising SEQ ID NO: 9 are formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4.

In some embodiments, the viral genome is single-stranded. In some embodiments, the viral genome is self-complementary. Certain embodiments of the AAV particles of the disclosure comprise two inverted terminal repeat (ITR) regions. In some embodiments, the ITRs are AAV2 ITRs. In some embodiments, one ITR comprises SEQ ID NO: 1811 and the other ITR comprises SEQ ID NO: 1812. Certain embodiments provide a viral genome comprising a first ITR region located 5' relative to the polynucleotide sequence and a second inverted terminal repeat region is located 3' relative to the polynucleotide sequence.

II. Viral Production

General Viral Production Process

Cells for the production of AAV, e.g., rAAV, particles may comprise, in some embodiments, mammalian cells (such as HEK293 cells) and/or insect cells (such as Sf9 cells).

In various embodiments, AAV production includes processes and methods for producing AAV particles and vectors which can contact a target cell to deliver a payload, e.g. a recombinant viral construct, which includes a nucleotide encoding a payload molecule. In certain embodiments, the viral vectors are adeno-associated viral (AAV) vectors such as recombinant adeno-associated viral (rAAV) vectors. In certain embodiments, the AAV particles are adeno-associated viral (AAV) particles such as recombinant adeno-associated viral (rAAV) particles.

In various embodiments, methods are provided herein of producing AAV particles or vectors by (a) contacting a viral production cell with one or more viral expression constructs encoding at least one AAV capsid protein, and one or more payload constructs encoding a payload molecule, which can be selected from: a transgene, a polynucleotide encoding protein, and a modulatory nucleic acid; (b) culturing the viral production cell under conditions such that at least one AAV particle or vector is produced, and (c) isolating the AAV particle or vector from the production stream.

In these methods, a viral expression construct may encode at least one structural protein and/or at least one non-structural protein. The structural protein may include any of the native or wild type capsid proteins VP1, VP2, and/or VP3, or a chimeric protein thereof. The non-structural protein may include any of the native or wild type Rep78, Rep68, Rep52, and/or Rep40 proteins or a chimeric protein thereof.

In certain embodiments, contacting occurs via transient transfection, viral transduction, and/or electroporation.

In certain embodiments, the viral production cell is selected from a mammalian cell and an insect cell. In certain embodiments, the insect cell includes a *Spodoptera frugiperda* insect cell. In certain embodiments, the insect cell includes a Sf9 insect cell. In certain embodiments, the insect cell includes a Sf21 insect cell.

The payload construct vector of the present disclosure may include, in various embodiments, at least one inverted terminal repeat (ITR) and may include mammalian DNA.

Also provided are AAV particles and viral vectors produced according to the methods described herein.

In various embodiments, the AAV particles of the present disclosure may be formulated as a pharmaceutical composition with one or more acceptable excipients.

In certain embodiments, an AAV particle or viral vector may be produced by a method described herein.

In certain embodiments, the AAV particles may be produced by contacting a viral production cell (e.g., an insect cell or a mammalian cell) with at least one viral expression construct encoding at least one capsid protein and at least one payload construct vector. The viral production cell may be contacted by transient transfection, viral transduction, and/or electroporation. The payload construct vector may include a payload construct encoding a payload molecule such as, but not limited to, a transgene, a polynucleotide encoding protein, and a modulatory nucleic acid. The viral production cell can be cultured under conditions such that at least one AAV particle or vector is produced, isolated (e.g., using temperature-induced lysis, mechanical lysis and/or chemical lysis) and/or purified (e.g., using filtration, chromatography, and/or immunoaffinity purification). As a non-limiting example, the payload construct vector may include mammalian DNA.

In certain embodiments, the AAV particles are produced in an insect cell (e.g., *Spodoptera frugiperda* (Sf9) cell) using a method described herein. As a non-limiting example, the insect cell is contacted using viral transduction which may include baculoviral transduction.

In certain embodiments, the AAV particles are produced in an mammalian cell (e.g., HEK293 cell) using a method described herein. As a non-limiting example, the mammalian cell is contacted using viral transduction which may include multiplasmid transient transfection (such as triple plasmid transient transfection).

In certain embodiments, the AAV particle production method described herein produces greater than $10^1$, greater than $10^2$, greater than $10^3$, greater than $10^4$, or greater than $10^5$ AAV particles in a viral production cell.

In certain embodiments, a process of the present disclosure includes production of viral particles in a viral production cell using a viral production system which includes at least one viral expression construct and at least one payload construct. The at least one viral expression construct and at least one payload construct can be co-transfected (e.g. dual transfection, triple transfection) into a viral production cell. The transfection is completed using standard molecular biology techniques known and routinely performed by a person skilled in the art. The viral production cell provides the cellular machinery necessary for expression of the proteins and other biomaterials necessary for producing the AAV particles, including Rep proteins which replicate the payload construct and Cap proteins which assemble to form a capsid that encloses the replicated payload constructs. The resulting AAV particle is extracted from the viral production cells and processed into a pharmaceutical preparation for administration.

In various embodiments, once administered, an AAV particle disclosed herein may, without being bound by theory, contact a target cell and enter the cell, e.g., in an endosome. The AAV particles, e.g., those released from the endosome, may subsequently contact the nucleus of the target cell to deliver the payload construct. The payload construct, e.g. recombinant viral construct, may be delivered to the nucleus of the target cell wherein the payload molecule encoded by the payload construct may be expressed.

In certain embodiments, the process for production of viral particles utilizes seed cultures of viral production cells that include one or more baculoviruses (e.g., a Baculoviral Expression Vector (BEV) or a baculovirus infected insect cell (BIIC) that has been transfected with a viral expression construct and a payload construct vector). In certain embodiments, the seed cultures are harvested, divided into aliquots and frozen, and may be used at a later time point to initiate an infection of a naïve population of production cells.

In some embodiments, large scale production of AAV particles utilizes a bioreactor. Without being bound by theory, the use of a bioreactor may allow for the precise measurement and/or control of variables that support the growth and activity of viral production cells such as mass, temperature, mixing conditions (impellor RPM or wave oscillation), $CO_2$ concentration, $O_2$ concentration, gas sparge rates and volumes, gas overlay rates and volumes, pH, Viable Cell Density (VCD), cell viability, cell diameter, and/or optical density (OD). In certain embodiments, the bioreactor is used for batch production in which the entire culture is harvested at an experimentally determined time point and AAV particles are purified. In some embodiments, the bioreactor is used for continuous production in which a portion of the culture is harvested at an experimentally determined time point for purification of AAV particles, and the remaining culture in the bioreactor is refreshed with additional growth media components.

In various embodiments, AAV viral particles can be extracted from viral production cells in a process which includes cell lysis, clarification, sterilization and purification. Cell lysis includes any process that disrupts the structure of the viral production cell, thereby releasing AAV particles. In certain embodiments, cell lysis may include thermal shock, chemical, or mechanical lysis methods. Clarification can include the gross purification of the mixture of lysed cells, media components, and AAV particles. In certain embodiments, clarification includes centrifugation and/or filtration, including but not limited to depth end, tangential flow, and/or hollow fiber filtration.

In various embodiments, the end result of viral production is a purified collection of AAV particles which include two components: (1) a payload construct (e.g. a recombinant AAV vector genome construct) and (2) a viral capsid.

In certain embodiments, a viral production system or process of the present disclosure includes steps for producing baculovirus infected insect cells (BIICs) using Viral Production Cells (VPC) and plasmid constructs. Viral Production Cells (VPCs) from a Cell Bank (CB) are thawed and expanded to provide a target working volume and VPC concentration. The resulting pool of VPCs is split into a Rep/Cap VPC pool and a Payload VPC pool. One or more Rep/Cap plasmid constructs (viral expression constructs) are processed into Rep/Cap Bacmid polynucleotides and transfected into the Rep/Cap VPC pool. One or more Payload plasmid constructs (payload constructs) are processed into Payload Bacmid polynucleotides and transfected into the Payload VPC pool. The two VPC pools are incubated to produce P1 Rep/Cap Baculoviral Expression Vectors (BEVs) and P1 Payload BEVs. The two BEV pools are expanded into a collection of Plaques, with a single Plaque being selected for Clonal Plaque (CP) Purification (also referred to as Single Plaque Expansion). The process can include a single CP Purification step or can include multiple CP Purification steps either in series or separated by other processing steps. The one-or-more CP Purification steps provide a CP Rep/Cap BEV pool and a CP Payload BEV pool. These two BEV pools can then be stored and used for future production steps, or they can be then transfected into VPCs to produce a Rep/Cap BIIC pool and a Payload BIIC pool.

In certain embodiments, a viral production system or process of the present disclosure includes steps for producing AAV particles using Viral Production Cells (VPC) and baculovirus infected insect cells (BIICs). Viral Production Cells (VPCs) from a Cell Bank (CB) are thawed and expanded to provide a target working volume and VPC concentration. The working volume of Viral Production Cells is seeded into a Production Bioreactor and can be further expanded to a working volume of 200-2000 L with a target VPC concentration for BIIC infection. The working volume of VPCs in the Production Bioreactor is then co-infected with Rep/Cap BIICs and Payload BIICs, with a target VPC:BIIC ratio and a target BIIC:BIIC ratio. VCD infection can also utilize BEVs. The co-infected VPCs are incubated and expanded in the Production Bioreactor to produce a bulk harvest of AAV particles and VPCs.

Viral Expression Constructs

In various embodiments, the viral production system of the present disclosure includes one or more viral expression constructs that can be transfected/transduced into a viral production cell. In certain embodiments, a viral expression construct or a payload construct of the present disclosure can be a bacmid, also known as a baculovirus plasmid or recombinant baculovirus genome. In certain embodiments, the viral expression includes a protein-coding nucleotide sequence and at least one expression control sequence for expression in a viral production cell. In certain embodiments, the viral expression includes a protein-coding nucleotide sequence operably linked to least one expression control sequence for expression in a viral production cell. In certain embodiments, the viral expression construct contains parvoviral genes under control of one or more promoters. Parvoviral genes can include nucleotide sequences encoding non-structural AAV replication proteins, such as Rep genes which encode Rep52, Rep40, Rep68, or Rep78 proteins. Parvoviral genes can include nucleotide sequences encoding structural AAV proteins, such as Cap genes which encode VP1, VP2, and VP3 proteins.

Viral expression constructs of the present disclosure may include any compound or formulation, biological or chemical, which facilitates transformation, transfection, or transduction of a cell with a nucleic acid. Exemplary biological viral expression constructs include plasmids, linear nucleic acid molecules, and recombinant viruses including baculovirus. Exemplary chemical vectors include lipid complexes. Viral expression constructs are used to incorporate nucleic acid sequences into virus replication cells in accordance with the present disclosure. (O'Reilly, David R., Lois K. Miller, and Verne A. Luckow. Baculovirus expression vectors: a laboratory manual. Oxford University Press, 1994.); Maniatis et al., eds. Molecular Cloning. CSH Laboratory, NY, N.Y. (1982); and, Philiport and Scluber, eds. Liposomes as tools in Basic Research and Industry. CRC Press, Ann Arbor, Mich. (1995), the contents of each of which are herein incorporated by reference in its entirety as related to viral expression constructs and uses thereof.

In certain embodiments, the viral expression construct is an AAV expression construct which includes one or more nucleotide sequences encoding non-structural AAV replication proteins, structural AAV capsid proteins, or a combination thereof.

In certain embodiments, the viral expression construct of the present disclosure may be a plasmid vector. In certain embodiments, the viral expression construct of the present disclosure may be a baculoviral construct.

The present disclosure is not limited by the number of viral expression constructs employed to produce AAV particles or viral vectors. In certain embodiments, one, two, three, four, five, six, or more viral expression constructs can be employed to produce AAV particles in viral production cells in accordance with the present disclosure. In certain embodiments of the present disclosure, a viral expression construct may be used for the production of an AAV particles in insect cells. In certain embodiments, modifications may be made to the wild type AAV sequences of the capsid and/or rep genes, for example to improve attributes of the viral particle, such as increased infectivity or specificity, or to enhance production yields.

In certain embodiments, the viral expression construct may contain a nucleotide sequence which includes start codon region, such as a sequence encoding AAV capsid proteins which include one or more start codon regions. In certain embodiments, the start codon region can be within an expression control sequence. The start codon can be ATG or a non-ATG codon (i.e., a suboptimal start codon where the start codon of the AAV VP1 capsid protein is a non-ATG).

In certain embodiments, the viral expression construct used for AAV production may contain a nucleotide sequence encoding the AAV capsid proteins where the initiation codon of the AAV VP1 capsid protein is a non-ATG, i.e., a suboptimal initiation codon, allowing the expression of a modified ratio of the viral capsid proteins in the production system, to provide improved infectivity of the host cell. In a non-limiting example, a viral construct vector may contain a nucleic acid construct comprising a nucleotide sequence encoding AAV VP1, VP2, and VP3 capsid proteins, wherein the initiation codon for translation of the AAV VP1 capsid protein is CTG, TTG, or GTG, as described in U.S. Pat. No. 8,163,543, the contents of which are herein incorporated by reference in its entirety as related to AAV capsid proteins and the production thereof.

In certain embodiments, the viral expression construct of the present disclosure may be a plasmid vector or a baculoviral construct that encodes the parvoviral rep proteins for expression in insect cells. In certain embodiments, a single coding sequence is used for the Rep78 and Rep52 proteins, wherein start codon for translation of the Rep78 protein is a suboptimal start codon, selected from the group consisting of ACG, TTG, CTG, and GTG, that effects partial exon skipping upon expression in insect cells, as described in U.S. Pat. No. 8,512,981, the contents of which are herein incorporated by reference in their entirety, for example to promote less abundant expression of Rep78 as compared to Rep52, which may promote high vector yields.

In certain embodiments, a VP-coding region encodes one or more AAV capsid proteins of a specific AAV serotype. The AAV serotypes for VP-coding regions can be the same or different. In certain embodiments, a VP-coding region can be codon optimized. In certain embodiments, a VP-coding region or nucleotide sequence can be codon optimized for a mammal cell. In certain embodiments, a VP-coding region or nucleotide sequence can be codon optimized for an insect cell. In certain embodiments, a VP-coding region or nucleotide sequence can be codon optimized for a *Spodoptera frugiperda* cell. In certain embodiments, a VP-coding region or nucleotide sequence can be codon optimized for Sf9 or Sf21 cell lines.

In certain embodiments, a nucleotide sequence encoding one or more VP capsid proteins can be codon optimized to have a nucleotide homology with the reference nucleotide sequence of less than 100%. In certain embodiments, the nucleotide homology between the codon-optimized VP nucleotide sequence and the reference VP nucleotide sequence is less than 100%, less than 99%, less than 98%, less than 97%, less than 96%, less than 95%, less than 94%, less than 93%, less than 92%, less than 91%, less than 90%, less than 89%, less than 88%, less than 87%, less than 86%, less than 85%, less than 84%, less than 83%, less than 82%, less than 81%, less than 80%, less than 78%, less than 76%, less than 74%, less than 72%, less than 70%, less than 68%, less than 66%, less than 64%, less than 62%, less than 60%, less than 55%, less than 50%, and less than 40%.

In certain embodiments, a viral expression construct or a payload construct of the present disclosure can be a bacmid, also known as a baculovirus plasmid or recombinant baculovirus genome. In certain embodiments, a viral expression construct or a payload construct of the present disclosure (e.g. bacmid) can include a polynucleotide incorporated by homologous recombination (transposon donor/acceptor system) into the bacmid by standard molecular biology techniques known and performed by a person skilled in the art.

In certain embodiments, the polynucleotide incorporated into the bacmid (i.e. polynucleotide insert) can include an expression control sequence operably linked to a protein-coding nucleotide sequence. In certain embodiments, the polynucleotide incorporated into the bacmid can include an expression control sequence which includes a promoter, such as p10 or polh, and which is operably linked to a nucleotide sequence which encodes a structural AAV capsid protein (e.g. VP1, VP2, VP3 or a combination thereof). In certain embodiments, the polynucleotide incorporated into the bacmid can include an expression control sequence which includes a promoter, such as p10 or polh, and which is operably linked to a nucleotide sequence which encodes a non-structural AAV capsid protein (e.g. Rep78, Rep52, or a combination thereof).

The method of the present disclosure is not limited by the use of specific expression control sequences. However, when a certain stoichiometry of VP products are achieved (close to 1:1:10 for VP1, VP2, and VP3, respectively) and also when the levels of Rep52 or Rep40 (also referred to as the p19 Reps) are significantly higher than Rep78 or Rep68 (also referred to as the p5 Reps), improved yields of AAV in production cells (such as insect cells) may be obtained. In certain embodiments, the p5/p19 ratio is below 0.6 more, below 0.4, or below 0.3, but always at least 0.03. These ratios can be measured at the level of the protein or can be implicated from the relative levels of specific mRNAs.

In certain embodiments, AAV particles are produced in viral production cells (such as mammalian or insect cells) wherein all three VP proteins are expressed at a stoichiometry approaching, about or which is: 1:1:10 (VP1:VP2:VP3); 2:2:10 (VP1:VP2:VP3); 2:0:10 (VP1:VP2:VP3); 1-2:0-2:10 (VP1:VP2:VP3); 1-2:1-2:10 (VP1:VP2:VP3); 2-3:0-3:10 (VP1:VP2:VP3); 2-3:2-3:10 (VP1:VP2:VP3); 3:3:10 (VP1:VP2:VP3); 3-5:0-5:10 (VP1:VP2:VP3); or 3-5:3-5:10 (VP1:VP2:VP3).

In certain embodiments, the expression control regions are engineered to produce a VP1:VP2:VP3 ratio selected from the group consisting of: about or exactly 1:0:10; about or exactly 1:1:10; about or exactly 2:1:10; about or exactly 2:1:10; about or exactly 2:2:10; about or exactly 3:0:10; about or exactly 3:1:10; about or exactly 3:2:10; about or exactly 3:3:10; about or exactly 4:0:10; about or exactly 4:1:10; about or exactly 4:2:10; about or exactly 4:3:10; about or exactly 4:4:10; about or exactly 5:5:10; about or exactly 1-2:0-2:10; about or exactly 1-2:1-2:10; about or exactly 1-3:0-3:10; about or exactly 1-3:1-3:10; about or exactly 1-4:0-4:10; about or exactly 1-4:1-4:10; about or exactly 1-5:1-5:10; about or exactly 2-3:0-3:10; about or exactly 2-3:2-3:10; about or exactly 2-4:2-4:10; about or exactly 2-5:2-5:10; about or exactly 3-4:3-4:10; about or exactly 3-5:3-5:10; and about or exactly 4-5:4-5:10.

In certain embodiments of the present disclosure, Rep52 or Rep78 is transcribed from the baculoviral derived polyhedron promoter (polh). Rep52 or Rep78 can also be transcribed from a weaker promoter, for example a deletion mutant of the ie-1 promoter, the Δie-1 promoter, has about 20% of the transcriptional activity of that ie-1 promoter. A promoter substantially homologous to the Δie-1 promoter may be used. In respect to promoters, a homology of at least 50%, 60%, 70%, 80%, 90% or more, is considered to be a substantially homologous promoter.

Mammalian Cells

Viral production of the present disclosure disclosed herein describes processes and methods for producing AAV particles or viral vector that contacts a target cell to deliver a payload construct, e.g. a recombinant AAV particle or viral construct, which includes a nucleotide encoding a payload molecule. The viral production cell may be selected from any biological organism, including prokaryotic (e.g., bacterial) cells, and eukaryotic cells, including, insect cells, yeast cells and mammalian cells.

In certain embodiments, the AAV particles of the present disclosure may be produced in a viral production cell that includes a mammalian cell. Viral production cells may comprise mammalian cells such as A549, WEH1, 3T3, 10T1/2, BHK, MDCK, COS 1, COS 7, BSC 1, BSC 40, BMT 10, VERO, W138, HeLa, HEK293, HEK293T (293T), Saos, C2C12, L cells, HT1080, Huh7, HepG2, C127, 3T3, CHO, HeLa cells, KB cells, BHK and primary fibroblast, hepatocyte, and myoblast cells derived from mammals. Viral production cells can include cells derived from any mammalian species including, but not limited to, human, monkey, mouse, rat, rabbit, and hamster or cell type, including but not limited to fibroblast, hepatocyte, tumor cell, cell line transformed cell, etc.

AAV viral production cells commonly used for production of recombinant AAV particles include, but is not limited to other mammalian cell lines as described in U.S. Pat. Nos. 6,156,303, 5,387,484, 5,741,683, 5,691,176, 6,428,988 and 5,688,676; U.S. patent application 2002/0081721, and International Patent Publication Nos. WO 00/47757, WO 00/24916, and WO 96/17947, the contents of each of which are herein incorporated by reference in their entireties insofar as they do no conflict with the present disclosure. In certain embodiments, the AAV viral production cells are trans-complementing packaging cell lines that provide functions deleted from a replication-defective helper virus, e.g., HEK293 cells or other Ea trans-complementing cells.

In certain embodiments, the packaging cell line 293-10-3 (ATCC Accession No. PTA-2361) may be used to produce the AAV particles, as described in U.S. Pat. No. 6,281,010, the contents of which are herein incorporated by reference in its entirety as related to the 293-10-3 packaging cell line and uses thereof.

In certain embodiments, of the present disclosure a cell line, such as a HeLA cell line, for trans-complementing E1 deleted adenoviral vectors, which encoding adenovirus E1a and adenovirus E1b under the control of a phosphoglycerate kinase (PGK) promoter can be used for AAV particle production as described in U.S. Pat. No. 6,365,394, the contents of which are incorporated herein by reference in their entirety as related to the HeLa cell line and uses thereof.

In certain embodiments, AAV particles are produced in mammalian cells using a multiplasmid transient transfection method (such as triple plasmid transient transfection). In certain embodiments, the multiplasmid transient transfection method includes transfection of the following three different constructs: (i) a payload construct, (ii) a Rep/Cap construct (parvoviral Rep and parvoviral Cap), and (iii) a helper construct. In certain embodiments, the triple transfection method of the three components of AAV particle production may be utilized to produce small lots of virus for assays including transduction efficiency, target tissue (tropism) evaluation, and stability. In certain embodiments, the triple transfection method of the three components of AAV particle production may be utilized to produce large lots of materials for clinical or commercial applications.

AAV particles to be formulated may be produced by triple transfection or baculovirus mediated virus production, or any other method known in the art. Any suitable permissive or packaging cell known in the art may be employed to produce the vectors. In certain embodiments, trans-complementing packaging cell lines are used that provide functions deleted from a replication-defective helper virus, e.g., 293 cells or other E1a trans-complementing cells.

The gene cassette may contain some or all of the parvovirus (e.g., AAV) cap and rep genes. In certain embodiments, some or all of the cap and rep functions are provided in trans by introducing a packaging vector(s) encoding the capsid and/or Rep proteins into the cell. In certain embodiments, the gene cassette does not encode the capsid or Rep proteins. Alternatively, a packaging cell line is used that is stably transformed to express the cap and/or rep genes.

Recombinant AAV virus particles are, in certain embodiments, produced and purified from culture supernatants according to the procedure as described in US2016/0032254, the contents of which are incorporated by reference in its entirety as related to the production and processing of recombinant AAV virus particles. Production may also involve methods known in the art including those using 293T cells, triple transfection or any suitable production method.

In certain embodiments, mammalian viral production cells (e.g. 293T cells) can be in an adhesion/adherent state (e.g. with calcium phosphate) or a suspension state (e.g. with polyethyleneimine (PEI)). The mammalian viral production cell is transfected with plasmids required for production of AAV, (i.e., AAV rep/cap construct, an adenoviral helper construct, and/or ITR flanked payload construct). In certain embodiments, the transfection process can include optional medium changes (e.g. medium changes for cells in adhesion form, no medium changes for cells in suspension form, medium changes for cells in suspension form if desired). In certain embodiments, the transfection process can include transfection mediums such as DMEM or F17. In certain embodiments, the transfection medium can include serum or can be serum-free (e.g. cells in adhesion state with calcium phosphate and with serum, cells in suspension state with PEI and without serum).

Cells can subsequently be collected by scraping (adherent form) and/or pelleting (suspension form and scraped adherent form) and transferred into a receptacle. Collection steps can be repeated as necessary for full collection of produced cells. Next, cell lysis can be achieved by consecutive freeze-thaw cycles (−80C to 37C), chemical lysis (such as adding detergent triton), mechanical lysis, or by allowing the cell culture to degrade after reaching ~0% viability. Cellular debris is removed by centrifugation and/or depth filtration. The samples are quantified for AAV particles by DNase resistant genome titration by DNA qPCR.

AAV particle titers are measured according to genome copy number (genome particles per milliliter). Genome particle concentrations are based on DNA qPCR of the vector DNA as previously reported (Clark et al. (1999) Hum. Gene Ther., 10:1031-1039; Veldwijk et al. (2002) Mol. Ther., 6:272-278, the contents of which are each incorporated by reference in their entireties as related to the measurement of particle concentrations).

Insect Cells

Viral production of the present disclosure includes processes and methods for producing AAV particles or viral vectors that contact a target cell to deliver a payload construct, e.g., a recombinant viral construct, which includes a nucleotide encoding a payload molecule. In certain embodiments, the AAV particles or viral vectors of the present disclosure may be produced in a viral production cell that includes an insect cell.

Growing conditions for insect cells in culture, and production of heterologous products in insect cells in culture are well-known in the art, see U.S. Pat. No. 6,204,059, the contents of which are herein incorporated by reference in their entirety as related to the growth and use of insect cells in viral production.

Any insect cell which allows for replication of parvovirus and which can be maintained in culture can be used in accordance with the present disclosure. AAV viral production cells commonly used for production of recombinant AAV particles include, but is not limited to, *Spodoptera frugiperda*, including, but not limited to the Sf9 or Sf21 cell lines, *Drosophila* cell lines, or mosquito cell lines, such as *Aedes albopictus* derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, Methods in Molecular Biology, ed. Richard, Humana Press, N J (1995); O'Reilly et al., Baculovirus Expression Vectors, A Laboratory Manual, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kimbauer et al., Vir. 219:37-44 (1996); Zhao et al., Vir. 272:382-93 (2000); and Samulski et al., U.S. Pat. No. 6,204,059, the contents of each of which are herein incorporated by reference in their entirety as related to the use of insect cells in viral production.

In some embodiments, the AAV particles are made using the methods described in WO2015/191508, the contents of which are herein incorporated by reference in their entirety insofar as they do not conflict with the present disclosure.

In certain embodiments, insect host cell systems, in combination with baculoviral systems (e.g., as described by Luckow et al., Bio/Technology 6: 47 (1988)) may be used.

In certain embodiments, an expression system for preparing chimeric peptide is *Trichoplusia ni*, Tn 5B1-4 insect cells/baculoviral system, which can be used for high levels of proteins, as described in U.S. Pat. No. 6,660,521, the contents of which are herein incorporated by reference in their entirety as related to the production of viral particles.

Expansion, culturing, transfection, infection and storage of insect cells can be carried out in any cell culture media, cell transfection media or storage media known in the art, including Hyclone™ SFX-Insect™ Cell Culture Media, Expression System ESF AF™ Insect Cell Culture Medium, ThermoFisher Sf-900™ media, ThermoFisher Sf-900III™ media, or ThermoFisher Grace's Insect Media. Insect cell mixtures of the present disclosure can also include any of the formulation additives or elements described in the present disclosure, including (but not limited to) salts, acids, bases, buffers, surfactants (such as Poloxamer 188/Pluronic F-68), and other known culture media elements. Formulation additives can be incorporated gradually or as "spikes" (incorporation of large volumes in a short time).

Baculovirus Production Systems

In certain embodiments, processes of the present disclosure can include production of AAV particles or viral vectors in a baculoviral system using a viral expression construct and a payload construct vector. In certain embodiments, the baculoviral system includes Baculovirus expression vectors (BEVs) and/or baculovirus infected insect cells (BIICs). In certain embodiments, a viral expression construct or a payload construct of the present disclosure can be a bacmid, also known as a baculovirus plasmid or recombinant baculovirus genome. In certain embodiments, a viral expression construct or a payload construct of the present disclosure can be polynucleotide incorporated by homologous recombination (transposon donor/acceptor system) into a bacmid by standard molecular biology techniques known and performed by a person skilled in the art. Transfection of separate viral replication cell populations produces two or more groups (e.g. two, three) of baculoviruses (BEVs), one or more group which can include the viral expression construct (Expression BEV), and one or more group which can include the payload construct (Payload BEV). The baculoviruses may be used to infect a viral production cell for production of AAV particles or viral vector.

In certain embodiments, the process includes transfection of a single viral replication cell population to produce a single baculovirus (BEV) group which includes both the viral expression construct and the payload construct. These baculoviruses may be used to infect a viral production cell for production of AAV particles or viral vector.

In certain embodiments, BEVs are produced using a Bacmid Transfection agent, such as Promega FuGENE® HD, WFI water, or ThermoFisher Cellfectin® II Reagent. In certain embodiments, BEVs are produced and expanded in viral production cells, such as an insect cell.

In certain embodiments, the method utilizes seed cultures of viral production cells that include one or more BEVs, including baculovirus infected insect cells (BIICs). The seed BIICs have been transfected/transduced/infected with an Expression BEV which includes a viral expression construct, and also a Payload BEV which includes a payload construct. In certain embodiments, the seed cultures are harvested, divided into aliquots and frozen, and may be used at a later time to initiate transfection/transduction/infection of a naïve population of production cells. In certain embodiments, a bank of seed BIICs is stored at −80° C. or in LN2 vapor.

Baculoviruses are made of several essential proteins which are essential for the function and replication of the Baculovirus, such as replication proteins, envelope proteins and capsid proteins. The Baculovirus genome thus includes several essential-gene nucleotide sequences encoding the essential proteins. As a non-limiting example, the genome can include an essential-gene region which includes an essential-gene nucleotide sequence encoding an essential protein for the Baculovirus construct. The essential protein can include: GP64 baculovirus envelope protein, VP39 baculovirus capsid protein, or other similar essential proteins for the Baculovirus construct.

Baculovirus expression vectors (BEV) for producing AAV particles in insect cells, including but not limited to *Spodoptera frugiperda* (Sf9) cells, provide high titers of viral vector product. Recombinant baculovirus encoding the viral expression construct and payload construct initiates a productive infection of viral vector replicating cells. Infectious baculovirus particles released from the primary infection secondarily infect additional cells in the culture, exponentially infecting the entire cell culture population in a number of infection cycles that is a function of the initial multiplicity of infection, see Urabe, M. et al. J Virol. 2006 February; 80(4):1874-85, the contents of which are herein incorporated by reference in their entirety as related to the production and use of BEVs and viral particles.

Production of AAV particles with baculovirus in an insect cell system may address known baculovirus genetic and physical instability.

In certain embodiments, the production system of the present disclosure addresses baculovirus instability over multiple passages by utilizing a titerless infected-cells preservation and scale-up system. Small scale seed cultures of viral producing cells are transfected with viral expression constructs encoding the structural and/or non-structural components of the AAV particles. Baculovirus-infected viral producing cells are harvested into aliquots that may be cryopreserved in liquid nitrogen; the aliquots retain viability and infectivity for infection of large scale viral producing cell culture. Wasilko D J et al. Protein Expr Purif. 2009 June; 65(2):122-32, the contents of which are herein incorporated by reference in their entirety as related to the production and use of BEVs and viral particles.

A genetically stable baculovirus may be used to produce a source of the one or more of the components for producing AAV particles in invertebrate cells. In certain embodiments, defective baculovirus expression vectors may be maintained episomally in insect cells. In such embodiments, the corresponding bacmid vector is engineered with replication control elements, including but not limited to promoters, enhancers, and/or cell-cycle regulated replication elements.

In certain embodiments, stable viral producing cells permissive for baculovirus infection are engineered with at least one stable integrated copy of any of the elements necessary for AAV replication and vector production including, but not limited to, the entire AAV genome, Rep and Cap genes, Rep genes, Cap genes, each Rep protein as a separate transcription cassette, each VP protein as a separate transcription cassette, the AAP (assembly activation protein), or at least one of the baculovirus helper genes with native or non-native promoters.

In some embodiments, the AAV particle of the present disclosure may be produced in insect cells (e.g., Sf9 cells).

In some embodiments, the AAV particle of the present disclosure may be produced using triple transfection.

In some embodiments, the AAV particle of the present disclosure may be produced in mammalian cells.

In some embodiments, the AAV particle of the present disclosure may be produced by triple transfection in mammalian cells.

In some embodiments, the AAV particle of the present disclosure may be produced by triple transfection in HEK293 cells.

The AAV viral genomes encoding frataxin described herein may be useful in the fields of human disease, veterinary applications and a variety of in vivo and in vitro settings. The AAV particles of the present disclosure may be useful in the field of medicine for the treatment, prophylaxis, palliation, or amelioration of neurological or neuromuscular diseases and/or disorders. In some embodiments, the AAV particles of the disclosure are used for the prevention and/or treatment of Friedreich's Ataxia.

Various embodiments of the disclosure herein provide a pharmaceutical composition comprising the AAV particle described herein and a pharmaceutically acceptable excipient.

Various embodiments of the disclosure herein provide a method of treating a subject in need thereof comprising administering to the subject a therapeutically effective amount of the pharmaceutical composition described herein.

Certain embodiments of the method provide that the subject is treated by a route of administration of the pharmaceutical composition selected from the group consisting of: intravenous, intracerebroventricular, intraparenchymal, intrathecal, subpial, and intramuscular, or a combination thereof. Certain embodiments of the method provide that the subject is treated for Friedreich's ataxia and/or other neurological disorder arising from a deficiency in the quantity or function of frataxin. In one aspect of the method, a pathological feature of the Friedreich's ataxia or the other neurological disorder is alleviated and/or the progression of the Friedreich's ataxia or the other neurological disorder is halted, slowed, ameliorated, or reversed.

Various embodiments of the disclosure herein describe a method of increasing the level of frataxin in the central nervous system of a subject in need thereof comprising administering to said subject via infusion, an effective amount of the pharmaceutical composition described herein.

Also described herein are compositions, methods, processes, kits and devices for the design, preparation, manufacture and/or formulation of AAV particles. In some embodiments, payloads, such as but not limited to FXN, may be encoded by payload constructs or contained within plasmids or vectors or recombinant adeno-associated viruses (AAVs).

The present disclosure also provides administration and/or delivery methods for vectors and viral particles, e.g., AAV particles, for the treatment or amelioration of Friedreich's ataxia. Such methods may involve gene replacement or gene activation. Such outcomes are achieved by utilizing the methods and compositions taught herein.

III. Pharmaceutical Compositions

The present disclosure additionally provides a method for treating FA and disorders related to deficiencies in the function or expression of the frataxin protein in a mammalian subject, including a human subject, comprising administering to the subject any of the AAV polynucleotides or AAV genomes described herein (i.e., "vector genomes," "viral genomes," or "VGs") or administering to the subject a particle comprising said AAV polynucleotide or AAV genome, or administering to the subject any of the described compositions, including pharmaceutical compositions.

As used herein the term "composition" comprises an AAV polynucleotide or AAV genome or AAV particle and at least one excipient.

As used herein the term "pharmaceutical composition" comprises an AAV polynucleotide or AAV genome or AAV particle and one or more pharmaceutically acceptable excipients.

Although the descriptions of pharmaceutical compositions, e.g., AAV comprising a payload encoding a FXN construct to be delivered, provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients, or subjects.

In some embodiments, the AAV particle formulations described herein may contain a nucleic acid encoding at least one payload. In some embodiments, the formulations may contain a nucleic acid encoding 1, 2, 3, 4, or 5 payloads. In some embodiments, the formulation may contain a nucleic acid encoding a payload construct encoding proteins selected from categories such as, but not limited to, human proteins, veterinary proteins, bacterial proteins, biological proteins, antibodies, immunogenic proteins, therapeutic peptides and proteins, secreted proteins, plasma membrane proteins, cytoplasmic proteins, cytoskeletal proteins, intracellular membrane bound proteins, nuclear proteins, proteins associated with human disease, and/or proteins associated with non-human diseases. In some embodiments, the formulation contains at least three payload constructs encoding proteins. Certain embodiments provide that at least one of the payloads is FXN or a variant thereof.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

IV. Formulations

Formulations of the AAV pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered.

For example, the composition may comprise between 0.1% and 99% (w/w) of the active ingredient. By way of example, the composition may comprise between 0.1% and 100%, e.g., between 0.5% and 50%, between 1-30%, between 5-80%, or at least 80% (w/w) active ingredient.

The AAV particles of the disclosure can be formulated using one or more excipients to: (1) increase stability; (2) increase cell transfection or transduction; (3) permit the sustained or delayed release; (4) alter the biodistribution (e.g., target the viral particle to specific tissues or cell types); (5) increase the translation of encoded protein in vivo; (6) alter the release profile of encoded protein in vivo and/or (7) allow for regulatable expression of the payload.

Formulations of the present disclosure can include, without limitation, saline, lipidoids, liposomes, lipid nanoparticles, polymers, lipoplexes, core-shell nanoparticles, peptides, proteins, cells transfected with viral vectors (e.g., for transplantation into a subject), nanoparticle mimics and combinations thereof. Further, the viral vectors of the present disclosure may be formulated using self-assembled nucleic acid nanoparticles.

In some embodiments, the viral vectors encoding FXN may be formulated to optimize baricity and/or osmolality. In some embodiments, the baricity and/or osmolality of the formulation may be optimized to ensure optimal drug distribution in the central nervous system or a region or component of the central nervous system.

In some embodiments, the AAV particles of the disclosure may be formulated in PBS with 0.001% of pluronic acid (F-68) at a pH of about 7.0.

In some embodiments, the AAV particles of the disclosure may be formulated in PBS, in combination with an ethylene oxide/propylene oxide copolymer (also known as pluronic or poloxamer).

In some embodiments, the AAV particles of the disclosure may be formulated in PBS with 0.001% pluronic acid (F-68) (poloxamer 188) at a pH of about 7.0.

In some embodiments, the AAV particles of the disclosure may be formulated in PBS with 0.001% pluronic acid (F-68) (poloxamer 188) at a pH of about 7.3.

In some embodiments, the AAV particles of the disclosure may be formulated in PBS with 0.001% pluronic acid (F-68) (poloxamer 188) at a pH of about 7.4.

In some embodiments, the AAV particles of the disclosure may be formulated in a solution comprising sodium chloride, sodium phosphate and an ethylene oxide/propylene oxide copolymer.

In some embodiments, the AAV particles of the disclosure may be formulated in a solution comprising sodium chloride, sodium phosphate dibasic, potassium chloride, potassium phosphate monobasic, and poloxamer 188/pluronic acid (F-68).

In some embodiments, the AAV particles of the disclosure may be formulated in a solution comprising 192 mM sodium chloride, 10 mM sodium phosphate (dibasic), 2.7 mM potassium chloride, 2 mM potassium phosphate (monobasic) and 0.001% pluronic F-68 (v/v), at pH 7.4. This formulation is referred to as Formulation 1 in the present disclosure.

In some embodiments, the AAV particles of the disclosure may be formulated in a solution comprising about 192 mM sodium chloride, about 10 mM sodium phosphate dibasic and about 0.001% poloxamer 188, at a pH of about 7.3. The concentration of sodium chloride in the final solution may be 150 mM-200 mM. As non-limiting examples, the concentration of sodium chloride in the final solution may be 150 mM, 160 mM, 170 mM, 180 mM, 190 mM or 200 mM. The concentration of sodium phosphate dibasic in the final solution may be 1 mM-50 mM. As non-limiting examples, the concentration of sodium phosphate dibasic in the final solution may be 1 mM, 2 mM, 3 mM, 4 mM, 5 mM, 6 mM, 7 mM, 8 mM, 9 mM, 10 mM, 15 mM, 20 mM, 25 mM, 30 mM, 40 mM, or 50 mM. The concentration of poloxamer 188 (pluronic acid (F-68)) may be 0.0001%-1%. As non-limiting examples, the concentration of poloxamer 188 (pluronic acid (F-68)) may be 0.0001%, 0.0005%, 0.001%, 0.005%, 0.01%, 0.05%, 0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

In one embodiment, the AAV particles of the disclosure may be formulated in a solution comprising about 1.05% sodium chloride, about 0.212% sodium phosphate dibasic, heptahydrate, about 0.025% sodium phosphate monobasic, monohydrate, and 0.001% poloxamer 188, at a pH of about 7.4. As a non-limiting example, the concentration of AAV particle in this formulated solution may be about 0.001%. The concentration of sodium chloride in the final solution may be 0.1-2.0%, with non-limiting examples of 0.1%, 0.25%, 0.5%, 0.75%, 0.95%, 0.96%, 0.97%, 0.98%, 0.99%, 1.00%, 1.01%, 1.02%, 1.03%, 1.04%, 1.05%, 1.06%, 1.07%, 1.08%, 1.09%, 1.10%, 1.25%, 1.5%, 1.75%, or 2%. The concentration of sodium phosphate dibasic in the final solution may be 0.100-0.300% with non-limiting examples including 0.100%, 0.125%, 0.150%, 0.175%, 0.200%, 0.210%, 0.211%, 0.212%, 0.213%, 0.214%, 0.215%, 0.225%, 0.250%, 0.275%, 0.300%. The concentration of sodium phosphate monobasic in the final solution may be 0.010-0.050%, with non-limiting examples of 0.010%, 0.015%, 0.020%, 0.021%, 0.022%, 0.023%, 0.024%, 0.025%, 0.026%, 0.027%, 0.028%, 0.029%, 0.030%, 0.035%, 0.040%, 0.045%, or 0.050%. The concentration of poloxamer 188 (pluronic acid (F-68)) may be 0.0001%-1%. As non-limiting examples, the concentration of poloxamer 188 (pluronic acid (F-68)) may be 0.0001%, 0.0005%, 0.001%, 0.005%, 0.01%, 0.05%, 0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

Excipients

The formulations of the disclosure can include one or more excipients, each in an amount that together increases the stability of the AAV particle, increases cell transfection or transduction by the viral particle, increases the expression of viral particle encoded protein, and/or alters the release profile of AAV particle encoded proteins. In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; the contents of which are herein incorporated by reference in their entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Inactive Ingredients

In some embodiments, AAV formulations may comprise at least one excipient which is an inactive ingredient. As used herein, the term "inactive ingredient" refers to one or more agents that do not contribute to the activity of the pharmaceutical composition included in formulations. In some embodiments, all, none, or some of the inactive ingredients which may be used in the formulations of the present disclosure may be approved by the US Food and Drug Administration (FDA).

Formulations of AAV particles disclosed herein may include cations or anions. In one embodiment, the formulations include metal cations such as, but not limited to, $Zn^{2+}$, $Ca^{2+}$, $Cu^{2+}$, $Mg^{2+}$, or combinations thereof. In some embodiments, formulations may include polymers or polynucleotides complexed with a metal cation (See, e.g., U.S. Pat. Nos. 6,265,389 and 6,555,525, the contents of each of which are herein incorporated by reference in their entirety).

V. Uses and Applications

The compositions of the disclosure herein may be administered to a subject or used in the manufacture of a medicament for administration to a subject having a deficiency in the quantity or function of FXN or having a disease or condition associated with decreased FXN expression. In some embodiments, the disease is FA. In certain embodiments, the AAV particles including FXN may be administered to a subject to treat FA. In some embodiments, administration of the AAV particles comprising viral genomes that encode a FXN may protect central pathways from degeneration.

In some embodiments, the payload carried by the AAV particle is a polynucleotide encoding a FXN polypeptide having at least 90% sequence identity to a human FXN sequence of SEQ ID NO: 1725-1727. In some embodiments the frataxin polypeptide is of a nonhuman primate. In some embodiments, the nonhuman primate polypeptide is FXN of cynomolgus monkey *Macaca fascicularis* (cynoFXN or cFXN) or a rhesus macaque (*Macaca mulatta*). In some embodiments the non-human primate frataxin polypeptide is at least partially humanized. In some embodiments, the payload carried by the AAV particle is a polynucleotide encoding a FXN polypeptide having at least 90% sequence identity to a sequence given by any of SEQ ID NO: 1731-1733.

In some embodiments, the delivery of the AAV particles may halt or slow progression of Friedreich's ataxia as measured by mFARS/SARA by 50% relative to a comparator group. In certain embodiments, the delivery of the AAV particles increases the presence of functional FXN, improves and stabilizes gait, improves ataxia-associated heart conditions, decreases feelings of exhaustion, and treats metabolic disorders such as diabetes.

In some embodiments, the present disclosure encompasses the delivery of pharmaceutical, prophylactic, diagnostic, or imaging compositions in combination with agents that may improve their bioavailability, reduce and/or modify their metabolism, and/or modify their distribution within the body.

In certain embodiments, the pharmaceutical compositions described herein are used as research tools, particularly in in vitro investigations using human cell lines such as HEK293T and in vivo testing in nonhuman primates which will occur prior to human clinical trials.

CNS Diseases

The present disclosure provides a method for treating a disease, disorder and/or condition in a mammalian subject, including a human subject, comprising administering to the subject any of the viral particles e.g., AAV, AAV particle, or AAV genome that produces FXN described herein (i.e., viral genomes or "VG") or administering to the subject a particle comprising said AAV particle or AAV genome, or administering to the subject any of the described compositions, including pharmaceutical compositions.

In some embodiments, AAV particles of the present disclosure, through delivery of a functional payload that is a therapeutic product comprising a FXN or variant thereof that can modulate the level or function of a gene product in the CNS.

A functional payload may alleviate or reduce symptoms that result from abnormal level and/or function of a gene product (e.g., an absence or defect in a protein) in a subject in need thereof or that otherwise confers a benefit to a CNS disorder in a subject in need thereof.

As non-limiting examples, companion or combination therapeutic products delivered by AAV particles of the present disclosure may include, but are not limited to, growth and trophic factors, cytokines, hormones, neurotransmitters, enzymes, anti-apoptotic factors, angiogenic factors, FXN polypeptides, and any protein known to be mutated in pathological disorders such as FA (e.g., brain specific Mir-128a, See Adlakha and Saini, Molecular cancer, 2014, 13:33, incorporated herein by reference in its entirety).

In some embodiments, the neurodegenerative disorder is Friedreich's ataxia resulting from expansion of an intronic GAA triplet repeat in the FXN gene, which reduces expression of the mitochondrial protein frataxin causing progressive damage to the nervous system.

In some embodiments, AAV particles of the present disclosure may be used to treat diseases that are associated with impairments of the growth and development of the CNS, i.e., neurodevelopmental disorders. In some aspects, such neurodevelopmental disorders may be caused by genetic mutations.

In some embodiments, the neurological disorders may be functional neurological disorders with motor and/or sensory symptoms which have neurological origin in the CNS. As non-limiting examples, functional neurological disorders may be chronic pain, seizures, speech problems, involuntary movements, or sleep disturbances.

In some embodiments, the neurological or neuromuscular disease, disorder, and/or condition is Friedreich's ataxia. In some embodiments, the delivery of the AAV particles may halt or slow the disease progression of Friedreich's ataxia by 10%, 20%, 30%, 40%, 50%, 60%, 70%, 80%, 90%, 95%, or more than 95% using a known analysis method and comparator group for Friedreich's ataxia. As a non-limiting example, the delivery of the AAV particles may halt or slow progression of Friedreich's ataxia as measured by mFARS/SARA by 50% relative to a comparator group.

In some embodiments, the AAV particle encoding a payload may increase the amount of FXN in a tissue by 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 97%, 99%, or more than 100%. In some embodiments, the AAV particle encoding a payload may increase the amount of FXN in a tissue to be comparable to (e.g., approximately the same as) the amount of FXN in the corresponding tissue of a healthy subject. In some embodiments, the AAV particle encoding a payload may increase the amount of FXN in a tissue effective to reduce one or more symptoms of a disease associated with decreased FXN expression or a deficiency in the quantity and/or function of FXN, e.g., FA.

VI. Dosing and Administration

Administration

In some aspects, the present disclosure provides administration and/or delivery methods for vectors and viral particles, e.g., AAV particles, encoding FXN or a variant thereof, for the prevention, treatment, or amelioration of diseases or disorders of the CNS. For example, administration of the AAV particles encoding FXN that prevents, treats, or ameliorates FA.

The AAV particles of the present disclosure may be administered by any route which results in a therapeutically effective outcome. These include, but are not limited to, enteral (into the intestine), gastroenteral, epidural (into the dura matter), oral (by way of the mouth), transdermal, peridural, intracerebral (into the cerebrum), intracerebroventricular (into the cerebral ventricles), intracranial (into the skull), picutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intraparenchymal (into the substance of), intrathecal (into the spinal canal), intraperitoneal, (infusion or injection into the peritoneum), intravesicular infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracoronal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, subpial, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

In some embodiments, AAV particles of the present disclosure are administered so as to be delivered to a target cell or tissue. While not wishing to be bound by theory, delivery to a target cell results in FXN expression. A target cell may be any cell in which it is considered desirable to increase FXN expression levels. A target cell may be a CNS cell. Non-limiting examples of such cells and/or tissues include, dorsal root ganglia and dorsal columns, proprioceptive sensory neurons, Clark's column, gracile and cuneate nuclei, cerebellar dentate nucleus, corticospinal tracts and the cells comprising the same, Betz cells, and cells of the heart.

In some embodiments, compositions may be administered in a way that allows them to cross the blood-brain barrier, vascular barrier, or other epithelial barrier.

In some embodiments, delivery of FXN by adeno-associated virus (AAV) particles to cells of the central nervous system (e.g., parenchyma) comprises infusion into cerebrospinal fluid (CSF). CSF is produced by specialized ependymal cells that comprise the choroid plexus located in the ventricles of the brain. CSF produced within the brain then circulates and surrounds the central nervous system including the brain and spinal cord. CSF continually circulates around the central nervous system, including the ventricles of the brain and subarachnoid space that surrounds both the brain and spinal cord, while maintaining a homeostatic balance of production and reabsorption into the vascular system. The entire volume of CSF is replaced approximately four to six times per day or approximately once every four hours, though values for individuals may vary.

In some embodiments, the AAV particles may be delivered by systemic delivery. In some embodiments, the systemic delivery may be by intravascular administration. In some embodiments, the systemic delivery may be by intravenous administration.

In some embodiments, the AAV particles may be delivered by intravenous delivery.

In some embodiments, the AAV particles may be delivered by injection into the CSF pathway. Non-limiting examples of delivery to the CSF pathway include intrathecal and intracerebroventricular administration.

In some embodiments, the AAV particles may be delivered by thalamic delivery.

In some embodiments, the AAV particles may be delivered by intracerebral delivery.

In some embodiments, the AAV particles may be delivered by intracardiac delivery.

In some embodiments, the AAV particles may be delivered by intracranial delivery.

In some embodiments, the AAV particles may be delivered by direct (intraparenchymal) injection into an organ (e.g., CNS (brain or spinal cord)). In some embodiments, the intraparenchymal delivery may be to any region of the brain or CNS, e.g., intrastriatal.

In some embodiments, the AAV particles of the present disclosure may be administered to the ventricles of the brain.

In some embodiments, the AAV particles of the present disclosure may be administered to the ventricles of the brain by intracerebroventricular delivery.

In some embodiments, the AAV particles of the present disclosure may be administered by intramuscular delivery.

In some embodiments, the AAV particles of the present disclosure are administered by more than one route described above. As a non-limiting example, the AAV particles may be administered by intravenous delivery and thalamic delivery.

In some embodiments, the AAV particles of the present disclosure are administered by more than one route described above. As a non-limiting example, the AAV particles may be administered by intravenous delivery and intracerebral delivery.

In some embodiments, the AAV particles of the present disclosure are administered by more than one route described above. As a non-limiting example, the AAV particles may be administered by intravenous delivery and intracranial delivery.

In some embodiments, the AAV particles of the present disclosure are administered by more than one route described above. In some embodiments, the AAV particles of the present disclosure may be delivered by intrathecal and intracerebroventricular administration.

In some embodiments, the AAV particles may be delivered to a subject to improve and/or correct mitochondrial dysfunction.

In some embodiments, the AAV particles may be delivered to a subject to preserve neurons. The neurons may be primary and/or secondary sensory neurons. In some embodiments, AAV particles are delivered to dorsal root ganglia and/or neurons thereof.

In some embodiments, administration of the AAV particles may preserve and/or correct function in the sensory pathways.

In some embodiments, the AAV particles may be delivered via intravenous (IV), intracerebroventricular (ICV), intraparenchymal, and/or intrathecal (IT) infusion and the therapeutic agent may also be delivered to a subject via intramuscular (IM) limb infusion in order to deliver the therapeutic agent to the skeletal muscle. Delivery of AAVs encoding at least one FXN or variants thereof by intravascular limb infusion is described by Gruntman and Flotte, Human Gene Therapy Clinical Development, 2015, 26(3), 159-164, the contents of which are herein incorporated by reference in their entirety.

In some embodiments, delivery of viral vector pharmaceutical compositions in accordance with the present disclosure to cells of the central nervous system (e.g., parenchyma) comprises a rate of delivery defined by VG/hour=mL/hour*VG/mL, wherein VG is viral genomes, VG/mL is composition concentration, and mL/hour is rate of infusion.

In some embodiments, delivery of AAV particle pharmaceutical compositions in accordance with the present disclosure to cells of the central nervous system (e.g., parenchyma) comprises infusion of up to 1 mL. In some embodiments, delivery of viral vector pharmaceutical compositions in accordance with the present disclosure to cells of the central nervous system (e.g., parenchyma) may comprise infusion of 0.0001, 0.0002, 0.001, 0.002, 0.003, 0.004, 0.005, 0.008, 0.010, 0.015, 0.020, 0.025, 0.030, 0.040, 0.050, 0.060, 0.070, 0.080, 0.090, 0.1, 0.2, 0.3, 0.4, 0.5, 0.6, 0.7, 0.8, or 0.9 mL.

In some embodiments, delivery of AAV particle pharmaceutical compositions in accordance with the present disclosure to cells of the central nervous system (e.g., parenchyma) comprises infusion of between about 1 mL to about 120 mL. In some embodiments, delivery of viral vector pharmaceutical compositions in accordance with the present disclosure to cells of the central nervous system (e.g., parenchyma) may comprise an infusion of 0.1, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 mL. In some embodiments delivery of AAV particles to cells of the central nervous system (e.g., parenchyma) comprises infusion of at least 3 mL. In one embodiment, delivery of AAV particles to cells of the central nervous system (e.g., parenchyma) consists of infusion of 3 mL. In one embodiment, delivery of AAV particles to cells of the central nervous system (e.g., parenchyma) comprises infusion of at least 10 mL. In some embodiments, delivery of AAV particles to cells of the central nervous system (e.g., parenchyma) consists of infusion of 10 mL.

In some embodiments, the volume of the AAV particle pharmaceutical composition delivered to the cells of the central nervous system (e.g., parenchyma) of a subject is 2 µl, 20 µl, 50 µl, 80 µl, 100 µl, 200 µl, 300 µl, 400 µl, 500 µl, 600 µl, 700 µl, 800 µl, 900 µl, 1000 µl, 1100 µl, 1200 µl, 1300 µl, 1400 µl, 1500 µl, 1600 µl, 1700 µl, 1800 µl, 1900 µl, 2000 µl, or more than 2000 µl.

In some embodiments, the volume of the AAV particle pharmaceutical composition delivered to a region in both hemispheres of a subject brain is 2 µl, 20 µl, 50 µl, 80 µl, 100 µl, 200 µl, 300 µl, 400 µl, 500 µl, 600 µl, 700 µl, 800 µl, 900 µl, 1000 µl, 1100 µl, 1200 µl, 1300 µl, 1400 µl, 1500 µl, 1600 µl, 1700 µl, 1800 µl, 1900 µl, 2000 µl, or more than 2000 µl. In some embodiments, the volume delivered to a region in both hemispheres is 200µ. As another non-limiting example, the volume delivered to a region in both hemispheres is 900 µl. As yet another non-limiting example, the volume delivered to a region in both hemispheres is 1800 µl.

In certain embodiments, AAV particle or viral vector pharmaceutical compositions in accordance with the present disclosure may be administered at about 10 to about 600 µl/site, about 50 to about 500 µl/site, about 100 to about 400 µl/site, about 120 to about 300 µl/site, about 140 to about 200 µl/site, or about 160 µl/site.

In some embodiments, the total volume delivered to a subject may be split between one or more administration sites e.g., 1, 2, 3, 4, 5, or more than 5 sites. In some embodiments, the total volume is split between administration to the left and right hemisphere.

Delivery of AAV Particles

In some embodiments, the AAV particles or pharmaceutical compositions of the present disclosure may be administered or delivered using the methods for treatment of disease described in U.S. Pat. No. 8,999,948, or International Publication No. WO2014178863, the contents of which are herein incorporated by reference in their entirety.

In some embodiments, the AAV particles or pharmaceutical compositions of the present disclosure may be administered or delivered using the methods for delivering gene therapy in Alzheimer's Disease or other neurodegenerative conditions as described in US Application No. 20150126590, the contents of which are herein incorporated by reference in their entirety.

In some embodiments, the AAV particles or pharmaceutical compositions of the present disclosure may be administered or delivered using the methods for delivery of a CNS gene therapy as described in U.S. Pat. Nos. 6,436,708, and 8,946,152, and International Publication No. WO2015168666, the contents of which are herein incorporated by reference in their entirety.

In some embodiments, the AAV particles of the present disclosure may be administered or delivered using the methods for the delivery of AAV virions described in European Patent Application No. EP1857552, the contents of which are herein incorporated by reference in their entirety.

In some embodiments, the AAV particle or pharmaceutical compositions of the present disclosure may be administered or delivered using the methods for delivering proteins using AAV vectors described in European Patent Application No. EP2678433, the contents of which are herein incorporated by reference in their entirety.

In some embodiments, the viral vector encoding FXN may be administered or delivered using the methods for delivering DNA molecules using AAV vectors described in U.S. Pat. No. 5,858,351, the contents of which are herein incorporated by reference in their entirety.

In some embodiments, the AAV particle or pharmaceutical compositions of the present disclosure may be administered or delivered using the methods for delivering DNA to the bloodstream described in U.S. Pat. No. 6,211,163, the contents of which are herein incorporated by reference in their entirety.

In some embodiments, the viral vector encoding FXN may be administered or delivered using the methods for delivering AAV virions described in U.S. Pat. No. 6,325,998, the contents of which are herein incorporated by reference in their entirety.

In some embodiments, the viral vector encoding FXN may be administered or delivered using the methods for delivering DNA to muscle cells described in U.S. Pat. No. 6,335,011, the contents of which are herein incorporated by reference in their entirety.

In some embodiments, the viral vector encoding FXN may be administered or delivered using the methods for delivering DNA to muscle cells and tissues described in U.S. Pat. No. 6,610,290, the contents of which are herein incorporated by reference in their entirety.

In some embodiments, the viral vector encoding FXN may be administered or delivered using the methods for delivering DNA to muscle cells described in U.S. Pat. No. 7,704,492, the contents of which are herein incorporated by reference in their entirety.

In some embodiments, the viral vector encoding FXN may be administered or delivered using the methods for delivering a payload to skeletal muscles described in U.S. Pat. No. 7,112,321, the contents of which are herein incorporated by reference in their entirety.

In some embodiments, the AAV particle or pharmaceutical compositions of the present disclosure may be administered or delivered using the methods for delivering a payload to the central nervous system described in U.S. Pat. No. 7,588,757, the contents of which are herein incorporated by reference in their entirety.

In some embodiments, the AAV particle or pharmaceutical compositions of the present disclosure may be administered or delivered using the methods for delivering a payload described in U.S. Pat. No. 8,283,151, the contents of which are herein incorporated by reference in their entirety.

In some embodiments, the viral vector encoding FXN may be administered or delivered using the methods for delivering a payload for the treatment of Alzheimer disease described in U.S. Pat. No. 8,318,687, the contents of which are herein incorporated by reference in their entirety.

In some embodiments, the viral vector encoding FXN may be administered or delivered using the methods for delivering a payload described in International Patent Publication No. WO2012144446, the contents of which are herein incorporated by reference in their entirety.

In some embodiments, the AAV particle or pharmaceutical compositions of the present disclosure may be administered or delivered using the methods for delivering a payload using a glutamic acid decarboxylase (GAD) delivery vector described in International Patent Publication No. WO2001089583, the contents of which are herein incorporated by reference in their entirety.

In some embodiments, the AAV particle or pharmaceutical compositions of the present disclosure may be administered or delivered using the methods for delivering a payload to neural cells described in International Patent Publication No. WO2012057363, the contents of which are herein incorporated by reference in their entirety.

In some embodiments, the viral vector encoding FXN may be administered or delivered using the methods for delivering a payload described in International Patent Publication No. WO2001096587, the contents of which are herein incorporated by reference in their entirety.

In some embodiments, the viral vector encoding FXN may be administered or delivered using the methods for delivering a payload to muscle tissue described in International Patent Publication No. WO2002014487, the contents of which are herein incorporated by reference in their entirety.

In some embodiments, a catheter may be used to administer the AAV particles. In certain embodiments, the catheter or cannula may be located at more than one site in the spine for multi-site delivery. The viral particles encoding FXN may be delivered in a continuous and/or bolus infusion. Each site of delivery may be a different dosing regimen or the same dosing regimen may be used for each site of delivery. In some embodiments, the sites of delivery may be in the cervical and the lumbar region. In some embodiments, the sites of delivery may be in the cervical region. In some embodiments, the sites of delivery may be in the lumbar region.

In some embodiments, a subject may be analyzed for spinal anatomy and pathology prior to delivery of the AAV particles encoding FXN described herein. As a non-limiting example, a subject with scoliosis may have a different dosing regimen and/or catheter location compared to a subject without scoliosis.

In some embodiments, the delivery method and duration is chosen to provide broad transduction in the spinal cord. In some embodiments, intrathecal delivery is used to provide broad transduction along the rostral-caudal length of the spinal cord. In some embodiments, multi-site infusions provide a more uniform transduction along the rostral-caudal length of the spinal cord.

Delivery to Cells

In some aspects, the present disclosure provides a method of delivering to a cell or tissue any of the above-described AAV particles, comprising contacting the cell or tissue with said AAV particle or contacting the cell or tissue with a formulation comprising said AAV particle, or contacting the cell or tissue with any of the described compositions, including pharmaceutical compositions. The method of delivering the AAV particle to a cell or tissue can be accomplished in vitro, ex vivo, or in vivo.

Delivery to Subjects

In some aspects, the present disclosure additionally provides a method of delivering to a subject, including a mammalian subject, any of the above-described AAV particles comprising administering to the subject said AAV particle, or administering to the subject a formulation comprising said AAV particle, or administering to the subject any of the described compositions, including pharmaceutical compositions.

In some embodiments, the AAV particles may be delivered to bypass anatomical blockages such as, but not limited to the blood brain barrier.

In some embodiments, the AAV particles may be formulated and delivered to a subject by a route which increases the speed of drug effect as compared to oral delivery.

In some embodiments, the AAV particles may be delivered by a method to provide uniform transduction of the spinal cord and dorsal root ganglion (DRG). In some embodiments, the AAV particles may be delivered using intrathecal infusion.

In some embodiments, a subject may be administered the AAV particles described herein using a bolus infusion. As used herein, a "bolus infusion" means a single and rapid infusion of a substance or composition.

In some embodiments, the AAV particles encoding FXN may be delivered in a continuous and/or bolus infusion. Each site of delivery may be a different dosing regimen or the same dosing regimen may be used for each site of delivery. As a non-limiting example, the sites of delivery may be in the cervical and the lumbar region. As another non-limiting example, the sites of delivery may be in the cervical region. As another non-limiting example, the sites of delivery may be in the lumbar region.

In some embodiments, the AAV particles may be delivered to a subject via a single route administration.

In some embodiments, the AAV particles may be delivered to a subject via a multi-site route of administration. For example, a subject may be administered the AAV particles at 2, 3, 4, 5, or more than 5 sites.

In some embodiments, a subject may be administered the AAV particles described herein using sustained delivery over a period of minutes, hours or days. The infusion rate may be changed depending on the subject, distribution, formulation or another delivery parameter known to those in the art.

In some embodiments, if continuous delivery (continuous infusion) of the AAV particles is used, the continuous infusion may be for 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or more than 24 hours.

In some embodiments, the intracranial pressure may be evaluated prior to administration. The route, volume, AAV particle concentration, infusion duration and/or vector titer may be optimized based on the intracranial pressure of a subject.

In some embodiments, the AAV particles may be delivered by systemic delivery. In some embodiments, the systemic delivery may be by intravascular administration.

In some embodiments, the AAV particles may be delivered by injection into the CSF pathway. Non-limiting examples of delivery to the CSF pathway include intrathecal and intracerebroventricular administration.

In some embodiments, the AAV particles may be delivered by direct (intraparenchymal) injection into the substance of an organ, e.g., one or more regions of the brain.

In some embodiments, the AAV particles may be delivered by subpial injection into the spinal cord. For example, subjects may be placed into a spinal immobilization apparatus. A dorsal laminectomy may be performed to expose the spinal cord. Guiding tubes and XYZ manipulators may be used to assist catheter placement. Subpial catheters may be placed into the subpial space by advancing the catheter from the guiding tube and AAV particles may be injected through the catheter (Miyanohara et al., Mol Ther Methods Clin Dev. 2016; 3: 16046). In some cases, the AAV particles may be injected into the cervical subpial space. In some cases, the AAV particles may be injected into the thoracic subpial space.

In some embodiments, the AAV particles may be delivered to a subject in order to increase the FXN protein levels in the dorsal root ganglion (DRG) as compared to endogenous levels. The increase may be 0.1× to 5×, 0.5× to 5×, 1× to 5×, 2× to 5×, 3× to 5×, 4× to 5×, 0.1× to 4×, 0.5× to 4×, 1× to 4×, 2× to 4×, 3× to 4×, 0.1× to 3×, 0.5× to 3×, 1× to 3×, 2× to 3×, 0.1× to 2×, 0.5× to 2×, 0.1× to 1×, 0.5× to 1×, 0.1× to 0.5×, 1× to 2×, 0.1×, 0.2×, 0.3×, 0.4×, 0.5×, 0.6×, 0.7×, 0.8×, 0.9×, 1.0×, 1.1×, 1.2×, 1.3×, 1.4×, 1.5×, 1.6×, 1.7×, 1.8×, 1.9×, 2.0×, 2.1×, 2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9×, 4.0×, 4.1×, 4.2×, 4.3×, 4.4×, 4.5×, 4.6×, 4.7×, 4.8×, 4.9× or more than 5× as compared to endogenous levels. The increase may be seen in the cervical, thoracic, and/or lumbar regions of the spine. As a non-limiting example, the increase of FXN in the DRG may be greater than 0.5× of endogenous levels. As a non-limiting example, the increase of FXN in the DRG may be between 0.5×-3× as compared to endogenous levels.

In some embodiments, the AAV particles may be delivered to a subject in order to increase the FXN protein levels in the dorsal root ganglion (DRG) by transducing the large DRG neurons in the cervical, thoracic, and/or lumbar regions. Transduction may also be referred to as the amount of DRGs that are positive. The transduction may be greater than or equal to 1%, 5%, 10%, 15%, 20%, 25%, 30%, 35%, 40%, 45%, 50%, 55%, 60%, 65%, 70%, 75%, 80%, 85%, 90%, 95%, or 99%. As a non-limiting example, the transduction of the large DRG neurons in the cervical, thoracic, and/or lumbar regions may be greater than or equal to 15%. As a non-limiting example, the transduction of the large DRG neurons in the cervical, thoracic, and/or lumbar regions may be greater than or equal to 20%. As a non-limiting example, the transduction of the large DRG neurons in the cervical, thoracic, and/or lumbar regions may be greater than or equal to 25%. As a non-limiting example, the transduction of the large DRG neurons in the cervical, thoracic, and/or lumbar regions may be greater than or equal to 30%. As a non-limiting example, the transduction of the large DRG neurons in the cervical, thoracic, and/or lumbar regions may be greater than or equal to 35%. As a non-limiting example, the transduction of the large DRG neurons in the cervical, thoracic, and/or lumbar regions may be greater than or equal to 40%. As a non-limiting example, the transduction of the large DRG neurons in the cervical, thoracic, and/or lumbar regions may be greater than or equal to 45%. As a non-limiting example, the transduction of the large DRG neurons in the cervical, thoracic, and/or lumbar regions may be greater than or equal to 50%. As a non-limiting example, the transduction of the large DRG neurons in the cervical, thoracic, and/or lumbar regions may be greater than or equal to 55%. As a non-limiting example, the transduction of the large DRG neurons in the cervical, thoracic, and/or lumbar regions may be greater than or equal to 60%. As a non-limiting example, the transduction of the large DRG neurons in the cervical, thoracic, and/or lumbar regions may be greater than or equal to 65%. As a non-limiting example, the transduction of the large DRG neurons in the cervical, thoracic, and/or lumbar regions may be greater than or equal to 70%.

In some embodiments, the AAV particles may be delivered to a subject in order to increase the FXN protein levels in the dorsal root ganglion (DRG) as compared to endogenous levels and transducing the large DRG neurons in the cervical, thoracic, and/or lumbar regions. The FXN protein levels in the DRG may be increased by 0.5× to 3× as compared to endogenous levels in the cervical, thoracic, and/or lumbar regions and the large DRG neurons in the cervical, thoracic, and/or lumbar regions may be transduced at least 20%.

In some embodiments, the AAV particles may be delivered to a subject in order to transduce the large neurons of the cerebellar dentate nucleus. Transduction may also be referred to as the number of large neurons that are positive. The transduction may be greater than or equal to 1%, 5%, 10%, 15%, 20%, 25%, 30%, 35%, 40%, 45%, 50%, 55%, 60%, 65%, 70%, 75%, 80%, 85%, 90%, 95%, or 99%. As a non-limiting example, the transduction of the large neurons of the cerebellar dentate nucleus may be greater than or equal to 15%. As a non-limiting example, the transduction of the large neurons of the cerebellar dentate nucleus may be greater than or equal to 20%. As a non-limiting example, the transduction of the large neurons of the cerebellar dentate nucleus may be greater than or equal to 25%. As a non-limiting example, the transduction of the large neurons of the cerebellar dentate nucleus may be greater than or equal to 30%. As a non-limiting example, the transduction of the large neurons of the cerebellar dentate nucleus may be greater than or equal to 35%. As a non-limiting example, the transduction of the large neurons of the cerebellar dentate nucleus may be greater than or equal to 40%. As a non-limiting example, the transduction of the large neurons of the cerebellar dentate nucleus may be greater than or equal to 45%. As a non-limiting example, the transduction of the large neurons of the cerebellar dentate nucleus may be greater than or equal to 50%. As a non-limiting example, the transduction of the large neurons of the cerebellar dentate nucleus may be greater than or equal to 55%. As a non-limiting example, the transduction of the large neurons of the cerebellar dentate nucleus may be greater than or equal to 60%. As a non-limiting example, the transduction of the large neurons of the cerebellar dentate nucleus may be greater than or equal to 65%. As a non-limiting example, the transduction of the large neurons of the cerebellar dentate nucleus may be greater than or equal to 70%.

In some embodiments, the AAV particles may be delivered to a subject in order to transduce the neurons of Clarke's Column. Transduction may also be referred to as the number of neurons that are positive. The transduction may be greater than or equal to 1%, 5%, 10%, 15%, 20%, 25%, 30%, 35%, 40%, 45%, 50%, 55%, 60%, 65%, 70%, 75%, 80%, 85%, 90%, 95%, or 99%. As a non-limiting example, the transduction of the neurons of Clarke's Column may be greater than or equal to 15%. As a non-limiting example, the transduction of the neurons of Clarke's Column may be greater than or equal to 20%. As a non-limiting example, the transduction of the neurons of Clarke's Column may be greater than or equal to 25%. As a non-limiting example, the transduction of the neurons of Clarke's Column may be greater than or equal to 30%. As a non-limiting example, the transduction of the neurons of Clarke's Column may be greater than or equal to 35%. As a non-limiting example, the transduction of the neurons of Clarke's Column may be greater than or equal to 40%. As a non-limiting example, the transduction of the neurons of Clarke's Column may be greater than or equal to 45%. As a non-limiting example, the transduction of the neurons of Clarke's Column may be greater than or equal to 50%. As a non-limiting example, the transduction of the neurons of Clarke's Column may be greater than or equal to 55%. As a non-limiting example, the transduction of the neurons of Clarke's Column may be greater than or equal to 60%. As a non-limiting example, the transduction of the neurons of Clarke's Column may be greater than or equal to 65%. As a non-limiting example, the transduction of the neurons of Clarke's Column may be greater than or equal to 70%.

In some embodiments, the AAV particles may be delivered to a subject in order to transduce the neurons of the gracile nuclei. Transduction may also be referred to as the number of neurons that are positive. The transduction may be greater than or equal to 1%, 5%, 10%, 15%, 20%, 25%, 30%, 35%, 40%, 45%, 50%, 55%, 60%, 65%, 70%, 75%, 80%, 85%, 90%, 95%, or 99%. As a non-limiting example, the transduction of the neurons of the gracile nuclei may be greater than or equal to 15%. As a non-limiting example, the transduction of the neurons of the gracile nuclei may be greater than or equal to 20%. As a non-limiting example, the transduction of the neurons of the gracile nuclei may be greater than or equal to 25%. As a non-limiting example, the transduction of the neurons of the gracile nuclei may be greater than or equal to 30%. As a non-limiting example, the transduction of the neurons of the gracile nuclei may be greater than or equal to 35%. As a non-limiting example, the transduction of the neurons of the gracile nuclei may be greater than or equal to 40%. As a non-limiting example, the transduction of the neurons of the gracile nuclei may be greater than or equal to 45%. As a non-limiting example, the transduction of the neurons of the gracile nuclei may be greater than or equal to 50%. As a non-limiting example, the transduction of the neurons of the gracile nuclei may be greater than or equal to 55%. As a non-limiting example, the transduction of the neurons of the gracile nuclei may be greater than or equal to 60%. As a non-limiting example, the transduction of the neurons of the gracile nuclei may be greater than or equal to 65%. As a non-limiting example, the transduction of the neurons of the gracile nuclei may be greater than or equal to 70%.

In some embodiments, the AAV particles may be delivered to a subject in order to transduce the neurons of the cuneate nuclei. Transduction may also be referred to as the number of neurons that are positive. The transduction may be greater than or equal to 1%, 5%, 10%, 15%, 20%, 25%, 30%, 35%, 40%, 45%, 50%, 55%, 60%, 65%, 70%, 75%, 80%, 85%, 90%, 95%, or 99%. As a non-limiting example, the transduction of the neurons of the cuneate nuclei may be greater than or equal to 15%. As a non-limiting example, the transduction of the neurons of the cuneate nuclei may be greater than or equal to 20%. As a non-limiting example, the transduction of the neurons of the cuneate nuclei may be greater than or equal to 25%. As a non-limiting example, the transduction of the neurons of the cuneate nuclei may be greater than or equal to 30%. As a non-limiting example, the transduction of the neurons of the cuneate nuclei may be greater than or equal to 35%. As a non-limiting example, the transduction of the neurons of the cuneate nuclei may be greater than or equal to 40%. As a non-limiting example, the transduction of the neurons of the cuneate nuclei may be greater than or equal to 45%. As a non-limiting example, the transduction of the neurons of the cuneate nuclei may be greater than or equal to 50%. As a non-limiting example, the transduction of the neurons of the cuneate nuclei may be greater than or equal to 55%. As a non-limiting example, the transduction of the neurons of the cuneate nuclei may be greater than or equal to 60%. As a non-limiting example, the transduction of the neurons of the cuneate nuclei may be greater than or equal to 65%. As a non-limiting example, the transduction of the neurons of the cuneate nuclei may be greater than or equal to 70%.

In some embodiments, the AAV particles may be delivered to a subject in order to increase the FXN protein levels in the heart as compared to endogenous levels. The increase may be 0.1× to 5×, 0.5× to 5×, 1× to 5×, 2× to 5×, 3× to 5×, 4× to 5×, 0.1× to 4×, 0.5× to 4×, 1× to 4×, 2× to 4×, 3× to 4×, 0.1× to 3×, 0.5× to 3×, 1× to 3×, 2× to 3×, 0.1× to 2×, 0.5× to 2×, 0.1× to 1×, 0.5× to 1×, 0.1× to 0.5×, 1× to 2×, 0.1×, 0.2×, 0.3×, 0.4×, 0.5×, 0.6×, 0.7×, 0.8×, 0.9×, 1.0×, 1.1×, 1.2×, 1.3×, 1.4×, 1.5×, 1.6×, 1.7×, 1.8×, 1.9×, 2.0×, 2.1×, 2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9×, 4.0×, 4.1×, 4.2×, 4.3×, 4.4×, 4.5×, 4.6×, 4.7×, 4.8×, 4.9×, or more than 5× as compared to endogenous levels. As a non-limiting example, the increase of FXN in the heart may be greater than 0.5× of endogenous levels. As a non-limiting example, the increase of FXN in the heart may be between 0.5×-3× as compared to endogenous levels.

In some embodiments, the AAV particles may be delivered to a subject in order to increase the FXN protein levels by transducing cardiomyocytes. Transduction may also be referred to as the number of cardiomyocytes that are positive. The transduction may be greater than or equal to 1%, 5%, 10%, 15%, 20%, 25%, 30%, 35%, 40%, 45%, 50%, 55%, 60%, 65%, 70%, 75%, 80%, 85%, 90%, 95%, or 99%. As a non-limiting example, the transduction of cardiomyocytes may be greater than or equal to 15%. As a non-limiting example, the transduction of cardiomyocytes may be greater than or equal to 20%. As a non-limiting example, the transduction of cardiomyocytes may be greater than or equal to 25%. As a non-limiting example, the transduction of cardiomyocytes may be greater than or equal to 30%. As a non-limiting example, the transduction of cardiomyocytes may be greater than or equal to 35%. As a non-limiting example, the transduction of cardiomyocytes may be greater than or equal to 40%. As a non-limiting example, the transduction of cardiomyocytes may be greater than or equal to 45%. As a non-limiting example, the transduction of cardiomyocytes may be greater than or equal to 50%. As a non-limiting example, the transduction of cardiomyocytes may be greater than or equal to 55%. As a non-limiting example, the transduction of cardiomyocytes may be greater than or equal to 60%. As a non-limiting example, the transduction of cardiomyocytes may be greater than or equal to 65%. As a non-limiting example, the transduction of cardiomyocytes may be greater than or equal to 70%.

In some embodiments, the AAV particles may be delivered to a subject in order to increase the FXN protein levels in the heart as compared to endogenous levels and to transduce cardiomyocytes. The FXN protein levels in the heart may be increased by 0.5× to 3× as compared to endogenous levels and/or cardiomyocytes may be transduced at least 30%.

In some embodiments, delivery of AAV particles comprising a viral genome encoding FXN described herein to sensory neurons in the dorsal root ganglion (DRG), ascending spinal cord sensory tracts, and cerebellum will lead to an increased expression of FXN. The increased expression may lead to improved survival and function of various cell types.

Specifically, in some embodiments, the increased expression of frataxin may lead to improved ataxia (balance) and gait, sensory capability, coordination of movement and strength, functional capacity, and/or quality of life.

Dosing

In some aspects, the present disclosure provides methods comprising administering viral vectors and their payloads in accordance with the disclosure to a subject in need thereof. Viral vector pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition associated with decreased FXN expression or a deficiency in the quantity and/or function of FXN). In some embodiments, the disease, disorder, and/or condition is FA. The exact amount required will vary from subject to subject, depending on the species, age, and general condition of the subject, the severity of the disease, the particular composition, its mode of administration, its mode of activity, and the like. Compositions in accordance with the disclosure are typically formulated in unit dosage form for ease of administration and uniformity of dosage. It will be understood, however, that the total daily usage of the compositions of the present disclosure may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex, and diet of the patient; the time of administration, route of administration, and rate of excretion of the specific FXN employed; the duration of the treatment; drugs used in combination or coincidental with the specific compound employed; and like factors well known in the medical arts.

In certain embodiments, AAV particle pharmaceutical compositions in accordance with the present disclosure may be administered at dosage levels sufficient to deliver FXN from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. It will be understood that the above dosing concentrations may be converted to VG or viral genomes per kg or into total viral genomes administered by one of skill in the art.

In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total daily dose into two or more doses, e.g., two or more administrations of the single unit dose. As used herein, a "single unit dose" is a dose of any therapeutic composition administered in one dose/at one time/single route/single point of contact, i.e., single administration event. In some embodiments, a single unit dose is provided as a discrete dosage form (e.g., a tablet, capsule, patch, loaded syringe, vial, etc.). As used herein, a "total daily dose" is an amount given or prescribed in 24-hour period. It may be administered as a single unit dose. The viral particles may be formulated in buffer only or in a formulation described herein.

A pharmaceutical composition described herein can be formulated into a dosage form described herein, such as a topical, intranasal, pulmonary, intratracheal, or injectable (e.g., intravenous, intraocular, intravitreal, intramuscular, intracardiac, intraperitoneal, and/or subcutaneous).

In some embodiments, delivery of the AAV particles described herein results in minimal serious adverse events (SAEs) as a result of the delivery of the AAV particles.

In some embodiments, delivery of AAV particle pharmaceutical compositions in accordance with the present disclosure to cells of the central nervous system (e.g., parenchyma) may comprise a total concentration between about $1 \times 10^6$ VG/mL and about $1 \times 10^{16}$ VG/mL. In some embodiments, delivery may comprise a composition concentration of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $1.6 \times 10^{11}$, $1.8 \times 10^{11}$, $2 \times 10^{11}$, $3 \times 10^{11}$, $4 \times 10^{11}$, $5 \times 10^{11}$, $5.5 \times 10^{11}$, $6 \times 10^{11}$, $7 \times 10^{11}$, $8 \times 10^{11}$, $9 \times 10^{11}$, $0.8 \times 10^{12}$, $0.83 \times 10^{12}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $2.1 \times 10^{12}$, $2.2 \times 10^{12}$, $2.3 \times 10^{12}$, $2.4 \times 10^{12}$, $2.5 \times 10^{12}$, $2.6 \times 10^{12}$, $2.7 \times 10^{12}$, $2.8 \times 10^{12}$, $2.9 \times 10^{12}$, $3 \times 10^{12}$, $3.1 \times 10^{12}$, $3.2 \times 10^{12}$, $3.3 \times 10^{12}$, $3.4 \times 10^{12}$, $3.5 \times 10^{12}$, $3.6 \times 10^{12}$, $3.7 \times 10^{12}$, $3.8 \times 10^{12}$, $3.9 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $2.3 \times 10^{13}$, $3 \times 10^{13}$, $4 \times 10^{13}$, $5 \times 10^{13}$, $6 \times 10^{13}$, $7 \times 10^{13}$, $8 \times 10^{13}$, $9 \times 10^{13}$, $1 \times 10^{14}$, $1.9 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/mL. In some embodiments, the concentration of the viral vector in the composition is $1 \times 10^{13}$ VG/mL. In some embodiments, the concentration of the viral vector in the composition is $1.1 \times 10^{12}$ VG/mL. In some embodiments, the concentration of the viral vector in the composition is $3.7 \times 10^{12}$ VG/mL. In some embodiments, the concentration of the viral vector in the composition is $8 \times 10^{11}$ VG/mL. In some embodiments, the concentration of the viral vector in the composition is $2.6 \times 10^{12}$ VG/mL. In some embodiments, the concentration of the viral vector in the composition is $4.9 \times 10^{12}$ VG/mL. In some embodiments, the concentration of the viral vector in the composition is $0.8 \times 10^{12}$ VG/mL. In some embodiments, the concentration of the viral vector in the composition is $0.83 \times 10^{12}$ VG/mL. In one embodiment, the concentration of the viral vector in the composition is the maximum final dose which can be contained in a vial. In some embodiments, the concentration of the viral vector in the composition is $1.6 \times 10^{11}$ VG/mL. In some embodiments, the concentration of the viral vector in the composition is $5 \times 10^{11}$ VG/mL. In some embodiments, the concentration of the viral vector in the composition is $2.3 \times 10^{13}$ VG/mL. In some embodiments, the concentration of the viral vector in the composition is $1.9 \times 10^{14}$ VG/mL.

In some embodiments, delivery of AAV particle pharmaceutical compositions in accordance with the present disclosure to cells of the central nervous system (e.g., parenchyma) may comprise a total concentration per subject between about $1 \times 10^6$ VG and about $1 \times 10^{16}$ VG. In some embodiments, delivery may comprise a composition concentration of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $1.6 \times 10^{11}$, $2 \times 10^{11}$, $2.1 \times 10^{11}$, $2.2 \times 10^{11}$, $2.3 \times 10^{11}$, $2.4 \times 10^{11}$, $2.5 \times 10^{11}$, $2.6 \times 10^{11}$, $2.7 \times 10^{11}$, $2.8 \times 10^{11}$, $2.9 \times 10^{11}$, $3 \times 10^{11}$, $4 \times 10^{11}$, $4.6 \times 10^{11}$, $5 \times 10^{11}$, $6 \times 10^{11}$, $7 \times 10^{11}$, $7.1 \times 10^{11}$, $7.2 \times 10^{11}$, $7.3 \times 10^{11}$, $7.4 \times 10^{11}$, $7.5 \times 10^{11}$, $7.6 \times 10^{11}$, $7.7 \times 10^{11}$, $7.8 \times 10^{11}$, $7.9 \times 10^{11}$, $8 \times 10^{11}$, $9 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $2.3 \times 10^{12}$, $3 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $7 \times 10^{12}$, $8 \times 10^{12}$, $8.1 \times 10^{12}$, $8.2 \times 10^{12}$, $8.3 \times 10^{12}$, $8.4 \times 10^{12}$, $8.5 \times 10^{12}$, $8.6 \times 10^{12}$, $8.7 \times 10^{12}$, $8.8 \times 10^{12}$, $8.9 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$ $2 \times 10^{15}$ $3 \times 10^{15}$ $4 \times 10^{15}$ $5 \times 10^{15}$ $6 \times 10^{15}$ $7 \times 10^{15}$ $8 \times 10^{15}$, $9 \times 10^{15}$, or $1 \times 10^{16}$ VG/subject. In some embodiments, the concentration of the viral vector in the composition is $2.3 \times 10^{11}$ VG/subject. In some embodiments, the concentration of the viral vector in the composition is $7.2 \times 10^{11}$ VG/subject. In some embodiments, the concentration of the viral vector in the composition is $7.5 \times 10^{11}$ VG/subject. In some embodiments, the concentration of the viral vector in the composition is $1.4 \times 10^{12}$ VG/subject. In some embodiments, the concentration of the viral vector in the composition is $4.8 \times 10^{12}$ VG/subject. In some embodiments, the concentration of the viral vector in the composition is $8.8 \times 10^{12}$ VG/subject. In some embodiments, the concentration of the viral vector in the composition is $2.3 \times 10^{12}$ VG/subject. In some embodiments, the concentration of the viral vector in the composition is $2 \times 10^{19}$ VG/subject. In some embodiments, the concentration of the viral vector in the composition is $1.6 \times 10^{11}$ VG/subject. In some embodiments, the concentration of the viral vector in the composition is $4.6 \times 10^{11}$ VG/subject.

In some embodiments, delivery of AAV particles to cells of the central nervous system (e.g., parenchyma) may comprise a total dose between about $1 \times 10^6$ VG and about $1 \times 10^{16}$ VG. In some embodiments, delivery may comprise a total dose of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $1.9 \times 10^{10}$, $2 \times 10^{10}$, $3 \times 10^{10}$, $3.73 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $2.5 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG. In some embodiments, the total dose is $1 \times 10^{13}$ VG. In some embodiments, the total dose is $3 \times 10^{13}$ VG. In some embodiments, the total dose is $3.73 \times 10^{10}$ VG. In some embodiments, the total dose is $1.9 \times 10^{10}$ VG. In some embodiments, the total dose is $2.5 \times 10^{11}$ VG. In some embodiments, the total dose is $5 \times 10^{11}$ VG. In some embodiments, the total dose is $1 \times 10^{12}$ VG. In some embodiments, the total dose is $5 \times 10^{12}$ VG.

Combinations

The AAV particles may be used in combination with one or more other therapeutic, prophylactic, diagnostic, or imaging agents. The phrase "in combination with," is not intended to require that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, and/or modify their distribution within the body.

Measurement of Expression

Expression of FXN from viral genomes may be determined using various methods known in the art such as, but not limited to immunochemistry (e.g., IHC), enzyme-linked immunosorbent assay (ELISA), affinity ELISA, ELISPOT, flow cytometry, immunocytology, surface plasmon resonance analysis, kinetic exclusion assay, liquid chromatography-mass spectrometry (LCMS), high-performance liquid chromatography (HPLC), BCA assay, immunoelectrophoresis, Western blot, SDS-PAGE, protein immunoprecipitation, PCR, and/or in situ hybridization (ISH). In some embodiments, transgenes encoding FXN delivered in different AAV capsids may have different expression levels in dorsal root ganglion (DRG).

In certain embodiments, the FXN polypeptide is detectable by Western blot.

VII. Kits and Devices

Kits

In some aspects, the present disclosure provides a variety of kits for conveniently and/or effectively carrying out methods of the present disclosure. Typically, kits will comprise sufficient amounts and/or numbers of components to allow a user to perform multiple treatments of a subject(s) and/or to perform multiple experiments.

Any of the vectors, constructs, or FXN of the present disclosure may be comprised in a kit. In some embodiments, kits may further include reagents and/or instructions for creating and/or synthesizing compounds and/or compositions of the present disclosure. In some embodiments, kits may also include one or more buffers. In some embodiments, kits of the disclosure may include components for making protein or nucleic acid arrays or libraries and thus, may include, for example, solid supports.

In some embodiments, kit components may be packaged either in aqueous media or in lyophilized form. The container means of the kits will generally include at least one vial, test tube, flask, bottle, syringe or other container means, into which a component may be placed, and suitably aliquoted. Where there is more than one kit component, (labeling reagent and label may be packaged together), kits may also generally contain second, third or other additional containers into which additional components may be separately placed. In some embodiments, kits may also comprise second container means for containing sterile, pharmaceutically acceptable buffers and/or other diluents. In some embodiments, various combinations of components may be comprised in one or more vial. Kits of the present disclosure may also typically include means for containing compounds and/or compositions of the present disclosure, e.g., proteins, nucleic acids, and any other reagent containers in close confinement for commercial sale. Such containers may include injection or blow-molded plastic containers into which desired vials are retained.

In some embodiments, kit components are provided in one and/or more liquid solutions. In some embodiments, liquid solutions are aqueous solutions, with sterile aqueous solutions being particularly used. In some embodiments, kit components may be provided as dried powder(s). When reagents and/or components are provided as dry powders, such powders may be reconstituted by the addition of suitable volumes of solvent. In some embodiments, it is envisioned that solvents may also be provided in another container means. In some embodiments, labeling dyes are provided as dried powders. In some embodiments, it is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least or at most those amounts of dried dye are provided in kits of the disclosure. In such embodiments, dye may then be resuspended in any suitable solvent, such as DMSO.

In some embodiments, kits may include instructions for employing kit components as well the use of any other reagent not included in the kit. Instructions may include variations that may be implemented.

Devices

In some embodiments, compounds and/or compositions of the present disclosure may be combined with, coated onto or embedded in a device. Devices may include, but are not limited to, dental implants, stents, bone replacements, artificial joints, valves, pacemakers and/or other implantable therapeutic device.

The present disclosure provides for devices which may incorporate viral vectors that encode one or more FXN molecules. These devices contain in a stable formulation the viral vectors which may be immediately delivered to a subject in need thereof, such as a human patient.

Devices for administration may be employed to deliver the viral vectors encoding FXN of the present disclosure according to single, multi- or split-dosing regimens taught herein.

Method and devices known in the art for multi-administration to cells, organs and tissues are contemplated for use in conjunction with the methods and compositions disclosed herein as embodiments of the present disclosure.

VIII. Definitions

At various places in the present specification, substituents of compounds of the present disclosure are disclosed in groups or in ranges. It is specifically intended that the present disclosure include each and every individual subcombination of the members of such groups and ranges. The following is a non-limiting list of term definitions.

Adeno-associated virus: The term "adeno-associated virus" or "AAV" as used herein refers to members of the dependovirus genus comprising any particle, sequence, gene, protein, or component derived therefrom. The term "AAV particle" as used herein comprises a capsid and a polynucleotide referred to as the AAV genome or viral (or vector) genome (VG). The AAV particle may be derived from any serotype, described herein or known in the art, including combinations of serotypes (i.e., "pseudotyped" AAV) or from various genomes (e.g., single stranded or self-complementary). In addition, the AAV particle may be replication defective and/or targeted.

Active Ingredient: As used herein, the term "active ingredient" refers to a molecule or complex thereof that is biologically active and responsible for a generating a biological effect. The active ingredient in a pharmaceutical composition may be referred to as an active pharmaceutical ingredient. For the purposes of the present disclosure, the phrase "active ingredient" generally refers either to the viral particle carrying the payload or to the payload (or its gene product) delivered by the viral particle as described herein. In contrast, an "inactive ingredient" refers to a substance which is biologically inert. An excipient is an example of an inactive ingredient.

Activity: As used herein, the term "activity" refers to the condition in which things are happening or being done. Compositions of the disclosure may have activity and this activity may involve one or more biological events.

Administered in combination: As used herein, the term "administered in combination" or "delivered in combination" or "combined administration" refers to exposure of two or more agents (e.g., AAV) administered at the same time or within an interval such that the subject is at some point in time exposed to both agents and/or such that there is an overlap in the effect of each agent on the patient. In some embodiments, at least one dose of one or more agents is administered within about 24 hours, 12 hours, 6 hours, 3 hours, 1 hour, 30 minutes, 15 minutes, 10 minutes, 5 minutes, or 1 minute of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatuses in administration. In some embodiments, the administration of individual doses of one or more compounds and/or compositions of the present disclosure, as described herein, are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of a neurodegenerative disorder, amelioration includes the reduction or stabilization of neuron loss.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.25%, 0.1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any substance (e.g., an AAV) that has activity in or on a biological system and/or organism. For instance, a substance that, when administered to an organism, has a biological effect on that organism, is considered to be biologically active. In particular embodiments, a compound, and/or a composition of the present disclosure may be considered biologically active if even a portion of it is biologically active or mimics an activity considered to be biologically relevant. In some embodiments, biological activity refers to inducing expression of frataxin or a variant thereof. In some embodiments, biological activity refers to preventing and/or treating a disease associated with decreased frataxin expression or a deficiency in the quantity and/or function of frataxin. In some embodiments, biological activity refers to preventing and/or treating Friedreich's ataxia.

Biological system: As used herein, the term "biological system" refers to a group of organs, tissues, cells, intracellular components, proteins, nucleic acids, molecules (including, but not limited to biomolecules) that function together to perform a certain biological task within cellular membranes, cellular compartments, cells, tissues, organs, organ systems, multicellular organisms, or any biological entity. In some embodiments, biological systems are cell signaling pathways comprising intracellular and/or extracellular cell signaling biomolecules. In some embodiments, biological systems comprise growth factor signaling events within the extracellular/cellular matrix and/or cellular niches.

Capsid: As used herein the term "capsid" refers to the protein shell of a virus. It consists of several capsid proteins (e.g., VP1, VP2, and/or VP3 for AAV). The capsid encloses the genetic material of the virus. A capsid may be a wild-type capsid or a recombinant or engineered capsid.

Central Nervous System or CNS: As used herein, "central nervous system" or "CNS" refers to one of the two major subdivisions of the nervous system, which in vertebrates includes the brain and spinal cord. The central nervous system coordinates the activity of the entire nervous system.

Cervical Region: As used herein, "cervical region" refers to the region of the spinal cord comprising the cervical vertebrae C1, C2, C3, C4, C5, C6, C7, and C8.

Cis-Elements: As used herein, cis-elements or the synonymous term "cis-regulatory elements" refer to regions of non-coding DNA which regulate the transcription of nearby genes. The Latin prefix "cis" translates to "on this side." Cis-elements are found in the vicinity of the gene, or genes, they regulate. Examples of cis-elements include a Kozak sequence, SV40 introns, or a portion of the backbone.

CNS tissue: As used herein, "CNS tissue" or "CNS tissues" refers to the tissues of the central nervous system, which in vertebrates, include the brain and spinal cord and sub-structures thereof.

CNS structures: As used herein, "CNS structures" refers to structures of the central nervous system and sub-structures thereof. Non-limiting examples of structures in the spinal cord may include, ventral horn, dorsal horn, white matter, and nervous system pathways or nuclei within. Non-limiting examples of structures in the brain include, forebrain, midbrain, hindbrain, diencephalon, telencephalon, myelencephalon, metencephalon, mesencephalon, prosencephalon, rhombencephalon, cortices, frontal lobe, parietal lobe, temporal lobe, occipital lobe, cerebrum, thalamus, hypothalamus, tectum, tegmentum, cerebellum, pons, medulla, amygdala, hippocampus, basal ganglia, corpus callosum, pituitary gland, putamen, striatum, ventricles and sub-structures thereof.

CNS Cells: As used herein, "CNS cells" refers to cells of the central nervous system and sub-structures thereof. Non-limiting examples of CNS cells include, neurons and sub-types thereof, glia, microglia, oligodendrocytes, ependymal cells and astrocytes. Non-limiting examples of neurons include sensory neurons, motor neurons, interneurons, unipolar cells, bipolar cells, multipolar cells, pseudounipolar cells, pyramidal cells, basket cells, stellate cells, Purkinje cells, Betz cells, amacrine cells, granule cell, ovoid cell, medium aspiny neurons and large aspiny neurons.

Codon optimization: As used herein, the term "codon optimization" refers to a process of changing codons of a given gene in such a manner that the polypeptide sequence encoded by the gene remains the same while the changed codons improve the process of expression of the polypeptide sequence. For example, if the polypeptide is of a human protein sequence and expressed in E. coli, expression will often be improved if codon optimization is performed on the DNA sequence to change the human codons to codons that are more effective for expression in E. coli.

Composition: As used herein, the term "composition" comprises an AAV polynucleotide, AAV genome or AAV particle and at least one excipient.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present disclosure. For example, compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Conserved: As used herein, the term "conserved" refers to nucleotides or amino acid residues of polynucleotide or polypeptide sequences, respectively, that are those that occur unaltered in the same position of two or more sequences being compared. Nucleotides or amino acids that are relatively conserved are those that are conserved among more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

In one embodiment, conserved sequences are not contiguous. Those skilled in the art are able to appreciate how to achieve alignment when gaps in contiguous alignment are present between sequences, and to align corresponding residues not withstanding insertions or deletions present.

Delivery: As used herein, "delivery" refers to the act or manner of delivering a parvovirus e.g., AAV compound, substance, entity, moiety, cargo or payload to a target. Such target may be a cell, tissue, organ, organism, or system (whether biological or production).

Delivery Agent: As used herein, "delivery agent" refers to any agent which facilitates, at least in part, the delivery of one or more substances (including, but not limited to a compounds and/or compositions of the present disclosure, e.g., viral particles or AAV vectors) to targeted cells.

Delivery route: As used herein, the term "delivery route" and the synonymous term "administration route" refers to any of the different methods for providing a therapeutic agent to a subject. Routes of administration are generally classified by the location at which the substance is applied and may also be classified based on where the target of action is. Examples include, but are not limited to: intravenous administration, subcutaneous administration, oral administration, parenteral administration, enteral administration, topical administration, sublingual administration, inhalation administration, and injection administration, or other routes of administration described herein.

Derivative: As used herein, the term "derivative" refers to a composition (e.g., sequence, compound, formulation, etc.) that is derived from, or finds its basis in, a parent composition. Non-limiting examples of a parent composition include a wild-type or original amino acid or nucleic acid sequence, or an undiluted formulation. In some embodiments, a derivative is a variant of a parent composition. A derivative may differ from the parent composition by less than about 1%, less than about 5%, less than about 10%, less than about 15%, less than about 20%, less than about 25%, less than about 30%, less than about 35%, less than about 40%, less than about 45%, or less than about 50%. In certain embodiments, a derivative may differ from a parent composition by more than about 50%. In certain embodiments, a derivative may differ from a parent composition by more than about 75%. In some embodiments, a derivative may be a fragment or truncation of a parent amino acid or nucleotide sequence. As a non-limiting example, a derivative may be a sequence with a nucleotide or peptide insert as compared to a parent nucleic acid or amino acid sequence (e.g., AAVPHP.B as compared to AAV9).

Effective amount: As used herein, the term "effective amount" of an agent is that amount sufficient to effect beneficial or desired results, for example, upon single or multiple dose administration to a subject or a cell, in curing, alleviating, relieving or improving one or more symptoms of a disorder and, as such, an "effective amount" depends upon the context in which it is being applied. For example, in the context of administering an agent that treats FA, an effective amount of an agent is, for example, an amount sufficient to achieve treatment, as defined herein, of FA as compared to the response obtained without administration of the agent.

Engineered: As used herein, embodiments of the disclosure are "engineered" when they are designed to have a feature or property, whether structural or chemical, that varies from a starting point, wild-type or native molecule. Thus, engineered agents or entities are those whose design and/or production include an act of the hand of man.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and/or (5) post-translational modification of a polypeptide or protein.

Excipient: As used herein, the term "excipient" refers to an inactive substance that serves as the vehicle or medium for an active pharmaceutical agent or other active substance.

Formulation: As used herein, a "formulation" includes at least a compound and/or composition of the present disclosure (e.g., a vector, AAV particle, etc.) and a delivery agent.

Fragment: A "fragment," as used herein, refers to a contiguous portion of a whole. For example, fragments of proteins may comprise polypeptides obtained by digesting full-length protein isolated from cultured cells. In some embodiments, a fragment of a protein includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250 or more amino acids. A fragment may also refer to a truncation (e.g., an N-terminal and/or C-terminal truncation) of a protein or a truncation (e.g., at the 5' and/or 3' end) of a nucleic acid. A protein fragment may be obtained by expression of a truncated nucleic acid, such that the nucleic acid encodes a portion of the full-length protein.

Gene expression: The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides, and peptides are well known in the art.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% identical for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is typically determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids. In many embodiments, homologous protein may show a large overall degree of homology and a high degree of homology over at least one short stretch of at least 3, 4, 5, 6, 7, 8, 9, 10, 11, 12, 13, 14, 15, 16, 17, 18, 19, 20, 25, 30, 35, 40, 45, 50, or more amino acids. In many embodiments, homologous proteins share one or more characteristic sequence elements. As used herein, the term "characteristic sequence element" refers to a motif present in related proteins. In some embodiments, the presence of such motifs correlates with a particular activity (such as biological activity).

Humanized: As used herein, the term "humanized" refers to a non-human sequence of a polynucleotide or a polypeptide which has been altered to increase its similarity to its corresponding human sequence.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, may be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference in its entirety. For example, the percent identity between two nucleotide sequences can be determined, for example using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference in its entirety. Techniques for determining identity are codified in publicly available computer programs. Computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molecular Biol.,* 215, 403 (1990)).

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated" but carries with it the inference that separation was carried out by the hand of man. The terms "isolated" and "substantially isolated" are herein used interchangeably. An isolated substance or entity is one that has been partially or entirely separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure.

Lumbar Region: As used herein, the term "lumbar region" refers to the region of the spinal cord comprising the lumbar vertebrae L1, L2, L3, L4, and L5.

Modified: As used herein, the term "modified" refers to a changed state or structure of a molecule or entity as compared with a parent or reference molecule or entity. Molecules may be modified in many ways including chemically, structurally, and functionally. In some embodiments, compounds and/or compositions of the present disclosure are modified by the introduction of non-natural amino acids, or non-natural nucleotides.

Mutation: As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids). In embodiments wherein mutations comprise the addition and/or substitution of amino acids and/or nucleotides, such additions and/or substitutions may comprise 1 or more amino acid and/or nucleotide residues and may include modified amino acids and/or nucleotides. One or more mutations may result in a "mutant," "derivative," or "variant," e.g., of a nucleic acid sequence or polypeptide or protein sequence.

Naturally occurring: As used herein, "naturally occurring" or "wild-type" means existing in nature without artificial aid, or involvement of the hand of man. "Naturally occurring" or "wild-type" may refer to a native form of a biomolecule, sequence, or entity.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid: As used herein, the terms "nucleic acid," "polynucleotide," and "oligonucleotide" refer to any nucleic acid polymers composed of either polydeoxyribonucleotides (containing 2-deoxy-D-ribose), or polyribonucleotides (containing D-ribose), or any other type of polynucleotide that is an N glycoside of a purine or pyrimidine base, or modified purine or pyrimidine bases. There is no intended distinction in length between the term "nucleic acid," "polynucleotide," and "oligonucleotide," and these terms will be used interchangeably. These terms refer only to the primary structure of the molecule. Thus, these terms include double- and single-stranded DNA, as well as double- and single-stranded RNA.

Operably linked: As used herein, the phrase "operably linked" refers to a functional connection between two or more molecules, constructs, transcripts, entities, moieties or the like.

Particle: As used herein, a "particle" is a virus comprised of at least two components, a protein capsid and a polynucleotide sequence enclosed within the capsid.

Patient: As used herein, "patient" refers to a subject who may seek or be in need of treatment, requires treatment, is receiving treatment, will receive treatment, or a subject who is under care by a trained (e.g., licensed) professional for a particular disease or condition.

Payload: As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide.

Payload construct: As used herein, "payload construct" is one or more polynucleotide regions encoding or comprising a payload that is flanked on one or both sides by an inverted terminal repeat (ITR) sequence. The payload construct is a template that is replicated in a viral production cell to produce a viral genome.

Payload construct vector: As used herein, "payload construct vector" is a vector encoding or comprising a payload construct, and regulatory regions for replication and expression in bacterial cells. The payload construct vector may also comprise a component for viral expression in a viral replication cell.

Peptide: As used herein, the term "peptide" refers to a chain of amino acids that is less than or equal to about 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: As used herein, the term "pharmaceutically acceptable excipient," as used herein, refers to any ingredient other than active agents (e.g., as described herein) present in pharmaceutical compositions and having the properties of being substantially nontoxic and non-inflammatory in subjects. In some embodiments, pharmaceutically acceptable excipients are vehicles capable of suspending and/or dissolving active agents. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and/or xylitol.

Pharmaceutically acceptable salts: Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments, a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, $17^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), the contents of each of which are incorporated herein by reference in their entirety.

Pharmaceutical Composition: As used herein, the term "pharmaceutical composition" or pharmaceutically acceptable composition" comprises AAV polynucleotides, AAV genomes, or AAV particle and one or more pharmaceutically acceptable excipients, solvents, adjuvants, and/or the like.

Polypeptide: As used herein, the term "polypeptide" refers to an organic polymer consisting of a large number of amino-acid residues bonded together in a chain. A monomeric protein molecule is a polypeptide.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Promoter: As used herein, the term "promoter" refers to a nucleic acid site to which a polymerase enzyme will bind to initiate transcription (DNA to RNA) or reverse transcription (RNA to DNA).

Protein of interest: As used herein, the terms "proteins of interest" or "desired proteins" include those provided herein and fragments, mutants, variants, or alterations thereof.

Purified: As used herein, the term "purify" means to make substantially pure or clear from one or more unwanted components, material defilement, admixture or imperfection. "Purified" refers to the state of being pure. "Purification" refers to the process of making pure. As used herein, a substance is "pure" if it is substantially free of (substantially isolated from) one or more components, e.g., one or more components found in a native context.

Region: As used herein, the term "region" refers to a zone or general area. In some embodiments, when referring to a protein or protein module, a region may comprise a linear sequence of amino acids along the protein or protein module or may comprise a three dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini. N-termini refer to the end of a protein comprising an amino acid with a free amino group. C-termini refer to the end of a protein comprising an amino acid with a free carboxyl group. N- and/or C-terminal regions may comprise the N- and/or C-termini as well as surrounding amino acids. In some embodiments, N- and/or C-terminal regions comprise from about 3 amino acids to about 30 amino acids, from about 5 amino acids to about 40 amino acids, from about 10 amino acids to about 50 amino acids, from about 20 amino acids to about 100 amino acids and/or at least 100 amino acids. In some embodiments, N-terminal regions may comprise any length of amino acids that includes the N-terminus, but does not include the C-terminus. In some embodiments, C-terminal regions may comprise any length of amino acids, which include the C-terminus, but do not comprise the N-terminus.

In some embodiments, when referring to a polynucleotide, a region may comprise a linear sequence of nucleic acids along the polynucleotide or may comprise a three dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and 3' termini. 5' termini refer to the end of a polynucleotide comprising a nucleic acid with a free phosphate group. 3' termini refer to the end of a polynucleotide comprising a nucleic acid with a free hydroxyl group. 5' and 3' regions may there for comprise the 5' and 3' termini as well as surrounding nucleic acids. In some embodiments, 5' and 3' terminal regions comprise from about 9 nucleic acids to about 90 nucleic acids, from about 15 nucleic acids to about 120 nucleic acids, from about 30 nucleic acids to about 150 nucleic acids, from about 60 nucleic acids to about 300 nucleic acids and/or at least 300 nucleic acids. In some embodiments, 5' regions may comprise any length of nucleic acids that includes the 5' terminus, but does not include the 3' terminus. In some embodiments, 3' regions may comprise any length of nucleic acids, which include the 3' terminus, but does not comprise the 5' terminus.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

Sample: As used herein, the term "sample" refers to an aliquot or portion taken from a source and/or provided for analysis or processing. In some embodiments, a sample is from a biological source such as a tissue, cell or component part (e.g. a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In some embodiments, a sample is or comprises a medium, such as a nutrient broth or gel, which may contain cellular components, such as proteins or nucleic acid molecules. In some embodiments, a "primary" sample is an aliquot of the source. In some embodiments, a primary sample is subjected to one or more processing (e.g., separation, purification, etc.) steps to prepare a sample for analysis or other use.

Serotype: As used herein, the term "serotype" refers to distinct variations in a capsid of an AAV based on surface antigens which allow epidemiologic classifications of the AAVs at the sub-species level.

Signal Sequences: As used herein, the phrase "signal sequences" refers to a sequence which can direct the transport or localization.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Stable: As used herein "stable" refers to a compound or entity that is sufficiently robust to survive isolation to a useful degree of purity from a reaction mixture, and capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the disclosure may be administered, e.g., for experimental, diagnostic, prophylactic, and/or therapeutic purposes. Similarly, "subject" or "patient" refers to an organism who may seek, who may require, who is receiving, or who will receive treatment or who is under care by a trained professional for a particular disease or condition. Typical subjects include animals (e.g., mammals such as mice, rats, rabbits, non-human primates, and humans). In certain embodiments, a subject or patient may be susceptible to or suspected of having Friedreich's ataxia. In certain embodiments, a subject or patient may be diagnosed with Friedreich's ataxia.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term typically means within about 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present disclosure may be chemical or enzymatic.

Targeting: As used herein, "targeting" means the process of design and selection of nucleic acid sequence that will hybridize to a target nucleic acid and induce a desired effect.

Targeted Cells: As used herein, "target cells" or "targeted cells" refers to any one or more cells of interest. The cells may be found in vitro, in vivo, in situ or in the tissue or organ of an organism. The organism may be an animal, a mammal, a human and/or a patient. The target cells may be CNS cells or cells in CNS tissue.

Therapeutic Agent: The term "therapeutic agent" refers to any agent that, when administered to a subject has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Thoracic Region: As used herein, a "thoracic region" refers to a region of the spinal cord comprising the thoracic vertebrae T1, T2, T3, T4, T5, T6, T7, T8, T9, T10, T11, and T12.

Treating: As used herein, the term "treating" refers to partially or completely alleviating, ameliorating, improving, relieving, reversing, delaying onset of, inhibiting progression of, reducing severity of, and/or reducing incidence of one or more symptoms or features of a particular infection, disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild-type or native form of a biomolecule or entity. Molecules or entities may undergo a series of modifications whereby each modified product may serve as the "unmodified" starting molecule or entity for a subsequent modification.

Vector: As used herein, a "vector" is any molecule or moiety which transports, transduces or otherwise acts as a carrier of a heterologous molecule. Vectors of the present disclosure may be produced recombinantly and may be based on and/or may comprise adeno-associated virus (AAV) parent or reference sequence(s). Such parent or reference AAV sequences may serve as an original, second, third or subsequent sequence for engineering vectors. In non-limiting examples, such parent or reference AAV sequences may comprise any one or more of the following sequences: a polynucleotide sequence encoding a polypeptide or multi-polypeptide, having a sequence that may be wild-type or modified from wild-type and which sequence may encode full-length or partial sequence of a protein, protein domain, or one or more subunits of a FXN and variants thereof; a polynucleotide encoding a FXN and variants thereof, having a sequence that may be wild-type or modified from wild-type; and a transgene encoding FXN and variants thereof that may or may not be modified from wild-type sequence.

Viral construct vector: As used herein, a "viral construct vector" is a vector which comprises one or more polynucleotide regions encoding or comprising Rep and or Cap protein. A viral construct vector may also comprise one or more polynucleotide region encoding or comprising components for viral expression in a viral replication cell.

Viral genome: As used herein, a "viral genome" or "vector genome" is a polynucleotide comprising at least one inverted terminal repeat (ITR) and at least one encoded payload. A viral genome encodes at least one copy of the payload.

Wild-type: As used herein, "wild-type" is a native form of a biomolecule, sequence, or entity.

Described herein are compositions, methods, processes, kits and devices for the design, preparation, manufacture and/or formulation of AAV particles.

The details of one or more embodiments of the disclosure are set forth in the accompanying description below. Although any materials and methods similar or equivalent to those described herein can be used in the practice or testing of the present disclosure, the materials and methods are now described.

The present disclosure is further illustrated by the following non-limiting examples.

IX. EXAMPLES

Example 1. Design of Promoter Variants

A. Promoters

Previous studies have shown that CMV promoters drive the highest level of frataxin expression, with CBA showing less efficacy in driving expression. PGK and FXN promoters have been shown to be even weaker promoters for driving protein expression. Variants of the CMV, CBA and FXN promoters were generated to determine which promoters would lead to the highest expression of a payload (e.g., frataxin or luciferase). The promoters were inserted into a vector expressing luciferase which was built using standard molecular cloning techniques.

The designed promoters are described in Table 3 above. In Table 3, CMV stands for "cytomegalovirus," CBA stands for "chicken β-actin" which may have a CMV IE enhancer region and a promoter region, CAG stands for CMV enhancer, CBA promoter, and rabbit beta-globin splice acceptor site, FXN stands for "Frataxin," and mCBA stands for a variant of the CBA promoter which was generated using PCR.

Each of the engineered promoter variants was analyzed by gel electrophoresis, digested (Sac1 and HindIII), verified and sequenced.

B. In Vitro Evaluation of Promoters

Seven frataxin promotor variants, 15 CBA promoter variants and 8 CMV promoter variants were evaluated for expression activity in vitro. HEK293 cells were plated in 96-well plates (3.0×10$^4$ cells/well with 0.3 ul per well of FuGENE® HD transfection reagent) and transfected (5 transfections) in either duplicate or triplicate with a plasmid comprising a promoter from Table 3 and a luciferase payload (either firefly (~75 ng) or renilla (25 ng)). 48 hours after transfection, the activity and expression of luciferase was determined using the DUAL-GLO® luciferase assay system. In short, an equal volume of Dual-Glo® Luciferase Reagent was added directly to cells in growth medium, incubated for 10 mins, then measured for firefly luciferase expression. The same volume of reagent was then added to quench the firefly luminescence and the renilla luciferase activity was measured 10 min later. A control of pGL3-basic promoterless vector was used as control.

The activity of the promoter variants as determined by firefly and renilla luciferase expression is shown in Tables 18-20, quantified in relative light units (RLU). Table 18 shows data for initial FXN, CBA and CMV promoter variants while Table 19 shows data for a second generation of PCR generated CBA promoter variants. Table 20 shows data for all promoter variants run together.

TABLE 18

Luciferase Activity: FXN, CBA, and CMV Promoters

| Promoter Name | SEQ ID NO of Promoter | Firefly Luciferase Activity | Renilla Luciferase Activity | Relative Luciferase Activity |
|---|---|---|---|---|
| Contol (pGL3-basic) | — | 5818.1 | 22280.2 | 0.3 |
| FXNproN1336 | 1759 | 39598.9 | 22747.0 | 2.6 |
| FXNpro1226 | 1757 | 34531.6 | 27263.4 | 2.6 |
| FXNpro1060 | 1756 | 41490.3 | 21445.3 | 2.5 |
| FXNpro907 | 1755 | 41025.0 | 20960.2 | 1.6 |
| FXNpro534 | 1754 | 29035.6 | 25628.5 | 2.2 |
| FXNpro363 | 1753 | 18861.3 | 25370.3 | 1.6 |
| FXNpro223 | 1752 | 36665.0 | 22399.8 | 1.4 |
| CBA | 1734 | $1.9 \times 10^6$ | 29991.5 | 90.0 |
| CBA-D1 | 1735 | $1.9 \times 10^6$ | 30389.3 | 76.7 |
| CBA-D2 | 1736 | $1.4 \times 10^6$ | 24396.2 | 68.3 |
| CBA-D3 | 1737 | $1.7 \times 10^6$ | 21590.0 | 41.7 |
| CBA-D4 | 1738 | $1.1 \times 10^6$ | 21131.4 | 24.8 |
| CBA-D5 | 1739 | 528925.0 | 33152.1 | 29.3 |
| CBA-D6 | 1740 | 701503.0 | 31690.0 | 28.0 |
| CBA-D7 | 1741 | 87118.2 | 29718.0 | 13.4 |
| CBA-D8 | 1742 | 142306.0 | 25404.8 | 14.9 |
| CMV | 1743 | $1.7 \times 10^6$ | 27365.4 | 158.8 |
| CMV-D1 | 1744 | $2.0 \times 10^6$ | 29305.7 | 83.1 |
| CMV-D2 | 1745 | $1.7 \times 10^6$ | 22804.9 | 80.6 |
| CMV-D3 | 1746 | $1.6 \times 10^6$ | 25367.4 | 71.5 |
| CMV-D4 | 1747 | 823269.0 | 31143.1 | 68.1 |
| CMV-D5 | 1748 | 656529.0 | 27455.9 | 26.5 |
| CMV-D6 | 1749 | 745160.0 | 24906.0 | 56.1 |
| CMV-D7 | 1750 | 455119.0 | 20416.5 | 14.0 |
| CMV-D8 | 1751 | 265574.0 | 26751.1 | 14.3 |

TABLE 19

Luciferase Activity: CBA Promoters

| Promoter Name | SEQ ID NO of Promoter | Firefly Luciferase Activity | Renilla Luciferase Activity | Relative Luciferase Activity |
|---|---|---|---|---|
| Contol (pGL3-basic) | — | 7805.3 | 21204.0 | 0.7 |
| mCBA | 1760 | $1.1 \times 10^6$ | 24315.1 | 70.2 |
| CBA | 1734 | $1.2 \times 10^6$ | 19496.6 | 80.4 |
| mCBA-D1 | 1761 | $1.2 \times 10^6$ | 21795.7 | 50.8 |
| CBA-D1 | 1735 | $1.2 \times 10^6$ | 23643.8 | 57.2 |
| mCBA-D2 | 1762 | 866445.0 | 24847.4 | 37.3 |
| CBA-D2 | 1736 | $1.1 \times 10^6$ | 26002.7 | 54.9 |
| mCBA-D3 | 1763 | 483938.0 | 22957.8 | 20.1 |
| CBA-D3 | 1737 | 394159.0 | 24134.9 | 20.1 |
| mCBA-D4 | 1764 | 378331.0 | 21767.5 | 20.0 |
| CBA-D4 | 1738 | 423313.0 | 25556.2 | 17.3 |
| mCBA-D5 | 1765 | 481034.0 | 21420.2 | 20.0 |
| CBA-D5 | 1739 | 512204.0 | 23063.8 | 22.6 |
| mCBA-D6 | 1766 | 600066.0 | 25365.9 | 21.1 |
| CBA-D6 | 1740 | 499860.0 | 28509.2 | 22.2 |
| CBA-D7 | 1741 | 397064.0 | 24788.7 | 17.0 |
| CBA-D8 | 1742 | 193978.0 | 19823.0 | 10.6 |
| CMV | 1743 | $1.2 \times 10^6$ | 21271.2 | 103.2 |
| CMV-D1 | 1744 | $1.5 \times 10^6$ | 18371.5 | 64.1 |
| CMV-D2 | 1745 | $1.3 \times 10^6$ | 20514.7 | 68.4 |
| CMV-D3 | 1746 | 753070.0 | 25375.3 | 52.8 |
| CMV-D4 | 1747 | 860089.0 | 21706.6 | 48.6 |
| CMV-D5 | 1748 | 607362.0 | 18944.0 | 44.7 |
| CMV-D6 | 1749 | 835859.0 | 22311.5 | 48.5 |

TABLE 19-continued

Luciferase Activity: CBA Promoters

| Promoter Name | SEQ ID NO of Promoter | Firefly Luciferase Activity | Renilla Luciferase Activity | Relative Luciferase Activity |
|---|---|---|---|---|
| CMV-D7 | 1750 | 257050.0 | 23927.6 | 14.2 |
| CMV-D8 | 1751 | 223323.0 | 18691.3 | 12.6 |

TABLE 20

Luciferase Activity: FXN, CBA, and CMV Promoters

| Promoter Name | SEQ ID NO of Promoter | Firefly Luciferase Activity | Renilla Luciferase Activity | Relative Luciferase Activity |
|---|---|---|---|---|
| Contol (pGL3-basic) | — | 7921.8 | 20459.1 | 0.4 |
| FXNproN1336 | 1759 | 63926.2 | 25025.5 | 2.6 |
| FXNpro1226 | 1757 | 36579.9 | 17960.0 | 2.0 |
| FXNpro1060 | 1756 | 46231.1 | 20049.1 | 2.3 |
| FXNpro907 | 1755 | 40450.8 | 20082.3 | 2.0 |
| FXNpro534 | 1754 | 40052.5 | 21713.7 | 1.9 |
| FXNpro363 | 1753 | 39193.8 | 22916.8 | 1.7 |
| FXNpro223 | 1752 | 32047.5 | 22625.3 | 1.4 |
| mCBA | 1760 | $1.8 \times 10^6$ | 23690.8 | 73.9 |
| CBA | 1734 | $1.8 \times 10^6$ | 19496.6 | 70.4 |
| mCBA-D1 | 1761 | 989155.0 | 19090.6 | 50.8 |
| CBA-D1 | 1735 | $1.2 \times 10^6$ | 23643.8 | 57.2 |
| mCBA-D2 | 1762 | 580926.0 | 24847.4 | 30.6 |
| CBA-D2 | 1736 | $1.1 \times 10^6$ | 26002.7 | 54.9 |
| mCBA-D3 | 1763 | 786194.0 | 22957.8 | 33.4 |
| CBA-D3 | 1737 | 410735.0 | 24134.9 | 20.1 |
| mCBA-D4 | 1764 | 495034.0 | 21767.5 | 20.0 |
| CBA-D4 | 1738 | 385259.0 | 25556.2 | 17.3 |
| mCBA-D5 | 1765 | 525189.0 | 21420.2 | 20.0 |
| CBA-D5 | 1739 | 472985.0 | 23062.8 | 22.6 |
| mCBA-D6 | 1766 | 481465.0 | 25365.9 | 21.1 |
| CBA-D6 | 1740 | 568296.0 | 25175.8 | 22.2 |
| CBA-D7 | 1741 | 407952.0 | 24788.7 | 17.0 |
| CBA-D8 | 1742 | 229847.0 | 19823.0 | 10.6 |
| CMV | 1743 | $3.2 \times 10^6$ | 19365.4 | 124.2 |
| CMV-D1 | 1744 | $1.4 \times 10^6$ | 23521.7 | 64.1 |
| CMV-D2 | 1745 | $1.6 \times 10^6$ | 25113.0 | 68.4 |
| CMV-D3 | 1746 | $1.0 \times 10^6$ | 22383.5 | 39.5 |
| CMV-D4 | 1747 | $1.2 \times 10^6$ | 19553.7 | 48.6 |
| CMV-D5 | 1748 | $1.1 \times 10^6$ | 20376.2 | 44.7 |
| CMV-D6 | 1749 | $1.0 \times 10^6$ | 22311.5 | 51.8 |
| CMV-D7 | 1750 | 274083.0 | 20989.1 | 14.2 |
| CMV-D8 | 1751 | 296686.0 | 25589.8 | 12.6 |

The activities of the promoters ranged from 0.4 to 125-fold increase as compared to the control. This is a 321-fold difference in activity between the promoter with the lowest expression and the promoter leading to the highest expression. The CMV (SEQ ID NO: 1743) promoter provided the greatest activity, with the CBA (SEQ ID NO: 1734), mCBA (SEQ ID NO: 1760), CMV-D2 (SEQ ID NO: 1745), CBA-D1 (SEQ ID NO: 1735), CBA-D2 (SEQ ID NO: 1736), CMV-D6 (SEQ ID NO: 1749), mCBA-D1 (SEQ ID NO: 1761), and CMV-D4 (SEQ ID NO: 1747) promoters each showing decreasing efficacy in inducing expression of luciferase. An overall activity ranking of the promoter variants was as follows, listed in order of promoter with the highest expression to the promoter with the least activity: CMV (SEQ ID NO: 1743), mCBA (SEQ ID NO: 1760), CBA (SEQ ID NO: 1734), CMV-D2 (SEQ ID NO: 1745), CMV-D1 (SEQ ID NO: 1744), CBA-D1 (SEQ ID NO: 1735), CBA-D2 (SEQ ID NO: 1736), CMV-D6 (SEQ ID NO: 1749), mCBA-D1 (SEQ ID NO: 1761), CMV-D4 (SEQ ID NO: 1747), CMV-D5 (SEQ ID NO: 1748), CMV-D3 (SEQ ID NO: 1746), mCBA-D3 (SEQ ID NO: 1763), mCBA-D2 (SEQ ID NO: 1762), CBA-D5 (SEQ ID NO: 1739), CBA-D6 (SEQ ID NO: 1740), mCBA-D6 (SEQ ID NO: 1766), CBA-D3 (SEQ ID NO: 1737), mCBA-D5 (SEQ ID NO: 1765), mCBA-D4 (SEQ ID NO: 1764), CBA-D4 (SEQ ID NO: 1738), CBA-D7 (SEQ ID NO: 1741), CMV-D7 (SEQ ID NO: 1750), CMV-D8 (SEQ ID NO: 1751), CBA-D8 (SEQ ID NO: 1742), pGL3-FXNpro1336 (SEQ ID NO: 1759), pGL3-FXNpro1060 (SEQ ID NO: 1756), pGL3-FXNpro1226 (SEQ ID NO: 1757), pGL3-FXNpro534 (SEQ ID NO: 1754), pGL3-FXNpro363 (SEQ ID NO: 1753), pGL3-FXNpro223 (SEQ ID NO: 1752) and pGL3-basic.

Based on these findings, 12 promoter variants were selected for further studies. These included CMV (SEQ ID NO: 1743), CBA (SEQ ID NO: 1734), CMV-D1 (SEQ ID NO: 1744), mCBA-D1 (SEQ ID NO: 1761), CMV-D3 (SEQ ID NO: 1746), mCBA-D2 (SEQ ID NO: 1762), CBA-D6 (SEQ ID NO: 1740), CBA-D4 (SEQ ID NO: 1738), CMV-D7 (SEQ ID NO: 1750), CBA-D8 (SEQ ID NO: 1742), pGL3-FXNpro1060 (SEQ ID NO: 1756), and pGL3-FXNpro534 (SEQ ID NO: 1754). Promoters were selected that demonstrated low, medium, and high expression.

Example 2. Design of Payload Constructs Encoding Frataxin

Payload constructs were designed to comprise at a minimum a nucleic acid sequence encoding a frataxin protein. Payload constructs were built using standard molecular cloning techniques. FXN-tag transgenes were cloned into an AAV expression vector and the resulting clones were further sequenced to confirm the correctness of all elements such as ITRs, promoters, and tags.

To build cynomolgus monkey frataxin (cFXN) payload constructs, hemagglutinin (HA) tagged cFXN transgene was cloned into a plasmid containing 5' and 3' ITR sequences (141 nucleotides) derived from an AAV2 genome, a CBA, CMV or FXN promoter, a hβglobin intron region, a hGH poly (A) signal and three miR-122 binding sites (miR-122 BS) for liver-detargeting. Deletion variants of the CBA, CMV or FXN promoter were evaluated. A human albumin sequence of 450 bp (Alb450) was tested as a filler sequence in three constructs (see Table 4; ITR to ITR sequences).

To build human frataxin (hFXN) payload constructs with different configurations, a starting construct comprising 5' and 3' ITR sequences (141 nucleotides) derived from an AAV2 genome, a CBA promoter, a hβglobin intron region, a hFXN gene, and a hGH poly (A) signal, was utilized. Subsequent payload constructs derived from the starting construct contained one of the following four promoter deletion variants: CBA-D8, CMV, CMV-D7, and FXN-pro1060. To have full genome size, human albumin was chosen to serve as a filler (Alb1384, Alb1856, Alb450, Alb2266, Alb2335, Alb1785, Alb2264, or Alb1313) and was added to the subsequent payload constructs. Human frataxin constructs containing the filler sequences were built with or without the miR-122 binding sites (miR-122 BS) for liver-detargeting (see Table 4).

Plasmids containing the payload constructs are described in Table 4. These payload constructs comprise a vector backbone, 5' and 3' ITR sequences (141 nucleotides) derived from an AAV2 genome, a human β-globin (hβglobin) intron region, a human growth hormone (hGH) poly (A) signal, and may also comprise the following components: a CBA, mCBA, CMV, or FXN promoter or a deletion variant thereof; a cynomolgus monkey frataxin (cFXN) or human frataxin (hFXN) gene; a hemagglutinin (HA) tag; three miR-122 binding sites (BS); and a filler sequence of various length derived from the human albumin gene. The hβglobin intron region comprises an immediate-early protein 1 (ie1) exon 1, a partial ie1 intron, a hβglobin intron 2 and a hβglobin exon 3. The components between the ITR sequences are presented from 5' to 3' in Table 4.

Construct ITR to ITR sequences were confirmed by sequencing and are given as SEQ ID NO: 1778-1804.

Example 3. Verification of cFXN Constructs and Components Thereof

A. Identification of Promoter Variants and Hβglobin Intron

To verify the promoter and hβglobin intron region in engineered cFXN constructs driven by CMV, CBA, and FXN promoter variants, the constructs were digested with the high-fidelity restriction enzymes MluI-HF and AgeI-HF. The double digestion yields a cleavage product consisting of the promoter and hβglobin intron region. The digested samples were analyzed by agarose gel electrophoresis. The variants tested included cFXN1-cFXN18 (SEQ ID NO: 1778-1795). Gel revealed bands with a pattern corresponding to the sizes of the promoter variants.

B. Identification of miR-122 and hGH Poly(A)

To verify the miR-122 and hGH poly(A) region in the engineered cFXN constructs driven by CMV, CBA, and FXN promoter variants, the constructs were digested with the restriction enzymes XhoI and ClaI. The double digestion yields a cleavage product consisting of the miR-122 binding sites, the hGH poly (A) sequence and in some cases the filler sequence. The digested samples were analyzed by agarose gel electrophoresis. The variants tested included cFXN1-cFXN18 (SEQ ID NO: 1778-1795). A band corresponding to the miR-122 and hGH poly(A) region was detected in most constructs. Variants lacking the miR-122 sequence exhibited a lower band compared to the constructs having a miR-122 sequence. Variants with a filler sequence exhibited a higher band, confirming the presence of the filler.

C. Identification of ITRs

To verify the inverted terminal repeats (ITRs) in the engineered cFXN constructs driven by CMV, CBA, and FXN promoter variants, the constructs were digested with the restriction enzymes XmaI or MscI individually. Both XmaI and MscI cleave within the ITRs and at one additional site in the construct. The digested samples were analyzed by agarose gel electrophoresis. The variants tested included cFXN1-cFXN18 (SEQ ID NO: 1778-1795). Both gels revealed three cleavage products in all constructs, confirming the presence of the ITRs.

Example 4. Production of cFXN Constructs in Mammalian Cells cFXN constructs (SEQ ID NO: 1778-1795) were used to transfect HEK-293T or Huh7 cells. Transfection was performed in a 12-well plate with approximately $1.5 \times 10^5$ cells per well. Cells were incubated with 1.0 µg cFXN construct, 1.0 µg control plasmid containing an EGFP gene, and 4.0 µl FUGENE® HD Transfection Reagent (Promega, Madison, WI). At 72 hours post-transfection, cells were analyzed for EGFP expression by fluorescence microscopy. Cells transfected with EGFP plasmid alone exhibited fluorescence and served as the positive control, whereas untransfected cells served as the negative control and did not exhibit any fluorescence. The various constructs exhibited similar levels of EGFP expression, demonstrating efficient transfection. Cells were then subjected to RNA and protein extraction for subsequent analysis.

Example 5. Detection of hβGlobin Intron Splicing

A forward primer and a reverse primer were used to amplify a fragment covering the hβglobin intron and cFXN-HA transgene sequence from the cFXN constructs. PCR reactions were performed and products were analyzed by agarose gel electrophoresis. All constructs exhibited an identical band corresponding to the fragment retaining the hβglobin intron.

cDNA was synthesized by reverse transcription from the RNA extracted from transfected HEK-293T or Huh7 cells. PCR reactions were repeated with the cDNA templates and products were analyzed by agarose gel electrophoresis. The cDNA reactions yielded a smaller fragment compared to the fragment amplified directly from the constructs. The size difference coincided with the length of ie1 intron and hβglobin intron 2. The result demonstrated successful splicing of hβglobin intron after transfection.

Example 6. Expression of cFXN Protein in HEK-293T and Huh7 Cells

A. HEK-293T Cells

The expression of cFXN (SEQ ID NO: 1778-1795) in HEK293T cells subsequent to introduction of different cFXN constructs was detected via Western blot. Total protein was extracted from HEK-293T cells transfected with different cFXN constructs including cFXN1-cFXN18 (SEQ ID NO: 1778-1795). A total of 10 µg protein was loaded for each sample. GAPDH served as the internal control. Western blot revealed three different species of the cFXN protein, namely, a precursor protein (~25 KDa), an intermediate protein (~20 KDa), and a mature protein (~15 KDa). cFXN protein was not detected in cells transfected with EGFP only. Almost all constructs exhibited robust expression of cFXN protein, except for cFXN17 (SEQ ID NO: 1794) and cFXN18 (SEQ ID NO: 1795). cFXN11 (SEQ ID NO: 1788), cFXN12 (SEQ ID NO: 1789), cFXN13 (SEQ ID NO: 1790), cFXN14 (SEQ ID NO: 1791) had the highest expression.

The amount of cFXN protein expressed was quantified via enzyme-linked immunosorbent assay (ELISA). A total of 20 ng protein was used per group. cFXN constructs expressed cFXN at different levels and the levels of cFXN expression were highly consistent with promoter activity of CBA/CMV/FXN promoter variants. Table 21 lists the cFXN protein concentration expressed by different cFXN constructs in HEK-293T cells.

TABLE 21

| cFXN protein concentration in HEK-293T cells | | |
|---|---|---|
| cFXN construct | SEQ ID NO: | Average cFXN concentration (ng/µg total protein) |
| EGFP control | — | 0 |
| cFXN1 | 1778 | 9 |
| cFXN2 | 1779 | 14 |
| cFXN8 | 1785 | 16.5 |
| cFXN9 | 1786 | 5 |
| cFXN3 | 1780 | 2 |
| cFXN4 | 1781 | 1 |
| cFXN6 | 1783 | 0.5 |
| cFXN11 | 1788 | 17.5 |
| cFXN12 | 1789 | 20 |
| cFXN13 | 1790 | 9.5 |
| cFXN14 | 1791 | 3.5 |
| cFXN15 | 1792 | 1 |
| cFXN18 | 1795 | 0.2 |
| cFXN17 | 1794 | 0.1 |

TABLE 21-continued cFXN protein concentration in HEK-293T cells

| cFXN construct | SEQ ID NO: | Average cFXN concentration (ng/µg total protein) |
|---|---|---|
| cFXN5 | 1782 | 2.5 |
| cFXN7 | 1784 | 2 |
| cFXN16 | 1793 | 2 |

B. Huh7 Cells

The expression of cFXN in Huh7 cells after introduction of different cFXN constructs was detected via Western blot. Total protein was extracted from Huh7 cells transfected with different cFXN constructs including cFXN1-cFXN18 (SEQ ID NO: 1778-1795). A total of 10 µg protein was loaded for each sample. GAPDH served as the internal control. Western blot revealed three different species of the cFXN protein, namely, a precursor protein (25 KDa), an intermediate protein (20 kDa), and a mature protein (15 kDa). cFXN protein was not detected in cells transfected with EGFP only. A light band was seen in cells transfected with constructs containing miR-122 binding sites indicating that miR-122 effectively reduced cFXN protein expression in liver cells.

The amount of cFXN protein expressed was quantified via enzyme-linked immunosorbent assay (ELISA). A total of 20 ng protein was used per construct. cFXN constructs expressed cFXN at different levels and the levels of cFXN expression were highly consistent with promoter activity of CBA/CMV/FXN promoter variants. Cells transfected with constructs containing miR-122 binding sites showed significantly lower levels of cFXN protein compared to cells transfected with non-miR-122 constructs. Table 22 lists the cFXN protein concentration expressed by different cFXN constructs in Huh7 cells.

TABLE 22 cFXN protein concentration in Huh7 cells

| cFXN construct | SEQ ID NO: | Average cFXN concentration (ng/µg total protein) |
|---|---|---|
| EGFP control | — | 0.1 |
| cFXN1 | 1778 | 4.8 |
| cFXN2 | 1779 | 1 |
| cFXN8 | 1785 | 0.8 |
| cFXN9 | 1786 | 0.8 |
| cFXN3 | 1780 | 0.2 |
| cFXN4 | 1781 | 0.2 |
| cFXN6 | 1783 | 0.2 |
| cFXN11 | 1788 | 7.8 |
| cFXN12 | 1789 | 0.8 |
| cFXN13 | 1790 | 0.6 |
| cFXN14 | 1791 | 0.3 |
| cFXN15 | 1792 | 0.3 |
| cFXN18 | 1795 | 0.3 |
| cFXN17 | 1794 | 0.2 |
| cFXN5 | 1782 | 0.3 |
| cFXN7 | 1784 | 0.2 |
| cFXN16 | 1793 | 0.3 |

Example 7. In Vitro Testing of hFXN1 Constructs hFXN1 (SEQ ID NO: 1796) was co-transfected with an AAV PHP.B packaging plasmid into HEK-293T cells. Four dishes of transfected cells were used to purify the AAV particles. AAV particles were purified by iodixanol gradient ultracentrifugation. The purified sample contained 1E12 vg/ml AAV particles. The sample was run on a sodium dodecyl sulfate (SDS)-gel followed by silver staining to visualize the transgene band and check for impurities. Gel revealed the copurified hFXN protein, confirming successful packaging of the transgene into AAV.

Three different AAV multiplicity of infections (MOIs) were utilized to transfect HEK-293T cells, namely $5\times10^5$, $1\times10^5$, and $2\times10^4$. Following transfection, protein was extracted from the cells and expression detected by performing a Western blot. Expression of hFXN was directly proportional to the MOI of the transfection. Robust hFXN expression was seen for cells infected with the highest MOI of $5\times10^5$. hFXN protein was not detected for HEK-293T cells transfected with a MOI of $2\times10^4$, whereas it was detected for HEK-293T cells transduced with a MOI of $1\times10^5$.

The size of the AAV viral genome was analyzed using denaturing agarose gel electrophoresis. A single band was detected that corresponds to the expected genome size (2881 bp).

Example 8. Generation of Human hFXN Constructs

A. Alternative Promoter Design for Constructs Encoding hFXN1

The hFXN1 (SEQ ID NO: 1796) construct was utilized as a starting template to generate four intermediate plasmids by swapping the promoters. The four intermediate plasmids generated each contained one of the following promoters: FXNpro1060 (SEQ ID NO: 1756), CMV (SEQ ID NO: 1743), CMV-D7 (SEQ ID NO: 1750), and CBA-D8 (SEQ ID NO: 1742). Intermediate plasmids were generated by subcloning the four promoter sequences into the hFXN1 template using MluI and Hind3 restriction sites. The ligation products were transformed into bacterial cells and plasmids were purified using standard miniprep protocol. Purified plasmids were verified by restriction digestion with MluI/Hind3 or MluI/AgeI followed by agarose gel electrophoresis.

B. Insertion of Human Albumin (Alb) Filler Sequences

To ensure full genome size, human albumin DNA was chosen to serve as filler.

Genomic DNA of human albumin was isolated from HEK-297T and HeLa cells. PCR reactions were carried out to amplify 8 different sizes of albumin DNA, namely, 1313 bp (SEQ ID NO: 1831), 1384 by (SEQ ID NO: 1832), 1785 by (SEQ ID NO: 1833), 1856 by (SEQ ID NO: 1835), 2264 bp (SEQ ID NO: 1840), 2266 bp (SEQ ID NO: 1841), and 2335 bp (SEQ ID NO: 1842). The four intermediate plasmids were digested with either one restriction enzyme AvrII, which makes a cut between the miR-122 binding sites and the 3' ITR, or two restriction enzymes AvrII and BspEI, which excise a fragment containing the miR-122 binding sites. The 8 albumin PCR products were ligated with the enzyme-digested plasmids with or without miR-122 binding sites via Gibson Assembly. The ligation products were transformed into bacterial cells and plasmids were purified using standard miniprep protocol. Purified plasmids were verified by restriction digestion with XbaI/KpnI followed by agarose gel electrophoresis.

The final 8 constructs having genome size of 4.6 kb were sequenced from inverted terminal repeat (ITR) to ITR to confirm sequence integrity.

Example 9. Expression of hFXN Protein in HEK-293T Cells

The hFXN constructs were transfected into HEK-293T cells and hFXN protein expression was assessed via Western blots and ELISA. Transfection was performed as described previously. A GFP plasmid was used as an internal control. A total of 10 µg protein was loaded per sample. Western blot detected three forms of hFXN protein: precursor, intermediate and mature hFXN. Construct hFXN4 and hFXN5 (SEQ ID NO: 1799 and 1800) had the strongest hFXN expression, whereas hFXN2, hFXN3, hFXN6, and hFXN7 (SEQ ID NO: 1797, 1798, 1801, and 1802) exhibited limited expression, and hFXN8-hFXN9 (SEQ ID NO: 1803-1804) had weak to non-detectable expression.

The amount of hFXN protein and GFP expression was quantified via ELISA. Among the hFXN constructs, hFXN4 (SEQ ID NO: 1799) and hFXN5 (SEQ ID NO: 1800) demonstrated the highest hFXN protein concentration with relative hFXN expression of >20 times higher than the others. Table 23 lists the hFXN protein concentration and GFP expression in HEK-293T cells. Relative hFXN expression was calculated as hFXN/GFP ratio, showing fold change to endogenous hFXN control.

TABLE 23 hFXN protein concentration

| hFXN construct | SEQ ID NO: | Average hFXN concentration (ng/ml) | Average GFP concentration (ng/ml) | Average fold change to internal control |
|---|---|---|---|---|
| hFXN8 | 1803 | 794.0 | 2354.7 | 1.6 |
| hFXN9 | 1804 | 2187.4 | 2331.4 | 4.5 |
| hFXN4 | 1799 | 73010.1 | 2133.7 | 166.0 |
| hFXN5 | 1800 | 87718.4 | 1777.6 | 236.1 |
| hFXN6 | 1801 | 8533.8 | 1864.9 | 22.6 |
| hFXN7 | 1802 | 7594.3 | 2186.5 | 16.3 |
| hFXN2 | 1797 | 6424.0 | 2364.7 | 13.0 |
| hFXN3 | 1798 | 6375.4 | 2234.9 | 13.7 |
| GFP control | — | 204.3 | 977.3 | 1.0 |

Example 10. In Vivo Promoter Selection Studies

ITR to ITR sequences comprising promoters were packaged into AAV6 capsids and delivered by intrastriatal injection to Sprague Dawley rats at a dose of $1 \times 10^{10}$ VG. Tissue samples were collected at 3 weeks or 10 weeks and frataxin protein levels quantified. Constructs cFXN2 (SEQ ID NO: 1779), cFXN3 (SEQ ID NO: 1780), cFXN4 (SEQ ID NO: 1781), cFXN13 (SEQ ID NO: 1790), cFXN14 (SEQ ID NO: 1791), cFXN17 (SEQ ID NO: 1794), cFXN18 (SEQ ID NO: 1795), hFXN2 (SEQ ID NO: 1797), hFXN4 (SEQ ID NO: 1799), hFXN5 (SEQ ID NO: 1800), and hFXN6 (SEQ ID NO: 1801) were used for these studies.

Based on the quantification of frataxin expression, constructs demonstrating 3-fold (hFXN4; SEQ ID NO: 1799), 5-fold (hFXN8; SEQ ID NO: 1803), 8-fold (hFXN2; SEQ ID NO: 1797) and 25-fold (hFXN6; SEQ ID NO: 1801) weaker expression than cFXN2 were selected for further study. Wildtype CBA and CMV promoter-containing constructs (e.g., cFXN1; SEQ ID NO: 1778) were used as controls. The viral genomes were packaged into capsid VOY201 (SEQ ID NO: 1724) and administered by intravenous delivery to Sprague Dawley rats at a dose of either $6.3 \times 10^{12}$ or $2 \times 10^{13}$ VG/kg. After 28 or 90 days, tissue samples were collected and processed for quantification of frataxin expression (ng/mg).

Promoters CMV-D7 (SEQ ID NO: 1750) and CBA-D8 (SEQ ID NO: 1742) demonstrated the target moderate frataxin expression as compared to the other constructs and were therefore selected for further study.

To test the durability and persistence of frataxin expression driven by the CMV-D7 (SEQ ID NO: 1750) and CBA-D8 (SEQ ID NO: 1742) promoters, a time course study was conducted. Viral genomes comprising a CMV-D7 (SEQ ID NO: 1750), CBA-D8 (SEQ ID NO: 1742), CBA (SEQ ID NO: 1734) or CMV (SEQ ID NO: 1743) promoter with a frataxin payload sequence were packaged into VOY101 (SEQ ID NO: 1) capsids to generate AAV particles. These AAV particles were administered by intravenous delivery via the tail vein to male Sprague Dawley rats at one of two doses ($6.3 \times 10^{12}$ or $2 \times 10^{13}$). At 28, 90, or 180 days after administration, tissue samples were collected (heart, liver, cerebellum, thoracic and lumbar DRG) and processed for quantification of vector genome per diploid cell and frataxin expression levels based on an Anti-Frataxin SimpleStep ELISA. Data are shown below in Tables 24 and 25, FIG. 1A, FIG. 1B, FIG. 1C and FIG. 1D.

TABLE 24

Frataxin expression (ng/mg)

| | CMV-D7 | | | | | | CBA-D8 | | | | | |
|---|---|---|---|---|---|---|---|---|---|---|---|---|
| | 6.3e12 | | | 2.3e13 | | | 6.3e12 | | | 2.3e13 | | |
| Tissue | 28 d | 90 d | 180 d | 28 d | 90 d | 180 d | 28 d | 90 d | 180 d | 28 d | 90 d | 180 d |
| Heart | 14.9 | 168.7 | 98.5 | 37.4 | 254.9 | 234.7 | 20.4 | 112.1 | 164.6 | 77.5 | 713.8 | 304.8 |
| Cerebellum | 1.0 | 1.9 | 4.3 | 5.8 | 13.6 | 23.6 | 0.9 | 2.2 | 3.1 | 6.9 | 11.5 | 21.4 |
| Lumbar DRG | 75.2 | 144.7 | 64.7 | 249.0 | 250 | 152.1 | 45.0 | 98.3 | 53.2 | 121.3 | 212.8 | 95.9 |

TABLE 25

Vector genome/diploid cell (VG/dc)

| | CMV-D7 | | | | | | CBA-D8 | | | | | |
|---|---|---|---|---|---|---|---|---|---|---|---|---|
| | 6.3e12 | | | 2.3e13 | | | 6.3e12 | | | 2.3e13 | | |
| Tissue | 28 d | 90 d | 180 d | 28 d | 90 d | 180 d | 28 d | 90 d | 180 d | 28 d | 90 d | 180 d |
| Heart | 1.8 | 2.1 | 1.8 | 3.3 | 8.11 | 7.2 | 1.1 | 2.2 | 1.8 | 3.6 | 9.6 | 6.1 |
| Liver | 0.7 | 0.6 | 0.6 | 4.2 | 2.4 | 2.9 | 0.7 | 0.5 | 0.5 | 3.2 | 1.4 | 0.9 |

TABLE 25-continued

| | Vector genome/diploid cell (VG/dc) | | | | | | | | | | | |
|---|---|---|---|---|---|---|---|---|---|---|---|---|
| Cerebellum | 0.0 | 0.0 | 0.00 | 0.1 | 0.0 | 0.0 | 0.0 | 0.0 | 0.0 | 0.1 | 0.0 | 0.0 |
| Thoracic DRG | 0.1 | 0.1 | 0.1 | 0.5 | 0.4 | 0.1 | 0.1 | 0.1 | 0.1 | 0.5 | 0.4 | 0.3 |

| | CBA (no miR-122) | | | | | | CMV | | | | | |
|---|---|---|---|---|---|---|---|---|---|---|---|---|
| | 6.3e12 | | | 2.3e13 | | | 6.3e12 | | | 2.3e13 | | |
| | 28 d | 90 d | 180 d | 28 d | 90 d | 180 d | 28 d | 90 d | 180 d | 28 d | 90 d | 180 d |
| Heart | 4.3 | 7.0 | 7.0 | — | — | — | — | — | — | 4.8 | — | — |
| Liver | 0.8 | 0.4 | 0.6 | — | — | — | — | — | — | 5.7 | — | — |
| Cerebellum | 0.1 | 0.0 | 0.0 | — | — | — | — | — | — | 0.1 | — | — |
| Thoracic DRG | 0.5 | 0.4 | 0.1 | — | — | — | — | — | — | 2.2 | — | — |

In tissue collected from the heart ventricle, driving frataxin expression using the CMV-D7 (SEQ ID NO: 1750) promoter enhanced frataxin expression 0.2-2.5×, while driving frataxin expression using the CBA-D8 (SEQ ID NO: 1742) promoter enhanced frataxin expression 0.3-7.8×. As comparison, the CBA (SEQ ID NO: 1734) promoter enhanced frataxin expression 41.2-70× and the CMV (SEQ ID NO: 1743) promoter enhanced frataxin expression 297× as compared to normal frataxin expression.

In tissue collected from the cerebellum, driving frataxin expression using the CMV-D7 (SEQ ID NO: 1750) promoter enhanced frataxin expression 0.01-0.31×, while driving frataxin expression using the CBA-D8 (SEQ ID NO: 1742) promoter enhanced frataxin expression 0.01-0.28×. As comparison, the CBA (SEQ ID NO: 1734) promoter enhanced frataxin expression 0.0-0.9× and the CMV (SEQ ID NO: 1743) promoter enhanced frataxin expression 0.21× as compared to normal frataxin expression.

In tissue collected from the lumbar DRG, driving frataxin expression using the CMV-D7 (SEQ ID NO: 1750) promoter enhanced frataxin expression 1.6-6.2×, while driving frataxin expression using the CBA-D8 (SEQ ID NO: 1742) promoter enhanced frataxin expression 1.1-5.2×. As comparison, the CBA (SEQ ID NO: 1734) promoter enhanced frataxin expression 0.0-5.4× and the CMV (SEQ ID NO: 1743) promoter enhanced frataxin expression 0.5× as compared to normal frataxin expression.

Immunohistochemical analysis was performed on 30 μm tissue samples collected 28 days after AAV particle administration. An anti-hFXN antibody (1/50,000) was used. Frataxin expression driven by the CMV-D7 (SEQ ID NO: 1750) and CBA-D8 (SEQ ID NO: 1742) promoters was detected in the dentate nucleus of treated rats.

Each of CMV-D7 (SEQ ID NO: 1750), CBA-D8 (SEQ ID NO: 1742) and CBA (SEQ ID NO: 1734) promoters showed similar distribution and expression patterns in the DRG and brain. In the heart, CMV-D7 and CBA-D8 promoters generated FXN expression approximately 50-260 fold lower than CBA-driven frataxin expression.

The CMV-D7 (SEQ ID NO: 1750) and CBA-D8 (SEQ ID NO: 1742) promoters both drive frataxin expression in the cerebellum, heart and DRG at 180 days after administration of the AAV particles. At this time point, expression in the cerebellum is approximately 3-fold greater than that achieved using the reference CBA promoter, indicating that the CMV-D7 and CBA-D8 promoters are active in target cells of the cerebellum.

Figure 2:
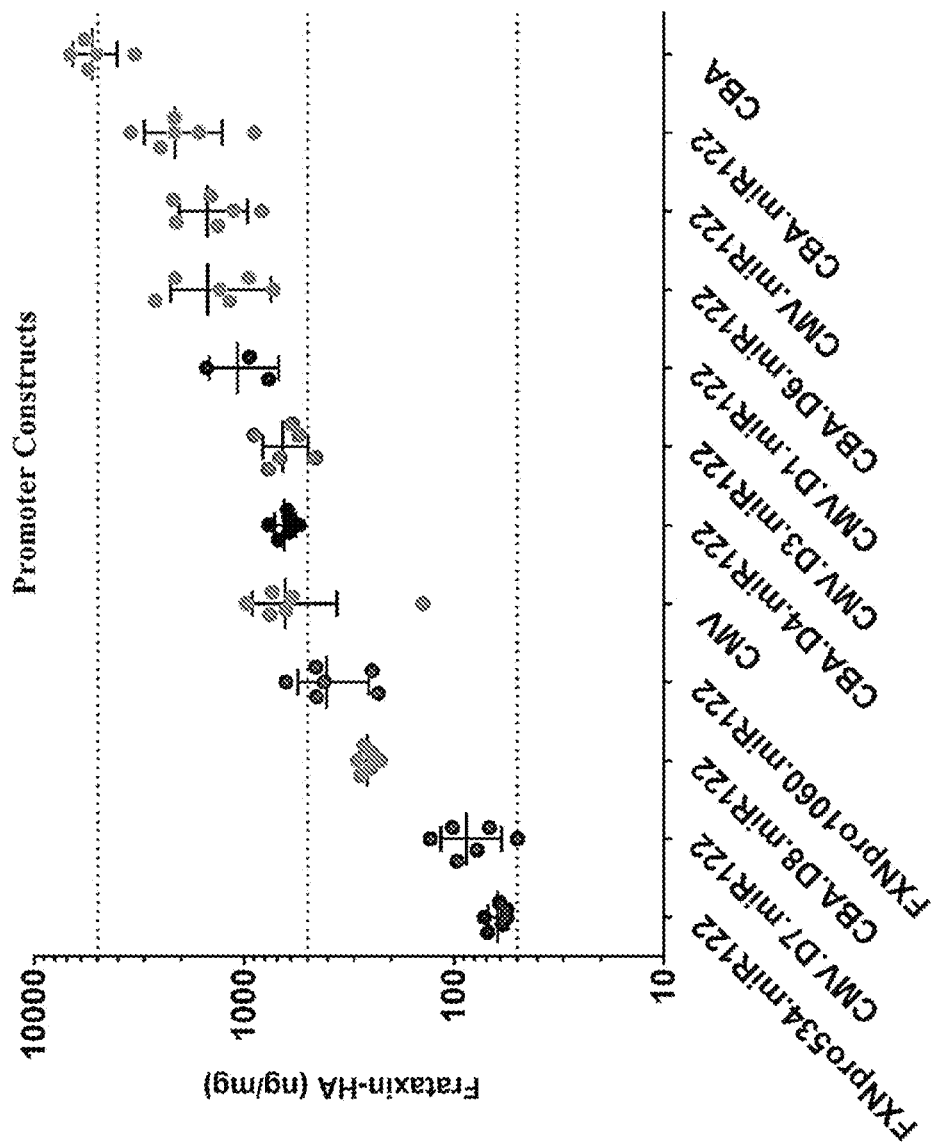
FIG. 2 presents a graph showing quantification results for striatal cFXN protein levels by ELISA for certain promoter constructs of the present disclosure.

Example 11. In Vivo cFXN Expression Levels Following Intra-Striatal Administration of a Viral Genome Comprising Alternative Promoter Variants in Rats To test frataxin expression driven by alternative promoter variants, a viral genome comprising one promoter selected from any of the following promoters: CMV-D1 (SEQ ID NO: 1744), CMV-D3 (SEQ ID NO: 1746), CBA-D4 (SEQ ID NO: 1738) and CBA-D6 (SEQ ID NO: 1740) (as taught in Table 3), AAV2 wild-type ITRs, *Macaca fascicularis* frataxin (cynoFXN or cFXN) with a HA-tag, triple repeat of a miR-122 target and a human growth hormone polyadenylation sequence was packaged into an AAV6 capsid and delivered by intra-striatal injection to Sprague Dawley rats at a dose of $1\times10^{10}$ VG/kg, unless noted otherwise. As controls, FXNpro534 (SEQ ID NO: 1754), FXNpro1060 (SEQ ID NO: 1756), CMV (SEQ ID NO: 1743), CBA (SEQ ID NO: 1734) promoters or their variants were used to drive cFXN expression from a viral genome and packaged into an AAV6 capsid. Tissue samples were collected 3 weeks after injection and striatal cFXN protein levels were quantified by ELISA. Data are shown below in Table 26 and FIG. 2.

TABLE 26

In vivo cFXN expression (ng/mg) driven by alternative promoters in rats.

| Promoters | Promoter SEQ ID NO: | Dose (VG/kg) | cFXN (ng/mg) | Fold change relative to the endogenous FXN |
|---|---|---|---|---|
| FXNpro534 | 1754 | 1e10 | 62.2 | 1 |
| CMV-D7 | 1750 | 6e9 | 87.5 | 1.4 |
| CBA-D8 | 1742 | 1e10 | 260 | 4.2 |
| FXNpro1060 | 1756 | 1e10. | 406 | 6.6 |
| CMV (without miR122) | 1743 | 1e10 | 640 | 10.4 |
| CBA-D4 | 1738 | 1e10 | 643.3 | 10.4 |
| CMV-D3 | 1746 | 1e10 | 657.5 | 10.7 |
| CMV-D1 | 1744 | 1e10 | 1076 | 17.5 |
| CBA-D6 | 1740 | 1e10 | 1496 | 24.3 |
| CMV | 1743 | 6e9 | 1504 | 24.4 |
| CBA | 1734 | 1e10 | 2142 | 34.7 |
| CBA (without miR122) | 1734 | 1e10 | 5302 | 86 |

Striatal cFXN expression driven by the FXNpro534 (SEQ ID NO: 1754) promoter was comparable to the endogenous frataxin level, while the FXNpro1060 (SEQ ID NO: 1756) promoter resulted in 6.6× of the endogenous FXN level. As controls, high levels of cFXN expression were achieved by CMV.miR122 (24.4×), CBA.miR122 (34.7×) or CBA (86×)

promoters, respectively. Moderate expression levels of cFXN driven by CMV-D7 (SEQ ID NO: 1750) or CBA-D8 (SEQ ID NO: 1742) promoters were observed by 1.4× and 4.2×, respectively, which were within the ranges of those driven by two FXN promoter variants. Alternative promoter variants CMV-D1 (SEQ ID NO: 1744), CMV-D3 (SEQ ID NO: 1746), CBA-D4 (SEQ ID NO: 1738) and CBA-D6 (SEQ ID NO: 1749) resulted in higher cFXN expression than either CMV-D7 (SEQ ID NO: 1750) or CBA-D8 (SEQ ID NO: 1742), but still much lower than CMV.miR122. In summary, these data indicated that additional promoter variants were effective to induce cFXN expression in rat striatum.

Example 12. In Vivo cFXN Expression and Vector Genome Biodistribution Following Intrathalamic Administration of VOY101-cFXN-HA AAV Vectors To achieve widespread expression of cFXN in deep cerebellar nuclei and associated cFXN levels in spinal cord and dorsal root ganglion, VOY101-cFXN-HA (SEQ ID NO: 1778) vectors were administered by bilateral intrathalamic injection into Sprague Dawley rats.

Single strand viral genome comprising a CBA promoter and cFXN-HA sequence were packaged into VOY101 particles and injected intrathalamically at the dose of $5 \times 10^{10}$ vg/injection. The injection volume and injection rate were 12 µl/injection and 0.5 µl/min, respectively. One rat was treated with vehicle control. Six weeks after treatment, immunohistochemical analysis was performed to assess the expression of cFXN-HA in the dentate nucleus of the cerebellum and spinal cord using anti-HA immunostaining. Compared to the vehicle control, strong HA staining was observed throughout the whole dentate nucleus of cerebellum in all treated animals. Furthermore, widespread cFXN expression were evident in dorsal column, central canal, ventral horn and Clarke's column of the cervical, thoracic and lumbar spinal cord distal from the injection site. These results together indicated that intrathalamic injection of VOY101-CBA-cFXN vectors could cause efficient transduction of deep cerebellar nuclei and neurons of spinal cord and drive the expression of FXN protein.

Example 13. Transgene Expression Levels of hFXN Following Intravenous Administration of Pvalb cKO Mice with VOY101-CMV-D7-hFXN or VOY101-CBA-D8-hFXN AAV Particles Friedreich's Ataxia (FA) is caused by an intronic GAA expansion in the frataxin gene which significantly reduces FXN expression in mitochondria. Patients at the early stage of Friedreich's Ataxia exhibit difficulty in walking and loss of balance due to the loss of large proprioceptive neurons in the peripheral dorsal root ganglia (DRG). Subsequently trunk and arm functions deteriorate because of increasing spino-cerebellar neuronal impairment. Patients become wheelchair bound and incapacitated, leading to a reduced average life span of about 40 years of age. To model the selective nature of neuronal loss in FA, a transgenic mouse was created in which FXN expression is abolished via the Cre Lox system in parvalbumin expressing cells (Pvalb cKO mice) (Piguet et al. 2018). The Pvalb cKO mice showed loss of proprioceptive sensory function and progressive ataxia within weeks after birth.

A viral genome comprising CMV-D7-hFXN (SEQ ID NO: 1801) or CBA-D8-hFXN (SEQ ID NO: 1797) was used to generate AAV particles, having a capsid serotype of VOY101 (SEQ ID NO: 1). The viral genome comprising a promoter (CMV-D7 or CBA-D8), two AAV2 ITRs, hFXN, triple repeat of a miR-122 target and a human growth hormone polyadenylation sequence was packaged into VOY101 AAV particles by triple transfection of HEK293 cells. The AAV particles were purified and formulated in phosphate buffered saline (PBS) with 0.001% F-68, and then administered intravenously to mice at the dose of $2 \times 10^{13}$ VG/kg.

To test hFXN expression levels in Pvalb cKO animals administrated intravenously with the single stranded VOY101-CMV-D7-hFXN or VOY101-CBA-D8-hFXN AAV particles, the particles were administered intravenously to Pvalb cKO mice at the age of 7.5 weeks at one of three doses of $6.32 \times 10^{12}$ VG/kg, or $2.0 \times 10^{13}$ VG/kg. A group of Pvalb cKO mice was treated intravenously with AAV9-hFXN particles at $7.0 \times 10^{12}$ VG/kg. WT or Pvalb cKO mice were also administered with vehicle control.

Figure 3A:
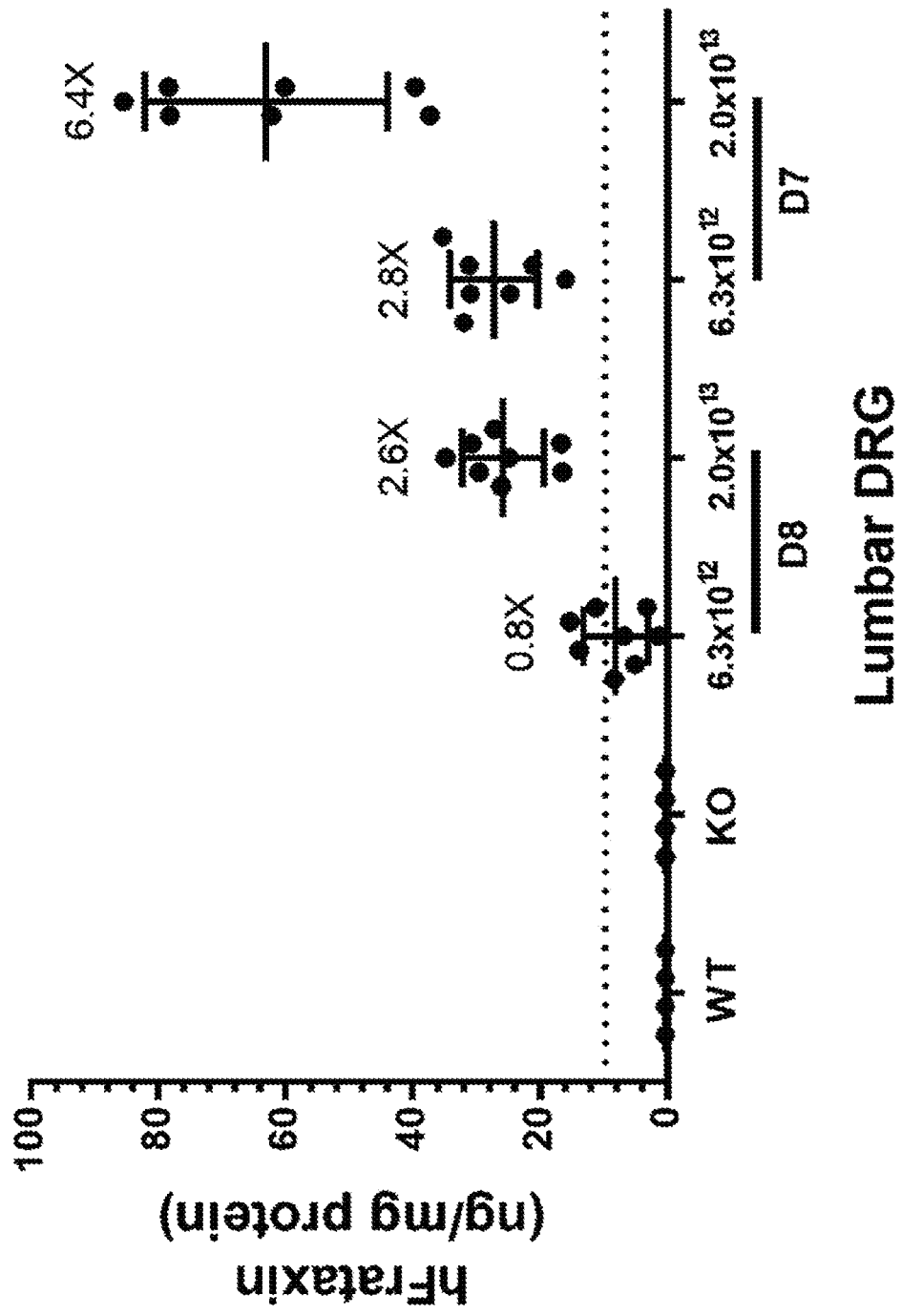
FIG. 3A presents a graph showing quantification results for frataxin expression levels (ng/mg) by ELISA for lumbar DRG tissues.
Figure 3B:
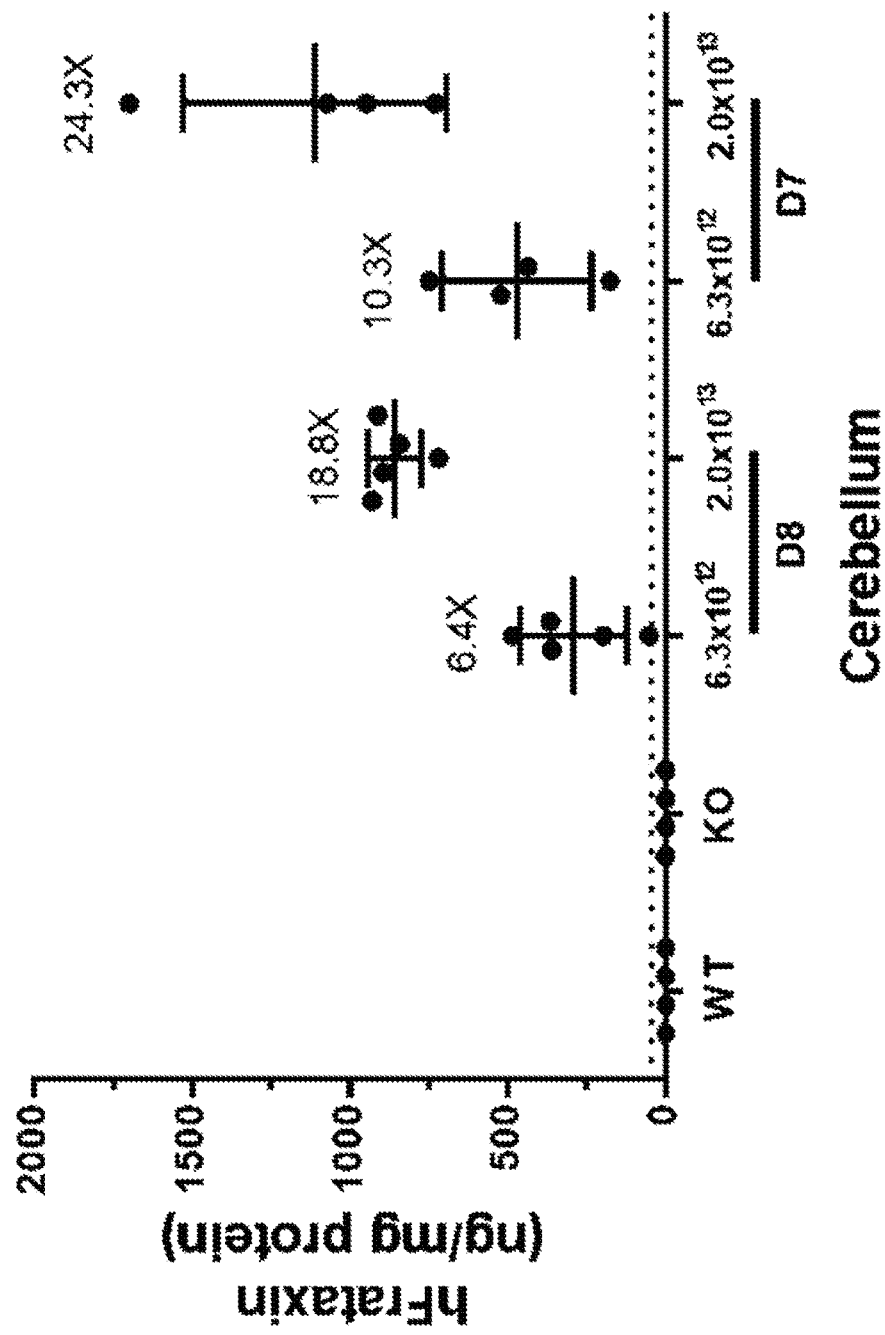
FIG. 3B presents a graph showing quantification results for frataxin expression levels (ng/mg) by ELISA for tissues of the cerebellum.

Four weeks after administration, mice 11.5 weeks old were euthanized. The cerebellum and lumbar DRG tissues were collected and processed for quantification of hFXN expression levels. hFXN protein levels were measured by ELISA and reported in ng hFXN/mg of total protein. Fold changes of hFXN expression in cerebellum or lumbar DRG relative to the WT endogenous FXN levels were calculated. Data are shown at Table 27, FIG. 3A, and FIG. 3B.

TABLE 27 hFXN expression in the cerebellum and lumbar DRG of Pvalb cKO mice

|  | WT | KO | CMV-D7 6.3e12 VG/kg | CMV-D7 2e13 VG/kg | CBA-D8 6.3e12 VG/kg | CBA-D8 2e13 VG/kg | AAV9 7e12 VG/kg |
|---|---|---|---|---|---|---|---|
| L-DRG (ng/mg) | 0.4 | 0.4 | 27.4 | 63.1 | 8.2 | 25.9 | 1.7 |
| Fold change in L-DRG | 1.0 | 0 | 2.8 | 6.4 | 0.8 | 2.6 | 0.1 |
| Cerebellum (ng/mg) | 0.7 | 0.7 | 472.2 | 1114.0 | 293.6 | 861.0 | 3.8 |
| Fold change in cerebellum | 1.0 | 0 | 10.3 | 24.3 | 6.4 | 18.8 | 0.1 |

In tissue collected from the lumbar DRG, intravenous administration of VOY101-CMV-D7-hFXN (SEQ ID NO: 1801) particles in Pvalb cKO animals enhanced hFXN expression by 2.8-6.4× as compared to the WT endogenous FXN levels 4 weeks after delivery. Intravenous administration of VOY101-CBA-D8-hFXN (SEQ ID NO: 1797) particles in Pvalb cKO animals enhanced hFXN expression by 0.8-2.6× 4 weeks after delivery.

In tissue collected from the cerebellum, intravenous administration of VOY101-CMV-D7-hFXN (SEQ ID NO: 1801) particles in Pvalb cKO animals enhanced hFXN expression by 10.3-24.3× as compared to the WT endogenous FXN levels 4 weeks after delivery. Intravenous administration of VOY101-CBA-D8-hFXN (SEQ ID NO: 1797) particles in Pvalb cKO animals enhanced hFXN expression by 6.4-18.8× as compared to the WT endogenous FXN levels 4 weeks after delivery.

In summary, high hFXN expression levels in the cerebellum and lumbar DRG of Pvalb cKO animals indicated that either VOY101-CMV-D7-hFXN (SEQ ID NO: 1801) or VOY101-CBA-D8-hFXN (SEQ ID NO: 1797) particles were capable of transducing these tissues.

Example 14. Correction of Proprioceptive Deficit and Rescue of Motor Function and Muscular Functions in Pvalb cKO Mice Following Intravenous Administration of VOY101-CMV-D7-hFXN or VOY101-CBA-D8-hFXN AAV Particles To evaluate the therapeutic efficacy of VOY101-CMV-D7-hFXN (SEQ ID NO: 1801) or VOY101-CBA-D8-hFXN (SEQ ID NO: 1797) vectors, the rescue of proprioceptive deficit in Pvalb cKO mice were tested by electromyogram analysis after intravenous (IV) delivery of these vectors at a dose of $6.32 \times 10^{12}$ VG/kg or $2.0 \times 10^{13}$ VG/kg.

The single-stranded VOY101-CMV-D7-hFXN (SEQ ID NO: 1801) or VOY101-CBA-D8-hFXN (SEQ ID NO: 1797) particles were purified and formulated in 192 mM sodium chloride, 2.7 mM potassium chloride, 2 mM potassium phosphate (monobasic) and 10 mM sodium phosphate (dibasic) with 0.001% pluronic acid (Pluronic F-68) and at pH 7.4, and administered via intravenous injection to adult Pvalb cKO mice at 7.5 weeks of age at a single dose of $6.32 \times 10^{12}$ VG/kg or $2.0 \times 10^{13}$ VG/kg. A control group received intravenous injection of AAV9-hFXN particle at the dose of $7 \times 10^{12}$ VG/kg.

Electromyogram analyses were performed using the Natus UltraProS100 apparatus (Mag2Health, France). Pvalb cKO mice were anesthetized using IP injection with ketamine/xylazine (130/13 mg/kg). Animals were maintained at 37° C. throughout the electrophysiological assessment. Latency and amplitude of the spinal somatosensory evoked response (H wave) were recorded in the plantar hind paw muscle after sciatic nerve stimulation (0.1 ms and 8 mA intensity). Electromyogram analysis was performed by recording spinal somatosensory evoked response (H wave) every week, two weeks or three weeks, depending on age of the mice, starting at 6.5 weeks of age according to Piguet et al 2018.

Figure 4:
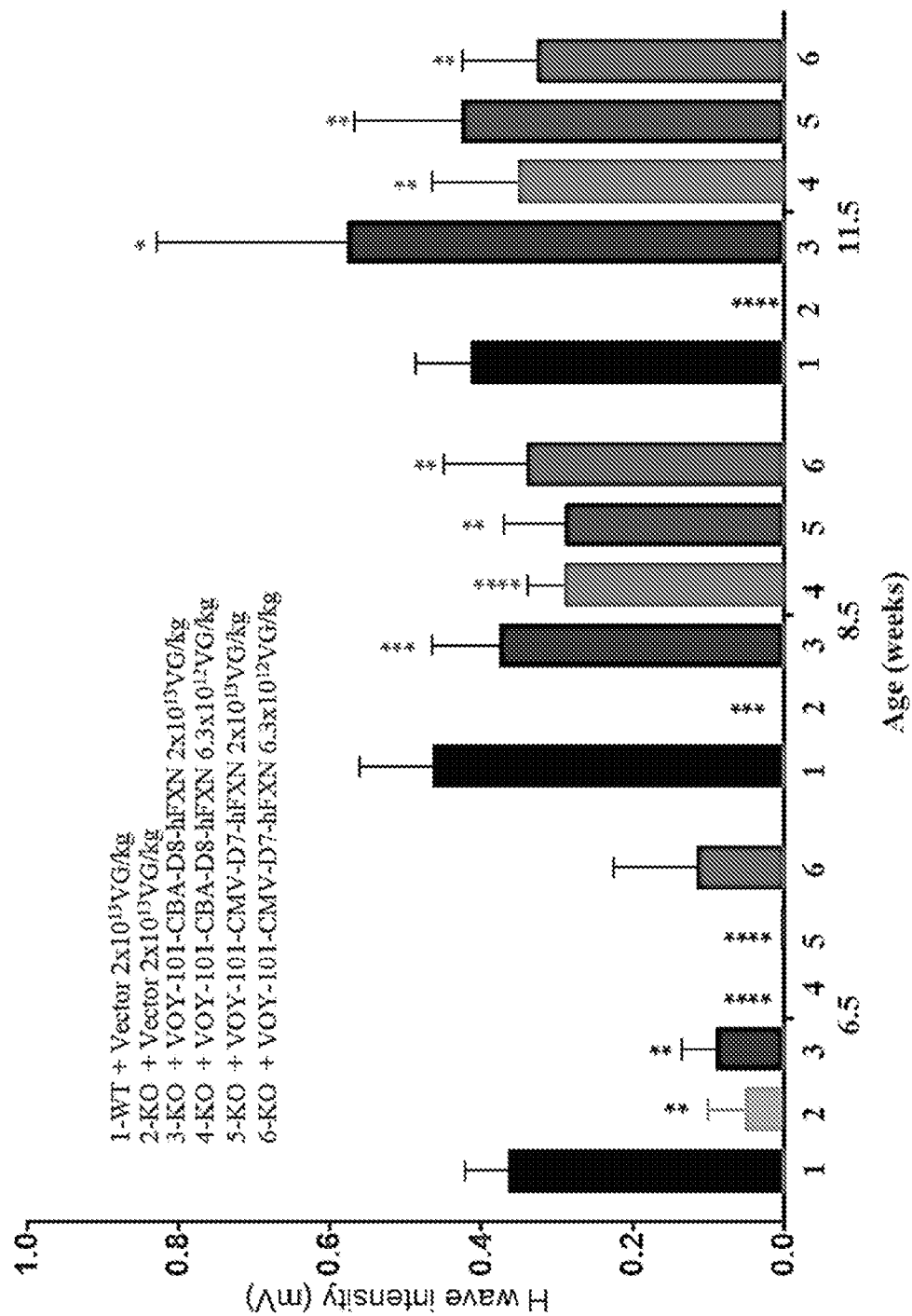
FIG. 4 presents a graph showing electromyographic (H wave intensity) measurements in Pvalb cKO animals treated intravenously with VOY101-CMV-D7-hFXN or with VOY101-CBA-D8-hFXN AAV particles, compared with Pvalb cKO mice and wild-type (WT) mice.

As shown in FIG. 4, H wave intensity in the Pvalb cKO mice at the age of 6.5 weeks was reduced significantly compared to the WT mice. In the cKO mice at the age of 8.5 weeks-one week after the injection, the H wave levels were no longer measurable. In contrast, intravenous injections of either VOY101-CMV-D7-hFXN (SEQ ID NO: 1801) or VOY101-CBA-D8-hFXN (SEQ ID NO: 1797) particles within a week of dosing almost completely restored H wave intensity to levels comparable to those seen in WT animals, indicating a reversal of the proprioceptive deficit of Pvalb cKO mice. Complete rescue was observed after 4 weeks of high dosing at $2.0 \times 10^{13}$ VG/kg using either of AAV particles.

These results demonstrated a dose-dependent effect of IV VOY101-CMV-D7-hFXN (SEQ ID NO: 1801) or VOY-CBA-D8-hFXN (SEQ ID NO: 1797) on spinal somatosensory evoked response, especially IV dose from $6.32 \times 10^{12}$ VG/kg to $2.00 \times 10^{13}$ VG/kg in mice at the age of weeks 11.5.

To test the rescue of motor and muscular function in Pvalb cKO animals after intravenous delivery of either VOY101-CMV-D7-hFXN (SEQ ID NO: 1801) or VOY101-CBA-D8-hFXN (SEQ ID NO: 1797) particles, a notched-bar experiment (scored number of slips of the upper or lower limbs—'falls') as previously described (Piguet el al. 2018) was conducted in cKO animals at 7.5, 8.5, 9.5 and 11.5 weeks of age. The VOY101 particles were administered by IV injection to cKO animals (7.5 weeks of age) as described as above.

Figure 5:
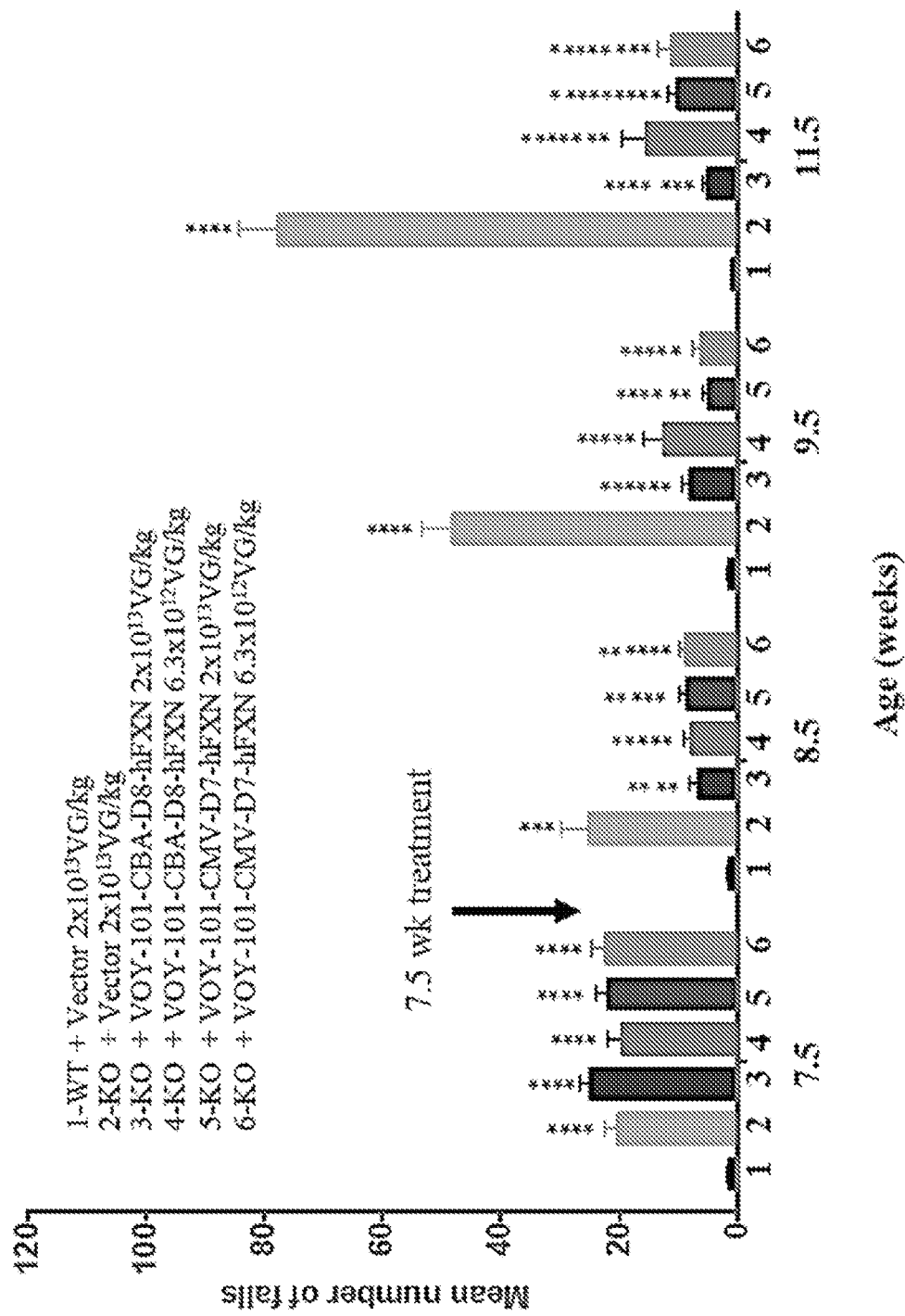
FIG. 5 presents a graph showing behavioral analysis through the notched-bar test in Pvalb cKO mice treated intravenously with VOY101-CMV-D7-hFXN or with VOY101-CBA-D8-hFXN AAV particles, compared with Pvalb cKO mice and wild-type (WT) mice.
Figure 6A:
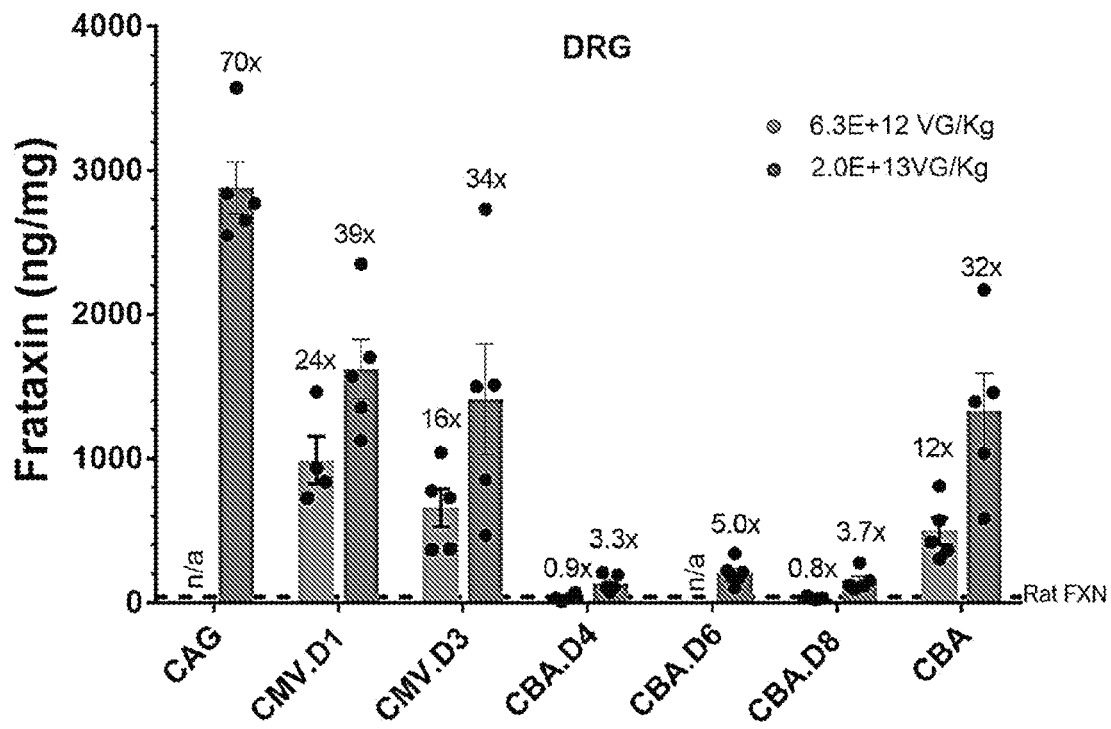
FIG. 6A presents a graph showing quantification results for frataxin expression levels (ng/mg) by ELISA for certain DRG tissue of the present disclosure.
Figure 6B:
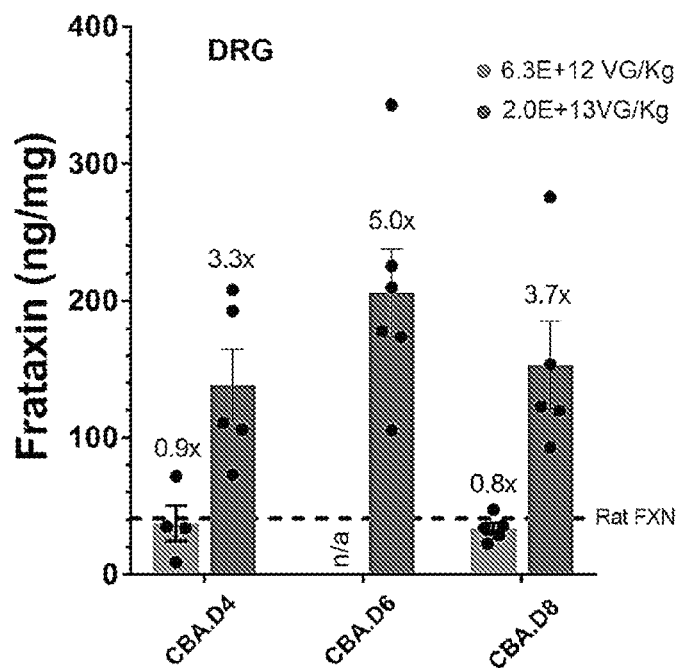
FIG. 6B presents an expanded view of the quantification results in FIG. 6A for hFXN13 (CBA.D4) having SEQ ID NO: 1808, hFXN14 (CBA.D6) having SEQ ID NO: 1809, and hFXN2 (CBA.D8) having SEQ ID NO: 1797.
Figure 6C:
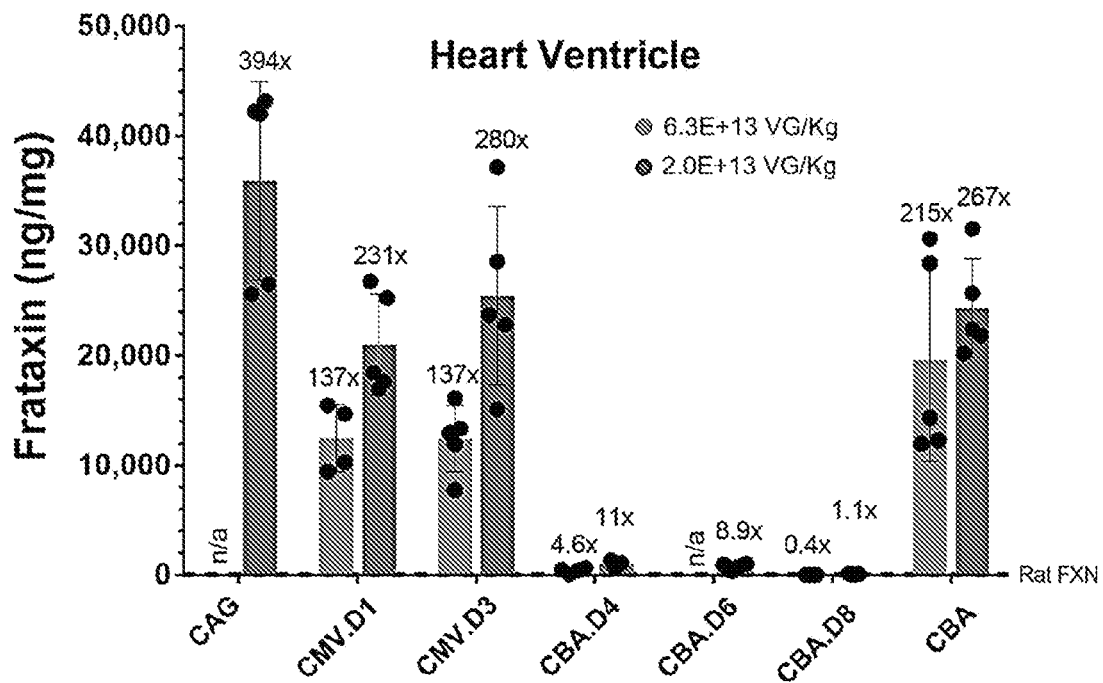
FIG. 6C presents a graph showing quantification results for frataxin expression levels (ng/mg) by ELISA for certain heart ventricle tissue of the present disclosure.
Figure 6D:
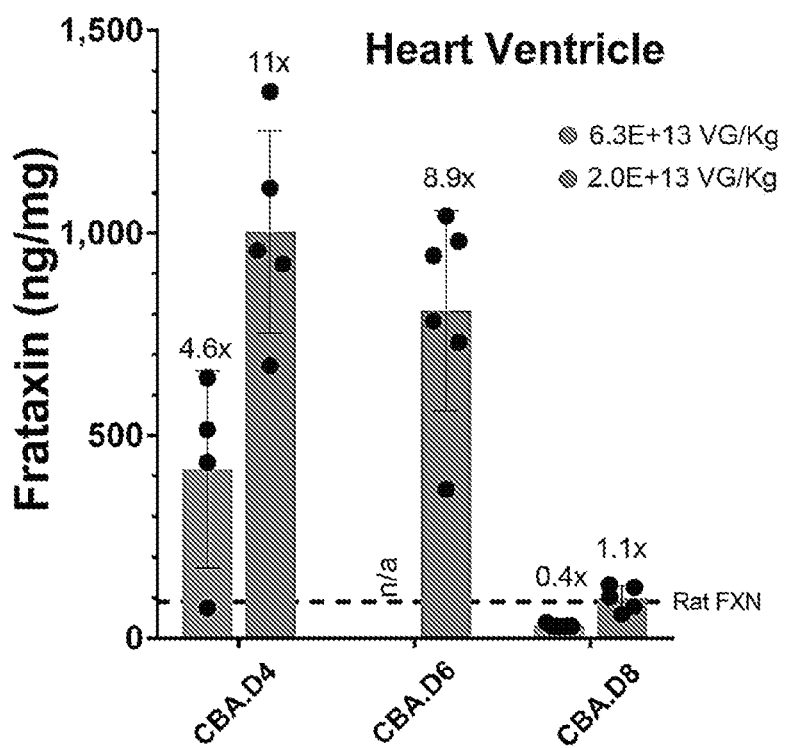
FIG. 6D presents an expanded view of the quantification results in FIG. 6C for hFXN13 (CBA.D4) having SEQ ID NO: 1808, hFXN14 (CBA.D6) having SEQ ID NO: 1809, and hFXN2 (CBA.D8) having SEQ ID NO: 1797.

As shown in FIG. 5, the Pvalb cKO mice quickly developed ataxic deficit from weeks 7.5 to 11.5. In contrast, intravenous administration of either VOY101-CMV-D7-hFXN (SEQ ID NO: 1801) or VOY101CBA-D8-hFXN (SEQ ID NO: 1797) particles at doses of $6.3 \times 10^{12}$ or $2.0 \times 10^{13}$ VG/kg rapidly reversed the ataxic phenotype one week after injection. The rescue effect still persisted in the cKO animals 4 weeks after treatment.

Example 15. In Vivo hFXN Expression and Vector Genome Biodistribution after Intravenous Dosing of VOY101-CMV-D7 or VOY101-CBA-D8-hFXN AAV Particles in Non-Human Primates (NHP)

A single stranded viral genome comprising two AAV2 ITRs, a promoter (CMV-D7 or CBA-D8), hFXN cDNA sequence, triple repeat of a miR-122 target, a human growth hormone polyA sequence, a fragment of human albumin as a stuffer sequence, is packaged into VOY101 capsids, produced by triple transfection, purified and formulated in phosphate buffered saline (PBS) with 0.001% F-68.

Three groups of adult cynomolgus monkeys (3 animals per group), approximately 2.7-5.8 years old, pre-screened for low anti-AAVvoy101 antibodies using both LEC2 nAb in vitro assay and IgG ELISA, will receive vehicle (PBS with 0.001% F-68), VOY101-CMV-D7-hFXN (SEQ ID NO: 1801) or VOY101-CBA-D8-hFXN (SEQ ID NO: 1797) at the dose of $5 \times 10^{13}$ VG/kg (titer $1.0 \times 10^{13}$VG/ml) via intravenous injection. The injection rate will be 3 ml/min and the dose volume will be 5 mL/kg (~17.5 mL/animal).

To test the distribution and expression of VOY101-CMV-D7-hFXN (SEQ ID NO: 1801) or VOY101-CBA-D8-hFXN (SEQ ID NO: 1797) in NHP, any test known in the art may be utilized. The hFXN protein and mRNA expression will be assessed by ELISA, PCR, immunohistochemistry, in situ hybridization (ISH) and liquid chromatography tandem mass spectrometry (LC-MS/MS). Vector genome levels in different tissues will be quantified using PCR and ISH.

The following samples may be collected: cervical, thoracic and/or lumbar DRG, cervical, thoracic, and/or lumbar spinal cord, frontal cortex, motor cortex, hippocampus, striatum, cerebellum, brainstem, liver, heart, heart atrium, heart ventricle. Tissues of the DRG, heart ventricle, lower lumbar spinal cord, upper lumbar spinal cord, frontal cortex, cerebellum and liver will be used to determine hFXN expression in target tissues using ELISA and LC-MS and digital droplet PCR to quantify vector genome/diploid cell. The expression and distribution of hFXN will be measured in cells of DRG, cerebellar dentate nucleus, Clarke's column, gracile and cuneate nuclei and heart by in situ hybridization (ISH). The resulting data will be used to confirm expected tissue biodistribution and transgene hFXN expression of VOY101-CMV-D7-hFXN (SEQ ID NO: 1801) or VOY101-CBA-D8-hFXN (SEQ ID NO: 1797) AAV particles in non-human primates.

Example 16. In Vivo Promoter Selection Studies in Non-Human Primate (NHP)

Select AAV particles with viral genomes comprising promoter variant sequences will be tested in non-human primates to determine frataxin expression in target cells and tissues. hFXN ITR-to-ITR constructs selected from Table 4 will be used, including hFXN2 (SEQ ID NO: 1797), hFXN3 (SEQ ID NO: 1798), hFXN6 (SEQ ID NO: 1801), hFXN7 (SEQ ID NO: 1802), hFXN13 (SEQ ID NO: 1808) and hFXN14 (SEQ ID NO: 1809).

AAV particles which include the selected hFXN ITR-to-ITR constructs in VOY101 capsids will be produced by triple transfection using mammalian HEK293 cells according to the present disclosure. The resulting AAV particles will be purified and then formulated into Formulation 1 (192 mM sodium chloride, 2.7 mM potassium chloride, 2 mM potassium phosphate (monobasic) and 10 mM sodium phosphate (dibasic) with 0.001% pluronic acid (Pluronic F-68) and at pH 7.4).

A group of juvenile cynomolgus monkeys (Chinese origin, pre-screened for low anti-AAVVoy101 antibodies using NAb assay) will be selected for each hFXN ITR-to-ITR construct being tested (two females and one male per group). The cynomolgus monkeys will receive AAV particles via intravenous injection (saphenous) according to the testing parameters of Table 28.

TABLE 28

Study design for testing hFXN promoter variants

| hFXN ITR-to-ITR Construct | SEQ ID NO: | AAV Dose (vg/kg) | Duration (days) | Dosing Regimen (ml/kg/h) |
|---|---|---|---|---|
| hFXN2 | 1797 | $2 \times 10^{13}$ | 30 | 5 ml/kg over 1 hour |
|  |  |  | 90 |  |
|  |  | $6.32 \times 10^{12}$ | 30 |  |
|  |  |  | 90 |  |
| hFXN3 | 1798 | $2 \times 10^{13}$ | 30 | 5 ml/kg over 1 hour |
|  |  |  | 90 |  |
|  |  | $6.32 \times 10^{12}$ | 30 |  |
|  |  |  | 90 |  |
| hFXN6 | 1801 | $2 \times 10^{13}$ | 30 | 5 ml/kg over 1 hour |
|  |  |  | 90 |  |
|  |  | $6.32 \times 10^{12}$ | 30 |  |
|  |  |  | 90 |  |
| hFXN7 | 1802 | $2 \times 10^{13}$ | 30 | 5 ml/kg over 1 hour |
|  |  |  | 90 |  |
|  |  | $6.32 \times 10^{12}$ | 30 |  |
|  |  |  | 90 |  |
| hFXN13 | 1808 | $2 \times 10^{13}$ | 30 | 5 ml/kg over 1 hour |
|  |  |  | 90 |  |
|  |  | $6.32 \times 10^{12}$ | 30 |  |
|  |  |  | 90 |  |
| hFXN14 | 1809 | $2 \times 10^{13}$ | 30 | 5 ml/kg over 1 hour |
|  |  |  | 90 |  |
|  |  | $6.32 \times 10^{12}$ | 30 |  |
|  |  |  | 90 |  |
| Formulation 1 (Vehicle) |  | 0 | 90 | 5 ml/kg over 1 hour |

The resulting distribution and expression of the selected hFXN constructs will be tested in various tissues, including one or more of the following: cervical DRG, thoracic DRG, lumbar DRG, cervical spinal cord, thoracic spinal cord, lumbar spinal cord, frontal cortex, motor cortex, hippocampus, striatum, cerebellum, brainstem, liver, heart, heart atrium, and heart ventricle.

The following primary readouts will be measured and collected from the test subjects: Complete Blood Count (CBC), serum chemistry, serum cytokine proteins, cage-side observations, Body Weight, AAV Vector Genome (VG) distribution, hFXN protein distribution, and hFXN protein expression. These primary readouts will be tested and measured according to various methods known in the art, including ELISA, PCR, immunohistochemistry, in situ hybridization (ISH) and liquid chromatography tandem mass spectrometry (LC-MS/MS).

Example 17. Testing of Promoter Constructs with Alternative Capsids

Viral genomes (e.g., hFXN2; SEQ ID NO: 1797, hFXN6; SEQ ID NO: 1801) comprising select promoter variant constructs from Table 4 will be incorporated into AAV particles having alternative capsids selected from Table 1. These capsids may have a sub-optimal or non-canonical initiation codon for translation of VP1, such as, but not limited to CTG. Such AAV particles will be used to deliver frataxin protein to target cells in a mouse by intravenous injection via the tail vein. Twenty-three male C57BL/6J mice will be given a $2 \times 10^{13}$ VG/kg dose of an AAV particle composition. Fourteen days after delivery, mice will undergo transcardiac perfusion with cold 1×PBS and tissue samples will be collected.

Any or all of the following tissue samples will be collected. Cervical, thoracic and/or lumbar DRG, cervical, thoracic, and/or lumbar spinal cord, frontal cortex, motor cortex, hippocampus, striatum, cerebellum, brainstem, liver, heart, heart atrium, heart ventricle, and/or gastrocnemius muscle. Tissue of the lumbar DRG, heart ventricle, lower lumbar spinal cord, frontal cortex and cerebellum will be used for ELISA to determine frataxin expression in the target tissue. Thoracic DRG, heart ventricle, upper lumbar spinal cord, frontal cortex, cerebellum, and/or liver will be used for digital droplet PCR to quantify vector genome/diploid cell. The resulting data will be used to confirm expected tissue biodistribution and transduction. It is anticipated that the use of an alternative capsid will result in similar if not better biodistribution and transduction as compared to VOY101, VOY201, and/or AAV9 or a variant thereof.

Example 18. In Vivo Promoter Selection Studies in Rats

Select AAV particles with viral genomes comprising promoter variant sequences were tested in rats to determine frataxin expression in target cells and tissues. The following hFXN ITR-to-ITR constructs selected from Table 4 were used: hFXN2 (SEQ ID NO: 1797), hFXN10 (SEQ ID NO: 1805), hFXN11 (SEQ ID NO: 1806), hFXN12 (SEQ ID NO: 1807), hFXN13 (SEQ ID NO: 1808), hFXN14 (SEQ ID NO: 1809), and hFXN15 (SEQ ID NO: 1810). AAV particles which included the selected hFXN ITR-to-ITR constructs in VOY101 capsids were produced by triple transfection using mammalian HEK293 cells according to the present disclosure. The resulting AAV particles were purified and then formulated into 192 mM sodium chloride, 2.7 mM potassium chloride, and 10 mM sodium phosphate (dibasic) with 0.001% pluronic acid (Pluronic F-68) and at pH 7.4).

The AAV particles were administered by intravenous delivery via the tail vein into male Sprague Dawley rats (5 per group) at one of two doses: $6.3 \times 10^{12}$ vg/kg or $2 \times 10^{13}$ vg/kg (5 ml/kg over 1 hour). At 28 days after administration, tissue samples were collected (heart ventricle and DRG) and analyzed for frataxin expression levels based on Anti-Frataxin SimpleStep ELISA. Data are shown in FIG. 6A, FIG. 6B, FIG. 6C, and FIG. 6D.

hFXN13 (CBA.D4), hFXN14 (CBA.D6) and hFXN2 (CBA.D8) were well tolerated at $6.3 \times 10^{12}$ vg/kg or $2 \times 10^{13}$ vg/kg, with low expression levels in both DRG and heart ventricle tissue compared to hFXN10, hFXN11, hFXN12 and hFXN15.

Example 19. In Vitro Evaluation of Promoter Variants

Seven promotor variant constructs including hFXN2 (SEQ ID NO: 1797), hFXN6 (SEQ ID NO: 1801), hFXN10 (SEQ ID NO: 1805), hFXN11 (SEQ ID NO: 1806), hFXN12 (SEQ ID NO: 1807), hFXN13 (SEQ ID NO: 1808), and hFXN14 (SEQ ID NO: 1809) were evaluated for expression activity in vitro in HEK293 cells. CMV and CBA promoter constructs were used as controls. The cells were transfected with a plasmid comprising one of the hFXN constructs or controls and a luciferase payload. The activity and expression of luciferase was determined using a luciferase assay system. 239T cells were used as a negative control.

Figure 7:
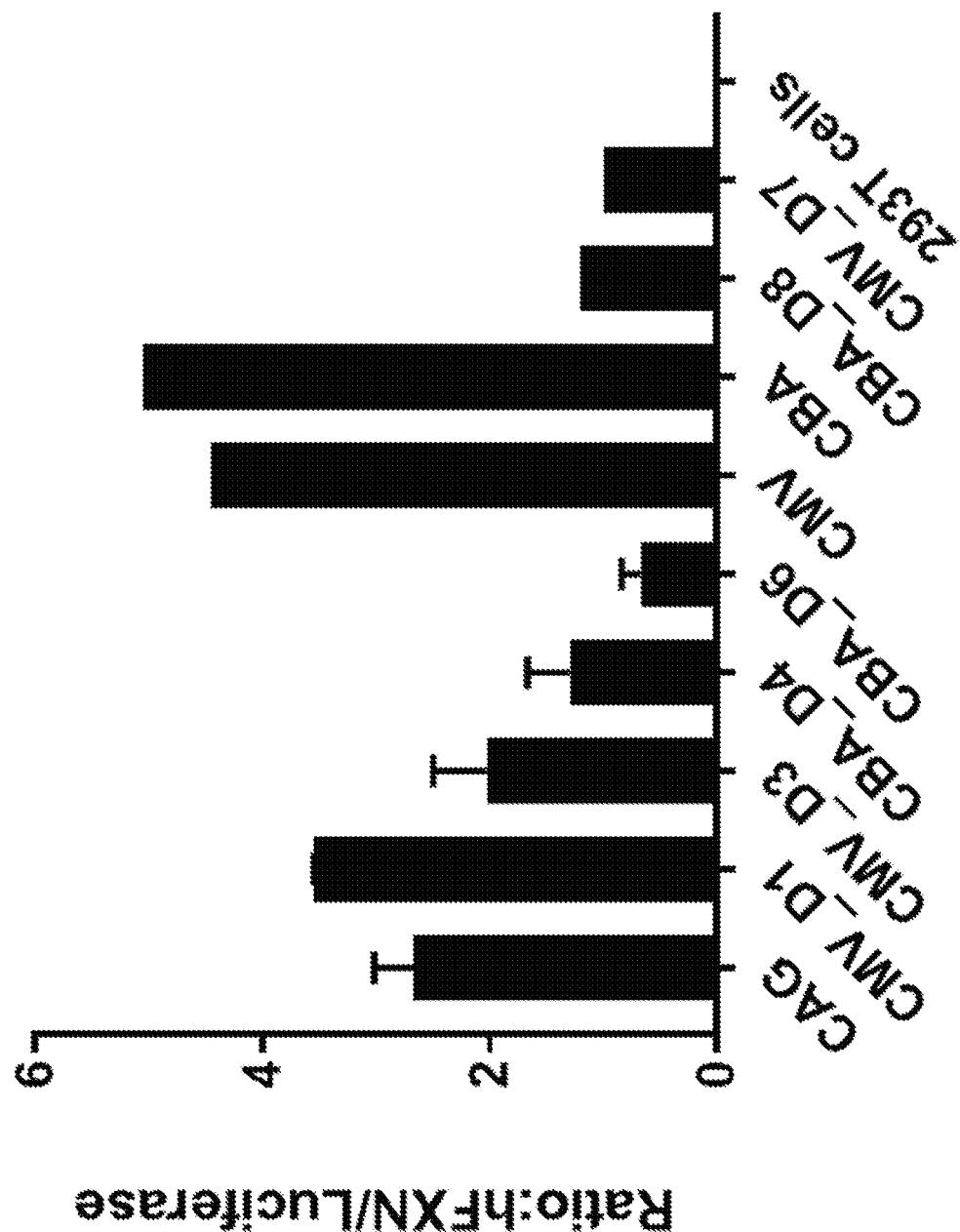
FIG. 7 presents a graph showing quantification results for frataxin expression levels by luciferase expression (FXN: Luciferase ratio) for promoter constructs of the present disclosure.

The activity of the promoter variants as determined by luciferase expression is shown in FIG. 7.

X. Equivalents and Scope

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

SEQUENCE LISTING

The patent contains a lengthy sequence listing. A copy of the sequence listing is available in electronic form from the USPTO web site (https://seqdata.uspto.gov/?pageRequest=docDetail&DocID=US12281321B2). An electronic copy of the sequence listing will also be available from the USPTO upon request and payment of the fee set forth in 37 CFR 1.19(b)(3).

The invention claimed is:

1. An adeno-associated viral (AAV) vector genome comprising an engineered promoter and a nucleic acid sequence encoding a frataxin protein, wherein the engineered promoter consists of a sequence that has at least 90% sequence identity to SEQ ID NO: 1742 over the full length of the engineered promoter.

2. The AAV vector genome of claim 1, wherein the engineered promoter consists of a sequence that has at least 95% sequence identity to SEQ ID NO: 1742 over the full length of the engineered promoter.

3. The AAV vector genome of claim 1, wherein the engineered promoter consists of a sequence that has at least 99% sequence identity to SEQ ID NO: 1742 over the full length of the engineered promoter.

4. The AAV vector genome of claim 1, wherein the engineered promoter consists of SEQ ID NO: 1742.

5. The AAV vector genome of claim 1, wherein the frataxin protein comprises an amino acid sequence having at least 80% sequence identity to SEQ ID NO: 1725, 1726, or 1727.

6. The AAV vector genome of claim 1, wherein the frataxin protein comprises an amino acid sequence of SEQ ID NO: 1725, 1726, or 1727.

7. The AAV vector genome of claim 1, wherein the frataxin protein comprises an amino acid sequence of SEQ ID NO: 1725.

8. The AAV vector genome of claim 1, wherein the nucleic acid sequence encoding the frataxin protein has at least 80% sequence identity to a fragment of SEQ ID NO: 1728, 1729, or 1730.

9. The AAV vector genome of claim 1, wherein the nucleic acid sequence encoding the frataxin protein comprises a fragment of SEQ ID NO: 1728, 1729, or 1730.

10. The AAV vector genome of claim 1, wherein the nucleic acid sequence encoding the frataxin protein comprises nucleotides 221-853 of SEQ ID NO: 1728.

11. The AAV vector genome of claim 1, wherein the nucleic acid sequence encoding the frataxin protein has at least 80% sequence identity to SEQ ID NO: 1823 or 1824.

12. The AAV vector genome of claim 1, wherein the nucleic acid sequence encoding the frataxin protein is SEQ ID NO: 1823 or 1824.

13. The AAV vector genome of claim 1, wherein the nucleic acid sequence encoding the frataxin protein comprises SEQ ID NO: 1823 or 1824.

14. The AAV vector genome of claim 1, wherein the AAV vector genome further comprises a 5' inverted terminal repeat (ITR).

15. The AAV vector genome of claim 14, wherein the 5' ITR is an AAV2 ITR.

16. The AAV vector genome of claim 1, wherein the AAV vector genome further comprises a 3' ITR.

17. The AAV vector genome of claim 16, wherein the 3' ITR is an AAV2 ITR.

18. The AAV vector genome of claim 1, wherein the AAV vector genome further comprises a 5' inverted terminal repeat (ITR), an intron, a microRNA (miR) binding site, a polyadenylation (polyA) sequence, a filler sequence, a 3' ITR.

19. The AAV vector genome of claim 18, wherein the intron comprises an enhancer sequence.

20. The AAV vector of claim 18, wherein: the 5' ITR has at least 95% sequence identity to SEQ ID NO: 1811, the intron has at least 90% sequence identity to SEQ ID NO: 1816, the nucleic acid sequence encoding the frataxin protein has at least 90% identity to SEQ ID NO: 1824, the miR binding site has at least 90% identity to SEQ ID NO: 1826 or 1827, the polyA sequence has at least 90% sequence identity to SEQ ID NO: 1828, the filler sequence has at least 90% sequence identity to SEQ ID NO: 1841, and/or the 3' ITR has at least 95% sequence identity to SEQ ID NO: 1812.

21. The AAV vector of claim 20, wherein: the 5' ITR comprises SEQ ID NO: 1811, the intron comprises SEQ ID NO: 1816, the nucleic acid sequence encoding the frataxin protein comprises SEQ ID NO: 1824, the miR binding site comprises SEQ ID NO: 1826 or 1827, the polyA sequence comprises SEQ ID NO: 1828, the filler sequence comprises SEQ ID NO: 1841, and/or the 3' ITR comprises SEQ ID NO: 1812.

22. The AAV vector genome of claim 18, wherein the AAV vector genome further comprises three copies of a microRNA (miR) binding site.

23. The AAV vector genome of claim 22, wherein the three copies of a miR binding site comprises SEQ ID NO: 1826.

24. The AAV vector genome of claim 1, wherein the AAV vector genome further comprises at least one microRNA (miR) binding site.

25. The AAV vector genome of claim 24, wherein the at least one miR binding site comprises a sequence that has at least 90% sequence identity to SEQ ID NO: 1827.

26. The AAV vector genome of claim 24, wherein the at least one miR binding site comprises SEQ ID NO: 1827.

27. An AAV particle comprising the AAV vector genome of claim 1.

28. A pharmaceutical composition comprising the AAV particle of claim 27 and a pharmaceutically acceptable excipient.

29. A method of treating Friedreich's Ataxia or another disorder associated with decreased frataxin protein levels in a subject in need thereof, comprising administering to the subject an effective amount of the AAV particle of claim 27.

30. The AAV vector genome of claim 1, wherein the nucleic acid sequence encoding the frataxin protein has at least 90% sequence identity to SEQ ID NO: 1823 or 1824.

31. The AAV vector genome of claim 1, wherein the nucleic acid sequence encoding the frataxin protein has at least 95% sequence identity to SEQ ID NO: 1823 or 1824.

32. An adeno-associated viral (AAV) vector genome comprising a sequence that has at least 90% sequence identity to SEQ ID NO: 1797.

33. The AAV vector genome of claim 32, wherein the AAV vector genome comprises a sequence that has at least 95% sequence identity to SEQ ID NO: 1797.

34. An AAV particle comprising the AAV vector genome of claim 32.

35. A cell comprising the AAV vector genome of claim 32.

36. A pharmaceutical composition comprising the AAV particle of claim 34 and a pharmaceutically acceptable excipient.

37. A method of treating Friedreich's Ataxia or another disorder associated with decreased frataxin protein levels in a subject in need thereof, comprising administering to the subject an effective amount of the AAV particle of claim 34.

38. An adeno-associated virus (AAV) vector genome comprising the sequence of SEQ ID NO: 1797.

39. An AAV particle comprising the AAV vector genome of claim 38.

40. A cell comprising the AAV vector genome of claim 38.

41. A pharmaceutical composition comprising the AAV particle of claim 39 and a pharmaceutically acceptable excipient.

42. A method of treating Friedreich's Ataxia or another disorder associated with decreased frataxin protein levels in a subject in need thereof, comprising administering to the subject an effective amount of the AAV particle of claim 39.

* * * * *

UNITED STATES PATENT AND TRADEMARK OFFICE
CERTIFICATE OF CORRECTION

PATENT NO. : 12,281,321 B2
APPLICATION NO. : 17/279878
DATED : April 22, 2025
INVENTOR(S) : Patzke et al.

Page 1 of 1

It is certified that error appears in the above-identified patent and that said Letters Patent is hereby corrected as shown below:

In the Claims

Claim 18, Column 211, Lines 38-39, "a filler sequence, a 3' ITR." should read --a filler sequence, and/or a 3' ITR.--.

Signed and Sealed this
Tenth Day of June, 2025

Coke Morgan Stewart
*Acting Director of the United States Patent and Trademark Office*